United States Patent [19]
Talley et al.

[11] Patent Number: 5,668,161
[45] Date of Patent: Sep. 16, 1997

[54] SUBSTITUTED THIAZOLES FOR THE TREATMENT OF INFLAMMATION

[75] Inventors: John J. Talley, Brentwood; Jeffery S. Carter, Chesterfield, both of Mo.; Paul W. Collins, Deerfield, Ill.; Steven W. Kramer, Des Plaines, Ill.; Thomas D. Penning, Elmhurst, Ill.; Donald J. Rogier, Jr., St. Louis; Roland S. Rogers, Richmond Heights, both of Mo.

[73] Assignee: G.D. Searle & Co., Skokie, Ill.

[21] Appl. No.: 679,462

[22] Filed: Jul. 9, 1996

Related U.S. Application Data

[63] Continuation of Ser. No. 281,288, Jul. 27, 1994, abandoned.

[51] Int. Cl.[6] ............... C07D 277/26; A61K 31/425
[52] U.S. Cl. ............... 514/365; 514/312; 514/326; 514/370; 546/209; 546/270.4; 546/256; 548/193; 548/194; 548/201; 548/203; 548/205
[58] Field of Search ............... 514/365, 370, 514/312, 326; 548/203, 201, 205, 193, 194; 546/280, 209

[56] References Cited

U.S. PATENT DOCUMENTS

| | | | |
|---|---|---|---|
| 4,346,088 | 8/1982 | Lang | 548/197 |
| 4,632,930 | 12/1986 | Carizi | 514/365 |
| 5,550,142 | 8/1996 | Ducharme et al. | 514/365 |

FOREIGN PATENT DOCUMENTS

87/06429  11/1987  WIPO.

OTHER PUBLICATIONS

Yagupolskii Zh.okh. 31 (4/1315, (1961).

Primary Examiner—Robert Gerstl
Attorney, Agent, or Firm—Joseph W. Bulock

[57] ABSTRACT

A class of substituted thiazolyl compounds is described for use in treating inflammation disorders. Compounds are defined by Formula II

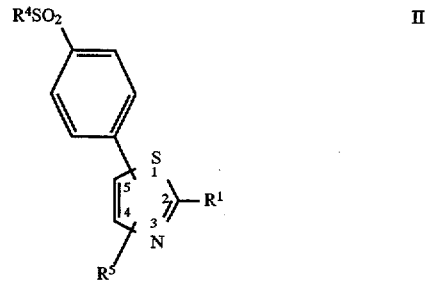

wherein $R^1$ is selected from hydrido, alkyl, haloalkyl, cyanoalkyl, alkylamino, aralkyl, arylamino, heteroarylsulfonylalkyl, heteroarylsulfonylhaloalkyl, aralkylamino, aryloxyalkyl, alkoxycarbonyl, aryl optionally substituted at a substitutable position with one or more radicals selected from halo and alkoxy, and heterocyclic optionally substituted at a substitutable position with one or more radicals selected from halo and alkyl; wherein $R^4$ is selected from alkyl and amino; and wherein $R^5$ is selected from aryl and heteroaryl; wherein $R^5$ is optionally substituted at a substitutable position with one or more radicals selected from halo, alkyl and alkoxy; provided $R^5$ is not phenyl at position 4 when $R^1$ is α,α-bis(trifluoromethyl)methanol and $R^4$ is methyl; or a pharmaceutically-acceptable salt thereof.

34 Claims, No Drawings

SUBSTITUTED THIAZOLES FOR THE TREATMENT OF INFLAMMATION

This is a continuation of application Ser. No. 08/281,288 filed Jul. 27, 1994, now abandoned.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, *Proc. Natl. Acad. Sci, USA*, 89, 7384 (1992) and named "cyclooxygenase II (COX II)" or "prostaglandin G/H synthase II". The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, *Proc. Natl. Acad. Sci, USA*, 89, 3917 (1992)). The 6-methoxy-2-napthylacetic acid metabolite of nabumetone has been found by E. Meade et al to selectively inhibit the COX II enzyme (*J. Biol. Chem.*, 268, 6610 (1993)). In addition, Futaki et al (*Prostaglandins*, 47, 55 (1994)) have reported that N-(2-cyclohexyloxy-4-nitrophenyl)methanesulfonamide inhibits the COX II enzyme.

The references below that disclose antiinflammatory activity, show continuing efforts to find a safe and effective antiinflammatory agent. The novel thiazoles disclosed herein are such safe and also effective antiinflammatory agents furthering such efforts. The invention compounds are found to show usefulness in vivo as antiinflammatory agents with minimal side effects. The substituted thiazolyl compounds disclosed herein preferably selectively inhibit cyclooxygenase II over cyclooxygenase I.

Diarylheterocycles having antiinflammatory activity are described in copending applications Ser. Nos. 08/160,594 and 08/065,730.

U.S. Pat. No. 5,232,921 to Biziere et al describes 2-alkylaminothiazoles as having an affinity for muscarinic cholinergic receptors.

PCT application WO 93/15071, published Aug. 5, 1993, describes 4-(2-pyridyl)thiazole derivatives as inhibiting gastric acid secretion. Specifically, 2-(phenylmethyl)-4-(2-pyridyl)-5-(2-methylphenyl)thiazole is described. U.S. Pat. No. 4,612,321 to S. Terao and Y. Maki describes 5-pyridylthiazole derivatives, and specifically 5-pyridyl-4-(4-methoxyphenyl)-2-thienylthiazole, as having antiinflammatory activity.

U.S. Pat. No. 4,659,726 to Yoshino et al, describes 4,5-bis(4-methoxyphenyl)-2-(2-pyrrolyl)thiazoles as being effective as platelet aggregation inhibitors. U.S. Pat. No. 5,217,971 to Takasugi et al describes 4,5-diphenylthiazole compounds as having antiinflammatory properties, and specifically 4,5-bis(4-methoxyphenyl)-2-(4-pyridyl)thiazole.

U.S. Pat. No. 4,168,315 to R. Rynbrandt and E. Nishizawa describes 4,5-diphenylthiazole derivatives as being blood platelet agglutination inhibitors. U.S. Pat. No. 4,322,428 to K. Matsumoto and P. Ho, describe 2-(4-halophenyl)-4,5-bis(4-methoxyphenyl)thiazoles as being antiinflammatory. U.S. Pat. No. 4,451,471 to P. Ferrini and R. Goschke describes 2-thio-4,5,diarylthiazole derivatives as having antiinflammatory activity. 4,5-Bis(4-methoxyphenyl) thiazole is described as a synthetic intermediate. PCT application WO 87/6429, published Nov. 5, 1987, describes thienylthiazole compounds, and specifically 4-(4-chlorophenyl)-2-(5-chloro-2-thienyl)-5-(4-methylphenyl)thiazole, as having insecticidal utility.

U.S. Pat. No. 4,051,250 to Dahm et al describes 4,5-diarylthiazole compounds as being antiinflammatory. Specifically, 2-chloro-4-(4 -chlorophenyl)-5-(4-methylmercaptophenyl)thiazole is described as a synthetic intermediate. European Application EP592,664, published Apr. 20, 1994, describes 4,5-diphenylthiazoles as having antiinflammatory activity, and specifically 4-[4-(methylsulfonyloxy)phenyl]-5-phenyl-2-[bis(N-methylsulfonyl)amino]thiazole. Seko et al [*Chem. Pharm. Bull.*, 39, 651 (1991)] describe the platelet aggregation and cyclooxygenase inhibitory activity of 4,5-diphenylthiazoles, and specifically of 4,5-bis(4-methylthiophenyl)-2-(1,5-dimethyl-2-pyrrolyl)thiazole.

U.S. Pat. No. 4,632,930 to D. Carini and R. Wexler describes alkylaryl thiazole derivatives, and specifically 5-phenyl-4-(methylsulfonylphenyl)-α,α-bis(trifluoromethyl)thiazole-2-methanol, as having antihypertensive properties.

DESCRIPTION OF THE INVENTION

A class of substituted thiazolyl compounds useful in treating inflammation-related disorders is defined by Formula I:

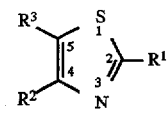

wherein $R^1$ is selected from hydrido, halo, amino, alkoxy, cyano, nitro, hydroxyl, aminocarbonyl, acyl, alkylaminocarbonyl, arylaminocarbonyl, alkyl, alkenyl, alkynyl, haloalkyl, haloalkoxy, alkylamino, arylamino, alkylarylamino, aralkylamino, carboxyl, carboxyalkyl, alkoxycarbonyl, alkoxycarbonylalkyl, alkylaminoalkyl, heterocyclicalkyl, aralkyl, cyanoalkyl, N-alkylsulfonylamino, heteroarylsulfonylalkyl, heteroarylsulfonylhaloalkyl, aryloxyalkyl, aralkyloxyalkyl, aryl optionally substituted at a substitutable position with one or more radicals selected from halo, alkyl, alkoxy, alkylthio, alkylsulfinyl, haloalkyl, haloalkoxy, carboxyalkyl, alkoxycarbonyl, aminocarbonyl, amino, acyl and alkylamino, and heterocyclic optionally substituted at a substitutable position with one or more radicals selected from halo, alkyl, alkoxy, alkylthio, alkylsulfinyl, haloalkyl, haloalkoxy, carboxyalkyl, alkoxycarbonyl, aminocarbonyl, amino, acyl and alkylamino;

wherein $R^2$ is selected from alkyl, alkenyl, aryl, cycloalkyl, cycloalkenyl and heterocyclic; wherein $R^2$ is optionally substituted at a substitutable position with one or more radicals selected from halo, alkylthio, alkylsulfinyl, alkylsulfonyl, haloalkylsulfonyl, sulfamyl, alkyl, alkenyl, alkynyl, cyano, carboxyl, carboxyalkyl, alkoxycarbonyl, aminocarbonyl, acyl, N-monoalkylaminocarbonyl, N-monoarylaminocarbonyl, N,N-dialkylaminocarbonyl, N-alkyl-N-arylaminocarbonyl, haloalkyl, hydroxyl, alkoxy, hydroxyalkyl, haloalkoxy, amino, N-alkylamino, N,N-dialkylamino, heterocyclic and nitro;

wherein $R^3$ is selected from alkyl, alkenyl, aryl, cycloalkyl, cycloalkenyl and heterocyclic; wherein $R^3$ is optionally substituted at a substitutable position with one or more radicals selected from halo, alkylthio, alkylsulfinyl, alkylsulfonyl, haloalkylsulfonyl, sulfamyl, alkyl, alkenyl, alkynyl, cyano, carboxyl, carboxyalkyl, alkoxycarbonyl, aminocarbonyl, acyl, N-monoalkylaminocarbonyl, N-monoarylaminocarbonyl, N,N-dialkylaminocarbonyl, N-alkyl-N-arylaminocarbonyl, haloalkyl, haloalkoxy, hydroxyl, alkoxy, hydroxyalkyl, amino, N-alkylamino, N,N-dialkylamino, heterocyclic and nitro;

provided one of $R^2$ and $R^3$ is substituted with alkylsulfonyl, haloalkylsulfonyl or sulfamyl; and further provided that $R^2$ is not methylsulfonylphenyl when $R^1$ is α,α-bis(trifluoromethyl)methanol;

or a pharmaceutically-acceptable salt thereof.

The phrase "further provided", as used in the above description, is intended to mean that the denoted proviso is not to be considered conjunctive with the other provisos.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects.

The present invention preferably includes compounds which selectively inhibit cyclooxygenase II over cyclooxygenase I. Preferably, the compounds have a cyclooxygenase II $IC_{50}$ of less than about 0.1 μM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 0.5 μM, and more preferably of greater than 5 μM. Such preferred selectivity may indicate an ability to reduce the incidence of common NSAID-induced side effects.

A preferred class of compounds consists of those compounds of Formula I wherein $R^1$ is selected from hydrido, halo, amino, alkoxy, cyano, nitro, hydroxyl, aminocarbonyl, acyl, alkylaminocarbonyl, arylaminocarbonyl, alkyl, alkenyl, alkynyl, haloalkyl, haloalkoxy, alkylamino, arylamino, aralkylamino, carboxyl, carboxyalkyl, alkoxycarbonyl, alkoxycarbonylalkyl, alkylaminoalkyl, heterocyclicalkyl, aralkyl, cyanoalkyl, N-alkylsulfonylamino, heteroarylsulfonylalkyl, heteroarylsulfonylhaloalkyl, aryloxyalkyl, aralkyloxyalkyl, aryl optionally substituted at a substitutable position with one or more radicals selected from halo, alkyl, alkoxy, alkylthio, alkylsulfinyl, haloalkyl, haloalkoxy, carboxyalkyl, alkoxycarbonyl, aminocarbonyl, amino, acyl and alkylamino, and heterocyclic optionally substituted at a substitutable position with one or more radicals selected from halo, alkyl, alkoxy, alkylthio, alkylsulfinyl, haloalkyl, haloalkoxy, carboxyalkyl, alkoxycarbonyl, aminocarbonyl, amino, acyl and alkylamino;

wherein $R^2$ is selected from alkyl, alkenyl, aryl, cycloalkyl, cycloalkenyl and heterocyclic; wherein $R^2$ is optionally substituted at a substitutable position with one or more radicals selected from halo, alkylthio, alkylsulfinyl, alkyl, alkenyl, alkynyl, cyano, carboxyl, carboxyalkyl, alkoxycarbonyl, aminocarbonyl, acyl, N-monoalkylaminocarbonyl, N-monoarylaminocarbonyl, N,N-dialkylaminocarbonyl, N-alkyl-N-arylaminocarbonyl, haloalkyl, hydroxyl, alkoxy, hydroxyalkyl, haloalkoxy, amino, N-alkylamino, N,N-dialkylamino, heterocyclic and nitro; and wherein $R^3$ is aryl substituted at a substitutable position with a radical selected from alkylsulfonyl, haloalkylsulfonyl and sulfamyl;

or a pharmaceutically-acceptable salt thereof.

A more preferred class of compounds consists of those compounds of Formula I wherein $R^1$ is selected from halo, amino, lower alkoxy, cyano, nitro, hydroxyl, aminocarbonyl, acyl, lower alkylaminocarbonyl, lower arylaminocarbonyl, lower alkyl, lower alkenyl, lower alkynyl, lower haloalkyl, lower haloalkoxy, lower alkylamino, lower arylamino, lower aralkylamino, carboxyl, lower carboxyalkyl, lower alkoxycarbonyl, lower alkoxycarbonylalkyl, lower alkylaminoalkyl, lower heterocyclicalkyl, lower aralkyl, lower cyanoalkyl, lower aryloxyalkyl, lower N-alkylsulfonylamino, lower heteroarylsulfonylalkyl, lower aralkyloxyalkyl, lower heteroarylsulfonylhaloalkyl, aryl selected from phenyl, naphthyl and biphenyl, optionally substituted at a substitutable position with one or more radicals selected from halo, lower alkyl, lower alkoxy, lower alkylthio, lower alkylsulfinyl, lower haloalkyl, lower haloalkoxy, lower carboxyalkyl, lower alkoxycarbonyl, aminocarbonyl, amino, acyl and lower alkylamino, and heterocyclic selected from thienyl, pyridyl, furyl, pyrazinyl, pyrrolyl, pyrazolyl and triazolyl, optionally substituted at a substitutable position with one or more radicals selected from halo, lower alkyl, lower alkoxy, lower alkylthio, lower alkylsulfinyl, lower haloalkyl, lower haloalkoxy, lower carboxyalkyl, lower alkoxycarbonyl, aminocarbonyl, amino, acyl and lower alkylamino;

wherein $R^2$ is selected from lower alkyl, lower alkenyl, aryl, lower cycloalkyl, lower cycloalkenyl and heterocyclic;

wherein $R^2$ is optionally substituted at a substitutable position with one or more radicals selected from halo, lower alkylthio, lower alkylsulfinyl, lower alkyl, lower alkenyl, lower alkynyl, cyano, carboxyl, lower carboxyalkyl, lower alkoxycarbonyl, aminocarbonyl, acyl, lower N-monoalkylaminocarbonyl, N-monoarylaminocarbonyl, lower N,N-dialkylaminocarbonyl, lower N-alkyl-N-arylaminocarbonyl, lower haloalkyl, hydroxyl, lower alkoxy, lower hydroxyalkyl, lower haloalkoxy, amino, lower N-alkylamino, lower N,N-dialkylamino, heterocyclic and nitro; and wherein $R^3$ is aryl selected from phenyl, naphthyl and biphenyl, substituted at a substitutable position with a radical selected from lower alkylsulfonyl, lower haloalkylsulfonyl and sulfamyl;

or a pharmaceutically-acceptable salt thereof.

A class of compounds of particular interest consists of those compounds of Formula I wherein $R^1$ is selected from fluoro, chloro, bromo, iodo, amino, methoxy, ethoxy, propoxy, butoxy, isopropoxy, tert-butoxy, cyano, nitro, hydroxy, aminocarbonyl, formyl, acetyl, N-methylaminocarbonyl, N-phenylaminocarbonyl, N,N-dimethylaminocarbonyl, N-methyl-N-phenylaminocarbonyl, methyl, ethyl, propyl, butyl, pentyl, isopropyl, isobutyl, tert-butyl, ethylenyl, propylenyl, butenyl, pentenyl, isopropylenyl, isobutylenyl, propargyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, N-methylamino, N-ethylamino, N-propylamino, N-butylamino, N-tert-butylamino, N-pentylamino, N-hexylamino, N,N-dimethylamino, carboxyl, N-benzylamino, carboxymethyl, methoxycarbonylmethyl, ethoxycarbonylmethyl, methylaminomethyl, morpholinomethyl, pyrrolidinylmethyl, piperazinylmethyl, piperidinylmethyl, pyridylmethyl, thienylmethyl, benzyl, phenethyl, phenpropyl, cyanomethyl, phenoxymethyl, benzyloxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylsulfonylamino, (2-thienyl)sulfonylmethyl, (2-thienyl)sulfonylbromomethyl, phenyl optionally substituted at a substitutable position with one or more radicals selected from fluoro, chloro, bromo, methyl, ethyl, propyl, butyl, pentyl, isopropyl, isobutyl, tert-butyl, methoxy, ethoxy, propoxy, butoxy, isopropoxy, tert-butoxy, methylthio, methylsulfinyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxymethyl, methoxycarbonyl, ethoxycarbonyl, aminocarbonyl, amino, formyl, methylamino and dimethylamino, and heterocyclic selected from morpholino, pyrrolidinyl, piperazinyl, piperidinyl, thienyl, pyridyl, furyl, pyrazinyl, pyrrolyl, pyrazolyl and triazolyl, optionally substituted at a substitutable position with one or more radicals selected from fluoro, chloro, bromo, methyl, ethyl, propyl, butyl, pentyl, isopropyl, isobutyl, tert-butyl, methoxy, ethoxy, propoxy, butoxy, isopropoxy, tert-butoxy, methylthio, methylsulfinyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxymethyl, methoxycarbonyl, ethoxycarbonyl, aminocarbonyl, amino, formyl, methylamino and dimethylamino;

wherein $R^2$ is selected from methyl, ethyl, propyl, butyl, pentyl, isopropyl, isobutyl, tert-butyl, ethylenyl, propylenyl, butenyl, pentenyl, isopropylenyl, isobutylenyl, phenyl, naphthyl, biphenyl, thienyl, pyridyl, furyl, pyrazinyl, pyrrolyl, pyrazolyl, triazolyl, cyclopropyl, cyclobutyl, cyclopentyl, cyclohexyl, cyclopropenyl, cyclobutenyl, cyclopentenyl, cyclohexenyl, morpholino, pyrrolidinyl, piperazinyl and piperidinyl; wherein $R^2$ is optionally substituted at a substitutable position with one or more radicals selected from fluoro, chloro, bromo, methylthio, methylsulfinyl, methyl, ethyl, propyl, butyl, pentyl, isopropyl, isobutyl, tert-butyl, ethylenyl, propylenyl, butenyl, pentenyl, isopropylenyl, isobutylenyl, propargyl, cyano, carboxyl, carboxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, formyl, acetyl, N-methylaminocarbonyl, N-phenylaminocarbonyl, N,N-dimethylaminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, ethoxy, propoxy, butoxy, isopropoxy, tert-butoxy, hydroxymethyl, trifluoromethoxy, amino, N-methylamino, N,N-dimethylamino, pyridyl, furyl, pyrazinyl, pyrrolyl, pyrazolyl, morpholino, pyrrolidinyl, piperazinyl, piperidinyl, triazolyl and nitro; and wherein $R^3$ is aryl selected from phenyl, naphthyl and biphenyl, substituted at a substitutable position with a radical selected from methylsulfonyl, fluoromethylsulfonyl and sulfamyl;

or a pharmaceutically-acceptable salt thereof.

A family of specific compounds of particular interest within Formula I consists of compounds and pharmaceutically-acceptable salts thereof as follows:

5-[(4-methylsulfonyl)phenyl]-4-(4-fluorophenyl)-2-phenylthiazole;

5-[(4-methylsulfonyl)phenyl]-4-(4-fluorophenyl)-2-(4-methoxyphenyl)thiazole;

5-[(4-methylsulfonyl)phenyl]-4-(4-fluorophenyl)-2-(4-chlorophenyl)thiazole;

5-[(4-methylsulfonyl)phenyl]-4-(4-fluorophenyl)-2-(N-hexylamino)thiazole;

5-[(4-methylsulfonyl)phenyl]-4-(4-fluorophenyl)-2-(N-methylamino)thiazole;

5-[(4-methylsulfonyl)phenyl]-4-(4-fluorophenyl)-2-(N-ethylamino)thiazole;

5-[(4-methylsulfonyl)phenyl]-4-(4-fluorophenyl)-2-(N-tert-butylamino)thiazole;

5-[(4-methylsulfonyl)phenyl]-4-(4-fluorophenyl)-2-(N-(4-phenoxyphenyl)amino)thiazole;

ethyl 4-[[5-[(4-methylsulfonyl)phenyl]-4-(4-fluorophenyl)-2-thiazolyl]amino]benzoate;

ethyl 3-[[5-[(4-methylsulfonyl)phenyl]-4-(4-fluorophenyl)-2-thiazolyl]amino]benzoate;

5-[(4-methylsulfonyl)phenyl]-4-(4-fluorophenyl)-2-(2-phenylethyl)thiazole;

5-[(4-methylsulfonyl)phenyl]-4-(4-fluorophenyl)-2-(N-(3,5-dichlorophenyl)amino)thiazole;

5-[(4-methylsulfonyl)phenyl]-4-(4-fluorophenyl)-2-(N-butylamino)thiazole;

4-[5-[(4-methylsulfonyl)phenyl]-4-(4-fluorophenyl)-2-thiazolyl]aminobenzoic acid;

3-[5-[(4-methylsulfonyl)phenyl]-4-(4-fluorophenyl)-2-thiazolyl]aminobenzoic acid;

5-[(4-methylsulfonyl)phenyl]-4-(4-fluorophenyl)-2-ethylthiazole;

5-[(4-methylsulfonyl)phenyl]-4-(4-fluorophenyl)-2-(3-phenylpropyl)thiazole;

5-[(4-methylsulfonyl)phenyl]-4-(4-fluorophenyl)-2-((3-chlorophenoxy)methyl)thiazole;

5-[(4-methylsulfonyl)phenyl]-4-(4-fluorophenyl)-2-(2-methyl-4-thiazolyl)thiazole;

5-[(4-methylsulfonyl)phenyl]-4-(2-fluorophenyl)-2-(2-chlorophenyl)thiazole;

5-[(4-methylsulfonyl)phenyl]-4-(2,5-difluorophenyl)-2-(2-chlorophenyl)thiazole;

5-[(4-methylsulfonyl)phenyl]-4-(4-fluorophenyl)-2-(2,3,4,5,6-pentafluorophenyl)thiazole;

5-[(4-methylsulfonyl)phenyl]-4-(4-fluorophenyl)-2-((2-chlorophenoxy)methyl)thiazole;

5-[(4-methylsulfonyl)phenyl]-4-(4-bromophenyl)-2-(2-chlorophenyl)thiazole;

5-[(4-methylsulfonyl)phenyl]-4-(2-fluorophenyl)-2-((3-chlorophenoxy)methyl)thiazole;

5-[(4-methylsulfonyl)phenyl]-4-(4-fluorophenyl)-2-((3,5-dichlorophenoxy)methyl)thiazole;

5-[(4-methylsulfonyl)phenyl]-4-(2-fluorophenyl)-2-((4-methoxyphenoxy)methyl)thiazole;

5-[(4-methylsulfonyl)phenyl]-4-(4-bromophenyl)- 2-(2-chlorophenyl)thiazole;

5-[(4-methylsulfonyl)phenyl]-4-(4-methylthiophenyl)-2-(2-chlorophenyl)thiazole;

5-[(4-methylsulfonyl)phenyl]-4-(3-fluoro-4-methoxyphenyl)-2-(2-chlorophenyl)thiazole;

5-[(4-methylsulfonyl)phenyl]-4-(3-chloro-4-methoxyphenyl)-2-(2-chlorophenyl)thiazole;

5-[(4-methylsulfonyl)phenyl]-4-(3-chloro-4-methylphenyl)-2-(2-chlorophenyl)thiazole;

5-[(4-methylsulfonyl)phenyl]-4-(3-methyl-4-chlorophenyl)-2-(2-chlorophenyl)thiazole;

5-[(4-methylsulfonyl)phenyl]-4-(3,4-methylenedioxyphenyl)-2-(2-chlorophenyl)thiazole;

5-[(4-methylsulfonyl)phenyl]-4-(3,5-difluoro-4-methoxyphenyl)-2-(2-chlorophenyl)thiazole;

5-[(4-methylsulfonyl)phenyl]-4-(3,5-dichloro-4-methoxyphenyl)-2-(2-chlorophenyl)thiazole;

5-[(4-methylsulfonyl)phenyl]-4-(4-fluorophenyl)-2-(difluoromethyl)thiazole;

5-[(4-methylsulfonyl)phenyl]-4-(4-fluorophenyl)-2-(methylthio)thiazole;

5-[(4-methylsulfonyl)phenyl]-4-(4-fluorophenyl)-2-(phenylthio)thiazole;

5-[(4-methylsulfonyl)phenyl]-4-(4-fluorophenyl)-2-((3-fluorophenyl)thio)thiazole;

5-[(4-methylsulfonyl)phenyl]-4-(4-fluorophenyl)-2-((3-chlorophenyl)thio)thiazole;

5-[(4-methylsulfonyl)phenyl]-4-(4-fluorophenyl)-2-((3-bromophenyl)thio)thiazole;

5-[(4-methylsulfonyl)phenyl]-4-(4-fluorophenyl)-2-((3,5-difluorophenyl)thio)thiazole;

5-[(4-methylsulfonyl)phenyl]-4-(4-fluorophenyl)-2-[(3,5-dichlorophenyl)thio]thiazole;

5-[(4-methylsulfonyl)phenyl]-4-(4-fluorophenyl)-2-[(4-fluorophenyl)thio]thiazole;

5-[(4-methylsulfonyl)phenyl]-4-(4-fluorophenyl)-2-[(4-chlorophenyl)thio]thiazole;

5-[(4-methylsulfonyl)phenyl]-4-(4-fluorophenyl)-2-[(4-bromophenyl)thio]thiazole;

5-[(4-methylsulfonyl)phenyl]-4-(4-fluorophenyl)-2-((4-methylphenyl)thio)thiazole;

5-[(4-methylsulfonyl)phenyl]-4-(4-fluorophenyl)-2-(benzylthio)thiazole;

5-[(4-methylsulfonyl)phenyl]-4-(4-fluorophenyl)-2-((3-fluorobenzyl)thio)thiazole;

5-[(4-methylsulfonyl)phenyl]-4-(4-fluorophenyl)-2-((3-chlorobenzyl)thio)thiazole;

5-[(4-methylsulfonyl)phenyl]-4-(4-fluorophenyl)-2-((3-bromobenzyl)thio)thiazole;

5-[(4-methylsulfonyl)phenyl]-4-(4-fluorophenyl)-2-((3,5-difluorobenzyl)thio)thiazole;

5-[(4-methylsulfonyl)phenyl]-4-(4-fluorophenyl)-2-((3,5-dichlorobenzyl)thio)thiazole;

5-[(4-methylsulfonyl)phenyl]-4-(4-fluorophenyl)-2-((4-fluorobenzyl)thio)thiazole;

5-[(4-methylsulfonyl)phenyl]-4-(4-fluorophenyl)-2-((4-chlorobenzyl)thio)thiazole;

5-[(4-methylsulfonyl)phenyl]-4-(4-fluorophenyl)-2-((4-bromobenzyl)thio)thiazole;

5-[(4-methylsulfonyl)phenyl]-4-(4-fluorophenyl)-2-((4-methylbenzyl)thio)thiazole;

5-[(4-methylsulfonyl)phenyl]-4-(4-fluorophenyl)-2-(ethylsulfonyl)thiazole;

5-[(4-methylsulfonyl)phenyl]-4-(4-fluorophenyl)-2-(methylsulfonyl)thiazole;

5-[(4-methylsulfonyl)phenyl]-4-(4-fluorophenyl)-2-(phenylsulfonyl)thiazole;

5-[(4-methylsulfonyl)phenyl]-4-(4-fluorophenyl)-2-((3-fluorophenyl)sulfonyl)thiazole;

5-[(4-methylsulfonyl)phenyl]-4-(4-fluorophenyl)-2-((3-chlorophenyl)sulfonyl)thiazole;

5-[(4-methylsulfonyl)phenyl]-4-(4-fluorophenyl)-2-((3-bromophenyl)sulfonyl)thiazole;

5-[(4-methylsulfonyl)phenyl]-4-(4-fluorophenyl)-2-((3,5-difluorophenyl)sulfonyl)thiazole;

5-[(4-methylsulfonyl)phenyl]-4-(4-fluorophenyl)-2-((3,5-dichlorophenyl)sulfonyl)thiazole;

5-[(4-methylsulfonyl)phenyl]-4-(4-fluorophenyl)-2-((4-fluorophenyl)sulfonyl)thiazole;

5-[(4-methylsulfonyl)phenyl]-4-(4-fluorophenyl)-2-((4-chlorophenyl)sulfonyl)thiazole;

5-[(4-methylsulfonyl)phenyl]-4-(4-fluorophenyl)-2-((4-bromophenyl)sulfonyl)thiazole;

5-[(4-methylsulfonyl)phenyl]-4-(4-fluorophenyl)-2-((4-methylphenyl)sulfonyl)thiazole;

5-[(4-methylsulfonyl)phenyl]-4-(4-fluorophenyl)-2-(benzylsulfonyl)thiazole;

5-[(4-methylsulfonyl)phenyl]-4-(4-fluorophenyl)-2-((3-fluorobenzyl)sulfonyl)thiazole;

5-[(4-methylsulfonyl)phenyl]-4-(4-fluorophenyl)-2-((3-chlorobenzyl)sulfonyl)thiazole;

5-[(4-methylsulfonyl)phenyl]-4-(4-fluorophenyl)-2-((3-bromobenzyl)sulfonyl)thiazole;

5-[(4-methylsulfonyl)phenyl]-4-(4-fluorophenyl)-2-((3,5-difluorobenzyl)sulfonyl)thiazole;

5-[(4-methylsulfonyl)phenyl]-4-(4-fluorophenyl)-2-((3,5-dichlorobenzyl)sulfonyl)thiazole;

5-[(4-methylsulfonyl)phenyl]-4-(4-fluorophenyl)-2-((4-fluorobenzyl)sulfonyl)thiazole;

5-[(4-methylsulfonyl)phenyl]-4-(4-fluorophenyl)-2-((4-chlorobenzyl)sulfonyl)thiazole;

5-[(4-methylsulfonyl)phenyl]-4-(4-fluorophenyl)-2-((4-bromobenzyl)sulfonyl)thiazole;

5-[(4-methylsulfonyl)phenyl]-4-(4-fluorophenyl)-2-((4-methylbenzyl)sulfonyl)thiazole;

5-[(4-methylsulfonyl)phenyl]-4-(4-fluorophenyl)-2-(fluoromethylsulfonyl)thiazole;

5-[(4-methylsulfonyl)phenyl]-4-(4-fluorophenyl)-2-(acetyl)thiazole;

5-[(4-methylsulfonyl)phenyl]-4-(4-fluorophenyl)-2-(trifluoroacetyl)thiazole;
5-[(4-methylsulfonyl)phenyl]-4-(4-fluorophenyl)-2-(benzoyl)thiazole;
5-[(4-methylsulfonyl)phenyl]-4-(4-fluorophenyl-2-(3-fluorobenzoyl)thiazole;
5-[(4-methylsulfonyl)phenyl]-4-(4-fluorophenyl)-2-(3-chlorobenzoyl)thiazole;
5-[(4-methylsulfonyl)phenyl]-4-(4-fluorophenyl)-2-(3-bromobenzoyl)thiazole;
5-[(4-methylsulfonyl)phenyl]-4-(4-fluorophenyl)-2-(3,5-difluorobenzoyl)thiazole;
5-[(4-methylsulfonyl)phenyl]-4-(4-fluorophenyl)-2-(3,5-dichlorobenzoyl)thiazole;
5-[(4-methylsulfonyl)phenyl]-4-(4-fluorophenyl)-2-(4-fluorobenzoyl)thiazole;
5-[(4-methylsulfonyl)phenyl]-4-(4-fluorophenyl)-2-(4-chlorobenzoyl)thiazole;
5-[(4-methylsulfonyl)phenyl]-4-(4-fluorophenyl)-2-(4-bromobenzoyl)thiazole;
5-[(4-methylsulfonyl)phenyl]-4-(4-fluorophenyl)-2-(4-methylbenzoyl)thiazole;
methyl [5-[(4-methylsulfonyl)phenyl]-4-(4-fluorophenyl)-2-thiazolyl]carboxylate;
ethyl [5-[(4-methylsulfonyl)phenyl]-4-(4-fluorophenyl)-2-thiazolyl]carboxylate;
propyl [5-[(4-methylsulfonyl)phenyl]-4-(4-fluorophenyl)-2-thiazolyl]carboxylate;
butyl [5-[(4-methylsulfonyl)phenyl]-4-(4-fluorophenyl)-2-thiazolyl]carboxylate;
5-[(4-methylsulfonyl)phenyl]-4-(4-fluorophenyl)-2-(hydroxymethyl)thiazole;
5-[(4-methylsulfonyl)phenyl]-4-(4-fluorophenyl)-2-(methoxymethyl)thiazole;
5-[(4-methylsulfonyl)phenyl]-4-(4-fluorophenyl)-2-(phenoxymethyl)thiazole;
5-[(4-methylsulfonyl)phenyl]-4-(4-fluorophenyl)-2-(3-fluorophenoxymethyl)thiazole;
5-[(4-methylsulfonyl)phenyl]-4-(4-fluorophenyl)-2-(3-chlorophenoxymethyl)thiazole;
5-[(4-methylsulfonyl)phenyl]-4-(4-fluorophenyl)-2-(3-bromophenoxymethyl)thiazole;
5-[(4-methylsulfonyl)phenyl]-4-(4-fluorophenyl)-2-(3,5-difluorophenoxymethyl)thiazole;
5-[(4-methylsulfonyl)phenyl]-4-(4-fluorophenyl)-2-(3,5-dichlorophenoxymethyl)thiazole;
5-[(4-methylsulfonyl)phenyl]-4-(4-fluorophenyl)-2-(4-fluorophenoxymethyl)thiazole;
5-[(4-methylsulfonyl)phenyl]-4-(4-fluorophenyl)-2-(4-chlorophenoxymethyl)thiazole;
5-[(4-methylsulfonyl)phenyl]-4-(4-fluorophenyl)-2-(4-bromophenoxymethyl)thiazole;
5-[(4-methylsulfonyl)phenyl]-4-(4-fluorophenyl)-2-(4-methylphenoxymethyl)thiazole;
5-[(4-methylsulfonyl)phenyl]-4-(4-fluorophenyl)-2-(benzyloxymethyl)thiazole;
5-[(4-methylsulfonyl)phenyl]-4-(4-fluorophenyl)-2-(cyanomethyl)thiazole;
5-[(4-methylsulfonyl)phenyl]-4-(4-fluorophenyl)-2-(2-quinolylmethyloxymethyl)thiazole;
5-[(4-methylsulfonyl)phenyl]-4-(4-fluorophenyl)-2-(2-naphthylmethyloxymethyl)thiazole;
5-[(4-methylsulfonyl)phenyl]-4-(4-fluorophenyl)-2-(N-phenylaminocarbonyl)thiazole;
5-[(4-methylsulfonyl)phenyl]-4-(4-fluorophenyl)-2-[(3-fluorophenyl)aminocarbonyl]thiazole;
5-[(4-methylsulfonyl)phenyl]-4-(4-fluorophenyl)-2-[(3-chlorophenyl)aminocarbonyl]thiazole;
5-[(4-methylsulfonyl)phenyl]-4-(4-fluorophenyl)-2-[(3-bromophenyl)aminocarbonyl]thiazole;
5-[(4-methylsulfonyl)phenyl]-4-(4-fluorophenyl)-2-[(3,5-difluorophenyl)aminocarbonyl]thiazole;
5-[(4-methylsulfonyl)phenyl]-4-(4-fluorophenyl)-2-[(3,5-dichlorophenyl)aminocarbonyl]thiazole;
5-[(4-methylsulfonyl)phenyl]-4-(4-fluorophenyl)-2-[(4-fluorophenyl)aminocarbonyl]thiazole;
5-[(4-methylsulfonyl)phenyl]-4-(4-fluorophenyl)-2-[(4-chlorophenyl)aminocarbonyl]thiazole;
5-[(4-methylsulfonyl)phenyl]-4-(4-fluorophenyl)-2-[(4-bromophenyl)aminocarbonyl]thiazole;
5-[(4-methylsulfonyl)phenyl]-4-(4-fluorophenyl)-2-([4-methylphenyl)aminocarbonyl]thiazole;
5-[(4-methylsulfonyl)phenyl]-4-(4-fluorophenyl)-2-(benzylaminocarbonyl)thiazole;
5-[(4-methylsulfonyl)phenyl]-4-(4-fluorophenyl)-2-((3-fluorobenzyl)aminocarbonyl)thiazole;
5-[(4-methylsulfonyl)phenyl]-4-(4-fluorophenyl)-2-((3-chlorobenzyl)aminocarbonyl)thiazole;
5-[(4-methylsulfonyl)phenyl]-4-(4-fluorophenyl)-2-((3-bromobenzyl)aminocarbonyl)thiazole;
5-[(4-methylsulfonyl)phenyl]-4-(4-fluorophenyl)-2-((3,5-difluorobenzyl)aminocarbonyl)thiazole;
5-[(4-methylsulfonyl)phenyl]-4-(4-fluorophenyl)-2-((3,5-dichlorobenzyl)aminocarbonyl)thiazole;
5-[(4-methylsulfonyl)phenyl]-4-(4-fluorophenyl)-2-((4-fluorobenzyl)aminocarbonyl)thiazole;
5-[(4-methylsulfonyl)phenyl]-4-(4-fluorophenyl)-2-((4-chlorobenzyl)aminocarbonyl)thiazole;
5-[(4-methylsulfonyl)phenyl]-4-(4-fluorophenyl)-2-((4-bromobenzyl)aminocarbonyl)thiazole;
5-[(4-methylsulfonyl)phenyl]-4-(4-fluorophenyl)-2-((4-methylbenzyl)aminocarbonyl)thiazole;
5-[(4-methylsulfonyl)phenyl]-4-(4-fluorophenyl)-2-(benzoylamino)thiazole;
5-[(4-methylsulfonyl)phenyl]-4-(4-fluorophenyl)-2-((3-fluorobenzoyl)amino)thiazole;
5-[(4-methylsulfonyl)phenyl]-4-(4-fluorophenyl)-2-((3-chlorobenzoyl)amino)thiazole;
5-[(4-methylsulfonyl)phenyl]-4-(4-fluorophenyl)-2-((3-bromobenzoyl)amino)thiazole;
5-[(4-methylsulfonyl)phenyl]-4-(4-fluorophenyl)-2-((3,5-difluorobenzoyl)amino)thiazole;
5-[(4-methylsulfonyl)phenyl]-4-(4-fluorophenyl)-2-((3,5-dichlorobenzoyl)amino)thiazole;
5-[(4-methylsulfonyl)phenyl]-4-(4-fluorophenyl)-2-((4-fluorobenzoyl)amino)thiazole;
5-[(4-methylsulfonyl)phenyl]-4-(4-fluorophenyl)-2-((4-chlorobenzoylamino)thiazole;
5-[(4-methylsulfonyl)phenyl]-4-(4-fluorophenyl)-2-((4-bromobenzoyl)amino)thiazole;
5-[(4-methylsulfonyl)phenyl]-4-(4-fluorophenyl)-2-((4-methylbenzoyl)amino)thiazole;
5-[(4-methylsulfonyl)phenyl]-4-(4-fluorophenyl)-2-(phenylacetyl)aminothiazole;
2-((4-chlorophenoxy)methyl)-4-(4-fluorophenyl)-5-[(4-methylsulfonyl)phenyl]thiazole;
2-(2-chlorophenyl)-4-phenyl-5-[(4-methylsulfonyl)phenyl]thiazole;
2-(2-chlorophenyl)-4-(3-fluorophenyl)-5-[(4-methylsulfonyl)phenyl]thiazole;
4-(2,4-difluorophenyl)-2-(2-chlorophenyl)-5-[(4-methylsulfonyl)phenyl]thiazole;
2-(2-chlorophenyl)-4-(2-methylphenyl)-5-[(4-methylsulfonyl)phenyl]thiazole;
2-(2-chlorophenyl)-5-[(4-methylsulfonyl)phenyl]-4-(2-thienyl)thiazole;

2-(2-chlorophenyl)-5-[(4-methylsulfonyl)phenyl]-4-(3-thienyl)thiazole;
4-(4-fluorophenyl)-5-[(4-methylsulfonyl)phenyl]-2-(4-pyridyl)thiazole;
2-(2-chlorophenyl)-4-(2-chlorophenyl)-5-[(4-methylsulfonyl)phenyl]thiazole;
2-(2-chlorophenyl)-4-(4-chlorophenyl)-5-[(4-methylsulfonyl)phenyl]thiazole;
2-(2-chlorophenyl)-4-(4-methoxyphenyl)-5-[(4-methylsulfonyl)phenyl]thiazole;
2-(3-chloro-4-fluorophenyl)-4-(4-fluorophenyl)-5-[(4-methylsulfonyl)phenyl]thiazole;
2-((2-thienyl)sulfonylmethyl)-4-(4-fluorophenyl)-5-[(4-methylsulfonyl)phenyl]thiazole;
2-((2-thienyl)sulfonylbromomethyl)-4-(4-fluorophenyl)-5-[(4-methylsulfonyl)phenyl]thiazole;
2-(2-chlorophenyl)-5-[(4-methylsulfonyl) phenyl]-4-(4-methylphenyl)thiazole;
2-(2-chlorophenyl)-4-(4-fluorophenyl)- 5-[(4-methylsulfonyl)phenyl]thiazole;
ethyl [4-(4-fluorophenyl)-5-(4-methylsulfonylphenyl)-2-thiazolyl]carboxylate;
2-(cyanomethyl)-4-(4-fluorophenyl)-5-[(4-methylsulfonyl)phenyl]thiazole;
2-(tert-butyl)-4-(4-fluorophenyl)-5-[(4-methylsulfonyl)phenyl]thiazole;
4-(4-fluorophenyl)-5-[(4-methylsulfonyl)phenyl]-2-benzylthiazole;
2-(3-[4-bromophenyl]propyl)-4-(4-fluorophenyl))-5-[(4-methylsulfonyl)phenyl]thiazole;
4-(4-fluorophenyl)-5-[(4-methylsulfonyl)phenyl]thiazole;
4-(4-fluorophenyl)-5-[(4-methylsulfonyl)phenyl]-2-trifluoromethylthiazole;
4-(4-fluorophenyl)-5-[(4-methylsulfonyl)phenyl]-2-(2-thienyl)thiazole;
4-(4-fluorophenyl)-5-[(4-methylsulfonyl)phenyl]-2-(5-bromo-2-thienyl)thiazole;
4-(4-fluorophenyl)-5-[(4-methylsulfonyl)phenyl]-2-(3-pyridyl)thiazole;
4-(4-fluorophenyl)-5-[(4-methylsulfonyl)phenyl]-2-methylthiazole;
4-(4-fluorophenyl)-5-[(4-methylsulfonyl)phenyl]-2-benzylaminothiazole;
4-(4-fluorophenyl)-5-[(4-methylsulfonyl)phenyl]-2-(1-piperidinyl)thiazole;
4-(4-fluorophenyl)-5-[(4-methylsulfonyl)phenyl]-2-(1-propylamino)thiazole;
4-[4-(4-bromophenyl)-2-(2-chlorophenyl)-5-thiazolyl]benzenesulfonamide;
4-[4-(4-fluorophenyl)-2-phenyl-5-thiazolyl]benzenesulfonamide;
4-[4-(4-fluorophenyl)-2-(4-methoxyphenyl)-5-thiazolyl]benzenesulfonamide;
4-[4-(4-fluorophenyl)-2-(4-chlorophenyl)-5-thiazolyl]benzenesulfonamide;
4-[4-(4-fluorophenyl)-2-(N-hexylamino)-5-thiazolyl]benzenesulfonamide;
4-[4-(4-fluorophenyl)-2-(N-methylamino)-5-thiazolyl]benzenesulfonamide;
4-[4-(4-fluorophenyl)-2-(N-ethylamino)-5-thiazolyl]benzenesulfonamide;
4-[4-(4-fluorophenyl)-2-(N-tert-butylamino)-5-thiazolyl]benzenesulfonamide;
4-[4-(4-fluorophenyl)-2-(N-(4-phenoxyphenyl)amino)-5-thiazolyl]benzenesulfonamide;
ethyl 4-[[5-[(4-aminosulfonyl)phenyl]-4-(4-fluorophenyl)-2-thiazolyl]amino]benzoate;
ethyl 3-[[5-[(4-aminosulfonyl)phenyl]-4-(4-fluorophenyl)-2-thiazolyl]amino]benzoate;
4-[4-(4-fluorophenyl)-2-(2-phenylethyl-5-thiazolyl]benzenesulfonamide;
4-[4-(4-fluorophenyl)-2-(N-(3,5-dichlorophenyl)amino)-5-thiazolyl]benzenesulfonamide;
4-[4-(4-fluorophenyl)-2-(N-butylamino)-5-thiazolyl]benzenesulfonamide;
4-[[5-[(4-aminosulfonyl)phenyl]-4-(4-fluorophenyl)-2-thiazolyl]amino]benzoic acid;
3-[[5-[(4-aminosulfonyl)phenyl]-4-(4-fluorophenyl)-2-thiazolyl]amino]benzoic acid;
4-[4-(4-fluorophenyl)-2-ethyl-5-thiazolyl]benzenesulfonamide;
4-[4-(4-fluorophenyl)-2-(3-phenylpropyl)-5-thiazolyl]benzenesulfonamide;
4-[4-(4-fluorophenyl)-2-((3-chlorophenoxy)methyl)-5-thiazolyl]benzenesulfonamide;
4-[4-(4-fluorophenyl)-2-(2-methyl-4-thiazolyl)-5-thiazolyl]benzenesulfonamide;
4-[4-(2-fluorophenyl)-2-(2-chlorophenyl)-5-thiazolyl]benzenesulfonamide;
4-[4-(2,5-difluorophenyl)-2-(2-chlorophenyl)-5-thiazolyl]benzenesulfonamide;
4-[4-(4-fluorophenyl)-2-(2,3,4,5,6-pentafluorophenyl)-5-thiazolyl]benzenesulfonamide;
4-[4-(4-fluorophenyl)-2-((2-chlorophenoxy)methyl)-5-thiazolyl]benzenesulfonamide;
4-[4-(2-fluorophenyl)-2-((3-chlorophenoxy)methyl)-5-thiazolyl]benzenesulfonamide;
4-[4-(4-fluorophenyl)-2-((3,5-dichlorophenoxy)methyl)-5-thiazolyl]benzenesulfonamide;
4-[4-(2-fluorophenyl)-2-((4-methoxyphenoxy)methyl)-5-thiazolyl]benzenesulfonamide;
4-[4-(4-bromophenyl)-2-(2-chlorophenyl)-5-thiazolyl]benzenesulfonamide;
4-[4-(4-methylthiophenyl)-2-(2-chlorophenyl)-5-thiazolyl]benzenesulfonamide;
4-[4-(3-fluoro-4-methoxyphenyl)-2-(2-chlorophenyl)-5-thiazolyl]benzenesulfonamide;
4-[4-(3-chloro-4-methoxyphenyl)-2-(2-chlorophenyl)-5-thiazolyl]benzenesulfonamide;
4-[4-(3-chloro-4-methylphenyl)-2-(2-chlorophenyl)-5-thiazolyl]benzenesulfonamide;
4-[4-(3-methyl-4-chlorophenyl)-2-(2-chlorophenyl)-5-thiazolyl]benzenesulfonamide;
4-[4-(3,4-methylenedioxyphenyl)-2-(2-chlorophenyl)-5-thiazolyl]benzenesulfonamide;
4-[4-(3,5-difluoro-4-methoxyphenyl)-2-(2-chlorophenyl)-5-thiazolyl]benzenesulfonamide;
4-[4-(3,5-dichloro-4-methoxyphenyl)-2-(2-chlorophenyl)-5-thiazolyl]benzenesulfonamide;
4-[4-(4-fluorophenyl)-2-(difluoromethyl)-5-thiazolyl]benzenesulfonamide;
4-[4-(4-fluorophenyl)-2-(methylthio)-5-thiazolyl]benzenesulfonamide;
4-[4-(4-fluorophenyl)-2-(phenylthio)-5-thiazolyl]benzenesulfonamide;
4-[4-(4-fluorophenyl)-2-((3-fluorophenyl)thio)-5-thiazolyl]benzenesulfonamide;
4-[4-(4-fluorophenyl)-2-((3-chlorophenyl)thio)-5-thiazolyl]benzenesulfonamide;
4-[4-(4-fluorophenyl)-2-((3-bromophenyl)thio)-5-thiazolyl]benzenesulfonamide;
4-[4-(4-fluorophenyl)-2-((3,5-difluorophenyl)thio)-5-thiazolyl]benzenesulfonamide;
4-[4-(4-fluorophenyl)-2-[(3,5-dichlorophenyl)thio]-5-thiazolyl]benzenesulfonamide;

4-[4-(4-fluorophenyl)-2-[(4-fluorophenyl)thio]-5-thiazolyl]
benzenesulfonamide;

4-[4-(4-fluorophenyl)-2-[(4-chlorophenyl)thio]-5-thiazolyl]
benzenesulfonamide;

4-[4-(4-fluorophenyl)-2-[(4-bromophenyl)thio]-5-thiazolyl]
benzenesulfonamide;

4-[4-(4-fluorophenyl)-2-((4-methylphenyl)thio)-5-
thiazolyl]benzenesulfonamide;

4-[4-(4-fluorophenyl)-2-(benzylthio)-5-thiazolyl]
benzenesulfonamide;

4-[4-(4-fluorophenyl)-2-((3-fluorobenzyl)thio)-5-thiazolyl]
benzenesulfonamide;

4-[4-(4-fluorophenyl)-2-((3-chlorobenzyl)thio)-5-thiazolyl]
benzenesulfonamide;

4-[4-(4-fluorophenyl)-2-((3-bromobenzyl)thio)-5-thiazolyl]
benzenesulfonamide;

4-[4-(4-fluorophenyl)-2-((3,5-difluorobenzyl)thio)-5-
thiazolyl]benzenesulfonamide;

4-[4-(4-fluorophenyl)-2-((3,5-dichlorobenzyl)thio)-5-
thiazolyl]benzenesulfonamide;

4-[4-(4-fluorophenyl)-2-((4-fluorobenzyl)thio)-5-thiazolyl]
benzenesulfonamide;

4-[4-(4-fluorophenyl)-2-((4-chlorobenzyl)thio)-5-thiazolyl]
benzenesulfonamide;

4-[4-(4-fluorophenyl)-2-((4-bromobenzyl)thio)-5-thiazolyl]
benzenesulfonamide;

4-[4-(4-fluorophenyl)-2-((4-methylbenzyl)thio)-5-thiazolyl]
benzenesulfonamide;

4-[4-(4-fluorophenyl)-2-(ethylsulfonyl)-5-thiazolyl]
benzenesulfonamide;

4-[4-(4-fluorophenyl)-2-(methylsulfonyl)-5-thiazolyl]
benzenesulfonamide;

4-[4-(4-fluorophenyl)-2-(phenylsulfonyl)-5-thiazolyl]
benzenesulfonamide;

4-[4-(4-fluorophenyl)-2-((3-fluorophenyl)sulfonyl)-5-
thiazolyl]benzenesulfonamide;

4-[4-(4-fluorophenyl)-2-((3-chlorophenyl)sulfonyl)-5-
thiazolyl]benzenesulfonamide;

4-[4-(4-fluorophenyl)-2-((3-bromophenyl)sulfonyl)-5-
thiazolyl]benzenesulfonamide;

4-[4-(4-fluorophenyl)-2-((3,5-difluorophenyl)sulfonyl)-5-
thiazolyl]benzenesulfonamide;

4-[4-(4-fluorophenyl)-2-((3,5-dichlorophenyl)sulfonyl)-5-
thiazolyl]benzenesulfonamide;

4-[4-(4-fluorophenyl)-2-((4-fluorophenyl)sulfonyl)-5-
thiazolyl]benzenesulfonamide;

4-[4-(4-fluorophenyl)-2-((4-chlorophenyl)sulfonyl)-5-
thiazolyl]benzenesulfonamide;

4-[4-(4-fluorophenyl)-2-((4-bromophenyl)sulfonyl)-5-
thiazolyl]benzenesulfonamide;

4-[4-(4-fluorophenyl)-2-((4-methylphenyl)sulfonyl)-5-
thiazolyl]benzenesulfonamide;

4-[4-(4-fluorophenyl)-2-(benzylsulfonyl)-5-thiazolyl]
benzenesulfonamide;

4-[4-(4-fluorophenyl)-2-((3-fluorobenzyl)sulfonyl)-5-
thiazolyl]benzenesulfonamide;

4-[4-(4-fluorophenyl)-2-((3-chlorobenzyl)sulfonyl)-5-
thiazolyl]benzenesulfonamide;

4-[4-(4-fluorophenyl)-2-((3-bromobenzyl)sulfonyl)-5-
thiazolyl]benzenesulfonamide;

4-[4-(4-fluorophenyl)-2-((3,5-difluorobenzyl)sulfonyl)-5-
thiazolyl]benzenesulfonamide;

4-[4-(4-fluorophenyl)-2-((3,5-dichlorobenzyl)sulfonyl)-5-
thiazolyl]benzenesulfonamide;

4-[4-(4-fluorophenyl)-2-((4-fluorobenzyl)sulfonyl)-5-
thiazolyl]benzenesulfonamide;

4-[4-(4-fluorophenyl)-2-((4-chlorobenzyl)sulfonyl)-5-
thiazolyl]benzenesulfonamide;

4-[4-(4-fluorophenyl)-2-((4-bromobenzyl)sulfonyl)-5-
thiazolyl]benzenesulfonamide;

4-[4-(4-fluorophenyl)-2-((4-methylbenzyl)sulfonyl)-5-
thiazolyl]benzenesulfonamide;

4-[4-(4-fluorophenyl)-2-(fluoromethylsulfonyl)-5-thiazolyl]
benzenesulfonamide;

4-[4-(4-fluorophenyl)-2-(acetyl)-5-thiazolyl]
benzenesulfonamide;

4-[4-(4-fluorophenyl)-2-(trifluoroacetyl)-5-thiazolyl]
benzenesulfonamide;

4-[4-(4-fluorophenyl)-2-(benzoyl)-5-thiazolyl]
benzenesulfonamide;

4-[4-(4-fluorophenyl)-2-(3-fluorobenzoyl)-5-thiazolyl]
benzenesulfonamide;

4-[4-(4-fluorophenyl)-2-(3-chlorobenzoyl)-5-thiazolyl]
benzenesulfonamide;

4-[4-(4-fluorophenyl)-2-(3-bromobenzoyl)-5-thiazolyl]
benzenesulfonamide;

4-[4-(4-fluorophenyl)-2-(3,5-difluorobenzoyl)-5-thiazolyl]
benzenesulfonamide;

4-[4-(4-fluorophenyl)-2-(3,5-dichlorobenzoyl)-5-thiazolyl]
benzenesulfonamide;

4-[4-(4-fluorophenyl)-2-(4-fluorobenzoyl)-5-thiazolyl]
benzenesulfonamide;

4-[4-(4-fluorophenyl)-2-(4-chlorobenzoyl)-5-thiazolyl]
benzenesulfonamide;

4-[4-(4-fluorophenyl)-2-(4-bromobenzoyl)-5-thiazolyl]
benzenesulfonamide;

4-[4-(4-fluorophenyl)-2-(4-methylbenzoyl)-5-thiazolyl]
benzenesulfonamide;

methyl [5-[(4-aminosulfonyl)phenyl]-4-(4-fluorophenyl)-2-
thiazolyl]carboxylate;

ethyl [5-[(4-aminosulfonyl)phenyl]-4-(4-fluorophenyl)-2-
thiazolyl]carboxylate;

propyl [5-[(4-aminosulfonyl)phenyl]-4-(4-fluorophenyl)-2-
thiazolyl]carboxylate;

butyl [5-[(4-aminosulfonyl)phenyl]-4-(4-fluorophenyl)-2-
thiazolyl]carboxylate;

4-[4-(4-fluorophenyl)-2-(hydroxymethyl)-5-thiazolyl]
benzenesulfonamide;

4-[4-(4-fluorophenyl)-2-(methoxymethyl)-5-thiazolyl]
benzenesulfonamide;

4-[4-(4-fluorophenyl)-2-(phenoxymethyl)-5-thiazolyl]
benzenesulfonamide;

4-[4-(4-fluorophenyl)-2-(3-fluorophenoxymethyl)-5-
thiazolyl]benzenesulfonamide;

4-[4-(4-fluorophenyl)-2-(3-chlorophenoxymethyl)-5-
thiazolyl]benzenesulfonamide;

4-[4-(4-fluorophenyl)-2-(3-bromophenoxymethyl)-5-
thiazolyl]benzenesulfonamide;

4-[4-(4-fluorophenyl)-2-(3,5-difluorophenoxymethyl)-5-
thiazolyl]benzenesulfonamide;

4-[4-(4-fluorophenyl)-2-(3,5-dichlorophenoxymethyl)-5-
thiazolyl]benzenesulfonamide;

4-[4-(4-fluorophenyl)-2-(4-fluorophenoxymethyl)-5-
thiazolyl]benzenesulfonamide;

4-[4-(4-fluorophenyl)-2-(4-chlorophenoxymethyl)-5-
thiazolyl]benzenesulfonamide;

4-[4-(4-fluorophenyl)-2-(4-bromophenoxymethyl)-5-
thiazolyl]benzenesulfonamide;

4-[4-(4-fluorophenyl)-2-(4-methylphenoxymethyl)-5-
thiazolyl]benzenesulfonamide;

4-[4-(4-fluorophenyl)-2-(benzyloxymethyl)-5-thiazolyl]
benzenesulfonamide;

4-[4-(4-fluorophenyl)-2-(cyanomethyl)-5-thiazolyl]
benzenesulfonamide;

4-[4-(4-fluorophenyl)-2-(2-quinolylmethyloxymethyl)-5-
thiazolyl]benzenesulfonamide;

4-[4-(4-fluorophenyl)-2-(2-naphthylmethyloxymethyl)-5-thiazolyl]benzenesulfonamide;
4-[4-(4-fluorophenyl)-2-(N-phenylaminocarbonyl)-5-thiazolyl]benzenesulfonamide;
4-[4-(4-fluorophenyl)-2-[(3-fluorophenyl)aminocarbonyl]-5-thiazolyl]benzenesulfonamide;
4-[4-(4-fluorophenyl)-2-[(3-chlorophenyl)aminocarbonyl]-5-thiazolyl]benzenesulfonamide;
4-[4-(4-fluorophenyl)-2-[(3-bromophenyl)aminocarbonyl]-5-thiazolyl]benzenesulfonamide;
4-[4-(4-fluorophenyl)-2-[(3,5-difluorophenyl)aminocarbonyl]-5-thiazolyl]benzenesulfonamide;
4-[4-(4-fluorophenyl)-2-[(3,5-dichlorophenyl)aminocarbonyl]-5-thiazolyl]benzenesulfonamide;
4-[4-(4-fluorophenyl)-2-[(4-fluorophenyl)aminocarbonyl]-5-thiazolyl]benzenesulfonamide;
4-[4-(4-fluorophenyl)-2-[(4-chlorophenyl)aminocarbonyl]-5-thiazolyl]benzenesulfonamide;
4-[4-(4-fluorophenyl)-2-[(4-bromophenyl)aminocarbonyl]-5-thiazolyl]benzenesulfonamide;
4-[4-(4-fluorophenyl)-2-[(4-methylphenyl)aminocarbonyl]-5-thiazolyl]benzenesulfonamide;
4-[4-(4-fluorophenyl)-2-(benzylaminocarbonyl)-5-thiazolyl]benzenesulfonamide;
4-[4-(4-fluorophenyl)-2-((3-fluorobenzyl)aminocarbonyl)-5-thiazolyl]benzenesulfonamide;
4-[4-(4-fluorophenyl)-2-((3-chlorobenzyl)aminocarbonyl)-5-thiazolyl]benzenesulfonamide;
4-[4-(4-fluorophenyl)-2-((3-bromobenzyl)aminocarbonyl)-5-thiazolyl]benzenesulfonamide;
4-[4-(4-fluorophenyl)-2-((3,5-difluorobenzyl)aminocarbonyl)-5-thiazolyl]benzenesulfonamide;
4-[4-(4-fluorophenyl)-2-((3,5-dichlorobenzyl)aminocarbonyl)-5-thiazolyl]benzenesulfonamide;
4-[4-(4-fluorophenyl)-2-((4-fluorobenzyl)aminocarbonyl)-5-thiazolyl]benzenesulfonamide;
4-[4-(4-fluorophenyl)-2-((4-chlorobenzyl)aminocarbonyl)-5-thiazolyl]benzenesulfonamide;
4-[4-(4-fluorophenyl)-2-((4-bromobenzyl)aminocarbonyl)-5-thiazolyl]benzenesulfonamide;
4-[4-(4-fluorophenyl)-2-((4-methylbenzyl)aminocarbonyl)-5-thiazolyl]benzenesulfonamide;
4-[4-(4-fluorophenyl)-2-(benzoylamino)-5-thiazolyl]benzenesulfonamide;
4-[4-(4-fluorophenyl)-2-((3-fluorobenzoyl)amino)-5-thiazolyl]benzenesulfonamide;
4-[4-(4-fluorophenyl)-2-((3-chlorobenzoyl)amino)-5-thiazolyl]benzenesulfonamide;
4-[4-(4-fluorophenyl)-2-((3-bromobenzoyl)amino)-5-thiazolyl]benzenesulfonamide;
4-[4-(4-fluorophenyl)-2-((3,5-difluorobenzoyl)amino)-5-thiazolyl]benzenesulfonamide;
4-[4-(4-fluorophenyl)-2-((3,5-dichlorobenzoyl)amino)-5-thiazolyl]benzenesulfonamide;
4-[4-(4-fluorophenyl)-2-((4-fluorobenzoyl)amino)-5-thiazolyl]benzenesulfonamide;
4-[4-(4-fluorophenyl)-2-((4-chlorobenzoylamino)-5-thiazolyl]benzenesulfonamide;
4-[4-(4-fluorophenyl)-2-((4-bromobenzoyl)amino)-5-thiazolyl]benzenesulfonamide;
4-[4-(4-fluorophenyl)-2-((4-methylbenzoyl)amino)-5-thiazolyl]benzenesulfonamide;
4-[4-(4-fluorophenyl)-2-(phenylacetyl)amino-5-thiazolyl]benzenesulfonamide;
4-[2-((4-chlorophenoxy)methyl)-4-(4-fluorophenyl)-5-thiazolyl]benzenesulfonamide;
4-[2-(2-chlorophenyl)-4-phenyl-5-thiazolyl]benzenesulfonamide;
4-[2-(2-chlorophenyl)-4-(3-fluorophenyl)-5-thiazolyl]benzenesulfonamide;
4-[4-(2,4-difluorophenyl)-2-(2-chlorophenyl)-5-thiazolyl]benzenesulfonamide;
4-[2-(2-chlorophenyl)-4-(2-methylphenyl)-5-thiazolyl]benzenesulfonamide;
4-[2-(2-chlorophenyl)-4-(2-thienyl)-5-thiazolyl]benzenesulfonamide;
4-[2-(2-chlorophenyl)-4-(3-thienyl)-5-thiazolyl]benzenesulfonamide;
4-[4-(4-fluorophenyl)-2-(4-pyridyl)-5-thiazolyl]benzenesulfonamide;
4-[2-(2-chlorophenyl)-4-(2-chlorophenyl)-5-thiazolyl]benzenesulfonamide;
4-[2-(2-chlorophenyl)-4-(4-chlorophenyl)-5-thiazolyl]benzenesulfonamide;
4-[2-(2-chlorophenyl)-4-(4-methoxyphenyl)-5-thiazolyl]benzenesulfonamide;
4-[2-(3-chloro-4-fluorophenyl)-4-(4-fluorophenyl)-5-thiazolyl]benzenesulfonamide;
4-[2-((2-thienyl)sulfonylmethyl)-4-(4-fluorophenyl)-5-thiazolyl]benzenesulfonamide;
4-[2-((2-thienyl)sulfonylbromomethyl)-4-(4-fluorophenyl)-5-thiazolyl]benzenesulfonamide;
4-[2-(2-chlorophenyl)-4-(4-methylphenyl)-5-thiazolyl]benzenesulfonamide;
ethyl [4-(4-fluorophenyl)-5-[(4-aminosulfonyl)phenyl]-2-thiazolyl]carboxylate;
4-[2-(cyanomethyl)-4-(4-fluorophenyl)-5-thiazolyl]benzenesulfonamide;
4-[2-(tert-butyl)-4-(4-fluorophenyl)-5-thiazolyl]benzenesulfonamide;
4-[4-(4-fluorophenyl)-2-benzyl-5-thiazolyl]benzenesulfonamide;
4-[2-(3-[4-bromophenyl]propyl)-4-(4-fluorophenyl))-5-thiazolyl]benzenesulfonamide;
4-[4-(4-fluorophenyl)-5-thiazolyl]benzenesulfonamide;
4-[4-(4-fluorophenyl)-2-trifluoromethyl-5-thiazolyl]benzenesulfonamide;
4-[4-(4-fluorophenyl)-2-(2-thienyl)-5-thiazolyl]benzenesulfonamide;
4-[4-(4-fluorophenyl)-2-(5-bromo-2-thienyl)-5-thiazolyl]benzenesulfonamide;
4-[4-(4-fluorophenyl)-2-(3-pyridyl)-5-thiazolyl]benzenesulfonamide;
4-[4-(4-fluorophenyl)-2-methyl-5-thiazolyl]benzenesulfonamide;
4-[4-(4-fluorophenyl)-2-benzylamino-5-thiazolyl]benzenesulfonamide;
4-[4-(4-fluorophenyl)-2-(1-piperidinyl)-5-thiazolyl]benzenesulfonamide;
4-[4-(4-fluorophenyl)-2-(1-propylamino)-5-thiazolyl]benzenesulfonamide;
4-[4-(4-fluorophenyl)-2-(2-chlorophenyl)thiazol-5-yl]benzenesulfonamide; and
4-[4-(4-fluorophenyl)-2-((3,5-dichlorophenoxy)methyl)-5-thiazolyl]benzenesulfonamide.

A second preferred class of compounds consists of those compounds of Formula I wherein $R^1$ is selected from hydrido, halo, amino, alkoxy, cyano, nitro, hydroxyl, aminocarbonyl, acyl, alkylaminocarbonyl, arylaminocarbonyl, alkyl, alkenyl, alkynyl, haloalkyl, haloalkoxy, alkylamino, arylamino, aralkylamino, carboxyl, carboxyalkyl, alkoxycarbonyl, alkoxycarbonylalkyl, alkylaminoalkyl, heterocyclicalkyl, aralkyl, cyanoalkyl, N-alkylsulfonylamino, heteroarylsulfonylalkyl, heteroarylsulfonylhaloalkyl, aryloxyalkyl and aralkyloxyalkyl; wherein $R^2$ is aryl substituted at a substitutable position with a radical selected from alkylsulfonyl, haloalkylsulfonyl and sulfamyl; and wherein $R^3$ is selected from alkyl, alkenyl, aryl, cycloalkyl, cycloalkenyl and heterocyclic; wherein $R^3$ is optionally substituted at a substitutable position with one or more radicals selected from halo, alkylthio, alkylsulfinyl, alkyl, alkenyl, alkynyl, cyano, carboxyl, carboxyalkyl, alkoxycarbonyl, aminocarbonyl, acyl, N-monoalkylaminocarbonyl, N-monoarylaminocarbonyl, N,N-dialkylaminocarbonyl, N-alkyl-N-arylaminocarbonyl, haloalkyl, haloalkoxy, hydroxyl, alkoxy, hydroxyalkyl, amino, N-alkylamino, N,N-dialkylamino, heterocyclic and nitro; or a pharmaceutically-acceptable salt thereof, provided $R^1$ is not α,α-bis (trifluoromethyl) methanol.

A second more preferred class of compounds consists of those compounds of Formula I wherein $R^1$ is selected from halo, amino, lower alkoxy, cyano, nitro, hydroxy, aminocarbonyl, acyl, lower alkylaminocarbonyl, lower arylaminocarbonyl, lower alkyl, lower alkenyl, lower alkynyl, lower haloalkyl, lower haloalkoxy, lower alkylamino, carboxyl, lower aralkylamino, lower carboxyalkyl, lower alkoxycarbonylalkyl, lower alkoxycarbonyl, lower alkylaminoalkyl, lower heterocyclicalkyl, lower N-alkylsulfonylamino, lower heteroarylsulfonylalkyl, lower heteroarylsulfonylhaloalkyl, lower aralkyl, lower cyanoalkyl, lower aryloxyalkyl and lower aralkyloxyalkyl;

wherein $R^2$ is aryl selected from phenyl, naphthyl and biphenyl, substituted at a substitutable position with a radical selected from lower alkylsulfonyl, lower haloalkylsulfonyl and sulfamyl; and wherein $R^3$ is selected from lower alkyl, lower alkenyl, aryl, lower cycloalkyl, lower cycloalkenyl and heterocyclic; wherein $R^3$ is optionally substituted at a substitutable position with one or more radicals selected from halo, lower alkylthio, lower alkylsulfinyl, lower alkyl, lower alkenyl, lower alkynyl, cyano, carboxyl, lower carboxyalkyl, lower alkoxycarbonyl, aminocarbonyl, acyl, lower N-monoalkylaminocarbonyl, N-monoarylaminocarbonyl, lower N,N-dialkylaminocarbonyl, lower N-alkyl-N-arylaminocarbonyl, lower haloalkyl, hydroxyl, lower alkoxy, lower hydroxyalkyl, lower haloalkoxy, amino, lower N-alkylamino, lower N,N-dialkylamino, heterocyclic and nitro;

or a pharmaceutically-acceptable salt thereof.

A second class of compounds of particular interest consists of those compounds of Formula I wherein $R^1$ is selected from fluoro, chloro, bromo, iodo, amino, methoxy, ethoxy, propoxy, butoxy, isopropoxy, tert-butoxy, cyano, nitro, hydroxy, aminocarbonyl, formyl, acetyl, N-methylaminocarbonyl, N-phenylaminocarbonyl, N,N-dimethylaminocarbonyl, N-methyl-N-phenylaminocarbonyl, methyl, ethyl, propyl, butyl, pentyl, isopropyl, isobutyl, tert-butyl, ethylenyl, propylenyl, butenyl, pentenyl, isopropylenyl, isobutylenyl, propargyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, N-methylamino, N-ethylamino, N-propylamino, N-butylamino, N-tert-butylamino, N-pentylamino, N-hexylamino, N,N-dimethylamino, carboxyl, N-benzylamino, carboxymethyl, methoxycarbonylmethyl, ethoxycarbonylmethyl, methylaminomethyl, morpholinomethyl, pyrrolidinylmethyl, piperazinylmethyl, piperidinylmethyl, pyridylmethyl, thienylmethyl, benzyl, phenethyl, phenpropyl, cyanomethyl, phenoxymethyl, benzyloxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, morpholino, pyrrolidinyl, piperazinyl, piperidinyl, (2-thienyl)sulfonylmethyl and (2-thienyl) sulfonylbromomethyl;

wherein $R^2$ is aryl selected from phenyl, naphthyl and biphenyl, substituted at a substitutable position with a radical selected from methylsulfonyl, fluoromethylsulfonyl and sulfamyl;

wherein $R^3$ is selected from methyl, ethyl, propyl, butyl, pentyl, isopropyl, isobutyl, tert-butyl, ethylenyl, propylenyl, butenyl, pentenyl, isopropylenyl, isobutylenyl, phenyl, naphthyl, biphenyl, thienyl, pyridyl, furyl, pyrazinyl, pyrrolyl, pyrazolyl, triazolyl, cyclopropyl, cyclobutyl, cyclopentyl, cyclohexyl, cyclopropenyl, cyclobutenyl, cyclopentenyl, cyclohexenyl, morpholino, pyrrolidinyl, piperazinyl and piperidinyl; wherein $R^3$ is optionally substituted at a substitutable position with one or more radicals selected from fluoro, chloro, bromo, methylthio, methylsulfinyl, methyl, ethyl, propyl, butyl, pentyl, isopropyl, isobutyl, tert-butyl, ethylenyl, propylenyl, butenyl, pentenyl, isopropylenyl, isobutylenyl, propargyl, cyano, carboxyl, carboxymethyl, carboxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, formyl, acetyl, N-methylaminocarbonyl, N-phenylaminocarbonyl, N,N-dimethylaminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, ethoxy, propoxy, butoxy, isopropoxy, tert-butoxy, hydroxymethyl, trifluoromethoxy, amino, N-methylamino, N,N-dimethylamino, pyridyl, furyl, pyrazinyl, pyrrolyl, pyrazolyl, morpholino, pyrrolidinyl, piperazinyl, piperidinyl, triazolyl and nitro;

or a pharmaceutically-acceptable salt thereof.

A second family of specific compounds of particular interest within Formula I consists of compounds and pharmaceutically-acceptable salts thereof as follows:

4-[(4-methylsulfonyl)phenyl]-5-(4-fluorophenyl)-2-(trifluoromethyl)thiazole;

4-[(4-methylsulfonyl)phenyl]-5-(4-chlorophenyl)-2-(2-chlorophenyl)thiazole;

4-[(4-methylsulfonyl)phenyl]-5-(4-methoxyphenyl)-2-(2-chlorophenyl)thiazole;

4-[(4-methylsulfonyl)phenyl]-5-(4-methylphenyl)-2-(2-chlorophenyl)thiazole;

4-[(4-methylsulfonyl)phenyl]-5-(4-bromophenyl)-2-(2-chlorophenyl)thiazole;

4-[(4-methylsulfonyl)phenyl]-5-(4-methylthiophenyl)-2-(2-chlorophenyl)thiazole;

4-[(4-methylsulfonyl)phenyl]-5-(3-fluoro-4-methoxyphenyl)-2-(2-chlorophenyl)thiazole;

4-[(4-methylsulfonyl)phenyl]-5-(3-chloro-4-methoxyphenyl)-2-(2-chlorophenyl)thiazole;

4-[(4-methylsulfonyl)phenyl]-5-(3-chloro-4-methylphenyl)-2-(2-chlorophenyl)thiazole;

4-[(4-methylsulfonyl)phenyl]-5-(3-methyl-4-chlorophenyl)-2-(2-chlorophenyl)thiazole;

4-[(4-methylsulfonyl)phenyl]-5-(3,4-methylenedioxyphenyl)-2-(2-chlorophenyl)thiazole;

4-[(4-methylsulfonyl)phenyl]-5-(3,5-difluoro-4-methoxyphenyl)-2-(2-chlorophenyl)thiazole;

4-[(4-methylsulfonyl)phenyl]-5-(3,5-dichloro-4-methoxyphenyl)-2-(2-chlorophenyl)thiazole;

4-[(4-methylsulfonyl)phenyl]-5-(4-fluorophenyl)-2-methylthiazole;

4-[(4-methylsulfonyl)phenyl]-5-(4-fluorophenyl)-2-(difluoromethyl)thiazole;

4-[(4-methylsulfonyl)phenyl]-5-(4-fluorophenyl)-2-(methylthio)thiazole;

4-[(4-methylsulfonyl)phenyl]-5-(4-fluorophenyl)-2-(phenylthio)thiazole;

4-[(4-methylsulfonyl)phenyl]-5-(4-fluorophenyl)-2-(3-fluoro-phenylthio)thiazole;

4-[(4-methylsulfonyl)phenyl]-5-(4-fluorophenyl)-2-(3-chloro-phenylthio)thiazole;

4-[(4-methylsulfonyl)phenyl]-5-(4-fluorophenyl)-2-(3-bromo-phenylthio)thiazole;

4-[(4-methylsulfonyl)phenyl]-5-(4-fluorophenyl)-2-(3,5-difluoro-phenylthio)thiazole;

4-[(4-methylsulfonyl)phenyl]-5-(4-fluorophenyl)-2-(3,5-dichloro-phenylthio)thiazole;

4-[(4-methylsulfonyl)phenyl]-5-(4-fluorophenyl)-2-(4-fluoro-phenylthio)thiazole;

4-[(4-methylsulfonyl)phenyl]-5-(4-fluorophenyl)-2-(4-chloro-phenylthio)thiazole;

4-[(4-methylsulfonyl)phenyl]-5-(4-fluorophenyl)-2-(4-bromo-phenylthio)thiazole;

4-[(4-methylsulfonyl)phenyl]-5-(4-fluorophenyl)-2-(4-methyl-phenylthio)thiazole;

4-[(4-methylsulfonyl)phenyl]-5-(4-fluorophenyl)-2-(benzylthio)thiazole;

4-[(4-methylsulfonyl)phenyl]-5-(4-fluorophenyl)-2-(3-fluorobenzylthio)thiazole;

4-[(4-methylsulfonyl)phenyl]-5-(4-fluorophenyl)-2-(3-chlorobenzylthio)thiazole;

4-[(4-methylsulfonyl)phenyl]-5-(4-fluorophenyl)-2-(3-bromobenzylthio)thiazole;

4-[(4-methylsulfonyl)phenyl]-5-(4-fluorophenyl)-2-(3,5-difluorobenzylthio)thiazole;

4-[(4-methylsulfonyl)phenyl]-5-(4-fluorophenyl)-2-(3,5-dichlorobenzylthio)thiazole;

4-[(4-methylsulfonyl)phenyl]-5-(4-fluorophenyl)-2-(4-fluorobenzylthio)thiazole;

4-[(4-methylsulfonyl)phenyl]-5-(4-fluorophenyl)-2-(4-chlorobenzylthio)thiazole;

4-[(4-methylsulfonyl)phenyl]-5-(4-fluorophenyl)-2-(4-bromobenzylthio)thiazole;

4-[(4-methylsulfonyl)phenyl]-5-(4-fluorophenyl)-2-(4-methylbenzylthio)thiazole;

4-[(4-methylsulfonyl)phenyl]-5-(4-fluorophenyl)-2-(ethylsulfonyl)thiazole;

4-[(4-methylsulfonyl) phenyl]-5-(4-fluorophenyl)-2-(methylsulfonyl)thiazole;

4-[(4-methylsulfonyl)phenyl]-5-(4-fluorophenyl)-2-(phenylsulfonyl)thiazole;

4-[(4-methylsulfonyl)phenyl]-5-(4-fluorophenyl)-2-(3-fluorophenylsulfonyl)thiazole;

4-[(4-methylsulfonyl)phenyl]-5-(4-fluorophenyl)-2-(3-chlorophenylsulfonyl)thiazole;

4-[(4-methylsulfonyl)phenyl]-5-(4-fluorophenyl)-2-(3-bromophenylsulfonyl)thiazole;

4-[(4-methylsulfonyl)phenyl]-5-(4-fluorophenyl)-2-(3,5-difluorophenylsulfonyl)thiazole;

4-[(4-methylsulfonyl)phenyl]-5-(4-fluorophenyl)-2-(3,5-dichlorophenylsulfonyl)thiazole;

4-[(4-methylsulfonyl)phenyl]-5-(4-fluorophenyl)-2-(4-fluorophenylsulfonyl)thiazole;

4-[(4-methylsulfonyl)phenyl]-5-(4-fluorophenyl)-2-(4-chlorophenylsulfonyl)thiazole;

4-[(4-methylsulfonyl)phenyl]-5-(4-fluorophenyl)-2-(4-bromophenylsulfonyl)thiazole;

4-[(4-methylsulfonyl)phenyl]-5-(4-fluorophenyl)-2-(4-methylphenylsulfonyl)thiazole;

4-[(4-methylsulfonyl)phenyl]-5-(4-fluorophenyl)-2-(benzylsulfonyl)thiazole;

4-[(4-methylsulfonyl)phenyl]-5-(4-fluorophenyl)-2-(3-fluorobenzylsulfonyl)thiazole;

4-[(4-methylsulfonyl)phenyl]-5-(4-fluorophenyl)-2-(3-chlorobenzylsulfonyl)thiazole;

4-[(4-methylsulfonyl)phenyl]-5-(4-fluorophenyl)-2-(3-bromobenzylsulfonyl)thiazole;

4-[(4-methylsulfonyl)phenyl]-5-(4-fluorophenyl)-2-(3,5-difluorobenzylsulfonyl)thiazole;

4-[(4-methylsulfonyl)phenyl]-5-(4-fluorophenyl)-2-(3,5-dichlorobenzylsulfonyl)thiazole;

4-[(4-methylsulfonyl)phenyl]-5-(4-fluorophenyl)-2-(4-fluorobenzylsulfonyl)thiazole;

4-[(4-methylsulfonyl)phenyl]-5-(4-fluorophenyl)-2-(4-chlorobenzylsulfonyl)thiazole;

4-[(4-methylsulfonyl)phenyl]-5-(4-fluorophenyl)-2-(4-bromobenzylsulfonyl)thiazole;

4-[(4-methylsulfonyl) phenyl]-5-(4-fluorophenyl)-2-(4-methylbenzylsulfonyl)thiazole;

4-[(4-methylsulfonyl)phenyl]-5-(4-fluorophenyl)-2-(fluoromethylsulfonyl)thiazole;

4-[(4-methylsulfonyl)phenyl]-5-(4-fluorophenyl)-2-(acetyl)thiazole;

4-[(4-methylsulfonyl)phenyl]-5-(4-fluorophenyl)-2-(trifluoroacetyl)thiazole;

4-[(4-methylsulfonyl)phenyl]-5-(4-fluorophenyl)-2-(benzoyl)thiazole;

4-[(4-methylsulfonyl)phenyl]-5-(4-fluorophenyl)-2-(3-fluorobenzoyl)thiazole;

4-[(4-methylsulfonyl)phenyl]-5-(4-fluorophenyl)-2-(3-chlorobenzoyl)thiazole;

4-[(4-methylsulfonyl)phenyl]-5-(4-fluorophenyl)-2-(3-bromobenzoyl)thiazole;

4-[(4-methylsulfonyl)phenyl]-5-(4-fluorophenyl)-2-(3,5-difluorobenzoyl)thiazole;

4-[(4-methylsulfonyl)phenyl]-5-(4-fluorophenyl)-2-(3,5-dichlorobenzoyl)thiazole;

4-[(4-methylsulfonyl)phenyl]-5-(4-fluorophenyl)-2-(4-fluorobenzoyl)thiazole;

4-[(4-methylsulfonyl)phenyl]-5-(4-fluorophenyl)-2-(4-chlorobenzoyl)thiazole;

4-[(4-methylsulfonyl)phenyl]-5-(4-fluorophenyl)-2-(4-bromobenzoyl)thiazole;

4-[(4-methylsulfonyl)phenyl]-5-(4-fluorophenyl)-2-(4-methylbenzoyl)thiazole;

[4-[(4-methylsulfonyl)phenyl]-5-(4-fluorophenyl)-2-thiazolyl]acetic acid;

[4-[(4-methylsulfonyl)phenyl]-5-(4-fluorophenyl)-2-thiazolyl]propanoic acid;

[4-[(4-methylsulfonyl)phenyl]-5-(4-fluorophenyl)-2-thiazolyl]butanoic acid;

[4-[(4-methylsulfonyl)phenyl]-5-(4-fluorophenyl)-2-thiazolyl]pentanoic acid;

4-[(4-methylsulfonyl)phenyl]-5-(4-fluorophenyl)-2-(hydroxymethyl)thiazole;

4-[(4-methylsulfonyl)phenyl]-5-(4-fluorophenyl)-2-(methoxymethyl)thiazole;

4-[(4-methylsulfonyl)phenyl]-5-(4-fluorophenyl)-2-(phenyloxymethyl)thiazole;

4-[(4-methylsulfonyl)phenyl]-5-(4-fluorophenyl)-2-(3-fluorophenyloxymethyl)thiazole;

4-[(4-methylsulfonyl)phenyl]-5-(4-fluorophenyl)-2-(3-chlorophenyloxymethyl)thiazole;
4-[(4-methylsulfonyl)phenyl]-5-(4-fluorophenyl)-2-(3-bromophenyloxymethyl)thiazole;
4-[(4-methylsulfonyl)phenyl]-5-(4-fluorophenyl)-2-(3,5-difluorophenyloxymethyl)thiazole;
4-[(4-methylsulfonyl)phenyl]-5-(4-fluorophenyl)-2-(3,5-dichlorophenyloxymethyl)thiazole;
4-[(4-methylsulfonyl)phenyl]-5-(4-fluorophenyl)-2-(4-fluorophenyloxymethyl)thiazole;
4-[(4-methylsulfonyl)phenyl]-5-(4-fluorophenyl)-2-(4-chlorophenyloxymethyl)thiazole;
4-[(4-methylsulfonyl)phenyl]-5-(4-fluorophenyl)-2-(4-bromophenyloxymethyl)thiazole;
4-[(4-methylsulfonyl)phenyl]-5-(4-fluorophenyl)-2-(4-methylphenyloxymethyl)thiazole;
4-[(4-methylsulfonyl)phenyl]-5-(4-fluorophenyl)-2-(benzyloxymethyl)thiazole;
4-[(4-methylsulfonyl)phenyl]-5-(4-fluorophenyl)-2-(cyanomethyl)thiazole;
4-[(4-methylsulfonyl)phenyl]-5-(4-fluorophenyl)-2-(2-quinolylmethyloxymethyl)thiazole;
4-[(4-methylsulfonyl)phenyl]-5-(4-fluorophenyl)-2-(2-naphthylmethyloxymethyl)thiazole;
4-[(4-methylsulfonyl)phenyl]-5-(4-fluorophenyl)-2-(N-phenylaminocarbonyl)thiazole;
4-[(4-methylsulfonyl)phenyl]-5-(4-fluorophenyl)-2-[(3-fluorophenyl)aminocarbonyl]thiazole;
4-[(4-methylsulfonyl)phenyl]-5-(4-fluorophenyl)-2-[(3-chlorophenyl)aminocarbonyl]thiazole;
4-[(4-methylsulfonyl)phenyl]-5-(4-fluorophenyl)-2-[(3-bromophenyl)aminocarbonyl]thiazole;
4-[(4-methylsulfonyl)phenyl]-5-(4-fluorophenyl)-2-[(3,5-difluorophenyl)aminocarbonyl]thiazole;
4-[(4-methylsulfonyl)phenyl]-5-(4-fluorophenyl)-2-[(3,5-dichlorophenyl)aminocarbonyl]thiazole;
4-[(4-methylsulfonyl)phenyl]-5-(4-fluorophenyl)-2-[(4-fluorophenyl)aminocarbonyl]thiazole;
4-[(4-methylsulfonyl)phenyl]-5-(4-fluorophenyl)-2-[(4-chlorophenyl)aminocarbonyl]thiazole;
4-(4-methylsulfonyl)-5-(4-fluorophenyl)-2-[(4-bromophenyl)aminocarbonyl]thiazole;
4-[(4-methylsulfonyl)phenyl]-5-(4-fluorophenyl)-2-[(4-methylphenyl)aminocarbonyl]thiazole;
4-[(4-methylsulfonyl)phenyl]-5-(4-fluorophenyl)-2-(benzylaminocarbonyl)thiazole;
4-[(4-methylsulfonyl)phenyl]-5-(4-fluorophenyl)-2-(3-fluorobenzylaminocarbonyl)thiazole;
4-[(4-methylsulfonyl)phenyl]-5-(4-fluorophenyl)-2-(3-chlorobenzylaminocarbonyl)thiazole;
4-[(4-methylsulfonyl)phenyl]-5-(4-fluorophenyl)-2-(3-bromobenzylaminocarbonyl)thiazole;
4-[(4-methylsulfonyl)phenyl]-5-(4-fluorophenyl)-2-(3,5-difluorobenzylaminocarbonyl)thiazole;
4-[(4-methylsulfonyl)phenyl]-5-(4-fluorophenyl)-2-(3,5-dichlorobenzylaminocarbonyl)thiazole;
4-[(4-methylsulfonyl)phenyl]-5-(4-fluorophenyl)-2-(4-fluorobenzylaminocarbonyl)thiazole;
4-[(4-methylsulfonyl)phenyl]-5-(4-fluorophenyl)-2-(4-chlorobenzylaminocarbonyl)thiazole;
4-[(4-methylsulfonyl)phenyl]-5-(4-fluorophenyl)-2-(4-bromobenzylaminocarbonyl)thiazole;
4-[(4-methylsulfonyl)phenyl]-5-(4-fluorophenyl)-2-(4-methylbenzylaminocarbonyl)thiazole;
4-[(4-methylsulfonyl)phenyl]-5-(4-fluorophenyl)-2-(benzoylamino)thiazole;
4-[(4-methylsulfonyl)phenyl]-5-(4-fluorophenyl)-2-(3-fluorobenzoylamino)thiazole;
4-[(4-methylsulfonyl)phenyl]-5-(4-fluorophenyl)-2-(3-chlorobenzoylamino)thiazole;
4-[(4-methylsulfonyl)phenyl]-5-(4-fluorophenyl)-2-(3-bromobenzoylamino)thiazole;
4-[(4-methylsulfonyl)phenyl]-5-(4-fluorophenyl)-2-(3,5-difluorobenzoylamino)thiazole;
4-[(4-methylsulfonyl)phenyl]-5-(4-fluorophenyl)-2-(3,5-dichlorobenzoylamino)thiazole;
4-[(4-methylsulfonyl)phenyl]-5-(4-fluorophenyl)-2-(4-fluorobenzoylamino)thiazole;
4-[(4-methylsulfonyl)phenyl]-5-(4-fluorophenyl)-2-(4-chlorobenzoylamino)thiazole;
4-[(4-methylsulfonyl)phenyl]-5-(4-fluorophenyl)-2-(4-bromobenzoylamino)thiazole;
4-[(4-methylsulfonyl)phenyl]-5-(4-fluorophenyl)-2-(4-methylbenzoylamino)thiazole;
4-[(4-methylsulfonyl)phenyl]-5-(4-fluorophenyl)-2-(phenylacetyl)aminothiazole;
4-[(4-methylsulfonyl)phenyl]-5-(4-fluorophenyl)-2-[(3-fluorophenyl)acetyl]aminothiazole;
4-[(4-methylsulfonyl)phenyl]-5-(4-fluorophenyl)-2-[(3-chlorophenyl)acetyl]aminothiazole;
4-[(4-methylsulfonyl)phenyl]-5-(4-fluorophenyl)-2-[(3-bromophenyl)acetyl]amino)thiazole;
4-[(4-methylsulfonyl)phenyl]-5-(4-fluorophenyl)-2-[(3,5-difluorophenyl)acetyl]amino)thiazole;
4-[(4-methylsulfonyl)phenyl]-5-(4-fluorophenyl)-2-[(3,5-dichlorophenyl)acetyl]amino)thiazole;
4-[(4-methylsulfonyl)phenyl]-5-(4-fluorophenyl)-2-[(4-fluorophenyl)acetyl]amino)thiazole;
4-[(4-methylsulfonyl)phenyl]-5-(4-fluorophenyl)-2-[(4-chlorophenyl)acetyl]amino)thiazole;
4-[(4-methylsulfonyl)phenyl]-5-(4-fluorophenyl)-2-[(4-bromophenyl)acetyl]amino)thiazole;
4-[(4-methylsulfonyl)phenyl]-5-(4-fluorophenyl)-2-[(4-methylphenyl)acetyl]amino)thiazole;
4-[(4-methylsulfonyl)phenyl]-5-(4-fluorophenyl)-2-(fluoromethylsulfonyl)aminothiazole;
4-[(4-methylsulfonyl)phenyl]-5-(4-fluorophenyl)-2-(methylsulfonyl)aminothiazole;
4-[5-(4-fluorophenyl)-2-(trifluoromethyl)-4-thiazolyl]benzenesulfonamide;
4-[5-(4-bromophenyl)-2-(2-chlorophenyl)-4-thiazolyl]benzenesulfonamide;
4-[5-(4-methylthiophenyl)-2-(2-chlorophenyl)-4-thiazolyl]benzenesulfonamide;
4-[5-(3-fluoro-4-methoxyphenyl)-2-(2-chlorophenyl)-5-thiazolyl]benzenesulfonamide;
4-[5-(3-chloro-4-methoxyphenyl)-2-(2-chlorophenyl)-5-thiazolyl]benzenesulfonamide;
4-[5-(3-chloro-4-methylphenyl)-2-(2-chlorophenyl)-4-thiazolyl]benzenesulfonamide;
4-[5-(3-methyl-4-chlorophenyl)-2-(2-chlorophenyl)-4-thiazolyl]benzenesulfonamide;
4-[5-(3,4-methylenedioxyphenyl)-2-(2-chlorophenyl)-5-thiazolyl]benzenesulfonamide;
4-[5-(3,5-difluoro-4-methoxyphenyl)-2-(2-chlorophenyl)-4-thiazolyl]benzenesulfonamide;
4-[5-(3,5-dichloro-4-methoxyphenyl)-2-(2-chlorophenyl)-4-thiazolyl]benzenesulfonamide;
4-[5-(4-chlorophenyl)-2-(2-chlorophenyl)-4-thiazolyl]benzenesulfonamide;
4-[5-(4-methoxyphenyl)-2-(2-chlorophenyl)-4-thiazolyl]benzenesulfonamide;
4-[5-(4-methylphenyl)-2-(2-chlorophenyl)-4-thiazolyl]benzenesulfonamide;
4-[5-(4-fluorophenyl)-2-(difluoromethyl)-4-thiazolyl]benzenesulfonamide;

4-[5-(4-fluorophenyl)-2-(methylthio)-4-thiazolyl]
benzenesulfonamide;
4-[5-(4-fluorophenyl)-2-(phenylthio)-4-thiazolyl]
benzenesulfonamide;
4-[5-(4-fluorophenyl)-2-((3-fluorophenyl)thio)-4-thiazolyl]
benzenesulfonamide;
4-[5-(4-fluorophenyl)-2-((3-chlorophenyl)thio)-4-thiazolyl]
benzenesulfonamide;
4-[5-(4-fluorophenyl)-2-((3-bromophenyl)thio)-4-thiazolyl]
benzenesulfonamide;
4-[5-(4-fluorophenyl)-2-((3,5-difluorophenyl)thio)-4-thiazolyl]benzenesulfonamide;
4-[5-(4-fluorophenyl)-2-[(3,5-dichlorophenyl)thio]-4-thiazolyl]benzenesulfonamide;
4-[5-(4-fluorophenyl)-2-[(4-fluorophenyl)thio]-4-thiazolyl]
benzenesulfonamide;
4-[5-(4-fluorophenyl)-2-[(4-chlorophenyl)thio]-4-thiazolyl]
benzenesulfonamide;
4-[5-(4-fluorophenyl)-2-[(4-bromophenyl)thio]-4-thiazolyl]
benzenesulfonamide;
4-[5-(4-fluorophenyl)-2-((4-methylphenyl thio)-4-thiazolyl]
benzenesulfonamide;
4-[5-(4-fluorophenyl)-2-(benzylthio)-4-thiazolyl]
benzenesulfonamide;
4-[5-(4-fluorophenyl)-2-((3-fluorobenzyl thio)-4-thiazolyl]
benzenesulfonamide;
4-[5-(4-fluorophenyl)-2-((3-chlorobenzyl thio)-4-thiazolyl]
benzenesulfonamide;
4-[5-(4-fluorophenyl)-2-((3-bromobenzyl)thio)-4-thiazolyl]
benzenesulfonamide;
4-[5-(4-fluorophenyl)-2-((3,5-difluorobenzyl)thio)-4-thiazolyl]benzenesulfonamide;
4-[5-(4-fluorophenyl)-2-((3,5-dichlorobenzyl)thio)-4-thiazolyl]benzenesulfonamide;
4-[5-(4-fluorophenyl)-2-((4-fluorobenzyl)thio)-4-thiazolyl]
benzenesulfonamide;
4-[5-(4-fluorophenyl)-2-((4-chlorobenzyl)thio)-4-thiazolyl]
benzenesulfonamide;
4-[5-(4-fluorophenyl)-2-((4-bromobenzyl)thio)-4-thiazolyl]
benzenesulfonamide;
4-[5-(4-fluorophenyl)-2-((4-methylbenzyl)thio)-4-thiazolyl]
benzenesulfonamide;
4-[5-(4-fluorophenyl)-2-(ethylsulfonyl)-4-thiazolyl]
benzenesulfonamide;
4-[5-(4-fluorophenyl)-2-(methylsulfonyl)-4-thiazolyl]
benzenesulfonamide;
4-[5-(4-fluorophenyl)-2-(phenylsulfonyl)-4-thiazolyl]
benzenesulfonamide;
4-[5-(4-fluorophenyl)-2-((3-fluorophenyl)sulfonyl)-4-thiazolyl]benzenesulfonamide;
4-[5-(4-fluorophenyl)-2-((3-chlorophenyl)sulfonyl)-4-thiazolyl]benzenesulfonamide;
4-[5-(4-fluorophenyl)-2-((3-bromophenyl)sulfonyl)-4-thiazolyl]benzenesulfonamide;
4-[5-(4-fluorophenyl)-2-((3,5-difluorophenyl)sulfonyl)-4-thiazolyl]benzenesulfonamide;
4-[5-(4-fluorophenyl)-2-((3,5-dichlorophenyl) sulfonyl)-4-thiazolyl]benzenesulfonamide;
4-[5-(4-fluorophenyl)-2-((4-fluorophenyl)sulfonyl)-4-thiazolyl]benzenesulfonamide;
4-[5-(4-fluorophenyl)-2-((4-chlorophenyl)sulfonyl)-4-thiazolyl]benzenesulfonamide;
4-[5-(4-fluorophenyl)-2-((4-bromophenyl)sulfonyl)-4-thiazolyl]benzenesulfonamide;
4-[5-(4-fluorophenyl)-2-((4-methylphenyl)sulfonyl)-4-thiazolyl]benzenesulfonamide;
4-[5-(4-fluorophenyl)-2-(benzylsulfonyl)-4-thiazolyl]
benzenesulfonamide;

4-[5-(4-fluorophenyl)-2-((3-fluorobenzyl)sulfonyl)-4-thiazolyl]benzenesulfonamide;
4-[5-(4-fluorophenyl)-2-((3-chlorobenzyl)sulfonyl)-4-thiazolyl]benzenesulfonamide;
4-[5-(4-fluorophenyl)-2-((3-bromobenzyl)sulfonyl)-4-thiazolyl]benzenesulfonamide;
4-[5-(4-fluorophenyl)-2-((3,5-difluorobenzyl) sulfonyl)-4-thiazolyl]benzenesulfonamide;
4-[5-(4-fluorophenyl)-2-((3,5-dichlorobenzyl) sulfonyl)-4-thiazolyl]benzenesulfonamide;
4-[5-(4-fluorophenyl)-2-((4-fluorobenzyl)sulfonyl)-4-thiazolyl]benzenesulfonamide;
4-[5-(4-fluorophenyl)-2-((4-chlorobenzyl)sulfonyl)-4-thiazolyl]benzenesulfonamide;
4-[5-(4-fluorophenyl)-2-((4-bromobenzyl)sulfonyl)-4-thiazolyl]benzenesulfonamide;
4-[5-(4-fluorophenyl)-2-((4-methylbenzyl)sulfonyl)-4-thiazolyl]benzenesulfonamide;
4-[5-(4-fluorophenyl)-2-(fluoromethylsulfonyl)-4-thiazolyl]
benzenesulfonamide;
4-[5-(4-fluorophenyl)-2-(acetyl)-4-thiazolyl]
benzenesulfonamide;
4-[5-(4-fluorophenyl)-2-(trifluoroacetyl)-4-thiazolyl]
benzenesulfonamide;
4-[5-(4-fluorophenyl)-2-(benzoyl)-4-thiazolyl]
benzenesulfonamide;
4-[5-(4-fluorophenyl)-2-(3-fluorobenzoyl)-4-thiazolyl]
benzenesulfonamide;
4-[5-(4-fluorophenyl)-2-(3-chlorobenzoyl)-4-thiazolyl]
benzenesulfonamide;
4-[5-(4-fluorophenyl)-2-(3-bromobenzoyl)-4-thiazolyl]
benzenesulfonamide;
4-[5-(4-fluorophenyl)-2-(3,5-difluorobenzoyl)-4-thiazolyl]
benzenesulfonamide;
4-[5-(4-fluorophenyl)-2-(3,5-dichlorobenzoyl)-4-thiazolyl]
benzenesulfonamide;
4-[5-(4-fluorophenyl)-2-(4-fluorobenzoyl)-4-thiazolyl]
benzenesulfonamide;
4-[5-(4-fluorophenyl)-2-(4-chlorobenzoyl)-4-thiazolyl]
benzenesulfonamide;
4-[5-(4-fluorophenyl)-2-(4-bromobenzoyl)-4-thiazolyl]
benzenesulfonamide;
4-[5-(4-fluorophenyl)-2-(4-methylbenzoyl)-4-thiazolyl]
benzenesulfonamide;
methyl [4-[(4-aminosulfonyl)phenyl]-5-(4-fluorophenyl)-2-thiazolyl]carboxylate;
ethyl [4-[(4-aminosulfonyl)phenyl]-5-(4-fluorophenyl)-2-thiazolyl]carboxylate;
propyl [4-[(4-aminosulfonyl)phenyl]-5-(4-fluorophenyl)-2-thiazolyl]carboxylate;
butyl [4-[(4-aminosulfonyl)phenyl]-5-(4-fluorophenyl)-2-thiazolyl]carboxylate;
4-[5-(4-fluorophenyl-2-(hydroxymethyl)-4-thiazolyl]
benzenesulfonamide;
4-[5-(4-fluorophenyl-2-(methoxymethyl)-4-thiazolyl]
benzenesulfonamide;
4-[5-(4-fluorophenyl-2-(phenoxymethyl)-4-thiazolyl]
benzenesulfonamide;
4-[5-(4-fluorophenyl-2-(3-fluorophenoxymethyl)-4-thiazolyl]benzenesulfonamide;
4-[5-(4-fluorophenyl-2-(3-chlorophenoxymethyl)-4-thiazolyl]benzenesulfonamide;
4-[5-(4-fluorophenyl)-2-(3-bromophenoxymethyl)-4-thiazolyl]benzenesulfonamide;
4-[5-(4-fluorophenyl)-2-(3,5-difluorophenoxymethyl)-4-thiazolyl]benzenesulfonamide;
4-[5-(4-fluorophenyl)-2-(3,5-dichlorophenoxymethyl)-4-thiazolyl]benzenesulfonamide;

4-[5-(4-fluorophenyl)-2-(4-fluorophenoxymethyl)-4-thiazolyl]benzenesulfonamide;
4-[5-(4-fluorophenyl)-2-(4-chlorophenoxymethyl)-4-thiazolyl]benzenesulfonamide;
4-[5-(4-fluorophenyl)-2-(4-bromophenoxymethyl)-4-thiazolyl]benzenesulfonamide;
4-[5-(4-fluorophenyl)-2-(4-methylphenoxymethyl)-4-thiazolyl]benzenesulfonamide;
4-[5-(4-fluorophenyl)-2-(benzyloxymethyl)-4-thiazolyl]benzenesulfonamide;
4-[5-(4-fluorophenyl)-2-(cyanomethyl)-4-thiazolyl]benzenesulfonamide;
4-[5-(4-fluorophenyl)-2-(2-quinolylmethyloxymethyl)-4-thiazolyl]benzenesulfonamide;
4-[5-(4-fluorophenyl)-2-(2-naphthylmethyloxymethyl)-4-thiazolyl]benzenesulfonamide;
4-[5-(4-fluorophenyl)-2-(N-phenylaminocarbonyl)-4-thiazolyl]benzenesulfonamide;
4-[5-(4-fluorophenyl)-2-[(3-fluorophenyl)aminocarbonyl]-4-thiazolyl]benzenesulfonamide;
4-[5-(4-fluorophenyl)-2-[(3-chlorophenyl)aminocarbonyl]-4-thiazolyl]benzenesulfonamide;
4-[5-(4-fluorophenyl)-2-[(3-bromophenyl)aminocarbonyl]-4-thiazolyl]benzenesulfonamide;
4-[5-(4-fluorophenyl)-2-[(3,5-difluorophenyl)aminocarbonyl]-4-thiazolyl]benzenesulfonamide;
4-[5-(4-fluorophenyl)-2-[(3,5-dichlorophenyl)aminocarbonyl]-4-thiazolyl]benzenesulfonamide;
4-[5-(4-fluorophenyl)-2-[(4-fluorophenyl) aminocarbonyl]-4-thiazolyl]benzenesulfonamide;
4-[5-(4-fluorophenyl)-2-[(4-chlorophenyl) aminocarbonyl]-4-thiazolyl]benzenesulfonamide;
4-[5-(4-fluorophenyl)-2-[(4-bromophenyl) aminocarbonyl]-4-thiazolyl]benzenesulfonamide;
4-[5-(4-fluorophenyl)-2-[(4-methylphenyl) aminocarbonyl]-4-thiazolyl]benzenesulfonamide;
4-[5-(4-fluorophenyl)-2-(benzylaminocarbonyl)-4-thiazolyl]benzenesulfonamide;
4-[5-(4-fluorophenyl)-2-((3-fluorobenzyl)aminocarbonyl)-4-thiazolyl]benzenesulfonamide;
4-[5-(4-fluorophenyl)-2-((3-chlorobenzyl)aminocarbonyl)-4-thiazolyl]benzenesulfonamide;
4-[5-(4-fluorophenyl)-2-((3-bromobenzyl)aminocarbonyl)-4-thiazolyl]benzenesulfonamide;
4-[5-(4-fluorophenyl)-2-((3,5-difluorobenzyl)aminocarbonyl)-4-thiazolyl]benzenesulfonamide;
4-[5-(4-fluorophenyl)-2-((3,5-dichlorobenzyl)aminocarbonyl)-4-thiazolyl]benzenesulfonamide;
4-[5-(4-fluorophenyl)-2-((4-fluorobenzyl)aminocarbonyl)-4-thiazolyl]benzenesulfonamide;
4-[5-(4-fluorophenyl)-2-chlorobenzyl)aminocarbonyl)-4-thiazolyl]benzenesulfonamide;
4-[5-(4-fluorophenyl)-2-((4-bromobenzyl)aminocarbonyl)-4-thiazolyl]benzenesulfonamide;
4-[5-(4-fluorophenyl)-2-((4-methylbenzyl)aminocarbonyl)-4-thiazolyl]benzenesulfonamide;
4-[5-(4-fluorophenyl)-2-(benzoylamino)-4-thiazolyl]benzenesulfonamide;
4-[5-(4-fluorophenyl)-2-((3-fluorobenzoyl)amino)-4-thiazolyl]benzenesulfonamide;
4-[5-(4-fluorophenyl)-2-((3-chlorobenzoyl)amino)-4-thiazolyl]benzenesulfonamide;
4-[5-(4-fluorophenyl)-2-((3-bromobenzoyl)amino)-4-thiazolyl]benzenesulfonamide;
4-[5-(4-fluorophenyl)-2-((3,5-difluorobenzoyl)amino)-4-thiazolyl]benzenesulfonamide;
4-[5-(4-fluorophenyl)-2-((3,5-dichlorobenzoyl)amino)-4-thiazolyl]benzenesulfonamide;
4-[5-(4-fluorophenyl)-2-((4-fluorobenzoyl)amino)-4-thiazolyl]benzenesulfonamide;
4-[5-(4-fluorophenyl)-2-((4-chlorobenzoylamino)-4-thiazolyl]benzenesulfonamide;
4-[5-(4-fluorophenyl)-2-((4-bromobenzoyl)amino)-4-thiazolyl]benzenesulfonamide;
4-[5-(4-fluorophenyl)-2-((4-methylbenzoyl)amino)-4-thiazolyl]benzenesulfonamide; and
4-[5-(4-fluorophenyl)-2-(phenylacetyl)amino-4-thiazolyl]benzenesulfonamide.

Within Formula I there is a subclass of compounds of high interest represented by Formula II:

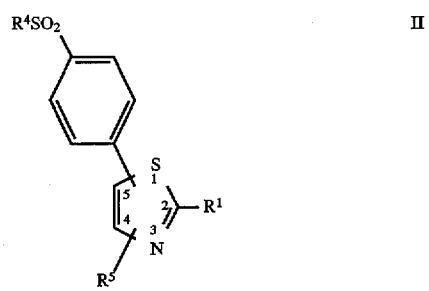

wherein $R^1$ is selected from hydrido, alkyl, haloalkyl, cyanoalkyl, alkylamino, aralkyl, arylamino, heteroarylsulfonylalkyl, heteroarylsulfonylhaloalkyl, aralkylamino, aryloxyalkyl, alkoxycarbonyl, aryl optionally substituted at a substitutable position with one or more radicals selected from halo and alkoxy, and heterocyclic optionally substituted at a substitutable position with one or more radicals selected from halo and alkyl;
wherein $R^4$ is selected from alkyl and amino; and
wherein $R^5$ is selected from aryl and heteroaryl; wherein $R^5$ is optionally substituted at a substitutable position with one or more radicals selected from halo, alkyl and alkoxy;
provided $R^5$ is not phenyl at position 4 when $R^1$ is α,α-bis(trifluoromethyl) methanol and $R^4$ is methyl;
or a pharmaceutically-acceptable salt thereof.

A preferred class of compounds consists of those compounds of Formula II wherein $R^1$ is selected from hydrido, lower alkyl, lower haloalkyl, lower cyanoalkyl, lower alkylamino, lower aralkyl, lower arylamino, lower heteroarylsulfonylalkyl, lower heteroarylsulfonylhaloalkyl, lower aralkylamino, lower aryloxyalkyl, lower alkoxycarbonyl, aryl optionally substituted at a substitutable position with one or more radicals selected from halo and lower alkoxy, and heterocyclic optionally substituted at a substitutable position with one or more radicals selected from halo and lower alkyl;
wherein $R^4$ is selected from lower alkyl and amino; and
wherein $R^5$ is selected from aryl and heteroaryl; wherein $R^5$ is optionally substituted at a substitutable position with one or more radicals selected from halo, lower alkyl and lower alkoxy;
or a pharmaceutically-acceptable salt thereof.

A class of compounds of particular interest consists of those compounds of Formula II wherein $R^1$ is selected from hydrido, methyl, ethyl, propyl, butyl, pentyl, isopropyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyanomethyl, cyanoethyl, cyanopropyl, methylamino, ethylamino, propylamino, butylamino, tert-butylamino, pentylamino, hexylamino, phenethyl, phenpropyl, benzyl, phenylamino, thienylsulfonylmethyl, thienylsulfonylbromomethyl, benzylamino, phenoxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, phenyl optionally substituted at a substitutable position with one or more radicals selected from fluoro, chloro, bromo, methoxy, ethoxy, propoxy, butoxy, isopropoxy and tert-butoxy, and a heterocyclic radical selected from thienyl, pyridyl, furyl, pyrazinyl, thiazolyl, pyrrolyl, pyrazolyl and triazolyl, optionally substituted at a substitutable position with one or more radicals selected from fluoro, chloro, bromo, methyl, ethyl, propyl, butyl, pentyl, isopropyl, isobutyl and tert-butyl;

wherein $R^4$ is methyl or amino; and wherein $R^5$ is selected from phenyl, pyridyl, furyl, pyrazinyl, pyrrolyl, pyrazolyl, triazolyl and thienyl; wherein $R^5$ is optionally substituted at a substitutable position with one or more radicals selected from fluoro, chloro, bromo, methyl, ethyl, propyl, butyl, pentyl, isopropyl, isobutyl, tert-butyl, methoxy, ethoxy, propoxy, butoxy, isopropoxy and tert-butoxy;

or a pharmaceutically-acceptable salt thereof.

A family of specific compounds of particular interest within Formula II consists of compounds and pharmaceutically-acceptable salts thereof as follows:

4-(4-fluorophenyl)-5-[(4-methylsulfonyl)phenyl]-2-phenylthiazole;

4-(4-fluorophenyl)-5-[(4-methylsulfonyl)phenyl]-2-(4-methoxyphenyl)thiazole;

4-(4-fluorophenyl)-5-[(4-methylsulfonyl)phenyl]-2-trifluoromethyl-thiazole;

4-(4-fluorophenyl)-2-(N-hexylamino)-5-[(4-methylsulfonyl)phenyl]thiazole;

2-(4-cyanophenylamino)-4-(4-fluorophenyl)-5[4-(methylsulfonyl)phenyl]thiazole;

4-(4-fluorophenyl)-2-(N-methylamino)-5-[(4-methylsulfonyl)phenyl]thiazole;

2-(N-ethylamino)-4-(4-fluorophenyl)-5-[(4-methylsulfonyl)phenyl]thiazole;

2-(N-tert-butylamino)4-(4-fluorophenyl)-5-[(4-methylsulfonyl)phenyl]thiazole;

ethyl 4-[[4-(4-fluorophenyl)-5-[(4-methylsulfonyl)phenyl]-2-thiazolyl]amino]benzoate;

ethyl 3-[[4-(4-fluorophenyl)-5-[(4-methylsulfonyl)phenyl]-2-thiazolyl]amino]benzoate;

4-(4-fluorophenyl)5-[(4-methylsulfonyl)phenyl]-2-(2-phenylethyl)thiazole;

2-(N-(3,5-dichlorophenyl)amino)-4-(4-fluorophenyl)-5-[(4-methylsulfonyl)phenyl]thiazole;

2-(N-butylamino)-4-(4-fluorophenyl)-5-[(4-methylsulfonyl)phenyl]thiazole;

2-ethyl-4-(4-fluorophenyl)-5-[(4-methylsulfonyl)phenyl]thiazole;

4-(4-fluorophenyl)-5-[(4-methylsulfonyl)phenyl]-2-(3-phenylpropyl)thiazole;

2-((3-chlorophenoxy)methyl)-4-(4-fluorophenyl)-5-[(4-methylsulfonyl)phenyl]thiazole;

4-(4-fluorophenyl)-5-[(4-methylsulfonyl)phenyl]-2-(2-methyl-4-thiazolyl)thiazole;

2-(2-chlorophenyl)-4-(2-fluorophenyl)-5-[(4-methylsulfonyl)phenyl]thiazole;

4-(4-fluorophenyl)-5-[(4-methylsulfonyl)phenyl]-2-(2,3,4,5,6-pentafluorophenyl)thiazole;

2-((2-chlorophenoxy)methyl)-4-(4-fluorophenyl)-5-[(4-methylsulfonyl)phenyl]thiazole;

2-(2-chlorophenyl)-4-(4-bromophenyl)-5-[(4-methylsulfonyl)phenyl]thiazole;

2-((3-chlorophenoxy)methyl)-4-(2-fluorophenyl)-5-[(4-methylsulfonyl)phenyl]thiazole;

4-(2-fluorophenyl)-5-[(4-methylsulfonyl)phenyl]-2-((4-methoxyphenoxy)methyl)thiazole;

2-((4-chlorophenoxy)methyl)-4-(4-fluorophenyl)-5-[(4-methylsulfonyl)phenyl]thiazole;

2-(2-chlorophenyl)-4-phenyl-5-[(4-methylsulfonyl)phenyl]thiazole;

2-(2-chlorophenyl)-4-(3-fluorophenyl)- 5-[(4-methylsulfonyl)phenyl]thiazole;

4-(2,4-difluorophenyl)-2-(2-chlorophenyl)-5-[(4-methylsulfonyl)phenyl]thiazole;

2-(2-chlorophenyl)-4-(2-methylphenyl)-5-[(4-methylsulfonyl)phenyl]thiazole;

2-(2-chlorophenyl)-5-[(4-methylsulfonyl)phenyl]-4-(2-thienyl)thiazole;

2-(2-chlorophenyl)-5-[(4-methylsulfonyl)phenyl]-4-(3-thienyl)thiazole;

4-(4-fluorophenyl)-5-[(4-methylsulfonyl)phenyl]-2-(4-pyridyl)thiazole;

2-(2-chlorophenyl)-4-(2-chlorophenyl)-5-[(4-methylsulfonyl)phenyl]thiazole;

2-(2-chlorophenyl)-4-(4-chlorophenyl)-5-[(4-methylsulfonyl)phenyl]thiazole;

2-(2-chlorophenyl)-4-(4-methoxyphenyl)-5-[(4-methylsulfonyl)phenyl]thiazole;

4-(3-chloro-4-fluorophenyl)-4-(4-fluorophenyl)-5-[(4-methylsulfonyl)phenyl]thiazole;

4-(4-fluorophenyl)-2-((2-thienyl)sulfonylmethyl)-5-[(4-methylsulfonyl)phenyl]thiazole;

2-(4-fluorophenyl)-2-((2-thienyl)sulfonylbromomethyl)-5-[(4-methylsulfonyl)phenyl]thiazole;

2-(2-chlorophenyl)-5-[(4-methylsulfonyl)phenyl]-4-(4-methylphenyl)thiazole;

2-(2-chlorophenyl)-4-(4-fluorophenyl)-5-[(4-methylsulfonyl)phenyl]thiazole;

ethyl [4-(4-fluorophenyl)-5-[(4-methylsulfonyl)phenyl]-2-thiazolyl]carboxylate;

2-(cyanomethyl)-4-(4-fluorophenyl)-5-[(4-methylsulfonyl)phenyl]thiazole;

2-(tert-butyl)-4-(4-fluorophenyl)-5-[(4-methylsulfonyl)phenyl]thiazole;

2-benzyl-4-(4-fluorophenyl)-5-[(4-methylsulfonyl)phenyl]-thiazole;

5-(4-fluorophenyl)-4-[(4-methylsulfonyl)phenyl]-2-methylthiazole;

2-(3-[4-bromophenyl]propyl)-4-(4-fluorophenyl))-5-[(4-methylsulfonyl)phenyl]thiazole;

4-(4-fluorophenyl)-5-[(4-methylsulfonyl)phenyl]thiazole;

4-(4-fluorophenyl)-5-[(4-methylsulfonyl)phenyl]-2-trifluoromethylthiazole;

4-(4-fluorophenyl)-5-[(4-methylsulfonyl)phenyl]-2-(2-thienyl)thiazole;

2-(5-bromo-2-thienyl)-4-(4-fluorophenyl)-5-[(4-methylsulfonyl)phenyl]thiazole;

4-(4-fluorophenyl)-5-[(4-methylsulfonyl)phenyl]-2-(3-pyridyl)thiazole;

4-(4-fluorophenyl)-5-[(4-methylsulfonyl)phenyl]-2-methylthiazole;

2-benzylamino-4-(4-fluorophenyl)-5-[(4-methylsulfonyl)phenyl]thiazole;

4-(4-fluorophenyl)-5-[(4-methylsulfonyl)phenyl]-2-(1-piperidinyl)thiazole;

4-(4-fluorophenyl)-5-[(4-methylsulfonyl)phenyl]-2-(1-propylamino)thiazole;

2-[(3,5-dichlorophenoxy)methyl]-4-(4-fluorophenyl)-5-[4-(methylsulfonyl)phenyl]thiazole;

4-[4-(4-fluorophenyl)-2-(2-chlorophenyl)-5-thiazolyl] benzenesulfonamide; and

4-[4-(4-fluorophenyl)-2-((3,5-dichlorophenoxy)methyl)-5-thiazolyl]benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where the term "alkyl" is used, either alone or within other terms such as "haloalkyl", "alkylsulfonyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Where the term "alkenyl" is used, it embraces linear or branched carbon carbon double bond-containing radicals having two to about twenty carbon atoms or, preferably, two to about twelve carbon atoms. More preferred alkenyl radicals are "lower alkenyl" radicals having two to about six carbon atoms. Suitable "lower alkenyl" may be a straight or branched one such as vinyl, allyl, isopropenyl, propenyl, butenyl, pentenyl or the like, in which preferably one is isopropenyl. Said lower alkenyl may be substituted with cyano. Where the term "alkynyl" is used, it embraces linear or branched carbon carbon triple bond-containing radicals having two to about twenty carbon atoms or, preferably, two to about twelve carbon atoms. More preferred alkynyl radicals are "lower alkynyl" radicals having two to about six carbon atoms. Suitable "lower alkynyl" may be a straight or branched one such as ethynyl, propynyl, propargyl or the like, in which preferably one is propargyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. The term "hydroxyalkyl" embraces linear or branched alkyl radicals having one to about ten carbon atoms any one of which may be substituted with one or more hydroxyl radicals. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, to provide haloalkoxy or haloalkoxyalkyl radicals. Examples of such radicals include trifluoromethoxy and trifluoroethoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronapthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.]etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. The term "heterocycloalkyl" embraces heterocyclic-substituted alkyl radicals such as pyridylmethyl and thienylmethyl. The term "alkylthio" embraces radicals containing a linear or branched alkyl radical, of one to about ten carbon atoms attached to a divalent sulfur atom, such as a methythio radical, (CH$_3$—S—). The term "alkylsulfinyl" embraces radicals containing a linear or branched alkyl radical, of one to ten carbon atoms, attached to a divalent —S(=O)— radical. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The terms "sulfamyl", "aminosulfonyl" and sulfonamidyl denotes NH$_2$O$_2$S—. The term "acyl" denotes a radical provided by the residue after removal of hydroxyl from an organic acid.

Examples of such acyl radicals include alkanoyl and aroyl radicals. The terms "carboxy" or "carboxyl", whether used alone or with other terms, such as "carboxyalkyl", denotes —CO$_2$H. The term "carboxyalkyl" embraces carboxylic acids substituted so as to have a free acid remaining. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" embraces radicals having "alkoxycarbonyl", as defined above substituted to an alkyl radical. Examples of similar radicals include substituted or unsubstituted "aryloxycarbonyl" [e.g. phenoxycarbonyl, 4-nitrophenoxycarbonyl, 2-naphthyloxycarbonyl, etc.], substituted or unsubstituted "aralkoxycarbonyl" [e.g. benzyloxycarbonyl, phenethyloxycarbonyl, benzhydryloxycarbonyl, 4-nitrobenzyloxycarbonyl, etc.] and the like. The "alkanoyl" embraces radicals having a carboxy radical as defined above, attached to an alkyl radical. The alkanoyl radicals may be a substituted or unsubstituted one such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The "aroyl" radicals may be benzoyl, naphthoyl, toluoyl, di(tert-butyl)benzoyl and the like and the aryl in said aroyl may be additionally substituted. The term "aralkyl" embraces aryl-substituted alkyl radicals such as benzyl, diphenylmethyl, triphenylmethyl, phenethyl, and diphenethyl. The aryl in said aralkyl may be additionally substituted at a substitutable position with one or more alkyl or halo radicals. The terms benzyl and phenylmethyl are interchangeable. The term "cycloalkyl" embraces radicals having three to ten carbon atoms, such as cyclopropyl cyclobutyl, cyclopentyl, cyclohexyl and cycloheptyl. The term "cycloalkenyl" embraces unsaturated radicals having three to ten carbon atoms, such as cylopropenyl, cyclobutenyl, cyclopentenyl, cyclohexenyl and cycloheptenyl. The term "aryloxy" embrace oxy-containing aryl radicals attached through an oxygen atom to other radicals. More preferred aryloxy radicals are "lower aryloxy" radicals having a phenyl radical. An example of such radicals is phenoxy. The term "aryloxyalkyl" embraces alkyl radicals having one or more aryloxy radicals attached to the alkyl radical, that is, to form monoaryloxyalkyl and diaryloxyalkyl radicals. The "aryloxy" or "aryloxyalkyl" radicals may be further substituted at a substitutable position with one or more alkyl, alkoxy or halo radicals. to provide haloaryloxyalkyl radicals alkylaryloxy radicals, and the like. Examples of such radicals include chlorophenoxy and methylphenoxy. The term "aralkyloxy" embrace oxy-containing aralkyl radicals attached through an oxygen atom to other radicals. The term "aralkyloxyalkyl" embraces alkyl radicals having one or more aralkyloxy radicals attached to the alkyl radical, that is, to form monoaralkyloxyalkyl and diaralkyloxyalkyl radicals. The "aralkyloxy" or "aralkyloxyalkyl" radicals may be further substituted on the aryl ring portion of the radical. The term "aminoalkyl" embraces alkyl radicals substituted with amino radicals. The term "alkylaminoalkyl" embraces aminoalkyl radicals having the nitrogen atom substituted with an alkyl radical. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. Arylamino radicals may be substituted at a substitutable position with one or more alkyl, cyano, alkoxy, alkoxycarbonyl or halo radicals. The term "aralkylamino" denotes amino groups which have been substituted with one or two aralkyl radicals, such as N-benzylamino, N-phenethylamino and phenpropylamino. The "aralkylamino" or "arylamino" radicals may be further substituted on the aryl ring portion of the radical. The terms "aminocarbonyl" and "amide", whether used by itself or with other terms such as "N-monoalkylaminocarbonyl", "N-monoarylaminocarbonyl", "N,N-dialkylaminocarbonyl" and "N-alkyl-N-arylaminocarbonyl", denotes a radical formed by an amino substituted carbonyl, or —C(=O)NH$_2$. The terms "N-alkylaminocarbonyl" and "N,N-dialkylaminocarbonyl" denote amido groups which have been substituted with one alkyl radical and with two alkyl radicals, respectively. The N-alkylaminocarbonyl may be substituted with halo or an unsubstituted one such as N-methylaminocarbonyl, N-ethylaminocarbonyl, N-propylaminocarbonyl, N,N-dimethylaminocarbonyl, 2,2, 2-trifluoroethylaminocarbonyl or the like. The terms "N-monoarylaminocarbonyl" and "N-alkyl-N-arylaminocarbonyl" denote amido radicals substituted, respectively, with one aryl radical, and one alkyl and one aryl radical. The N-arylaminocarbonyl may be phenylaminocarbonyl, naphthylaminocarbonyl, tolylaminocarbonyl, xylylaminocarbonyl, mesitylaminocarbonyl, cumenylaminocarbonyl, and the like, in which the preferable one is phenylaminocarbonyl. The term "alkylsulfonylamino" embraces radicals having an alkylsulfonyl radical attached to a nitrogen atom. More preferred are "lower alkylsulfonylamino" having alkylsulfonyl radicals of one to six carbon atoms attached to the nitrogen.

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–VIII, wherein the $R^1$–$R^5$ substituents are as defined for Formulas I–II, above, except where further noted.

SCHEME I

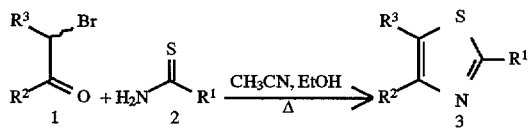

Synthetic Scheme I shows the procedure used to prepare the antiinflammatory substituted thiazoles 3 of the present invention from α-haloketones 1. The α-haloketones 1, such as 2-bromo-ethanone, are reacted with a thioamide 2 or thiourea in acetonitrile and an alcohol, such as methanol and ethanol, to give the 4,5-substituted thiazoles 3 via the Hantzsch synthesis (R. Wiley et al, *The Preparation of Thiazoles*, ORGANIC REACTIONS, VOLUME 6, (1951)).

SCHEME II

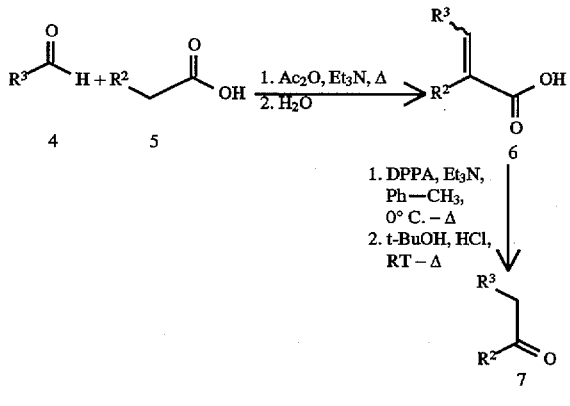

Synthetic Scheme II shows the four step procedure which can be used to prepare the substituted ketone compounds 7 from aldehyde 4 and acid 5. In step one, aldehyde 4 and substituted acetic acid 5 are heated in acetic anhydride and triethylamine to form the 2,3-disubstituted acrylic acids 6 via a Perkin condensation. In step two, the addition of water produces the corresponding 2,3-disubstituted acrylic acids 6. In step three, the acrylic acids 6 are reacted with diphenylphosphorylazide (DPPA) and triethyl amine in toluene at 0° C. and then at room temperature to form acylazides. In step four, the crude acylazides are heated to form an isocyanate via a Curtius rearrangement. The isocyanate is trapped as the N-tert-butyloxycarbonyl enamine derivative via the addition of tert-butanol. Acidic hydrolysis using concentrated HCl provides the substituted ketone 7 intermediates.

SCHEME III

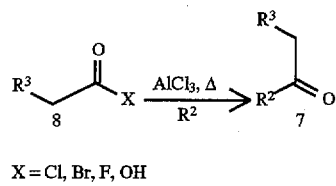

X = Cl, Br, F, OH

Synthetic Scheme III shows an alternative approach which can be used to prepare the substituted ketone intermediates 7 via the use of Friedel Crafts acylation. An acylating agent 8, such as an acid chloride is treated with aluminum chloride in an inert solvent, such as methylene chloride, chloroform, nitrobenzene, dichlorobenzene or chlorobenzene, and reacted with $R^2$ to form ketone 7.

Other synthetic approaches are possible to form the desired ketones. These alternatives include reacting appropriate Grignard or lithium reagents with substituted acetic acids or corresponding esters.

SCHEME IV

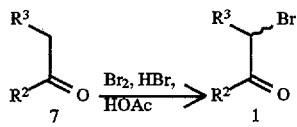

Synthetic Scheme IV shows the procedure which can be used to prepare the substituted haloketone compounds 1. 1,2-Disubstituted ketone intermediates 7 from Synthetic Schemes II or II are readily brominated via the addition of bromine in acetic acid to form the 2-bromo-1,2-disubstituted ethanone intermediates 1.

Alternative means of forming 2-haloketones include the conversion of benzoins such as substituted 2-hydroxyethanones via use of reagents such as thionyl chloride, sulfuryl chloride, methylsulfonyl chloride/lithium chloride, triphenylphosphine dichloride or triphenylphosphine dibromide, among others. The conversion of simple desoxy benzions to the haloketones 1 is readily accomplished via use of halogenating reagents such as bromine, N-bromosuccinimide, N-chlorosuccinimide.

SCHEME V

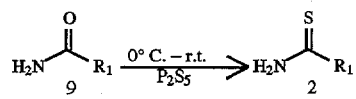

Synthetic Scheme V shows a procedure for the preparation of thioamides 2 by the thiation of the oxygen carboxamide 9 counterparts. The carboxamide 9 is dissolved in a solvent, such as diethyl ether, and cooled to about 0° C. The thiation reagent, such as phosphorous pentasulfide ($P_2S_5$ or $P_4S_{10}$) is added and maintained at a temperature below room temperature. The reaction is warmed to room temperature and stirred. The ethereal solution of the thioamide 2 can be decanted from the reaction mixture and used "as is".

Alternative means of forming the thioaides 2 includes the use of 2,4-bis(4-methoxyphenyl)-1,3-dithia-2,4-diphosphetane-2,4-disulfide (Lawesson's Reagent) as the thiation reagent. The reaction is heated at reflux. In addition, thioamides 2 can be formed by the reaction of a suitable nitrile with hydrogen sulfide.

peroxide, periodate, peracetic acid and the like. Alternatively, the procedure can be utilized to produce thiazoles having an alkylsulfonylphenyl radical at $R^2$.

SCHEME VI

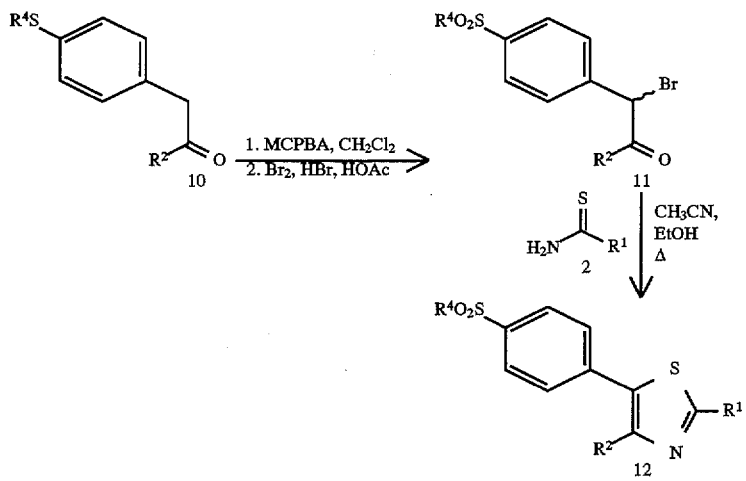

Synthetic Scheme VI shows a three step procedure which can be used to prepare alkylsulfonyl substituted thiazoles 12 from alkylthio substituted ketones 10. In step one, the alkylthioether of ethanone 10, where the thioether radical is located at $R^3$ and $R^4$ is an alkyl radical, is first oxidized to an alkylsulfone using meta-chloroperoxybenzoic acid (MCPBA) (2 eq) in methylene chloride at 0° C. and warmed to room temperature. In step two, the alkylsulfonylketone, where the alkylsulfone radical is located at $R^3$, is brominated alpha to the carbonyl using bromine in HBr/HOAc to form the alkylsulfonyl-2-bromoethanone 11. Condensation of 11 with an appropriate thioamide or thiourea 2 provides the corresponding substituted 5-(4-alkylsulfonylphenyl)thiazole 12. Alternatively, the procedure can be utilized to produce thiazoles having an alkylsulfonyl radical at $R^2$.

SCHEME VII

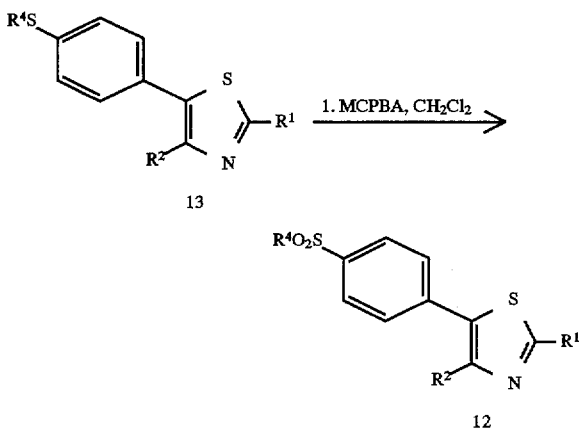

An alternative synthesis of the alkylsulfonyl substituted thiazoles 13 is accomplished as shown in Synthetic Scheme VII. Thiazole 13, having an alkylthiophenyl radical at $R^3$ where $R^4$ is an alkyl radical, is oxidized with MCPBA (2 equivalents) in methylene chloride to form the alkylsulfone 12. Other suitable oxidizing agents include oxone, hydrogen peroxide, periodate, peracetic acid and the like. Alternatively, the procedure can be utilized to produce thiazoles having an alkylsulfonylphenyl radical at $R^2$.

SCHEME VIII

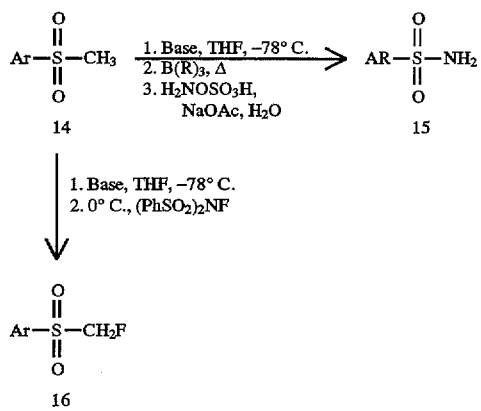

Synthetic Scheme VIII shows the three step procedure used to prepare sulfonamide antiinflammatory agents 15 and the two step procedure used to prepare fluoromethylsulfone antiinflammatory agents 16 from their corresponding methylsulfones 14. In step one, a THF solution of the methylsulfones 14 at −78° C. is treated with an alkyllithium or organo magnesium (Grignard) reagent (RMgX), e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxyamine-O-sulfonic acid is added to provide the corresponding sulfonamide antiinflammatory agents 15 of this invention. Alternatively, the anion solutions generated in step one may be warmed to 0° C. and treated with N-fluorodibenzenesulfonamide to provide the corresponding fluoromethylsulfone antiinflammatory agents 16 of this invention.

The following examples contain detailed descriptions of the methods of preparation of compounds of Formula I–II.

These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

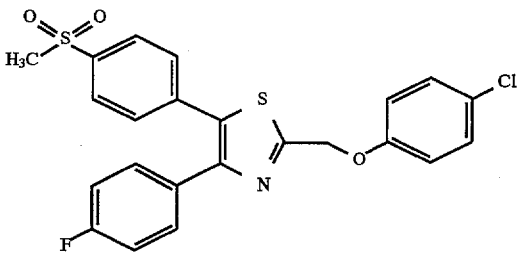

2-((4-Chlorophenoxy)methyl)-4-(4-fluorophenyl)-5-(4-methylsulfonylphenyl)thiazole Step 1

Preparation of 2-(4-Fluorophenyl)-3-(4-methylthiophenyl)propenoic Acid

Acetic anhydride (500 mL), 4-(methylthio) benzaldehyde (100.2 g, 0.66 mol), 4-fluorophenylacetic acid (101.6 g, 0.66 mol), and triethylamine (68.1 g, 0.67 mol) were placed in a 3 L round bottom flask and heated to reflux for 1.75 hours. The reaction was cooled to 110° C., and water (500 mL) was added cautiously through an addition funnel. This caused the solution to reflux vigorously and the temperature to rise to 135° C. A yellow precipitate formed, and after cooling to room temperature, was collected by filtration, washed with water, and recrystallized from ethyl acetate/isooctane to provide the diarylpropenoic acid as yellow needles (135.2 g, 71%): mp 172°–176° C. $^1$H NMR (acetone-$d_6$) 300 MHz 7.84 (s,1H), 7.03–7.28 (m, 10H), 2.46 (s, 3H); $^{19}$F NMR (acetone-$d_6$) –116.11 (m). Mass spectrum: M$^+$ 288.

Step 2

Preparation of 1-(4-Fluorophenyl)-2-(4-methylthiophenyl)ethanone

The diarylpropenoic acid from Step 1 (226.5 g, 0.78 mol) was placed in a 2 L round bottom flask with anhydrous toluene (800 mL) and triethylamine (81.2 g, 0.80 mol). After cooling to 0° C., diphenylphosphoryl azide (217.4 g, 0.79 mol) was added. The solution was stirred at 0° C. for twenty minutes and at room temperature for 2.5 hours. The reaction was poured into water, extracted with ether, dried over magnesium sulfate, and concentrated in vacuo to remove the ether. The remaining toluene solution was heated to reflux and a vigorous evolution of gas occurred. After 1.25 hours, tert-butyl alcohol (80 mL, 0.84 mol) was added to the reaction. After an additional twenty minutes, concentrated hydrochloric acid (41 mL) was added slowly causing the reaction to foam. The reaction was heated at 90° C. overnight (14 hours) and after cooling, a white precipitate formed. The precipitate was isolated by filtration, washed with cold ether, and air dried to yield the desired ketone (182.7 g, 89%): mp 134.5°–138° C. $^1$H NMR (acetone-$d_6$) 300 MHz 8.16 (m,2H), 7.24 (m, 6H), 4.34 (s, 2H), 2.46 (s, 3H); $^{19}$F NMR (acetone-$d_6$) –107.88 (m).

Step 3

Preparation of 1-(4-Fluorophenyl)-2-(4-methylthiophenyl)-2-bromoethanone

A 1 L three necked round bottomed flask equipped with reflux condenser, magnetic stir bar, thermometer adapter, and constant pressure addition funnel was charged with the ketone from Step 2, (55.5 g, 0.21 mol), acetic acid (250 mL) and 33% HBr in acetic acid (120 mL). The solution was stirred and treated with bromine (11.1 mL, 0.21 mol) from the addition funnel at such a rate that the bromine color was discharged rapidly, ca. 15 minutes. After an additional 10 minutes at room temperature, the solution was filtered through a Buchner funnel and the filtrate concentrated in vacuo to give the bromoketone as an orange solid. The crude bromoketone was dissolved in dichloromethane and washed with 1N NaHSO$_3$, dried over anhydrous MgSO$_4$, filtered and concentrated in vacuo to give 68.8 g of 1-(4-fluorophenyl)-2-(4-methylthiophenyl)-2-bromoethanone as a yellow solid which was used directly in the next step.

Step 4

Preparation of 2-((4-Chlorophenoxy)methyl)-4-(4-fluorophenyl)-5-(4-methylthiophenyl)thiazole A solution of the bromoketone from Step 3 (2.51 g, 7.4 mmol) and 4-chlorophenoxy thioacetamide (1.27 g, 7.3 mmol) in 25 mL of acetonitrile was heated to reflux for 4 hours and concentrated in vacuo, the residue was taken up in ethyl acetate and washed successively with sat. aq. NaHCO$_3$, brine, dried over anhydrous MgSO$_4$, filtered and concentrated in vacuo to give the crude thiazole. The thiazole was purified by flash chromatography on silica gel, eluting with 5% ethyl acetate in hexane. The appropriate fractions were combined, concentrated in vacuo and then the crude solid was recrystallized from methanol to give pure thiazole (1.71 g, 61%): mp 91°–95° C. $^1$H NMR (CDCl$_3$) 300 MHz 7.49 (m,2H), 7.22 (m, 6H), 6.99 (m, 4H), 5.37 (s, 2H), 2.49 (s,3H); $^{19}$F NMR (CDCl$_3$) –113.53 (m). High resolution field desorption mass spectrum Calc'd. for C$_{23}$H$_{17}$ClFNOS$_2$Li (M$^+$+Li): 448.0584. Found: 448.0554.

Step 5

Preparation of 2-((4-Chlorophenoxy)methyl)-4-(4-fluorophenyl)-5-(4-methylsulfonylphenyl)thiazole A solution of the thiazole from Step 4 (1.39 g, 3.1 mmol) in 20 mL of dichloromethane was treated with m-chloroperbenzoic acid (MCPBA) (2.22 g, 6.4 mmol) at 0° C. for 1 hour. The solution was washed with 10% aq. NaHSO$_3$, 10% Na$_2$CO$_3$, dried over anhydrous MgSO$_4$, filtered and concentrated in vacuo to give a white foam that was purified by recrystallization from a mixture of dichloromethane and isooctane to give pure product (1.24 g, 83%): mp 140°–43° C. $^1$H NMR (CDCl$_3$) 300 MHz 7.87 (d, J=8.5 Hz, 2H), 7.53 (d, J=8.5 Hz, 2H), 7.45 (m, 2H), 7.27 (d, J=9.2 Hz, 2H), 6.99 (m,4H), 5.38 (s, 2H), 3.08 (s,3H); $^{19}$F NMR (CDCl$_3$) –112.40 (m). Mass spectrum: M+H=474.

EXAMPLE 2

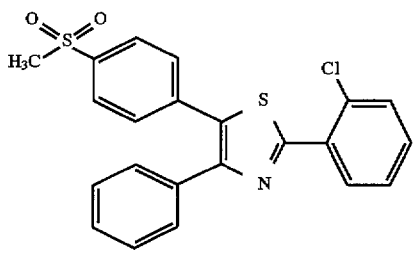

2-(2-Chlorophenyl)-4-phenyl-5-(4-methylsulfonylphenyl)thiazole

Step 1

Preparation of 2-Phenyl-3-(4-methylthiophenyl) propenoic Acid

A mixture of acetic anhydride (500 mL), 4-(methylthio) benzaldehyde (113.1 g, 0.743 mol), phenylacetic acid (101.2 g, 0.743 mol), and triethylamine (75.8 g, 0.75 mol) was placed in a 3 L round bottom flask and heated to reflux for 5 hours. The reaction was cooled to 110° C., and water (500 mL) was added through an addition funnel. A yellow precipitate formed, and after further cooling to room temperature, the solid was collected by filtration, washed with water, and recrystallized from isopropyl alcohol to give the diarylpropenoic acid as white needles (94.2 g, 57%): mp 167°–169° C. $^1$H NMR (CDCl$_3$) 300 MHz 12.00 (br s,1H), 7.91 (s,1H), 7.38 (m, 3H), 7.24 (m, 2H), 7.00 (d, 2H), 6.99 (d, 2H), 2.43 (s, 3H).

Step 2

Preparation of 2-(4-Methylthiophenyl)-1-phenylethanone

The diarylpropenoic acid from Step 1 (12.27 g, 45.4 mmol) and triethylamine (8.44 g, 84 mmol) were dissolved in 110 mL of anhydrous toluene, cooled to 0° C. and treated with diphenylphosphoryl azide (12.6 g, 83.4 mmol). The solution was maintained at 0° C. for twenty minutes and warmed to room temperature for 2.5 hours. The reaction was poured into water, extracted with ether, dried over magnesium sulfate, and concentrated in vacuo to remove the ether. The remaining toluene solution was heated to reflux for 1.25 hours. tert-Butyl alcohol (5 mL, 53 mmol) was added to the solution, after an additional twenty minutes, concentrated hydrochloric acid (4 mL) was cautiously added and the reaction maintained at 90° C. overnight (14 hours). After cooling the solution to room temperature, a white precipitate formed which was isolated by filtration, washed with cold ether, and air dried to yield the desired ketone which was crystallized from a mixture of dichloromethane and isooctane (5.16 g, 47%): mp 123°–127° C. $^1$H NMR (CDCl$_3$) 300 MHz 7.99 (d, J=7.3 Hz,2H), 7.56 (m, 1H), 7.46 (m, 2H), 7.22 (d, J=8.4 Hz 2H), 7.20 (d, J=8.5 Hz, 2H), 4.24 (s, 2H), 2.46 (s, 3H).

Step 3

Preparation of 2-Bromo-2-(4-methylthiophenyl)-1-phenylethanone

A solution of the ketone from Step 2 (2.35 g, 9.7 mmol) in acetic acid (50 mL) and 33% HBr in acetic acid (4 mL) was treated with a 1.1M solution of bromine in acetic acid (9 mL, 9.9 mmol) and then stirred at room temperature for 1 hour. The solution was diluted with dichloromethane and washed with 1N NaHSO$_3$, dried over anhydrous MgSO$_4$, filtered and concentrated in vacuo to give the bromoketone which was used directly in the next step (2.38 g, 76%): mp 93°–95° C. $^1$H NMR (CDCl$_3$) 300 MHz 7.97 (d, J=7.3 Hz, 2H), 7.57 (m, 1H), 7.46 (m, 4H), 7.24 (d, J=8.5 Hz, 2H), 6.35 (s, 1H), 2.47 (s, 3H).

Step 4

Preparation of 2-(2-Chlorophenyl)-4-phenyl-5-(4-methylthiophenyl)thiazole

A solution of the bromoketone from Step 3 (2.38 g, 7.4 mmol) and 4-chlorothiobenzamide (1.29 g, 7.5 mmol) in 25 mL of acetonitrile was heated to reflux for 14 hours. The solution was cooled to room temperature and poured into 25 mL of methanol whereupon crystals of pure diaryl thiazole formed which were isolated by filtration and air dried to afford the pure diaryl thiazole (2.01 g, 69%): mp 107°–109.5° C. $^1$H NMR (CDCl$_3$) 300 MHz 8.37 (m, 1H), 7.62 (m, 2H), 7.49 (d, J=7.7 Hz, 1H), 7.32 (m, 7H), 7.22 (d, J=8.5 Hz, 2H), 2.51 (s, 3H). Mass spectrum M+H=394.

Step 5

Preparation of 2-(2-chlorophenyl)-4-phenyl-5-(4-methylsulfonylphenyl)thiazole

A solution of the diaryl thiazole from Step 4 (1.90 g, 4.8 mmol) in 10 mL of dichloromethane was treated with MCPBA (3.40 g, 9.9 mmol) at 0° C. for 1 hour. The solution was washed with 10% aq. NaHSO$_3$, 10% Na$_2$CO$_3$, dried over anhydrous MgSO$_4$, filtered and concentrated in vacuo to give a yellow solid that was purified by flash chromatography on silica gel eluting with 1:1 hexane:ethyl acetate to provide 1.5 g, 73% of pure product: mp 191.5°–195° C. $^1$H NMR (CDCl$_3$) 300 MHz 8.40 (m, 1H), 7.88 (d, J=8.5 Hz, 2H), 7.51–7.62 (m, 5 H), 7.35–7.41 (m, 5H), 3.09 (s, 3H). High resolution mass spectrum Calc'd. for C$_{22}$H$_{16}$ClNO$_2$S$_2$: 425.0311. Found: 425.0315.

EXAMPLE 3

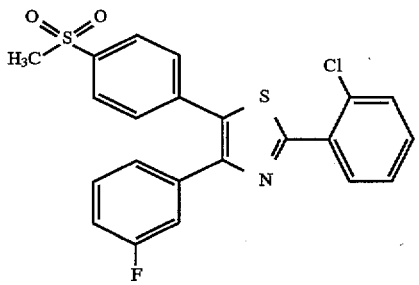

2-(2-Chlorophenyl)-4-(3-fluorophenyl)-5-(4-methylsulfonylphenyl)thiazole

Step 1

Preparation of 2-(3-fluorophenyl)-3-(4-methylthiophenyl)propenoic Acid

A mixture of acetic anhydride (60 mL), 4-(methylthio) benzaldehyde (4.99 g, 33 mmol), 3-fluorophenylacetic acid (5.08 g, 33 mmol), and triethylamine (3.98 g, 39 mmol) was heated to reflux for 4 hours. The reaction was cooled to 120° C., and water (120 mL) was added through an addition funnel. A yellow precipitate formed and, after further cooling to room temperature, was collected by filtration, washed with water, and recrystallized from toluene to give the desired intermediate as a yellow solid (3.72 g, 39%): mp 184°–187° C. $^1$H NMR (CDCl$_3$) 300 MHz 7.92 (s,1H), 7.35 (m, 1H), 7.26 (d, J=6.3 Hz, 1H), 7.19 (d, J=7.7 Hz, 1H) 7.00 (m, 5H), 2.44 and 2.36 (s, 3H); $^{19}$F NMR (CDCl$_3$) –112.61 (m). Mass spectrum M+H=289.

Step 2

Preparation of 1-(3-Fluorophenyl)-2-(4-methylthiophenyl)ethanone

A solution of the intermediate from Step 1 (3.57 g, 12.4 mmol) and triethylamine (1.41 g, 13.9 mmol) dissolved in 35 mL of anhydrous toluene was cooled to 0° C. and treated with diphenylphosphoryl azide (3.53 g, 12.8 mmol). The solution was maintained at 0° C. for twenty minutes and warmed to room temperature for 3 hours. The reaction was poured into water, extracted with ether, dried over magnesium sulfate, and concentrated in vacuo to remove the ether. The remaining toluene solution was heated to reflux for 1 hour. tert-Butyl alcohol (4 mL, 42 mmol) was added to the reaction mixture. After an additional twenty minutes, concentrated hydrochloric acid (4 mL) was cautiously added and the reaction maintained at 80° C. overnight (14 hours). After cooling the solution to room temperature, the mixture was poured into a separatory funnel and washed with water. The toluene layer was dried with anhydrous MgSO$_4$, filtered and concentrated in vacuo to give a yellow powder. The crude solid was crystallized from a mixture of dichloromethane and isooctane to provide 1.30 g (40%) of the desired ketone: mp 116°–120° C. $^1$H NMR (CDCl$_3$) 300 MHz 7.77 (d, J=7.9 Hz, 1H), 7.68 (dt, J=9.4 Hz 2.6 Hz, 1H), 7.43 (m, 1H), 7.21–7.29 (m, 3H), 7.18 (d, J=8.3 Hz, 2H), 4.22 (s, 2H), 2.46 (s, 3H); $^{19}$F NMR (CDCl$_3$) –111.82 (m). Mass spectrum M+H=261.

Step 3

Preparation of 2-Bromo-1-(3-fluorophenyl)2-(4-methylthiophenyl)ethanone

A solution of the ketone from Step 2 (1.53 g, 5.9 mmol) in acetic acid (20 mL) and 33% HBr in acetic acid (0.5 mL) was treated with a 0.99M solution of bromine in acetic acid (6.1 mL, 6.0 mmol) and stirred at room temperature for twenty minutes. The contents of the flask solidified and the precipitate was isolated by filtration. The filtrate solution was diluted with dichloromethane and washed with 1N NaHSO$_3$, dried over anhydrous MgSO$_4$, filtered and concentrated in vacuo to give a solid that was combined with the original precipitate to provide 1.92 g (96%) of bromoketone: mp 101°–104° C. $^1$H NMR (CDCl$_3$) 300 MHz 7.73 (d, J=7.9 Hz, 1H), 7.67 (dt, J=9.4 Hz 2.3 Hz, 1H), 7.41 (m, 3H), 7.24 (m, 3H), 6.27 (s, 1H), 2.47 (s, 3H); $^{19}$F NMR (CDCl$_3$) –111.18 (m). Mass spectrum: M+H=340.

Step 4

Preparation of 2-(2-Chlorophenyl)-4-(3-fluorophenyl)-5-(4-methylthiophenyl)thiazole A solution of the bromoketone intermediate from Step 3 (0.77 g, 2.3 mmol) and 4-chlorothiobenzamide (0.40 g, 2.3 mmol) in 10 mL of acetonitrile was heated to reflux for 4 hours. The solution was cooled to room temperature and poured into 25 mL of methanol whereupon crystals of thiazole formed which were isolated by filtration and air dried to afford the pure thiazole (0.66 g, 71%): mp 106.5°–108° C. $^1$H NMR (CDCl$_3$) 300 MHz 8.37 (dd, J=7.4 Hz 2.2 Hz, 1H), 7.49 (d, J=7.0 Hz, 1H), 7.21–7.42 (m, 9H), 7.00 (t, J=8.5 Hz, 1H), 2.51 (s,3H); $^{19}$F NMR (CDCl$_3$) –113.10 (m). Mass spectrum: M$^+$=412.

Step 5

Preparation of 2-(2-Chlorophenyl)-4-(3-fluorophenyl)-5-(4-methylsulfonylphenyl)thiazole A solution of the thiazole from Step 4 (610 mg, 1.48 mmol) in 15 mL of dichloromethane was treated with MCPBA (1.05 g) at room temperature for 72 hours. The solution was washed with 10% aq. NaHSO$_3$, 10% Na$_2$CO$_3$, dried over anhydrous MgSO$_4$, filtered and concentrated in vacuo to give a yellow oil that was crystallized from toluene to give yellow needles (320 mg, 48%): mp 133.5°–135° C. $^1$H NMR (CDCl$_3$) 300 MHz 8.39 (m, 1H), 7.91 (d, J=8.5 Hz, 2H), 7.63 (d, J=8.5 Hz 2H), 7.51 (m, 1H), 7.40 (m, 3H), 7.28 (m, 2H), 7.10 (m, 1H) 3.10 (s,3H); $^{19}$F NMR (CDCl$_3$) –112.70 (m). Mass spectrum: M$^+$=444.

EXAMPLE 4

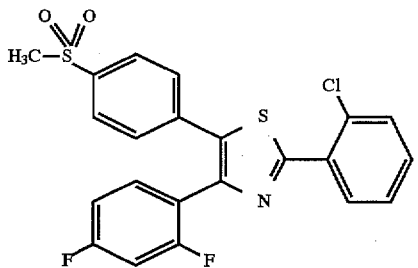

4-(2,4-Difluorophenyl)-2-(2-chlorophenyl)-5-(4-methylsulfonylphenyl)thiazole

Step 1

Preparation of 2-(2,4-Difluorophenyl)-3-(4-methylthiophenyl)propenoic Acid

A mixture of acetic anhydride (50 mL), 4-(methylthio)benzaldehyde (3.75 g, 24.6 mmol), 2,4-difluorophenylacetic acid (4.41 g, 24.6 mmol), and triethylamine (2.80 g, 27.7 mmol) was heated to reflux for 3.5 hours. The reaction was cooled to 90° C., and water (100 mL) was added through an addition funnel. A yellow oil formed that solidified upon stirring. The solid was collected by filtration, and dissolved in ethyl acetate, dried over anhydrous MgSO$_4$, filtered and concentrated in vacuo. The solid thus obtained was recrystallized from toluene to give the desired acid (3.18 g, 42%): mp 165°–171° C. $^1$H NMR (acetone-d$_6$) 300 MHz 7.95 (s,1H), 7.08–7.18 (m, 7H), 2.47 and 2.31 (s, 3H); $^{19}$F NMR (acetone-d$_6$) –110.81 (m) –111.75 (m). Mass spectrum: M+H=306.

Step 2

Preparation of 1-(2,4-Difluorophenyl)-2-(4-methylthiophenyl)ethanone

A solution of the acid from Step 1 (3.11 g, 10.2 mmol) and triethylamine (1.23 g, 10.8 mmol) dissolved in 15 mL of anhydrous toluene, was cooled to 0° C. and treated with diphenylphosphoryl azide (2.98 g, 10.8 mmol). The solution was maintained at 0° C. for twenty minutes and warmed to room temperature for 1 hour. The reaction was poured into water, extracted with ether, dried over magnesium sulfate, and concentrated in vacuo to remove the ether. The remaining toluene solution was diluted with an additional 10 mL of toluene and heated to 90° C. for 1.5 hours. tert-Butyl alcohol (4 mL, 42 mmol) was added to the reaction mixture. After an additional twenty minutes, concentrated hydrochloric acid (4 mL) was cautiously added and the reaction maintained at 90° C. overnight (16 hours). After cooling the solution to room temperature, the mixture was poured into a separatory funnel, diluted with ethyl acetate, and washed with water. The organic layer was dried with anhydrous MgSO$_4$, filtered and concentrated in vacuo to give a yellow solid. The crude solid was crystallized from a mixture of ethyl acetate and hexane to provide the desired ketone (2.19 g, 77%): mp 82°–88.5° C. $^1$H NMR (CDCl$_3$) 300 MHz 7.91 (q, J=6.0 Hz, 1H), 7.22 (d, J=8.1 Hz, 2H), 7.15 (d, J=8.5 Hz, 2H), 6.82–6.97 (m, 2H), 4.21 (d, J=2.6 Hz, 2H), 2.46 (s, 3H); $^{19}$F NMR (CDCl$_3$) −101.74 (m), −104.15 (m). Mass spectrum: M$^+$=278.

Step 3

Preparation of 1-(2,4-Difluorophenyl)-2-bromo-2-(4-methylthiophenyl)ethanone A solution of the ketone intermediate from Step 2 (2.05 g, 7.4 mmol) in acetic acid (30 mL) and 33% HBr in acetic acid (0.5 mL) was treated with a 0.99M solution of bromine in acetic acid (7.6 mL, 7.5 mmol) and stirred at room temperature for 1 hour. The solution was concentrated in vacuo and the residue was taken up in dichloromethane, washed with 1N NaHSO$_3$, brine, dried over anhydrous MgSO$_4$, filtered, and concentrated in vacuo to give a brown solid (2.39 g, 90%) that was unstable and used directly in the next step without further purification. $^1$H NMR (CDCl$_3$) 300 MHz 7.94 (q, J=6.3 Hz, 1H), 7.37 (d, J=8.5 Hz, 2H), 7.21 (d, J=8.5 Hz, 2H), 6.97 (m, 1H), 6.84 (m, 1H), 6.28 (s, 1H), 2.46 (s, 3H); $^{19}$F NMR (CDCl$_3$) −100.31 (m), −103.50 (m). Mass spectrum: M+H=358.

Step 4

Preparation of 4-(2,4-difluorophenyl)-2-(2-chlorophenyl)-5-(4-methylthiophenyl)thiazole A solution of the bromoketone intermediate from Step 3 (0.49 g, 1.3 mmol) and 4-chlorothiobenzamide (0.24 g, 1.4 mmol) in 5 mL of acetonitrile was heated to reflux for 3 hours. The solution was cooled to room temperature and poured into 20 mL of methanol, chilled with an ice bath, whereupon crystals of the thiazole formed which were isolated by filtration and air dried (0.31 g, 52%): mp 103°–105° C. $^1$H NMR (CDCl$_3$) 300 MHz 8.31 (m, 1H), 7.50–7.60 (m, 2H), 7.36 (m, 2H), 7.23 (d, J=8.5 Hz, 2H), 7.19 (d, J=8.5 Hz, 2H), 6.94 (t, J=8.5 Hz, 1H), 6.83 (t, J=9.2 Hz, 1H) 2.48 (S,3H). $^{19}$F NMR (CDCl$_3$) −108.50 (m), −109.49 (m). Mass spectrum M+H=430.

Step 5

Preparation of 4-(2,4-Difluorophenyl)-2-(2-chlorophenyl)-5-(4-methylsulfonylphenyl)thiazole A solution of the thiazole from Step 4 (260 mg, 0.60 mmol) in 4 mL of dichloromethane was treated with MCPBA (0.42 g) at room temperature for 1.5 hours. The solution was diluted with additional dichloromethane, washed with 10% aq. NaHSO$_3$, 10% Na$_2$CO$_3$, dried over anhydrous MgSO$_4$, filtered and concentrated in vacuo to give a white solid that was recrystallized from a mixture of dichloromethane and isooctane to give white needles (250 mg, 89%): mp 166°–169° C. $^1$H NMR (CDCl$_3$) 300 MHz 8.34 (m, 1H), 7.88 (d, J=8.5 Hz, 2H) 7.65 (q, J=6.6 Hz, 1H), 7.55 (d, J=8.1 Hz, H), 7.41 (m, 2H), 7.26 (s,1H), 6.99 (t, J=8.1 Hz, 1H), 6.83 (t, J=8.9 Hz, 1H) 3.08 (s,3H); $^{19}$F NMR (CDCl$_3$) −108.40 (m), −108.69 (m). Mass spectrum: M+H=462.

EXAMPLE 5

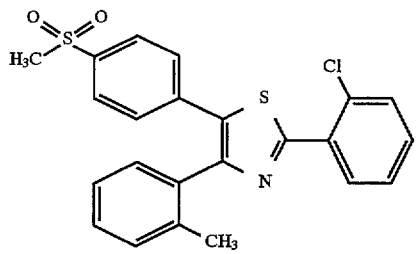

2-(2-Chlorophenyl)-4-(2-methylphenyl)-5-(4-methylsulfonylphenyl)thiazole

Step 1

Preparation of 2-(2-methylphenyl)-3-(4-methylthiophenyl)propenoic Acid

A mixture of acetic anhydride (160 mL), 4-(methylthio)benzaldehyde (25.32 g, 166 mmol), 2-methylphenylacetic acid (24.95 g, 166 mmol), and triethylamine (17.89 g, 176 mmol) was heated to reflux for 2.67 hours. The reaction was cooled to 100° C., and water (200 mL) was added through an addition funnel. A clear oil formed that solidified upon chilling with an ice bath. The solid was collected by filtration, and recrystallized from a mixture of ethyl acetate and isooctane to give the desired acid in two crops (18.6 g, 39%): mp 134°–137° C. $^1$H NMR (CDCl$_3$) 300 MHz 9.80 (br s, 1H), 7.91 (s,1H), 7.28 (m, 3H), 7.12 (d,J=7.5 Hz, 1H), 7.00 (d, J=8.5 Hz, 2H), 6.93 (d, J=8.5 Hz, 2H), 2.42 (s, 3H), 2.16 (s, 3H). High resolution mass spectrum Calc'd. for C$_{17}$H$_{16}$O$_2$S: 284.0871. Found: 284.0863.

Step 2

Preparation of 1-(2-Methylphenyl)2-(4-methylthiophenyl)ethanone

A solution of the acid from Step 1 (8.29 g, 9.2 mmol) and triethylamine (3.46 g, 34.2 mmol) dissolved in 30 mL of anhydrous toluene, was cooled to 0° C. and treated with diphenylphosphoryl azide (8.23 g, 9.9 mmol). The solution was maintained at 0° C. for 45 minutes and warmed to room temperature for 3.75 hours. The reaction was poured into water, extracted with ether, dried over magnesium sulfate, and concentrated in vacuo to remove the ether. The remaining toluene solution was heated to 110° C. for 1 hour. Tert-Butyl alcohol (6 mL, 63 mmol) was added to the reaction mixture, after an additional twenty minutes, concentrated hydrochloric acid (2.6 mL) was cautiously added and the reaction maintained at 90° C. overnight (16 hours). After cooling the solution to room temperature, the mixture was concentrated in vacuo and the residue taken up in ethyl acetate, washed successively with water, sat. aq. NaHCO$_3$ and brine, dried over anhydrous MgSO$_4$, filtered and concentrated in vacuo to give a yellow solid (6.44 g, 86%): mp 54°–61° C. $^1$H NMR (CDCl$_3$) 300 MHz 7.69 (d, J=7.7 Hz, 1H), 7.36 (m, 1H), 7.20–7.26 (m, 4H), 7.16 (d, J=8.5 Hz, 2H), 4.17 (s, 2H), 2.46 (s, 3H), 2.44 (s, 3H). Mass spectrum M+H=257.

Step 3

Preparation of 2-Bromo-1-(2-methylphenyl)-2-(4-methylthiophenyl)ethanone

A solution of the ketone from Step 2 (5.92 g, 23.1 mmol) in acetic acid (50 mL) and 33% HBr in acetic acid (2 mL)

was treated with a 1.1M solution of bromine in acetic acid (21.7 mL, 23.8 mmol) and stirred at room temperature for 2 hours. The solution was concentrated in vacuo and the residue taken up in dichloromethane, washed with 1N NaHSO₃ and sat. aq. NaHCO₃, dried over anhydrous MgSO₄, filtered and concentrated in vacuo to give a yellow solid which was used directly in the next step without further purification (5.97 g, 77%): mp 85°–89° C. ¹H NMR (CDCl₃) 300 MHz 7.56 (d, J=7.9 Hz, 1H), 7.41 (d, J=8.5 Hz, 2H), 7.37 (d, J=7.7 Hz, 1H), 7.22 (m, 4H), 6.18 (s, 1H), 2.47 (s, 3H), 2.44 (s, 3H). Mass spectrum M+H=341.

Step 4

Preparation of 2-(2-Chlorophenyl)-4-(2-methylphenyl)-5-(4-methylthiophenyl)thiazole A solution of the bromoketone intermediate from Step 3 (0.68 g, 2.03 mmol) and 4-chlorothiobenzamide (0.34 g, 1.98 mmol) in 10 mL of acetonitrile was heated to reflux for 16 hours. The solution was cooled to room temperature and poured into 30 mL of methanol, chilled with an ice bath whereupon crystals of pure thiazole formed which were isolated by filtration and air dried to afford the desired thiazole (220 mg, 27%): mp 116°–119° C. ¹H NMR (CDCl₃) 300 MHz 8.33 (m, 1H), 7.50 (m, 1H), 7.16–7.36 (m, 8H), 7.12 (d, J=8.7 Hz, 2H), 2.46 (s, 3H), 2.18 (s, 3H). Mass spectrum: M⁺=407.

Step 5

Preparation of 2-(2-Chlorophenyl)-4-(2-methylphenyl)-5-(4-methylsulfonylphenyl)thiazole A solution of the thiazole from Step 4 (220 mg, 0.54 mmol) in 5 mL of dichloromethane was treated with MCPBA (390 mg, 1.13 mmol) at room temperature for 55 minutes. The solution was diluted with additional dichloromethane, washed with 10% aq. NaHSO₃, and 10% Na₂CO₃, dried over anhydrous MgSO₄, filtered and concentrated in vacuo to give a yellow powder that was recrystallized from a mixture of dichloromethane and isooctane to give a yellow solid (44 mg, 18%): mp 156.5°–157° C. ¹H NMR (CDCl₃) 300 MHz 8.38 (m, 1H), 7.79 (d, J=8.6 Hz, 2H), 7.52 (m, 1H), 7.46 (d, J=8.3 Hz, 2H), 7.39 (m, 2H), 7.21–7.34 (m, 4H), 3.05 (s, 3H), 2.19 (s, 3H). High resolution mass spectrum Calc'd. for C₂₃H₁₈ClNO₂S₂: 439.0468. Found: 439.0476.

EXAMPLE 6

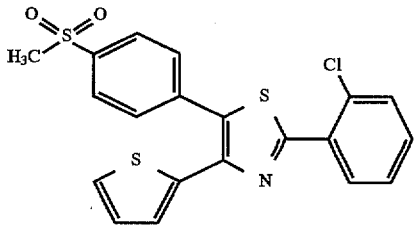

2-(2-Chlorophenyl)-5-(4-methylsulfonylphenyl)-4-(2-thienyl)thiazole

Step 1

Preparation of 3-(4-methylthiophenyl)-2-(2-thienyl) propenoic Acid

A mixture of acetic anhydride (90 mL), 4-(methylthio) benzaldehyde (13.17 g, 82.2 mmol), 2-(2-thienyl)acetic acid (12.09 g, 83.3 mmol), and triethylamine (8.60 g, 85 mmol) was heated to reflux for 4 hours. The reaction was cooled to 85° C., and water (80 mL) was added through an addition funnel. A brown solid was isolated by filtration and air dried to afford the propenoic acid (8.48 g, 37%): mp 201°–206° C. ¹H NMR (DMSO-d₆) 300 MHz 12.80 (br s, 1H), 7.77 (s,1H), 7.60 (d, J=5.2 Hz, 1H), 7.09 (m, 5H), 6.92 (d, J=3.3 Hz, 1H), 2.42 (s, 3H). ¹³C NMR (DMSO-d₆) 168.24, 141.60, 141.30, 136.84, 131.08, 130.86, 128.46, 127.86, 125.51, 125.28, 14.52. Mass spectrum: M+H=277.

Step 2

Preparation of 2-(4-methylthiophenyl)-1-2-thienyl) ethanone

A solution of the propenoic acid intermediate from Step 1 (8.13 g, 29.4 mmol) and triethylamine (3.33 g, 32.9 mmol) dissolved in 40 mL of anhydrous toluene, was cooled to 0° C. and treated with diphenylphosphoryl azide (8.15 g, 29.6 mmol). The solution was maintained at 0° C. for twenty minutes and warmed to room temperature for 4 hours. The reaction was poured into water, extracted with ether, dried over magnesium sulfate, and concentrated in vacuo to remove the ether. The remaining toluene solution was heated to 110° C. for 1.5 hours. tert-Butyl alcohol (8.5 mL, 85.6 mmol) was added to the reaction mixture. After an additional twenty minutes, concentrated hydrochloric acid (5 mL) was cautiously added and the reaction maintained at 90° C. overnight (16 hours). After cooling with an ice bath, a solid separated and was isolated by filtration. The filtrate was concentrated in vacuo and the residue taken up in dichloromethane washed with water, sat. aq. NaHCO₃ and brine, dried over anhydrous MgSO₄, filtered and concentrated in vacuo to give a brown solid. The two batches of solid were combined and recrystallized from a mixture of dichloromethane and isooctane to give the ketone as a light brown solid (3.02 g, 41%): mp 100°–101° C. ¹H NMR (CDCl₃) 300 MHz 7.76 (dd, J=3.8 Hz, 1.1 Hz, 1H), 7.63 (dd, J=4.9 Hz, 1.1 Hz, 1H), 7.22 (s, 4H), 7.12 (dd, J=4.9 Hz, 3.8 Hz, 1H), 4.15 (s, 2H), 2.46 (s, 3H). 13C NMR (CDCl₃) 300 MHz 190.28, 143.80, 137.22, 134.05, 132.61, 131.18, 129.89, 128.19, 127.08, 45.85, 15.99. Mass spectrum: M+H=249.

Step 3

Preparation of 2-Bromo-2-(4-methylthiophenyl)-1-(2-thienyl)ethanone

A solution of the ketone from Step 2 (3.02 g, 12 mmol) in acetic acid (70 mL) and 33% HBr in acetic acid (4 mL) was treated with a 0.99M solution of bromine in acetic acid (13 mL, 12.8 mmol) and stirred at room temperature for 2 hours. The solution was concentrated in vacuo and the residue taken up in dichloromethane, washed with 1N NaHSO₃, and 10% Na₂CO₃, dried over anhydrous MgSO₄, filtered and concentrated in vacuo to give the bromoketone as a brown solid (2.95 g, 74%): mp 60°–64.5° C. ¹H NMR (CDCl₃) 300 MHz 7.75 (d, J=4.0 Hz, 1H), 7.66 (d, J=4.8 Hz, 1H), 7.45 (d, J=8.3 Hz, 2H), 7.22 (d, J=8.3 Hz, 2H), 7.10 (m, 1H), 6.19 (s, 1H), 2.46 (s, 3H); ¹³C NMR (CDCl₃) 300 MHz 184.08, 140.67, 140.62, 135.39, 133.53, 132.26, 129.52, 128.53, 126.50, 51.30, 15.42. Mass spectrum: M+H=328.

Step 4

Preparation of 2-(2-Chlorophenyl)-5-(4-methylthiophenyl)-4-(2-thienyl)thiazole

A solution of the bromoketone from Step 3 (340 mg, 1.0 mmol) and 4-chlorothiobenzamide (180 mg, 1.0 mmol) in 3 mL of acetonitrile was heated to reflux for 5 hours. The solution was cooled to room temperature, poured into 30 mL of methanol and chilled with an ice bath whereupon crystals of pure thiazole formed which were isolated by filtration and air dried to afford the desired thiazole (180 mg, 42%) which was used directly in the next step. $^1$H NMR (CDCl$_3$) 300 MHz 8.39 (d, J=6.2 Hz, 1H), 7.22–7.51 (m, 8H), 7.14 (d, J=3.4 Hz, 1H), 6.94 (m, 1H), 2.54 (s, 3H).

Step 5

Preparation of 2-(2-Chlorophenyl)-5-(4-methylsulfonylphenyl)-4-(2-thienyl)thiazole A solution of the thiazole from Step 4 (140 mg, 0.35 mmol) in 3 mL of dichloromethane was treated with MCPBA (250 mg, 0.72 mmol) at room temperature for 2 hours. The solution was diluted with additional dichloromethane, washed with 10% aq. NaHSO$_3$, and 10% Na$_2$CO$_3$, dried over anhydrous MgSO$_4$, filtered and concentrated in vacuo to give a green solid that was purified by flash chromatography on silica gel eluting with hexane ethyl acetate to give white solid (100 mg, 67%): mp 171°–174° C. $^1$H NMR (CDCl$_3$) 300 MHz 8.41 (dd, J=7.3 Hz 1.8 Hz, 1H), 7.99 (d, J=8.3 Hz, 2H), 7.77(d, J=8.5 Hz, 2H), 7.50 (d, J=7.7 Hz, 1H), 7.40 (m, 2H), 7.30 (d, J=4.0 Hz, 1H), 7.09 (d, J=3.6 Hz, 1H), 6.95 (m, 1H), 3.12 (s, 3H). High resolution mass spectrum Calc'd. for C$_{20}$H$_{15}$ClNO$_2$S$_3$ (M+H): 431.9953. Found: 431.9954.

EXAMPLE 7

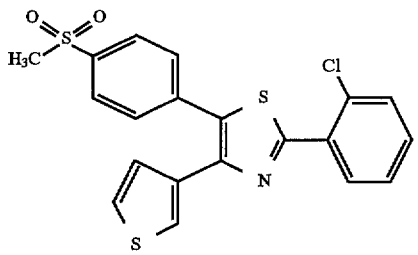

2-(2-Chlorophenyl)-5-(4-methylsulfonylphenyl)-4-(3-thienyl)thiazole

Step 1

Preparation of 3-(4-Methylthiophenyl)-2-(3-thienylpropenoic Acid

A mixture of acetic anhydride (100 mL), 4-(methylthio)benzaldehyde (11.06 g, 72.7 mmol), 3-thiopheneacetic acid (10.33 g, 72.7 mmol), and triethylamine (7.68 g, 75.9 mmol) was heated to reflux for 3 hours. The reaction was cooled to 90° C., and water (100 mL) was added through an addition funnel. A white solid separated from the solution was isolated by filtration and air dried to afford the acid (11.0 g, 55%): mp 184°–189° C. $^1$H NMR (DMSO-d$_6$) 300 MHz 12.61 (br s, 1H), 7.69 (s,1H), 7.54 (d, J=4.7 Hz, 1H), 7.31 (s,1H), 7.08 (d, J=8.7 Hz, 2H), 7.02 (d, J=8.7 Hz, 2H), 6.89 (d, J=5.1 Hz, 1H), 2.41 (s, 3H); $^{13}$C NMR (DMSO-d$_6$) 168.63, 140.70, 139.70, 136.22, 131.29, 130.89, 129.35, 127.74, 126.57, 125.53, 125.06, 14.57. Mass spectrum: M+H=277.

Step 2

Preparation of 2-(4-methylthiophenyl)-1-(3-thienyl)ethanone

A solution of the acid from Step 1 (7.20 g, 26.1 mmol) and triethylamine (2.83 g, 28 mmol) dissolved in 30 mL of anhydrous toluene, was cooled to 0° C. and treated with diphenylphosphoryl azide (7.72 g, 28.1 mmol). The solution was maintained at 0° C. for thirty minutes and warmed to room temperature for 3 hours. The reaction was poured into water, extracted with ether, dried over magnesium sulfate, and concentrated in vacuo to remove the ether. The remaining toluene solution was heated to 100° C. for 1.5 hours. Tert-Butyl alcohol (3 mL, 31.8 mmol) was added to the reaction mixture. After an additional fifteen minutes, concentrated hydrochloric acid (2 mL) was cautiously added and the reaction maintained at 80° C. for 72 hours. After cooling with an ice bath, a solid separated and was isolated by filtration. The filtrate was concentrated in vacuo and the residue taken up in dichloromethane, washed with water, sat. aq. NaHCO$_3$, and brine, dried over anhydrous MgSO$_4$, filtered and concentrated in vacuo to give a brown solid. The two batches of solid were combined and recrystallized from a mixture of ethyl acetate and hexane to give a light brown solid. Washing the solid with ether afforded pure white ketone (5.0 g, 77%): mp 119°–122° C. $^1$H NMR (CDCl$_3$) 300 MHz 8.08 (m, 1H), 7.55 (d, J=5.2 Hz, 1H), 7.30 (m, 1H), 7.21 (m, 4H), 4.13 (s,2H), 2.46 (s, 3H). Mass spectrum: M+H=249.

Step 3

Preparation of 2-Bromo-2-(4-methylthiophenyl)-1-(3-thienyl)ethanone

A solution of the ketone from Step 2 (4.0 g, 16.1 mmol) in acetic acid (100 mL) and 33% HBr in acetic acid (5 mL) was treated with a 0.99M solution of bromine in acetic acid (16.5 mL, 16.3 mmol) and stirred at room temperature for 1 hour. The solution was concentrated in vacuo and the residue taken up in dichloromethane, washed with 1N NaHSO$_3$, and 10% Na$_2$CO$_3$, dried over anhydrous MgSO$_4$, filtered and concentrated in vacuo to give a gray solid which was recrystallized from a mixture of ethyl acetate and isooctane to provide the bromoketone intermediate (4.22 g, 80%): mp 74°–76.5° C. Mass spectrum: M+H=328.

Step 4

Preparation of 2-(2-Chlorophenyl)-5-(4-methylthiophenyl)-4-(3-thienyl)thiazole

A solution of the bromoketone from Step 3 (330 mg, 1.0 mmol) and 4-chlorothiobenzamide (180 mg, 1.0 mmol) in 10 mL of acetonitrile was heated to reflux for 15 hours. The solution was cooled to room temperature and poured into 30 mL of methanol, chilled with an ice bath, whereupon crystals of pure thiazole formed which were isolated by filtration and air dried to afford the thiazole which was used directly in the next step (230 mg, 58%): mp 102°–103.5° C. $^1$H NMR (CDCl$_3$) 300 MHz 8.39 (d, 1H), 7.57 (m, 1H), 7.49 (d, 1H), 7.39 (m, 4H), 7.26 (m, 4H), 2.53 (s, 3H). Mass spectrum: M+H=401.

Step 5

Preparation of 2-(2-Chlorophenyl)-5-(4-methylsulfonylphenyl)-4-(3-thienyl)thiazole A solution of the thiazole from Step 4 (180 mg, 0.45 mmol) in 2 mL of dichloromethane was treated with MCPBA (330 mg, 0.95 mmol) at room temperature for 4 hours. The solution was diluted with additional dichloromethane, washed with 10% aq. NaHSO$_3$, and 10% Na$_2$CO$_3$, dried over anhydrous MgSO$_4$, filtered and concentrated in vacuo to give a yellow solid that was purified by flash chromatography on silica gel, eluting with hexane and ethyl acetate to give a white solid (60 mg, 32%) $^1$H NMR (CDCl₃) 300 MHz 8.39 (m, 1H), 7.94 (d, J=8.5 Hz, 2H), 7.70 (d, J=8.5 Hz, 2H), 7.56 (m, 2H), 7.39 (m, 2H), 7.28 (m, 1H), 7.17 (d, J=5.0 Hz, 1H), 3.11 (s, 3H). Mass spectrum: M+H=432.

EXAMPLE 8

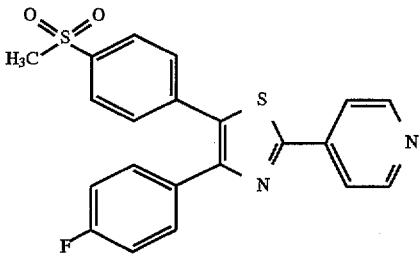

4-(4-Fluorophenyl)-5-(4-methylsulfonylphenyl)-2-(4-pyridyl)thiazole

Step 1

Preparation of 4-(4-Fluorophenyl)-5-(4-methylthiophenyl)-2-(4-pyridyl)thiazole A solution of the intermediate from Example 1, Step 3, 1-(4-fluorophenyl)-2-(4-methylthiophenyl)-2-bromoethanone, (1.58 g, 4.66 mmol) and thioisonicotinamide (670 mg, 4.84 mmol) in 25 mL of acetonitrile was heated to reflux for 23 hours. The solution was filtered, concentrated in vacuo and the residue taken up in dichloromethane. The dichloromethane solution was washed with sat. aq. NaHCO₃, and brine, dried over anhydrous MgSO₄, filtered and concentrated in vacuo to give a brown oil that was purified by flash chromatography on silica gel eluting with 20% ethyl acetate in hexane to provide the desired thiazole as an oil that solidified upon standing (640 mg, 36%): mp 107°–109° C. ¹H NMR (CDCl₃) 300 MHz 8.75 (br s, 2H), 7.85 (d, J=5.9 Hz, 2H), 7.56 (m, 2H), 7.26 (d, J=8.5 Hz, 2H), 7.22 (d, J=8.5 Hz, 2H), 7.01 (t, J=8.5 Hz, 2H), 2.50 (s, 3H); ¹⁹F NMR (CDCl₃) −113.23 (m). High resolution mass spectrum Calc'd. for C₂₁H₁₅FN₂S₂: 379.0661. Found: 379.0691.

Step 2

Preparation of 4-(4-Fluorophenyl)-5-(4-methylsulfonylphenyl)-2-(4-pyridyl)thiazole A solution of the thiazole from Step 1 (450 mg, 1.19 mmol) in 10 mL of dichloromethane was treated with MCPBA (850 mg, 2.46 mmol) at room temperature for 2.5 hours. The solution was diluted with additional dichloromethane, washed with 10% aq. NaHSO₃, and 10% Na₂CO₃, dried over anhydrous MgSO₄, filtered and concentrated in vacuo to give a yellow solid that was purified by recrystallization from a mixture of dichloromethane, ethanol and isooctane to provide the pure product (310 mg, 63%): mp 171°–176° C. ¹H NMR (CDCl₃) 300 MHz 8.25 (d, J=7.2 Hz, 2H), 7.90 (m, 4H), 7.56 (d, J=8.7 Hz, 2H), 7.50 (m, 2H), 7.04 (t, J=8.7 Hz, 2H), 3.09 (s, 3H). ¹⁹F NMR (CDCl₃) −111.83 (m). High resolution mass spectrum Calc'd. for C₂₁H₁₅FN₂O₂S₂: 410.0559. Found: 410.0576.

EXAMPLE 9

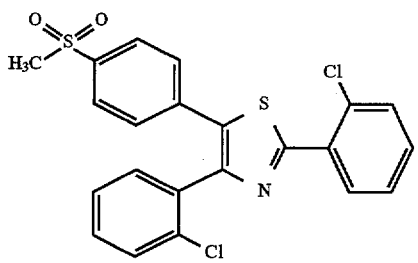

2-(2-Chlorophenyl)-4-(2-chlorophenyl)-5-(4-methylsulfonylphenyl)thiazole

Step 1

Preparation of 2-(2-Chlorophenyl)-3-(4-methylthiophenyl)propenoic Acid

A mixture of acetic anhydride (170 mL), 4-(methylthio) benzaldehyde (20.93 g, 137 mmol), 2-chlorophenylacetic acid (23.43 g, 137 mmol), and triethylamine (14.97 g, 147 mmol) was heated to reflux for 2 hours. The reaction was cooled to 90° C., and water (180 mL) was added through an addition funnel. A yellow solid that separated from the solution was isolated by filtration and air dried to afford the desired acid. The acid was recrystallized from a mixture of ethyl acetate and isooctane to afford 24.62 g (59%): mp 159°–164° C. ¹H NMR (CDCl₃) 300 MHz 7.97 (s, 1H), 7.48 (d, J=7.9 Hz, 1H), 7.17–7.35 (m, 3H), 7.02 (d, J=8.7 Hz 2H), 6.97 (d, J=8.7 Hz, 2H), 2.43 (s, 3H). High resolution mass spectrum Calc'd. for C₁₆H₁₃ClO₂S: 304.0325. Found: 304.0334.

Step 2

Preparation of 1-(2-Chlorophenyl)2-(4-methylthiophenyl)ethanone

A solution of the acid from Step 1 (17.88 g, 58.7 mmol) and triethylamine (9.53 g, 94.2 mmol) was dissolved in 50 mL of anhydrous toluene, cooled to 0° C. and treated with diphenylphosphoryl azide (16.46 g, 59.8 mmol). The solution was maintained at 0° C. for 36 minutes and warmed to room temperature for 4 hours. The reaction was poured into water, extracted with ether, dried over magnesium sulfate, and concentrated in vacuo to remove the ether. The remaining toluene solution was heated to 110° C. for 1 hour. Tert-Butyl alcohol (7 mL, 74 mmol) was added to the reaction mixture. After an additional twenty minutes, concentrated hydrochloric acid (5 mL) was cautiously added and the reaction maintained at 90° C. for 16 hours. The solution was concentrated in vacuo and the residue taken up in ethyl acetate, washed with water, sat. aq. NaHCO₃, and brine, dried over anhydrous MgSO₄, filtered and concentrated in vacuo to provide the ketone as an orange oil (14.62 g, 90%) that was used in the next step without further purification: ¹H NMR (CDCl₃) 300 MHz 7.40–7.10 (m,8H), 4.20 (s, 2H), 2.46 (s, 3H).

Step 3

Preparation of 2-Bromo-1-(2-chlorophenyl)-2-(4-methylthiophenyl)ethanone

A solution of the ketone from Step 2 (13.82 g, 49.9 mmol) in acetic acid (80 mL) and 33% HBr in acetic acid (4 mL) was treated with a 1.1M solution of bromine in acetic acid (46.8 mL, 51.3 mmol) and stirred at room temperature for 1.5 hours. The solution was concentrated in vacuo and the residue taken up in dichloromethane, washed with 1N NaHSO₃, and 10% Na₂CO₃, dried over anhydrous MgSO₄, filtered and concentrated in vacuo to give the bromoketone as an orange solid (6.07 g, 34%) of sufficient purity to be used directly in the next step without further purification: mp 93°–99° C. ¹H NMR (CDCl₃) 300 MHz 7.37–7.43 (m, 5H), 7.41 (m, 1H), 7.22 (d, J=8.5 Hz, 2H), 6.21 (s, 1H), 2.47 (s, 3H). Mass spectrum: M+H=357.

Step 4

Preparation of 2-(2-Chlorophenyl)-4-(2-chlorophenyl)-5-(4-methylthiophenyl)thiazole A solution of the bromoketone from Step 3, (1.14 g, 3.2 mmol) and 2-chlorothiobenzamide (550 mg, 3.2 mmol) in 10 mL of acetonitrile was heated to reflux for 16 hours. The solution was cooled to room temperature and poured into methanol. This solution was chilled whereupon a yellow solid separated that was isolated by filtration. The solid was air dried to provide pure thiazole (440 mg, 32%): mp 116°–120° C. ¹H NMR (CDCl₃) 300 MHz 8.33 (m, 1H), 7.29–7.52 (m, 7H), 7.19(d, J=8.3 Hz, 2H), 7.14 (d, J=8.5 Hz, 2H), 2.46 (s, 3H). Mass spectrum: M⁺=427.

Step 5

Preparation of 2-(2-Chlorophenyl)-4-(2-chlorophenyl)-5-(4-methylsulfonylphenyl)thiazole A solution of the thiazole from Step 4 (440 mg, 1.02 mmol) in 5 mL of dichloromethane was treated with MCPBA (720 mg, 2.08 mmol) at room temperature for 0.9 hour. The solution was diluted with additional dichloromethane, washed with 10% aq. NaHSO₃, and 10% Na₂CO₃, dried over anhydrous MgSO₄, filtered and concentrated in vacuo to give a yellow solid. The solid was recrystallized from a mixture of dichloromethane and isooctane to provide pure product (270 mg, 57%): mp 143°–147° C. ¹H NMR (CDCl₃) 300 MHz 8.36 (m, 1H), 7.82 (d, J=8.3 Hz, 2H), 7.52 (m, 1H), 7.45 (m, 4H), 7.38 (m, 4H), 3.05 (s, 3H). High resolution mass spectrum Calc'd. for C₂₂H₁₅Cl₂NO₂S₂: 458.9921. Found: 458.9903.

EXAMPLE 10

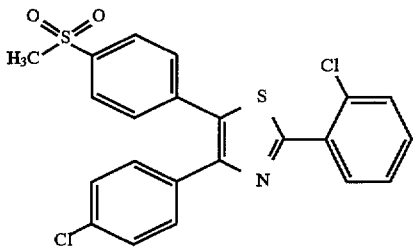

2-(2-Chlorophenyl)-4-(4-chlorophenyl)-5-(4-methylsulfonylphenyl)thiazole

Step 1

Preparation of 2-(4-Chlorophenyl)-3-(4-methylthiophenyl)propenoic Acid

A mixture of acetic anhydride (80 mL), 4-(methylthio)benzaldehyde (9.81 g, 61.2 mmol), 4-chlorophenylacetic acid (12.03 g, 70.5 mmol), and triethylamine (7.49 g, 7.42 mmol) was heated to reflux for 7 hours. The reaction was cooled to 90° C., and water (100 mL) was added through an addition funnel. A yellow solid separated from the solution which was isolated by filtration and air dried to afford the desired acid. The acid was recrystallized from toluene (9.59 g, 51%): mp 185°–187° C. ¹H NMR (CDCl₃) 300 MHz 7.91 (s, 1H), 7.35 (d, J=8.3 Hz, 1H), 7.17–7.35 (m, 3H), 7.03 (d, 2H), 7.00 (d, J=8.7 Hz, 2H), 2.44 and 2.36 (s, 3H). Mass spectrum: M+H=305.

Step 2

Preparation of 1-(4-Chlorophenyl)-2-(4-methylthiophenyl)ethanone

The acid from Step 1 (9.01 g, 29.6 mmol) and triethylamine (3.03 g, 29.9 mmol) were dissolved in 45 mL of anhydrous toluene, cooled to 0° C. and treated with diphenylphosphoryl azide (8.22 g, 29.9 mmol). The solution was maintained at 0° C. for 10 minutes and warmed to room temperature for 2 hours. The reaction was poured into water, extracted with ether, dried over anhydrous MgSO₄, and concentrated in vacuo to remove the ether. The remaining toluene solution was heated to 90° C. for 15 minutes. Tert-Butyl alcohol (10 mL) was added to the reaction mixture. After an additional twenty minutes, concentrated hydrochloric acid (8 mL) was cautiously added and the reaction maintained at 90° C. for 15 minutes. The solution was cooled to room temperature and a precipitate formed that was isolated by filtration, washed with ether and air dried to provide the desired ketone as a white solid (2.43 g, 30%): mp 143°–147.5° C. ¹H NMR (CDCl₃) 300 MHz 8.08 (d, J=8.8 Hz, 2H), 7.55 (d, J=8.5 Hz, 2H), 7.24 (m, 4H), 4.35 (s, 2H), 2.05 (s, 3H). Mass spectrum: M+H=277.

Step 3

Preparation of 2-Bromo-1-(4-chlorophenyl)- 2-(4-methylthiophenyl)ethanone

A solution of the ketone from Step 2 (2.04 g, 7.37 mmol) in acetic acid (15 mL) and 48% HBr in acetic acid (2 mL) was treated with a 0.99M solution of bromine in acetic acid (7.6 mL, 7.5 mmol) and stirred at room temperature for 2.25 hours. The desired product precipitated from the solution, was isolated by filtration and air dried to provide the bromoketone intermediate for use in the next step (0.91 g, 35%): mp 114°–115° C. ¹H NMR (CDCl₃) 300 MHz 7.90 (d, J=8.8 Hz, 2H), 7.40 (d, J=8.5 Hz, 4H), 7.23 (d, J=8.5 Hz, 2H), 6.28 (s, 1H), 2.47 (s, 3H); ¹³C NMR (CDCl₃) 400 MHz 189.76, 140.68, 140.30, 132.44, 131.88, 130.54, 129.51, 129.19, 126.51, 50.57, 15.33. High resolution mass spectrum Calc'd. for C₁₅H₁₂BrClOS: 353.9481. Found: 353.9516.

Step 4

Preparation of 2-(2-Chlorophenyl)-4-(4-chlorophenyl)-5-(4-methylthiophenyl)thiazole A solution of the bromoketone intermediate from Step 3, (890 mg, 2.5 mmol) and 2-chlorothiobenzamide (430 mg, 2.5 mmol) in 15 mL of acetonitrile was heated to reflux for 16 hours. The solution was diluted with ethyl acetate washed with sat. aq. NaHCO₃, dried over anhydrous MgSO₄, filtered and concentrated in vacuo to afford a white solid. The crude material was purified by flash chromatography on silica gel eluting with 8% ethyl acetate in hexane to give the desired thiazole as a white solid (370 mg, 34%): mp 122°–124° C. ¹H NMR (CDCl₃) 300 MHz 8.37 (m, 1H), 7.56 (d, J=8.5 Hz, 2H), 7.50 (m, 1H), 7.20–7.39 (m, 8H), 2.51 (s, 3H). Mass spectrum: M+H=429.

Step 5

Preparation of 2-(2-Chlorophenyl)-4-(4-chlorophenyl)-5-(4-methylsulfonylphenyl)thiazole A solution of the thiazole from Step 4 (300 mg, 0.7 mmol) in 10 mL of dichloromethane was treated with MCPBA (530 mg, 1.5 mmol) at room temperature for 1 hour. The solution was diluted with additional dichloromethane, washed successively with 10% aq. NaHSO₃, and 10% Na₂CO₃, dried over anhydrous MgSO₄, filtered and concentrated in vacuo to give a yellow solid. The solid was recrystallized from a mixture of dichloromethane and isooctane to provide pure product (180 mg, 56%): mp 177°–179° C. $^1$H NMR (CDCl₃) 300 MHz 8.37 (m, 1H), 7.91 (d, J=8.7 Hz, 2H), 7.62 (d, J=8.5 Hz, 2H), 7.50 (d, 3H), 7.40 (m, 2H), 7.34 (d, J=8.7 Hz, 2H), 3.10 (s, 3H). High resolution mass spectrum Calc'd. for $C_{22}H_{15}Cl_2NO_2S_2$: 458.9921. Found: 458.9922.

EXAMPLE 11

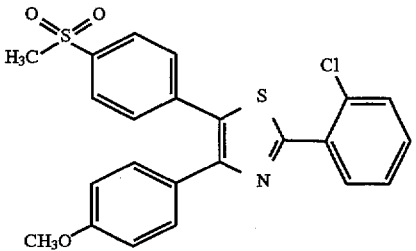

2-(2-Chlorophenyl)-4-(4-methoxyphenyl)-5-(4-methylsulfonylphenyl)thiazole

Acetic anhydride (350 mL), 4-(methylthio)benzaldehyde (61.6 g, 0.61 mol), 4-methoxyphenylacetic acid (100.0 g, 0.60 mol) and triethylamine (68.1 g, 0.67 mol) were placed in a 3 L round bottom flask and heated to reflux for 4 hours. The reaction was cooled to 110° C., and water (350 mL) was added through an addition funnel. This caused the solution to reflux vigorously and the temperature to rise to 135° C. A yellow precipitate formed and, after cooling to room temperature, was collected by filtration, washed with water and air dried. The product was crystallized from ethyl acetate/ethanol to give the desired acid as bright yellow needles (127.6 g, 71%): mp 174°–177° C. $^1$H NMR (CDCl₃) 300 MHz 8.89 (s, 1H), 7.16 (d, J=8.6 Hz, 2H), 7.02 (s, 4H), 6.92 (d, J=8.6 Hz, 2H), 3.84 (s, 3H), 2.43 (s, 3H). Mass spectrum: M+H=300.

Step 2

Preparation of 1-(4-Methoxyphenyl)-2-(4-methylthiophenyl)ethanone

The acid from Step 1 (23.0 g, 76.6 mmol) was placed in a 500 mL round bottom flask with anhydrous toluene (100 mL) and triethylamine (7.98 g, 79 mmol). After cooling to 0° C., diphenylphosphoryl azide (21.27 g, 79 mmol) was added, the solution was stirred at 0° C. for twenty minutes at room temperature for 2.50 hours. The mixture was poured into water, extracted with ether, dried over magnesium sulfate, and concentrated in vacuo to remove the ether. The remaining toluene solution was heated to 100° C. whereupon a vigorous evolution of gas occurred. After 1.25 hours, tert-butyl alcohol (8.2 mL) was added to the reaction, and after an additional twenty minutes, concentrated hydrochloric acid (7 mL) was added. The reaction was heated at 75° C. overnight (14 hours) and after cooling a white precipitate formed. The precipitate was filtered, washed with cold ether, and air dried to yield the light yellow ketone (19.3 g, 93%): mp 134.5°–138° C. $^1$H NMR (CDCl₃) 300 MHz 7.99 (d, J=8.9 Hz, 2H), 7.20 (m, 4H), 6.93 (d, J=8.9 Hz, 2H), 4.18 (s, 2H), 3.84 (s, 3H), 2.44 (s, 3H); $^{13}$C NMR (CDCl₃) 300 MHz 196.18, 163.65, 136.87, 131.92, 131.00, 129.97, 129.64, 127.15, 113.92, 55.58, 44.78, 16.11. Mass spectrum: M+H=273.

Step 3

Preparation of 2-Bromo-1-(4-methoxyphenyl)-2-(4-methylthiophenyl)ethanone

The ketone from Step 2 (19.3 g, 71 mmol) was dissolved in a mixture of glacial acetic acid (125 mL) and 33% HBr in acetic acid (3.4 mL) and treated with a 0.99M solution of bromine in acetic acid (73 mL, 72 mmol) at room temperature for 3 hours. The solution was diluted with dichloromethane, washed successively with water, and 10% aq. NaHSO₃, dried over anhydrous MgSO₄, filtered and concentrated in vacuo to give the desired bromoketone intermediate which was crystallized from a mixture of dichloromethane and isooctane (14.3 g, 57%): mp 90°–93° C. $^1$H NMR (CDCl₃) 300 MHz 7.95 (d, J=9.1 Hz, 2H), 7.42 (d, J=8.5 Hz, 2H), 7.22 (d, J=8.5 Hz, 2H), 6.92 (d, J=9.1 Hz, 2H), 6.33 (s, 1H), 3.85 (s, 3H), 2.46 (s, 3H). Mass spectrum: M+H=352.

Step 4

Preparation of 2-(2-Chlorophenyl)-4-(4-methoxyphenyl)-5-(4-methylthiophenyl)thiazole A mixture of the bromoketone intermediate from Step 3 (3.22 g, 9.17 mmol) and 2-chlorothiobenzamide (1.65 g, 9.62 mmol) in acetonitrile (40 mL) was stirred at room temperature for 24 hours. During this time a solid precipitated from solution which was isolated by filtration and air dried to give the desired thiazole (3.26 g, 84%): mp 159°–161° C. $^1$H NMR (CDCl₃) 300 MHz 8.38 (m, 1H), 7.54 (d, J=8.9 Hz, 2H) 7.48 (d, 1H), 7.33 (m, 4H), 7.22 (d, J=8.5 Hz, 2H), 6.88 (d, J=8.9 Hz, 2H), 3.82 (s, 3H), 2.51 (s, 3H). Mass spectrum: M+H=424.

Step 5

Preparation of 2-(2-Chlorophenyl)-4-(4-methoxyphenyl)-5-(4-methylsulfonylphenyl)thiazole A dichloromethane (5 mL) solution of the thiazole from Step 4 (0.30 g, 0.7 mmol) was treated with MCPBA (0.53 g, 1.5 mmol) and stirred at room temperature for 24 hours. The solution was successively washed with 10% aq. NaHSO₃, and 10% Na₂CO₃, dried over anhydrous MgSO₄, filtered and concentrated in vacuo to give a yellow solid that was crystallized from a mixture of dichloromethane and isooctane to afford pure product (190 mg, 59%): mp 171.5°–173.5° C. $^1$H NMR (CDCl₃) 300 MHz 8.39 (m, 1H), 7.88 (d, J=8.5 Hz, 2H) 7.63 (d, J=8.3 Hz, 2H), 7.49 (m, 3H), 7.38 (m, 2H), 6.90 (d, J=8.9 Hz, 2H), 3.83 (s, 3H), 3.09 (s, 3H). High resolution mass spectrum Calc'd for $C_{23}H_{18}ClNO_3S_2$: 455.0417. Found: 455.0416. Mass spectrum: M+H=455.0461.

EXAMPLE 12

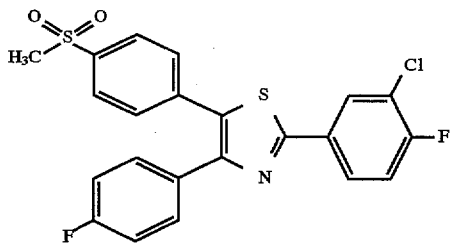

2-(3-Chloro-4-fluorophenyl)-4-(4-fluorophenyl)-5-(4-methylsulfonylphenyl)thiazole Step 1

Preparation of 2-(3-Chloro-4-fluorophenyl)-4-(4-fluorophenyl)-5-(4-methylthiophenyl)thiazole A solution of the intermediate from Example 1 Step 3, 1-(4-fluorophenyl)-2-(4-methylthiophenyl)-2-bromoethanone, (1.96 g, 5.78 mmol) and 3-fluoro-4-chlorothiobenzamide (1.14 g, 6.01 mmol) in 15 mL of acetonitrile was heated to reflux for 16 hours. The solution was cooled to room temperature, poured into 50 mL of methanol and chilled in an ice bath whereupon the desired product precipitated. The crude thiazole was recrystallized from methanol to provide the desired thiazole (1.44 g, 58%): mp 113°–118° C. $^1$H NMR (CDCl$_3$) 300 MHz 8.10 (dd, J=7.0 Hz,2.2 Hz, 1H), 7.85 (m, 1H), 7.57 (m, 2H), 7.26 (m, 5H), 7.02 (t, J=8.5 Hz, 2H), 2.51 (s, 3H). $^{19}$F NMR (CDCl$_3$) –112.92 (m), –113.44 (m). Mass spectrum M+H=429.

Step 2

Preparation of 2-(3-Chloro-4-fluorophenyl)-4-(4-fluorophenyl)-5-(4-methylsulfonylphenyl)thiazole A dichloromethane (20 mL) solution of the thiazole from Step 1 (910 mg, 2.12 mmol) was treated with MCPBA (1.48 g, 4.29 mmol) and stirred at room temperature for 30 minutes. The solution was successively washed with 10% aq. NaHSO$_3$, and 10% Na$_2$CO$_3$, dried over anhydrous MgSO$_4$, filtered and concentrated in vacuo to give a yellow solid that was crystallized from a mixture of dichloromethane and isooctane to afford pure product (770 mg, 79%): mp 165°–167° C. $^1$H NMR (CDCl$_3$) 300 MHz 8.10 (d, 1H), 7.90 (d, J=8.1 Hz, 2H), 7.85 (m, 1H), 7.54 (m, 4H), 7.24 (t, 1H), 7.05 (t, J=8.5 Hz, 2H), 3.10 (s, 3H); $^{19}$F NMR (CDCl$_3$) –112.06 (m), –112.29 (m). High resolution mass spectrum Calc'd. for C$_{22}$H$_{14}$ClF$_2$NO$_2$S$_2$: 462.0201. Found: 462.0138.

EXAMPLE 13

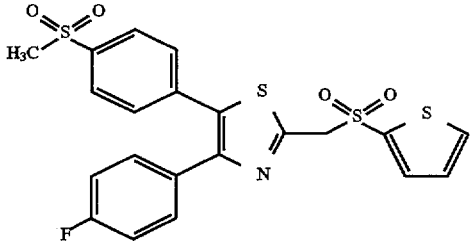

4-(4-Fluorophenyl)-5-(4-methylsulfonylphenyl)-2-(2-thienyl)sulfonylmethyl)thiazole Step 1

Preparation of 4-(4-fluorophenyl)-5-(4-methylthiophenyl)-2-(2-thienyl)sulfonylmethylthiazole A solution of the intermediate from Example 1 Step 3, 1-(4-fluorophenyl)-2-(4-methylthiophenyl)-2-bromoethanone, (4.33 g, 12.76 mmol) and (2-thienyl)sulphonylthioacetamide (2.55 g, 11.5 mmol) in 25 mL of acetonitrile was heated to reflux for 16 hours. The solution was cooled in an ice bath and a precipitate formed that was removed by filtration. The filtrate was concentrated in vacuo and the residue was dissolved in ethyl acetate, washed successively with sat. aq. NaHCO$_3$, and brine, dried over anhydrous MgSO$_4$, filtered and concentrated in vacuo to provide a brown oil that was purified by flash chromatography on silica gel, eluting with 30% ethyl acetate in hexane. The appropriate fractions were combined and concentrated and finally recrystallized from a mixture of dichloromethane and isooctane to provide 2.16 g (41%) of pure thiazole: mp 120°–121° C. $^1$H NMR (CDCl$_3$) 300 MHz 7.74 (d, J=4.9 Hz, 1H), 7.67 (m, 1H), 7.33 (m, 2H), 7.21 (m, 5H), 6.95 (t, J=8.7 Hz, 2H), 4.87 (s, 2H), 2.49 (s, 3H); $^{19}$F NMR (CDCl$_3$) –113.33 (m). High resolution mass spectrum Calc'd. for C$_{21}$H$_{16}$FNO$_2$S$_4$: 461.0048. Found: 461.0090.

Step 2

Preparation of 4-(4-Fluorophenyl)-5-(4-methylsulfonylphenyl)-2-(2-thienyl)sulfonylmethyl)-thiazole A dichloromethane (15 mL) solution of the thiazole from Step 1 (1.74 g, 3.8 mmol) was treated with MCPBA (2.68 g, 7.8 mmol) and stirred at room temperature for 1 hour. The solution was successively washed with 10% aq. NaHSO$_3$, and 10% Na$_2$CO$_3$, dried over anhydrous MgSO$_4$, filtered and concentrated in vacuo to give a yellow foam. The foam was crystallized from a mixture of dichloromethane and isooctane to afford 1.55 g, (86%) of pure product as a white solid: mp 98°–105° C. $^1$H NMR (CDCl$_3$) 300 MHz 7.91 (d, J=8.5 Hz, 2H), 7.77 (dd, J=4.8 Hz 1.4 Hz, 1H), 7.68 (dd, J=3.7 Hz 1.1 Hz, 1H), 7.51 (d, J=8.1 Hz, 2H), 7.29 (m, 2H), 7.17 (t, J=4.8 Hz, 1H), 6.98 (t, J=8.8 Hz, 2H), 4.89 (s, 2H), 3.09 (s,3H); $^{19}$F NMR (CDCl$_3$) –112.13 (m). High resolution mass spectrum Calc'd. for C$_{21}$H$_{17}$FNO$_4$S$_4$ (MH$^+$): 494.0025. Found: 494.0005.

EXAMPLE 14

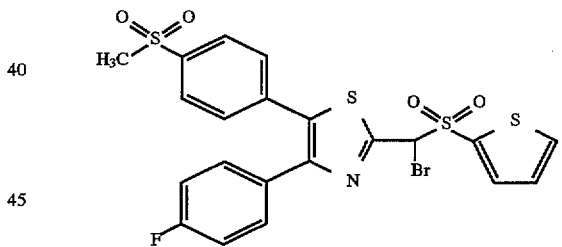

4-(4-Fluorophenyl)-5-(4-methylsulfonylphenyl)-2-(2-thienyl)sulfonylbromomethyl)-thiazole To a 50 mL round bottom flask was added the product from Example 13 Step 2, [4-(4-fluorophenyl)-5-(4-methylsulfonylphenyl)-2-(2-thienyl)sulfonylmethyl) thiazole], (0.38 g, 0.76 mmol) dissolved in chloroform (20 mL). The solution was treated with 0.80 mL of a solution of bromine in acetic acid (0.99M, 0.78 mmol) and stirred at room temperature for 0.58 hour and was treated with a 10% solution of NaHSO$_3$. The organic layer was collected, washed with saturated NaHCO$_3$, dried over magnesium sulfate and concentrated in vacuo to give a white foam (0.46 g) which was a mixture of the brominated compound and starting material. This mixture was purified by flash chromatography on silica gel, eluting with 30% ethyl acetate in hexane to give the product as a white foam (0.20 g, 45%): $^1$H NMR (CDCl$_3$) 300 MHz 7.90 (d, J=8.5 Hz, 2H), 7.86 (dd, J=4.8 Hz 1.1 Hz, 1H), 7.79 (dd, J=3.7 Hz 1.1 Hz, 1H), 7.55 (d, J=8.5 Hz, 2H), 7.31 (m, 2H), 7.21 (t, J=4.7 Hz, 1H), 6.98 (t, J=8.8 Hz, 2H), 6.24 (s, 2H), 3.09 (s, 3H); $^{19}$F NMR (CDCl$_3$) −111.85 (m). Field desorption mass spectrum: M+Li=579.

EXAMPLE 15

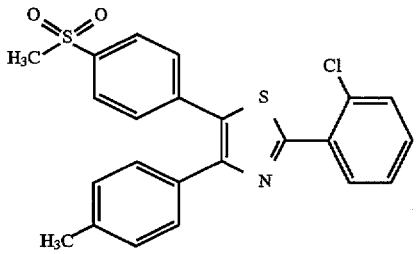

2-(2-Chlorophenyl)-5-(4-methylsulfonylphenyl)-4-(4-methylphenyl)thiazole

Step 1

Preparation of 3-(4-Methylthiophenyl-2-(4-methylphenyl)propenoic Acid

A 500 mL round-bottomed flask, equipped with magnetic stirrer, nitrogen inlet and reflux condenser was charged with 4-methylthiobenzaldehyde (16.4 mL, 123.7 mmol), 4-methylphenylacetic acid (26.0 g, 173.1 mmol), triethylamine (17.2 mL, 123.7 mmol) and 250 mL of acetic acid. The reaction was warmed to reflux and held at reflux for four hours. Upon cooling to approximately 110° C., water (250 mL) was added over ten minutes, such that foaming was controlled and the reaction temperature remained ≧90° C. This temperature was maintained for 16 hours, the thick suspension formed was cooled to room temperature and filtered. The solid was washed with water and dried to yield the acid intermediate as orange crystals (32.2 g; 91%): mp 144°–160° C. $^1$H NMR (CDCl$_3$) 300 MHz 7.87(s, 1H), 7.41 −7.02(m, 9H), 2.43 (s, 3H), 2.40 (s, 3H).

Step 2

Preparation of 2-(4-Methylthiophenyl)-1-(4-methylphenyl)ethanone

A 1000 mL four-necked round-bottomed flask equipped with mechanical stirrer, reflux condenser, nitrogen inlet, constant pressure addition funnel and thermometer was charged with 3-(4-methylthiophenyl-2-(4-methylphenyl) propenoic acid from Step 1 (25 g, 87.91 mmol), triethylamine (12.9 mL, 92.31 mmol) and toluene (200 mL). The addition funnel was charged with diphenylphosphoryl azide (19 mL, 87.91 mmol) dissolved in toluene (100 mL), and the reaction vessel was cooled to 0° C. Over approximately ten minutes, the diphenylphosphoryl azide solution was added to the reaction flask, keeping the reaction temperature ≧10° C. After holding the reaction temperature at 0° C. for 30 minutes, water (100 mL) was added, and the biphasic solution was transferred to a separatory funnel and extracted with toluene (2×200 mL). The combined organic solution was dried over anhydrous MgSO$_4$ and filtered. Over approximately thirty minutes, the solution was carefully warmed to reflux and held for one hour. Upon removing the heat source, tert-butanol (9 mL, 96.7 mmol) was added, and reflux was continued for an additional thirty minutes. Concentrated HCl (8 mL, 96.8 mmol) was added with extreme caution, producing copious evolution of gas. After continuing reflux for a final twenty minutes, the reaction was cooled to room temperature, and held for 16 hours. The solvent volume was reduced in vacuo, until crystals appeared. Diethyl ether (300 mL) was added, and the suspension was cooled to 0° C., held for 30 minutes, filtered and washed with diethyl ether to provide, after air-drying, pure 2-(4-methylthiophenyl)-1-(4-methylphenyl) ethanone (11.3 g, 50%): mp 120°–121° C. $^1$H NMR (CDCl$_3$) 300MHz 7.89 (d, J=8.26 Hz, 2H), 7.23–7.15(m, 6H), 4.21(s, 2H), 2.45(s, 3H), 2.40(s, 3H).

Step 3

Preparation of 2-Bromo-2-(4-methylthiophenyl)-1-(4-methylphenyl)ethanone

A 500 mL round-bottomed flask equipped with a pressure-equalizing addition funnel and provisions for magnetic stirring was charged with 2-(4-methylthiophenyl)-1-(4-methylphenyl)ethanone from Step 2 (10.0 g, 39.0 mmol), 33% HBr in acetic acid (70 mL) and glacial acetic acid (100 mL). Over approximately 20 minutes, a solution of bromine in acetic acid (1M, 39 mL) was added to the suspension, and the reaction was held at room temperature for one hour. Any undissolved solids were removed by filtration, and the reaction was concentrated in vacuo, to a residue. The residue was dissolved in methylene chloride (100 mL), washed with 5% Na$_2$S$_2$O$_5$ (2×100 mL), dried over MgSO$_4$, filtered, and concentrated in vacuo to a colorless oil. The oil was held under vacuum for 16 hours, yielding 2-bromo-2-(4-methylthiophenyl)-1-(4-methylphenyl)ethanone (8.38 g, 64%) as a dirty white solid: mp 97°–98° C. $^1$H NMR (CDCl$_3$) 300 MHz 7.86 (d, J=8.46 Hz, 2H), 7.80(d, J=8.26 Hz, 2H), 7.33–7.16(m, 4H), 5.88(s, 1H), 2.43(s, 3H), 2.36(s, 3H).

Step 4

Preparation of 2-(2-Chlorophenyl)-4-(4-methylphenyl)-5-(4-methylthiophenyl)thiazole A 100 mL one-neck round-bottom flask equipped for magnetic stirring was charged with 2-bromo-2-(4-methylthiophenyl)-1(4-methylphenyl)ethanone from Step 3 (0.300 g, 0.895 mmol) and acetonitrile (20 mL). 2-Chlorothiobenzamide (0.154 g, 0.895 mmol) was added, and the suspension was heated and held at reflux for three hours. The reaction was cooled to room temperature, diluted with ethyl acetate (50 mL) and poured into water(50 mL). The layers were separated, and the aqueous layer was extracted with ethyl acetate (2×30 mL). The combined organic solution was dried over MgSO$_4$, filtered and evaporated in vacuo. The residue was purified via flash chromatography (silica gel; 5% ethyl acetate in hexane) to yield 2-(2-chlorophenyl)-4-(4-methylphenyl)-5-(4-methylthiophenyl)thiazole (0.284 g, 78%) as a white solid: mp 125°–126° C. $^1$H NMR (CDCl$_3$) 300 MHz 8.40(m, 1H), 7.62–7.11(m, 11H), 2.50 (s, 3H), 3.36(s, 3H). Mass spectrum: MH$^+$=407.

Step 5

Preparation of 2-(2-Chlorophenyl)-5-(4-methylsulfonylphenyl)-4-(4-methylphenyl)thiazole A 100 mL one-neck round-bottom flask, equipped with provisions for magnetic stirring, was charged with 2-(2-chlorophenyl)-4-(4-methylphenyl)-5-(4-methylthiophenyl) thiazole from Step 4 (0.243 g, 0.596 mmol) and aqueous ethanol (25 mL). Oxone®(1.10 g, 1.787 mmol) was added, and the suspension was stirred at room temperature for 16 hours. Water (25 mL) was added, and the product precipitated. The suspension was cooled to 0° C. and held for one hour. The product was filtered, washed with water (25 mL), and dried to yield 2-(2-chlorophenyl)-5-methylsulfonylphenyl)-4-(4-methylphenyl)thiazole (0.236 g, 90%) as a white solid: mp 185°–187 ° C. $^1$H NMR (CDCl$_3$) 300 MHz 8.40(m, 1H), 7.89(d, J=8.26 Hz, 2H), 7.61 (d, J=8.46 Hz, 2H), 7.54–7.37 (m, 5H), 7.16 (d, J=7.85 Hz, 2H), 3.09(s, 3H), 2.38(s, 3H). Mass spectrum: MH$^+$= 439.

EXAMPLE 16

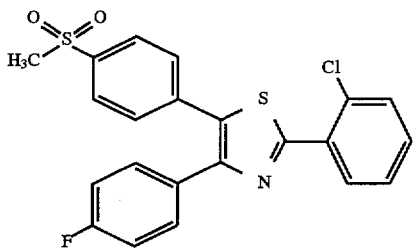

2-(2-Chlorophenyl)-4-(4-fluorophenyl)-5-(4-methylsulfonylphenyl)thiazole

Step 1

Preparation of 2-(2-Chlorophenyl)-4-(4-fluorophenyl)-5-(4-methylthiophenyl)thiazole To a solution of 2-bromo-1-(4-fluorophenyl)-2-(4-methylthiophenyl)ethanone (2.03 g, 5.98 mmol) (Example 1, Step 3) in acetonitrile (60mL) in a 125 mL round bottom flask was added 2-chlorothiobenzamide (1.08 g, 6.28 mmol) and the suspension heated to 80° C. for 4 hours. The reaction was cooled to room temperature and the suspension filtered through a fritted funnel. The solid was recrystallized from hot acetonitrile (50 mL) and methanol (150 mL) yielding 2-(2-chlorophenyl)-4-(4-fluorophenyl)-5-(4-methylthiophenyl)thiazole as a tan solid (1.23 g, 50 %): mp 133°–134° C. $^1$H NMR (CDCl$_3$) 300 mHz δ8.37 (d, J=6.17 Hz, 1H), 7.60 (dd, J=8.68, 5.28, 2H) 7.51 (d, J=9.44 Hz, 1H), 7.32–7.42 (m, 2H), 7.32 (d, J=8.68 Hz, 2H), 7.21 (d, J=8.68 Hz, 2H), 7.02 (t, J=8.68, 2H), 2.51 (s, 3H). MS (EI): m/z 412 (MH$^+$).

Step 2

Preparation of 2-(2-Chlorophenyl)-4-(4-fluorophenyl)-5-(4-methylsulfonylphenyl)thiazole To a solution of 2-(2-chlorophenyl)-4-(4-fluorophenyl)-5-(4-methylthiophenyl)thiazole from Step 1 (1.30 g, 3.16 mmol) in methylene chloride (30 mL) at room temperature was added MCPBA (2.03 g, 67% peroxide content, 7.89 mmol) in two portions (T=0 hour and 1 hour). After stirring for 6 hours, the hazy reaction mixture was diluted with methylene chloride (50 mL) and the resulting clear yellow solution was washed successively with NaHSO$_3$ solution (0.1M, 3×20 mL), NaHCO$_3$ saturated solution (3×50 mL), and brine, dried over Na$_2$SO$_4$, filtered and concentrated in vacuo yielding 2-(2-chlorophenyl)-4-(4-fluorophenyl)-5-(4-methylsulfonylphenyl)thiazole (1.2 g, 86%) as a yellow solid: mp 133°–134° C. $^1$H NMR (CDCl$_3$) 400 mHz δ8.42–8.38 (m, 1H), 7.92 (d, J=8.40 Hz, 2H), 7.61 (d, J=8.40 Hz, 2H), 7.56–7.45 (m, 3H), 7.38 (m, 2H), 7.05 (t, J=8.69 Hz, 2H), 3.10 (s, 3H). MS (EI-thermospray): m/z 443 (M+H). HRMS Δ=–2.5 mmu.

EXAMPLE 17

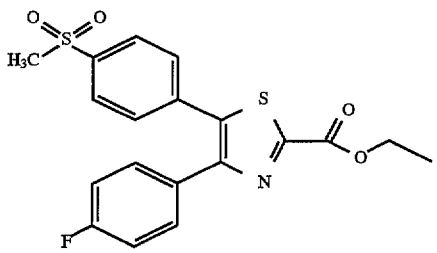

Ethyl [4-(4-fluorophenyl)-5-(4-methylsulfonylphenyl)-2-thiazolyl]carboxylate

Step 1

Synthesis of Ethyl [4-(4-Fluorophenyl)-5-(4-methylthiophenyl)-2-thiazolyl]carboxylate To a solution of 2-bromo-1-(4-fluorophenyl)-2-(4-methylthiophenyl) ethanone (1.014 g, 2.99 mmol) (Example 1, Step 3) in ethanol (30 mL) in a 50 mL round bottom flask was added ethyl thiooxamate (0.428 g, 3.21 mmol) and the suspension heated to reflux for 12 hours. The reaction was cooled to room temperature and let stand for 2 days. The crude reaction mixture was concentrated in vacuo, diluted with methylene chloride, washed with saturated NaHCO$_3$ solution, dried over Na$_2$SO$_4$, filtered and concentrated in vacuo. The residue was purified by flash chromatography (9:1 hexane:ethyl acetate) and recrystallized from methylene chloride and isooctane yielding the ethyl [4-(4-fluorophenyl)-5-(4-methylthiophenyl)-2-thiazolyl] carboxylate as a pale yellow solid (0.352 g, 32 %): mp 115°–116° C. $^1$H NMR (CDCl$_3$) 400 mHz δ7.54–7.48 (m, 2H), 7.25–7.20 (m, 4H), 7.00 (t, J=8.56 Hz, 2H), 4.50 (q, J=7.00 Hz, 2H), 2.50 (s, 3H). 1.46 (t, J=7.09 Hz, 3H). MS (EI): m/z 373 (M$^+$). HRMS Δ=0.000 mmu.

Step 2

Preparation of Ethyl [4-(4-Fluorophenyl)-5-(4-methylsulfonylphenyl)-2-thiazolyl]carboxylate To a solution of ethyl [4-(4-fluorophenyl)-5-(4-methylsulfonylphenyl)-2-thiazolyl]carboxylate from Step 1 (0.203 g, 0.544 mmol) in methylene chloride 10 mL) was added at 0° C. MCPBA (0.294 g of 67% peroxide content MCPBA, 1.14 mmol). The reaction was warmed to room temperature and let stand for 3 days. The crude reaction mixture was diluted with methylene chloride (50 mL) and the resulting solution was washed successively with NaHSO$_3$ solution (0.1M), NaHCO$_3$ saturated solution and brine. The solution was dried over Na$_2$SO$_4$, filtered and concentrated in vacuo yielding a white foam. This foam was crystallized from methylene chloride and isooctane to yield ethyl [4-(4-fluorophenyl)-5-(4-methylsulfonylphenyl)-2-thiazolyl]carboxylate as pale yellow small needles (0.150 g, 69 %): mp 173°–174° C. $^1$H NMR (CDCl$_3$) 400 mHz δ7.93 (d, J=8.30 Hz, 2 H), 7.55 (d, J=8.30 Hz, 2H), 7.48 (t, J=8.79 Hz, 2H), 7.03 (t, J=8.79 Hz, 2H), 4.52 (q, J=7.32 Hz, 2H), 3.09 (s, 3H), 1.46 (t, J=7.33 Hz, 3H). MS (EI): m/z 405 (M$^+$). HRMS Δ=–0.5 mmu.

EXAMPLE 18

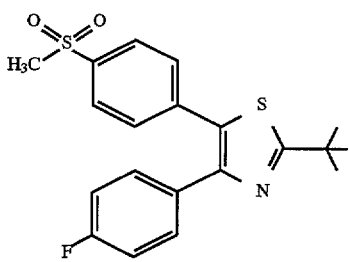

2-(tert-Butyl)-4-(4-fluorophenyl)-5-(4-methylsulfonylphenyl)thiazole

Step 1

Preparation of 2,2-Dimethylthiopropionamide

To a solution of 2,2-dimethylpropionamide (2.00 g, 19.77 mmol) in toluene (60 mL) in a 125 mL round bottom flask fitted with a calcium chloride drying tube was added Lawesson's reagent (4.00 g, 9.89 mmol) and the solution was heated to reflux for 12 hours. The crude reaction mixture was cooled to room temperature and was concentrated in vacuo. The crude product was flash chromatographed twice. The first column utilized 3:1 hexane:ethyl acetate yielding a white solid having a strong sulfurous aroma. This solid was flash chromatographed 1:1 methylene chloride:hexane with 1% acetic acid. The eluant, which contained the desired thioamide, was diluted with toluene and concentrated in vacuo yielding an oil. Treatment of this oil with isooctane yielded 2,2-dimethylthiopropionamide (0.190 g, 8%) as a white powder which was used immediately. $^1$H NMR (CDCl$_3$) 300 mHz δ9.40 (br s, 1H), 8.65 (br s, 1H), 1.19 (s, 9H).

Step 2 Preparation of 2-(tert-butyl)-4-(4-fluorophenyl)-4-(4-methylthiophenyl) thiazole:

To a solution of 2-bromo-1-(4-fluorophenyl)-2-(4-methylthiophenyl)ethanone (Example 1, Step 3) (0.196 g, 0.578 mmol) in ethanol (6 mL) in a 25 mL round bottom flask was added 2,2-dimethylthiopropionamide from Step 1 (0.071 g, 0.606 mmol) and the mixture heated to reflux overnight. The reaction was cooled to room temperature, diluted with ethyl acetate (50 mL) and this solution washed successively with Na$_2$CO$_3$ (10% solution) and brine, dried over Na$_2$SO$_4$, filtered and concentrated in vacuo yielding 2-(tert-butyl)-4-(4-fluorophenyl)-5-(4-methylthiophenyl) thiazole as a pale yellow oil (0.162 g, 78%): 1H NMR (CDCl$_3$) 300 mHz δ7.56–7.51 (m, 2H), 7.24 (d, J=8.48 Hz, 2H), 7.20 (d, J=8.48 Hz, 2H), 6.98 (t, J=8.85 Hz, 2H), 2.49 (s, 3H), 1.52 (s, 9H). MS (EI): m/e 357 (M+). HRMS Δ=0.1 mmu.

Stem 3 Preparation of 2-(tert-butyl)-4-(4-fluorophenyl)-5-(4-methylsulfonylphenyl) thiazole;

To a solution of 2-(tert-butyl)-4-(4-fluorophenyl)-5-(4-methylthiophenyl)thiazole from Step 2 (0.110 g, 0.31 mmol) in methylene chloride (5 mL) at 0° C. was added MCPBA (67 % peroxide content MCPBA) (0.080 g, 0.62 mmol initially) and the reaction was warmed to room temperature. Additional MCPBA was added (0.020 g, 0.15 mmol) later that day, more (0.040 g, 0.31 mmol) on day 4, and more (0.020 g, 0.15 mmol) later on day 4. The crude reaction mixture was diluted with methylene chloride (50 mL) and the resulting solution was washed successively with NaHSO$_3$ solution (0.1M), NaHCO$_3$ saturated solution and brine, dried over Na$_2$SO$_4$, filtered and concentrated in vacuo. The crude product was recrystallized from methylene chloride and isooctane yielding 2-(tert-butyl)-4-(4-fluorophenyl)-5-(4-methylsulfonylphenyl)thiazole as a white powder (0.059 g, 49%): mp 144°–145° C. $^1$HNMR (CDCl$_3$) 400 mHz δ7.87 (d, J=8.30 Hz, 2H), 7.51–7.45 (m, 4H), 7.00 (t, J=8.79, 2H), 3.08 (s, 3H), 1.50 (s, 9H). MS (EI): m/z 390 (MH$^+$). HRMS Δ=1.9 mmu.

EXAMPLE 19

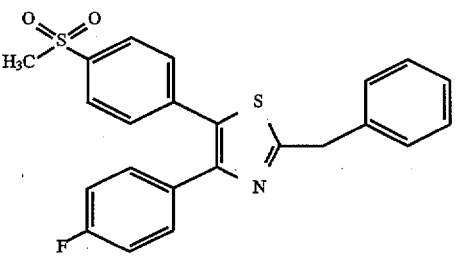

2-Benzyl-4-(4-fluorophenyl)-5-(4-methylsulfonylphenyl)thiazole

Step 1 Preparation of 2-benzyl-4-(4-fluorophenyl)-5-(4-methylthiophenyl)thiazole:

To a solution of 2-bromo-1-(4-fluorophenyl)-2-(4-methylthiophenyl)ethanone (Example 1, Step 3) (0.250 g, 0.737 mmol) in ethanol (9 mL) in a 25 mL round bottom flask was added 2-phenylthioacetamide (0.111 g, 0.737 mmol) and the mixture heated to reflux overnight. The reaction was cooled to room temperature, diluted with ethyl acetate (50 mL), washed successively with Na$_2$CO$_3$ (10 % solution) and brine, dried over Na$_2$SO$_4$, filtered and concentrated in vacuo yielding an oil. This oil was dissolved in methylene chloride and isooctane yielding a suspension. The solid was removed by filtration and the filtrate reconcentrated in vacuo yielding 2-benzyl-4-(4-fluorophenyl)-5-(4-methylthiophenyl)thiazole as a yellow oil which was suitable based upon $^1$H NMR to be used without further purification.

Step 2 Preparation of 2-benzyl-4-(4-fluorophenyl)-5-(4-methylsulfonylphenyl)thiazole:

To a solution of 2-(benzyl)-4-(4-fluorophenyl)-5-(4-methylthiophenyl)thiazole from Step 1 (0.20 g, 0.50 mmol) in methylene chloride (10 mL) was added, at room temperature, MCPBA (0.29 g of 67% peroxide content MCPBA, 1.00 mmol) and the reaction was warmed to room temperature and let stand for 2 hours. The crude reaction mixture was diluted with methylene chloride (50 mL) and the resulting solution was washed successively with NaHSO$_3$ solution (0.1M), NaHCO$_3$ saturated solution, and brine, dried over Na$_2$SO$_4$, filtered and concentrated in vacuo yielding a solid. This solid was recrystallized from methylene chloride and isooctane yielding 2-benzyl-4-(4-fluorophenyl)-5-(4-methylsulfonylphenyl)thiazole as white needles (0.130 g, 56%): mp 117°–118° C. 1H NMR (CDCl$_3$) 400 mHz δ7.83 (d, J=8.56 Hz, 2H), 7.5–7.3 (m, 9H), 7.02 (t, 8.67 Hz, 2H), 4.38 (s, 2H), 3.06 (s, 3H). MS (FAB): m/z 424 (MH+).

EXAMPLE 20

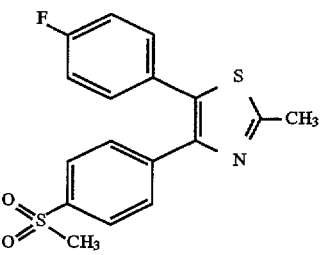

5-(4-Fluorophenyl)-4-(4-methylsulfonylphenyl)-2-methylthiazole

Step 1 Preparation of 1-(4-methylthiophenyl)-2-(4-fluorophenyl)ethanone;

To a stirred solution of thioanisole (380 mL, 3.2 mol) and 4-fluorophenylacetyl chloride (300 g, 1.6 mol) in carbon disulfide (1.2 L), cooled to 5° C., was added anhydrous aluminum chloride portionwise at such a rate that the internal temperature did not rise above 15° C. The reaction was stirred at room temperature for 16 hours. The solution was cautiously poured into 2 L of ice and water. The aqueous solution was extracted with methylene chloride (6×150 mL), the combined extracts were dried over anhydrous $MgSO_4$, filtered and concentrated in vacuo. The residue was dissolved in 800 mL of ether and cooled to 0° C. whereupon crystals of pure product formed which were isolated by filtration on a Buchner funnel and air dried to provide the ketone (199.6 g, 48%): mp 135°–138° C. $^1$H NMR (CDCl$_3$/TMS) 300 MHz 8.00 (d, J=8.7 Hz, 2H), 7.40–7.30 (m, 4H), 7.13–7.03 (m, 2H), 4.34 (s, 2H), 2.56 (s, 3H). Mass spectrum $M^+$=260.

Step 2 Preparation of 2-bromo-2-(4-fluorophenyl)-1-(4-methylthiophenyl)ethanone:

To a stirred slurry of 2-(4-fluorophenyl)-1-(4-methylthiophenyl)ethanone from Step 1 (5.04 g, 19.36 mmol) in acetic acid (100 mL) was added HBr in acetic acid (45 mL, 48% by wt.) and bromine (1.0 mL, 3.09 g, 19.36 mmol). The resulting green slurry became homogeneous within 30 minutes. After 4 hours, the reaction was concentrated in vacuo, the residue diluted with toluene, and reconcentrated in vacuo. The crude haloketone was purified by flash chromatography (2:1 hexane:methylene chloride) and recrystallized from ethyl acetate and isooctane yielding 2-bromo-2-(4-fluorophenyl)-1-(4-methylthiophenyl) ethanone as an off-white solid (4.51 g, 69%): mp 108°–111° C. $^1$H NMR (CDCl$_3$) 300 mHz δ7.94 (d, J=8.79 Hz, 2H), 7.60–7.50 (m, 2H), 7.25 (d, J=8.79 Hz, 2H), 7.10 (t, J=8.67 Hz, 2H), 6.34 (s, 1H), 2.56 (s, 3 H).

Step 3 Preparation of 5-(4-fluorophenyl)-4-(4-methylthiophenyl)-2-methylthiazole:

To a solution of 2-bromo-2-(4-fluorophenyl)-1-(4-methylthiophenyl) ethanone from Step 2 (0.70 g, 2.10 mmol) in ethanol (20 mL) in a 50 mL round bottom flask was added thioacetamide (0.16 g, 2.10 mmol) and the mixture heated to reflux for 20 hours. The reaction was cooled to room temperature and concentrated in vacuo and dissolved in methylene chloride. This solution was washed with NaHCO$_3$ saturated solution and dried over Na$_2$SO$_4$, filtered and reconcentrated in vacuo yielding a white crystalline solid. Flash chromatography of this solid (2:1 methylene chloride: hexane) yielded 5-(4-fluorophenyl)-4-(4-methylthiophenyl) -2-methylthiazole as a white solid (0.45 g, 68%): mp 104°–105° C. $^1$H NMR (CDCl$_3$) 400 mHz δ7.39 (d, J=8.32, 2H), 7.28 (dd, J=8.80, 5.14, 2H), 7.15 (d, J=8.32, 2H), 7.00 (t, J=8.80, 2H), 2.74 (s, 3H), 2.47 (s, 3H). MS (EI): m/z 316 (M+H). HRMS Δ=0.000 mmu.

Step 4 Preparation of 5-(4-fluorophenyl)-4-(4-methylsulfonylphenyl)-2 -methylthiazole:

To a solution of 2-(methyl)-5-(4-fluorophenyl)-4-(4-methylthiophenyl)thiazole from Step 3 (0.440 g, 1.39 mmol) in methylene chloride (15 mL) at 0° C. in a 25 mL round bottom flask was added MCPBA (0.90 g of 67% peroxide content MCPBA, 3.49 mmol) and the reaction was warmed to room temperature and let stand overnight. The crude reaction mixture was diluted with methylene chloride (70 mL) and the resulting solution was washed successively with NaHSO$_3$ solution (0.1M) and NaHCO$_3$ saturated solution, dried over Na$_2$SO$_4$, filtered and concentrated in vacuo. The crude product was purified by flash chromatography (1:1 methylene chloride:hexane) and the product thus obtained was recrystallized from methylene chloride and isooctane yielding 5-(4-fluorophenyl)-4-(4-methylsulfonylphenyl)-2-methylthiazole as clear colorless needles (0.274 g, 57%): mp 134°–135° C. $^1$H NMR (CDCl$_3$) 400 mHz δ7.84 (d, J=8.56 Hz, 2H), 7.69 (d, J=8.56 Hz, 2H), 7.28 (m, 2H), 7.06 (t, J=8.68, 2H), 3.04 (s, 3H), 2.76 (s, 3H). MS (EI): m/z 348 (MH+); HRMS Δ=−2.5 mmu.

EXAMPLE 21

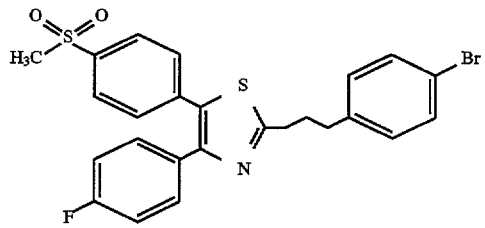

2-(3-[4-Bromophenyl]propyl)-4-(4-fluorophenyl))-5-(4-methylsulfonylphenyl)thiazole Step 1 Preparation of 4-(4-bromophenyl) thiobutyramide:

To a solution of 4-(4-bromophenyl)butyramide (1.653 g, 6.827 mmol) in toluene (35 mL) was added Lawesson's reagent (1.381 g, 3.414 mmol). The reaction was refluxed overnight, cooled to room temperature, and concentrated yielding an orange oil. Flash chromatography of this oil (1:1 hexane:methylene chloride with 1% acetic acid) yielded 4-(4-bromophenyl) thiobutyramide as off-white needles (0.196 g): mp 104°–105° C. $^1$H NMR (DMSO-d$_6$) 300 mHz δ9.33 (br s, 1H), 9.12 (br s, 1H), 7.44 (d, J=8.11 Hz, 2H), 7.14 (d, J=8.48 H z, 2H), 2.56–2.41 (m, 4H), 1.95–1.85 (m, 2H).

Step 2 Preparation of 2-(3-[4-bromophenyl]propyl)-4-(4-fluorophenyl))-5-(4-methylthiophenyl) thiazole:

To a solution of 2-bromo-2-(4-fluorophenyl)-1-(4-methylthiophenyl) ethanone (Example 1, Step 3 ) (2.70 g, 7.90 mmol) in acetonitrile (90 mL) and ethanol (10 mL) in a 125 mL round bottom flask was added 4-(4-bromophenyl) thiobutyramide from Step 1, (1.4 g, 7.90 mmol) and the mixture was heated to reflux for 7 hours. The reaction was cooled to room temperature and let stand overnight. The crude product was concentrated in vacuo yielding an oil which was purified by flash chromatography (1: 1 hexane:methylene chloride) yielding 2-(3-[4-bromophenyl]propyl)-4-(4-fluorophenyl))-5-(4-methylthiophenyl)thiazole (1.4 g, 36%) as a clear colorless oil (ca. 90% purity by $^1$H NMR): $^1$H NMR (CDCl$_3$) 3 00 mHz δ7.50–7.46 (m, 2H), 7.41 (d, J=8.46 Hz, 2H), 7.22 (d, J=8.66 Hz, 2H), 7.16 (d, J=8.66 Hz, 2H), 7.10 (d, J=8.26 Hz, 2H), 6.97 (t, J=8.86, 2H), 3.03 (t, J=7.45 Hz, 2H), 2.74 (t, J=7.45 Hz, 2H), 2.49 (s, 3H), 2.20–2.09 (m, 2H). MS (EI): m/z 529, 531 (M+) 497, 499. HRMS Δ=−2.1 mmu.

Step 3 Preparation of 2-(3-[4-bromophenyl]propyl)-4-(4-fluorophenyl))-5-(4-methylsulfonylphenyl)thiazole:

To a solution of 2-(3-[4-bromophenyl]propyl)-4-(4-fluorophenyl))-5-(4-methythiophenyl)thiazole from Step 2 (0.20 g, 0.48 mmol) in methylene chloride (5 mL) in a 10 mL round bottom flask at 0° C. was added MCPBA (0.17 g of 67% peroxide reagent, 0.65 mmol) and the solution was warmed to room temperature and let stand overnight. The reaction mixture was diluted with methylene chloride (50 mL) and was washed successively with NaHSO$_3$ solution (0.1M), and NaHCO$_3$ saturated solution, dried over Na$_2$SO$_4$, filtered and concentrated in vacuo. The product was recrystallized from methylene chloride and isooctane yielding 2-(3-[4-bromophenyl]propyl)-4-(4-fluorophenyl))-5-(4-methylsulfonylphenyl) thiazole as a white crystalline solid (0.113 g, 44%): mp 132°–133° C. $^1$H NMR (CDCl$_3$) 300 mHz δ7.86 (d, J=8.46 Hz, 2H), 7.49–7.40 (m, 6H), 7.11–7.08 (m, 2H), 7.01 (t, J=8.66 Hz, 2H), 3.08 –3.03 (m, 5H), 2.75 (t, J=7.45 Hz, 2H), 2.18 (m, 2H). MS (EI): m/z 529,5311 (M+). HRMS Δ=−3.117 mmu.

EXAMPLE 22

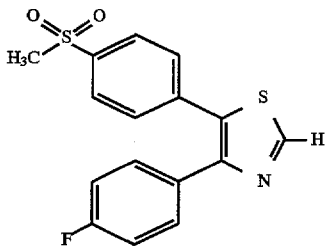

4-(4-Fluorophenyl)-5-(4-methylsulfonylphenyl) thiazole

Step 1 Preparation of 4-(4-fluorophenyl))-5-(4-methylthiophenyl)thiazole;

To a solution of formamide (3.4 g, 3.0 mL, 75.5 mmol) in diethyl ether was added, with ice bath cooling and stirring solid, phosophorous pentasulfide (2.35 g, 5.3 mmol) in several portions. The flask was refrigerated at 5° C. for 72 hours, warmed to room temperature and stirred for an additional 16 hours. The ethereal solution of resulting thioformamide was decanted from the reaction mixture and used "as is". One half of this ethereal solution was concentrated in vacuo. The resulting straw colored oil was diluted with acetonitrile (10 mL) and the solution was cooled to 0° C. (ice bath). Solid 2-bromo-1-(4-fluorophenyl)-2-(4-methylthiophenyl) ethanone (Example 1, Step 3) (0.518 g, 1.53 mmol) was added and the reaction was stirred at room temperature for 8 days. The reaction mixture was concentrated in vacuo, diluted with methylene chloride and washed successively with NaHCO$_3$ saturated solution, and brine, dried over Na$_2$SO$_4$, filtered and reconcentrated in vacuo. The crude thiazole was purified by flash chromatographed (1:1 hexane:methylene chloride) yielding 4-(4-fluorophenyl))-5-(4-methylthiophenyl)thiazole as a clear viscous oil (0.37 g, 80%): $^1$H NMR (CDCl$_3$) 300 mHz δ8.75 (s, 1H), 7.52 (dd, J=8.87, 5.47 Hz, 2H), 7.22 (d, J=8.68, 2H), 7.17 (d, J=8.68, 2H), 6.98 (t, J=8.87 Hz, 2H), 2.45 (s, 3H). MS (EI): m/e 301 (M+). HRMS Δ=5.0 63 mmu.

Step 2 Preparation of 4-(4-fluorophenyl)-2-(4-methylsulfonylphenyl)thiazole:

To a solution of 4-(4-fluorophenyl))-5-(4-methylthiophenyl)thiazole from Step 1 (0.35 g, 1.16 mmol) in methylene chloride (12 mL) at 0° C. was added MCPBA (0.75 g of 67% peroxide content reagent, 2.90 mmol). The solution was warmed to room temperature and stirred overnight. The reaction was diluted with methylene chloride (40 mL) and this solution was successively washed with NaHSO$_3$ solution (0.1M), and NaHCO$_3$ saturated solution, dried over Na$_2$SO$_4$, filtered and concentrated in vacuo. The product was recrystallized from methylene chloride and isooctane yielding 4-(4-fluorophenyl)-5-(4-methylsulfonylphenyl)thiazole as long pale yellow needles (0.253 g, 65%): mp 138°–139° C. $^1$H NMR (CDCl$_3$) 300 mHz δ8.89 (s, 1H), 7.91 (d, J=8.68, 2H), 7.55 (d, J=8.68, 2H), 7.48 (dd, J=9.06, 5.28Hz, 2H), 7.03 (t, J=9.06 Hz, 2 H), 3.09 (s, 3H). MS (EI): m/z 333 (M+). HRMS Δ=−5.342 mmu.

EXAMPLE 23

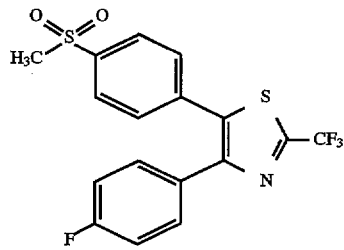

4-(4-Fluorophenyl)-5-(4-methylsulfonylphenyl)-2-trifluoromethylthiazole

Step 1 Preparation of 4-(4-fluorophenyl)-5-(4-methylthiophenyl)-2-trifluoromethylthiazole:

To a solution of trifluoroacetamide (13.7 g, 121.2 mmol) in toluene (30 mL) was added solid phosphorous pentasulfide (5.4 g, 12.1 mmol) and the mixture was heated to reflux for 60 hours. The resulting orange "coarse" suspension was cooled to room temperature and pulverized to form a fine suspension. One fourth of this toluene suspension (7.5 mL, ca. 30 mmol of theory) was transferred to a 25 mL round bottom flask and 2-bromo-1-(4-fluorophenyl)-2-(4-methylthiophenyl)ethanone (Example 1, Step 3) (1.53 g, 4.50 mmol) was added in one portion. This suspension was heated to reflux for 1.5 hours, cooled to 50° C., and 1.0 N HCl solution (1 mL) was added carefully. The solution was reheated to reflux for 1 hour more. This reaction was cooled to room temperature and let stand overnight. To this solution was added 2 N NaOH solution until the exotherm subsided and the reaction was stirred for 1 hour longer. The resulting black suspension was diluted with methylene chloride and washed with NaHCO$_3$ saturated solution, dried over Na$_2$SO$_4$, filtered and concentrated in vacuo yielding an orange oily semi-solid. This crude intermediate was purified by flash chromatography with 3:1 hexane:ethyl acetate and 9:1 hexane:methylene chloride yielding 4-(4-fluorophenyl)-5-(4-methylthiophenyl)-2-trifluoromethylthiazole (1.1 g, 72%) as a pale brown oil: $^1$H NMR (CDCl$_3$) 300 mHz δ7.52 (dd, J=5.28, 9.06, 2H), 7.24 (m, 4H), 7.01 (t, J=8.68 Hz, 2H), 2.51 (s, 3H). MS (EI): m/z 369 (M+H). HRMS Δ=−1.446 mmu.

Step 2 Preparation of 4-(4-fluorophenyl)-5-(4-methylsulfonylphenyl)-2-trifluoromethylthiazole;

To a solution of 2-trifluoromethyl-5-(4-fluorophenyl))-4-(4-methylthiophenyl)thiazole from Step 1 (1.10 g, 3.30 mmol) in methylene chloride (30 mL) at 0° C. was added MCPBA (2.10 g of 67% peroxide content reagent, 8.20 mmol) in three portions over 2 hours. After 3 hours total reaction time, the reaction was diluted with methylene chloride (150 mL) and the solution was washed with NaHSO$_3$ solution (0.1 M):NaHCO$_3$ saturated solution (1:1 ration 3×50 mL), dried over MgSO$_4$, filtered and concentrated in vacuo. The resulting solid was recrystallized from methylene chloride and isooctane yielding 4-(4-fluorophenyl)-5-( 4-methylsulfonylphenyl)-2-trifluoromethylthiazole as opaque white crystals (1.1 g, 90%): mp 168°–170° C. $^1$H NMR (CDCl$_3$) 300 mHz δ7.97 (d, J=8.84, 2H), 7.57 (d, J=8.84, J=8.84, 2H), 7.47 (dd, J=8.85, J=5.16, 2H), 7.04 (t, J=8.85 Hz, 2H), 3.11 (s, 3H); $^{19}$F NMR (CDCl$_3$) 300 mHz δ61.55, −111.42. MS (EI): m/z 402 (MH$^+$). HRMS Δ=1.938 mmu.

EXAMPLE 24

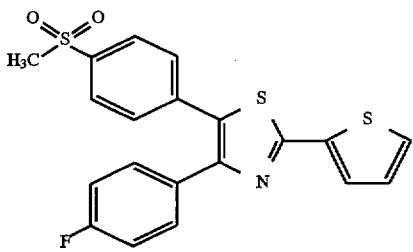

4-(4-Fluorophenyl)-5-(4-methylsulfonylphenyl)-2-(2-thienyl)thiazole

Step 1 Preparation of 4-(4-fluorophenyl)-5-(4-methylthiophenyl)-2-(2-thienyl)thiazole:

To a solution of 2-bromo-1-(4-fluorophenyl)-2-(4-methylthiophenyl)ethanone (Example 1, Step 3) (0.249 g, 0.734 mmol) in ethanol (9 mL) in a 25 mL round bottom flask was added thiophene-2-thiocarboxamide (0.110 g, 0.771 mmol) and the mixture was heated to reflux 14 hours. The reaction was cooled to room temperature, diluted with ethyl acetate (50 mL) and this solution washed successively with Na$_2$CO$_3$ (10% solution, 3×20 mL) and brine, dried over Na$_2$SO$_4$, filtered and concentrated in vacuo yielding an orange crystalline solid. This solid was purified by flash chromatography (9:1 hexane:ethyl acetate) yielding 4-(4 4-fluorophenyl)-5-(4-methylthiophenyl)-2-(2-thienyl] thiazole (0.228 g, 82%) as a viscous yellow oil: $^1$H NMR (CDCl$_3$) 300 mHz δ7.53–7.58 (m, 3H), 7.40 (dd, J=5.29, 1.17 Hz, 1H), 7.28 (d, J=8.30 Hz, 2H), 7.19 (d, J=8.30 Hz, 2H), 7.09 (dd, J=4.91, 3.78 Hz, 1H), 7.00 (t, J=8.68 Hz, 2H), 2.50 (s, 3H). MS (EI): m/e 383 (M$^+$). HRMS Δ=0.1 mmu.

Step 2 Preparation of 4-(4-fluorophenyl)-2-(4-methylsulfonylphenyl)-2-(2-thienyl)thiazole:

To a solution of 2-(2-thienyl)-4-(4-fluorophenyl)-5-(4-methylthiophenyl)thiazole from Step 1 (0.20 g, 0.52 mmol) in methylene chloride (5 mL), MCPBA was added at 0° C. ( 0.27 g of 67% peroxide content MCPBA, 1.1 mmol) and the reaction was warmed to room temperature. The crude reaction mixture was diluted with methylene chloride (50 mL) and the resulting solution was washed successively with NaHSO$_3$ solution (0.1M), NaHCO$_3$ saturated solution and brine, dried over Na$_2$SO$_4$, filtered and concentrated in vacuo. The crude product was recrystallized from methylene chloride and isooctane yielding 4-(4-fluorophenyl)-5-(4-methylsulfonylphenyl)-2-(2-thienyl)thiazole as a pale green solid (0.170 g, 79%): mp 194°–195° C. $^1$H NMR (DMSO-d$_6$) 400mHz δ 7.90 (d, J=8.30 Hz, 2H), 7.58 (d, J=3.91 Hz, 1H), 7.55–7.50 (m, 4H), 7.45 (d, J=3.91 Hz, 1H), 7.13–7.11 (m, 1H), 7.04 (t, J=8.79 Hz, 2H), 3.09 (s, 3H). MS (EI):m/z 416 (MH$^+$). HRMS Δ=0.9 mmu.

EXAMPLE 25

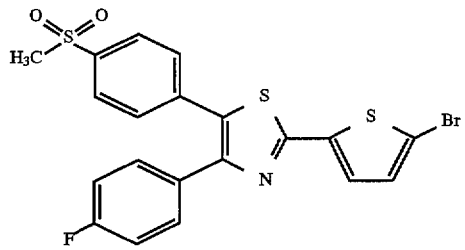

2-(5'-Bromo-2'-thienyl)-4-(4-fluorophenyl)-5-(4-methylsulfonylphenyl)thiazole

To a solution of 4-(4-fluorophenyl)-5-(4-methylthiophenyl)-2-(2-thienyl]thiazole (Example 24, Step 1) (0.057 g, 0.149 mmol) suspended in acetic acid (2 mL) and methylene chloride (2.0 mL) was added excess bromine in acetic acid (1.4M, 0.51 mL, 0.714 mmol). The reaction was concentrated in vacuo, diluted with ethyl acetate, and washed successively with NaHSO$_3$ solution (0.1M), NaHCO$_3$ saturated solution and brine, dried over Na$_2$SO$_4$, filtered and reconcentrated in vacuo. The resulting compound was diluted with methylene chloride (1 mL) and MCPBA (0.064 g of 67% peroxide reagent, 2.48 mmol) and allowed to stand for 4 hours. The crude reaction mixture was diluted with methylene chloride (50 mL) and the resulting solution was washed successively with NaHSO$_3$ solution (0.1M), NaHCO$_3$ saturated solution and brine, dried over Na$_2$SO$_4$, filtered and again concentrated in vacuo. The crude product was recrystallized from methylene chloride and isooctane yielding 2-(5-bromo-2-thienyl)-4-(4-fluorophenyl)-5-(4-methylsulfonylphenyl)-thiazole as fine yellow needles (0.039 g, 53%): mp 190°–191° C. $^1$H NMR (CDCl$_3$) 300 mHz δ7.89 (d, J=8.46 Hz, 2H), 7.54 (d, J=8.46 Hz, 2H), 7.49 (m, 2H), 7.30 (d, J=4.03 Hz, 1H), 7.08 (m 1H), 7.04 (t, J=8.66 Hz, 2H), 3.09 (s, 3H). MS (EI): m/z 496 (M+H).

EXAMPLE 26

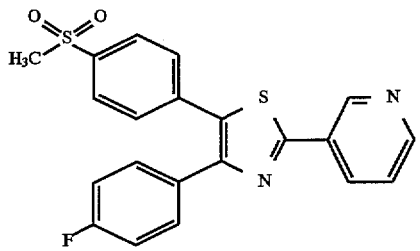

4-(4-Fluorophenyl)-5-(4-methylsulfonylphenyl)-2-(3-pyridyl)thiazole

Step 1 Preparation of 1-(4-fluorophenyl)-2-(4-methylsulfonylphenyl)ethanone:

To a stirred solution of 1-(4-fluorophenyl)-2-(4-methylthiophenyl)ethanone (Example 1, Step 3) (15.00 g, 57.62 mmol) in methylene chloride (500 mL) at 5° C. (ice-bath) was added MCPBA (29.64 g, ca. 67% peroxide, ca. 113 mmol), portionwise over 30 minutes. The solution was warmed to room temperature. The reaction solution was stirred vigorously with NaHSO₃ solution for 10 minutes to quench any unreacted MCPBA. The layers were separated and ethyl acetate was added to aid in dissolution of the precipitate which began to form. The partial suspension was filtered and the solid saved. The organic phase was washed successively with NaHCO₃ solution and brine, dried over Na₂SO₄, and diluted with isooctane until a solid began to precipitate. Upon removal of most of the ethyl acetate and methylene chloride in vacuo more solid precipitated. All of the precipitates were combined yielding 1-(4-fluorophenyl)-2-(4-methylsulfonylphenyl)ethanone (14.5 g, 86%). mp 182°–183° C. ¹H NMR (CDCl₃) 300 mHz δ8.04 (dd, J=5.24, 8.46, 2H), 7.92 (d, J=8.26 Hz, 2H), 7.46 (d, J=8.46 Hz, 2H), 7.17 (t, J=8.46, 2H), 4.37 (s, 2H), 3.05 (s, 3H). MS: m/z 293 (MH+); HRMS A =1.6 mmu.

Step 2 Preparation of 2-bromo-1-(4-fluorophenyl)-2-(4-methylsulfonylphenyl)ethanone:

To a stirred slurry of 1-(4-fluorophenyl)-2-(4-methylsulfonylphenyl) ethanone from Step 1 (3.03 g, 10.38 mmol) in acetic acid (40 mL) was added HBr in acetic acid (2 mL, 48% by wt. ) and bromine (0.64 mL, 1.99 g, 12.45 mmol). Within minutes the slurry became homogeneous. After 1 hour, the reaction was concentrated in vacuo, diluted with methylene chloride and reconcentrated in vacuo yielding 2-bromo-1-(4-fluorophenyl)-2-(4-methylsulfonylphenyl) ethanone as a tan solid (3.53 g, 95%) which could be used without further purification. mp 140°–141° C., ¹H NMR (CDCl₃) 300 mHz δ8.05 (dd, J=5.16, 8.84 Hz, 2H), 7.96 (d, J=8.48 Hz, 2H), 7.75 (d, J=8.48 Hz, 2H), 7.17 (t, J=8.48 Hz, 2H), 6.29 (s, 1H), 3.06 ( s, 3H). MS: m/e 371/373 (MH⁺). HRMS Δ=5.5 mmu.

Step 3 Preparation of 4- (4-fluorophenyl)-1-(4-methylsulfonylphenyl)-2-(3-pyridyl)thiazole:

To a solution of 2-bromo-1-(4-fluorophenyl)-2-(4-methylsulfonylphenyl)ethanone from Step 2 (0.732 g, 1.97 mmol) in acetonitrile (20 mL) in a 50 mL round bottom flask was added thionicotinamide ( 0.273 g, 1.97 mmol) with stirring. The resulting solution was heated to reflux for 1 hour and additional 2-bromo-1-(4-fluorophenyl)-3-(methylsulfonylphenyl)ethanone (0.031 g, 0.05 mmol) was added and stirred at ruflux for an additional hour. The reaction was cooled to room temperature and concentrated in vacuo yielding an orange semi-solid. This was purified by flash chromatography (2:1 hexane:ethyl acetate with 1% acetic acid). The product fractions were combined, toluene added, and the resulting solution reconcentrated in vacuo yielding 4-(4-fluorophenyl)-5-(4-methylsulfonylphenyl)-2-(3-pyridyl) thiazole as a pale yellow crystalline solid (0.351 g, 43%): mp 143°–146° C. ¹H NMR (CDCl₃) 400 mHz δ9.20 (d, J=1.81 Hz, 1H), 8.68 (dd, J=1.46, 4.89 Hz, 1H), 8.30 (dr, J=2.00, 9.42 Hz, 1H), 7.91 (d, J=8.55 Hz, 2H), 7.60–7.52 (m, 4H), 7.42 (m, 1), 7.05 (t, J=8.70 Hz, 2H), 3.10 (s, 3H). MS (EI): m/z 410 (M⁺). HRMS Δ=-4.3

EXAMPLE 27

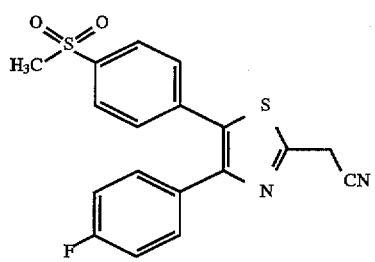

2-(Cyanomethyl)-4-(4-fluorophenyl)-5-(4-methylsulfonylphenyl)thiazole

Step 1 Preparation of 2-(cyanomethyl)-4-(4-fluorophenyl)-5-(4-methylthiophenyl) thiazole;

To a solution of 2-bromo-1-(4-fluorophenyl)-2-(4-methylsulfonylphenyl)ethanone (Example 26, Step 2) (0.249 g, 0.734 mmol) in ethanol (9 mL) in a 25 mL round bottom flask was added 2-cyanothioacetamide (0.077 g, 0.771 mmol) and the solution heated to reflux for 14 hours. The reaction was cooled to room temperature, was was concentrated in vacuo and the residue dissolved in ethyl acetate. This solution was washed successively with Na₂CO₃ (10% solution) and brine, dried over Na₂SO₄, filtered and reconcentrated in vacuo yielding an orange crystalline solid. This solid was purified by flash chromatography (4:1 hexane:ethyl acetate ) yielding 2-(cyanomethyl)-4-(4-fluorophenyl)-5-(4-methylthiophenyl)thiazole as very fine pink crystals (0.090 g, 36%): mp 118°–119° C. ¹H NMR (CDCl₃) 400 mHz δ7.50 (d, J=5.38, 2H), 7.47 (d, J=5.38, 2H), 7.24–7.18 (m, 4H), 7.00 (t, J=8.80, 2H), 4.16 (s, 2H), 2.50 (s, 3H). MS (EI): m/z 340 (ᴹ⁺). HRMS Δ=2.7 mmu.

Step 2 Preparation of 2-(cyanomethyl)-4-(4-fluorophenyl)-5-(4-methylsulfonylphenyl) thiazole;

To a solution of 2-cyanomethyl-4-(4-fluorophenyl)-5-(4-methylthiophenyl)thiazole from Step 1 (0.08 g, 0.24 mmol) in methylene chloride (3 mL) at 0° C. was added MCPBA (0.13 g of 67% peroxide content MCPBA, 0.48 mmol) and the reaction was warmed to room temperature. The crude reaction mixture was diluted with methylene chloride (50 mL), washed successively with NaHSO₃ solution (0.1M), NaHCO₃ saturated solution, and brine, dried over Na₂SO₄, filtered and concentrated in vacuo. The crude product was recrystallized from methylene chloride and isooctane yielding 2-(cyanomethyl)-4-(4-fluorophenyl)-5-(4-methylsulfonylphenyl)thiazole as light orange needles (0.064 g, 72%): mp 151°–152° C. ¹H NMR (CDCl₃) 400 mHz δ7.92 (d, J=8.79, 2H), 7.52 ( d, J=8.79, 2H), 7.44 (m, 2H), 7.03 (t, J=8.30, 2H), 4.17 (s, 2H), 3.09 (s, 3H). MS (EI): m/z 373 (M+H). HRMS Δ=4.8 mmu.

EXAMPLE 28

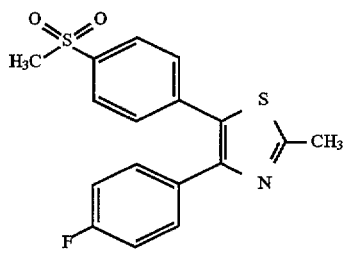

4-(4-Fluorophenyl)-5-(4-methylsulfonylphenyl)-2-methylthiazole

To a solution of 2-bromo-1-(4-fluorophenyl)-2-(4-methylsulfonylphenyl)ethanone (0.437 g, 1.18 mmol) (Example 26, Step 2) in acetonitrile (10 mL) in a 25 mL round bottom flask was added thioacetamide (0.088 g, 1.18 mmol) and the solution heated to reflux (2 hours) until all solid dissolved. The reaction was cooled to room temperature. The acetonitrile was removed in vacuo and the resulting product precipitated from methanol by the addition of water yielding 4-(4-fluorophenyl)-5-(4-methylsulfonylphenyl)-2-methylthiazole (0.226 g, 55%, ca. 85% purity by $^1$H NMR): mp 229°–233° C. $^1$HNMR (CDCl$_3$) 300 mHz δ7.98 (d, J=8.11 Hz, 2H ), 7.66–7.61 (m, 2H), 7.52 (d, J=8.48 Hz, 2H), 7.13 (t, J=8.48 Hz, 2H), 3.31 (s, 1H), 3.10 ( s, 3H). MS (EI-thermospray): m/z 348 (M+). HRMS Δ=–2.3 mmu.

EXAMPLE 29

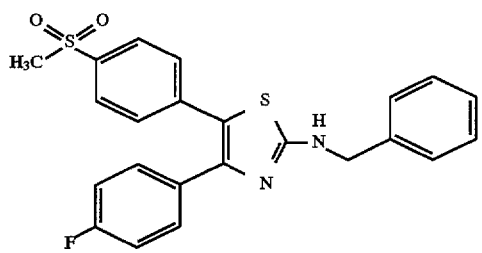

4-(4-Fluorophenyl)-5-(4-methylsulfonylphenyl)-2-benzylaminothiazole

To a solution of 2-bromo-1-(4-fluorophenyl)-2-(4-methylsulfonylphenyl)ethanone (Example 26, Step 2) (0.415 g, 1.12 mmol) in isopropanol (12 mL) in a 25 mL round bottom flask was added N-benzyl thiourea (0.186 g, 1.12 mmol). The solution was heated to reflux (30 hours), cooled to room temperature and let stand for 7 days. The resulting suspension was concentrated in vacuo. The resulting residue was suspended in methylene chloride (100 mL) and washed with NaHCO$_3$ saturated solution (3×10 mL), dried over sodium sulfate, filtered and reconcentrated in vacuo yielding 4-(4-fluorophenyl)-5-(4-methylsulfonylphenyl)-2-benzylaminothiazole as a pale yellow solid (0.34 g, 69%): mp 112° C. $^1$H NMR (CDCl$_3$ 400 mHz δ7.74 (d, J=8.56 Hz, 2H), 7.43–7.25 (m, 10H), 6.92 (t, J=8.56 Hz, 2H), 4.33 (s, 2H), 3.02 (s, 3H). MS (EI-thermospray): m/z 439 (MH+). HRMS Δ=1.6 mmu.

EXAMPLE 30

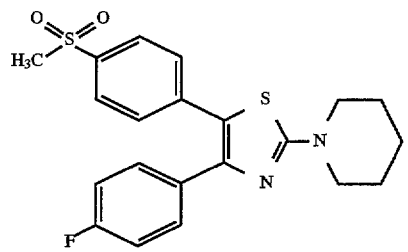

4-(4-Fluorophenyl)-5-(4-methylsulfonylphenyl)-2-(1-piperidinyl)thiazole

To a solution of 2-bromo-1-(4-fluorophenyl)-2-(4-methylsulfonylphenyl)ethanone (0.462 g, 1.24 mmol) (Example 26, Step 2) in ethanol (10 mL) in a 25 mL round bottom flask was added piperidine thiocarboxamide (0.198 g, 1.37 mmol) and the solution was heated to reflux for 14 hours. The reaction was cooled to room temperature and concentrated in vacuo yielding a foam. This foam was dissolved in methylene chloride and washed successively with NaHCO$_3$ saturated solution (3 portions) and brine, dried over Na$_2$SO$_4$, filtered and reconcentrated in vacuo yielding 4-(4-fluorophenyl)-5-(4-methylsulfonylphenyl)-2-(1-piperidinyl)-thiazole (0.371 g, 72%) as a yellow-green fluffy solid: mp 173°–175° C., $^1$H NMR (CDCl$_3$) 400 mHz δ7.77 (d, J=8.56 Hz, 2H), 7.46 (dd, J=5.60, 8.80), 7.38 (d, J=8.56 Hz, 2H), 6.99 (t, J=8.80 Hz, 2H), 3.53 (s (broad), 4H), 3.05 (s, 3H), 1.70 (s (broad), 6H). MS (EI): m/z 417 (MH+). HRMS Δ=–1.5 mmu.

EXAMPLE 31

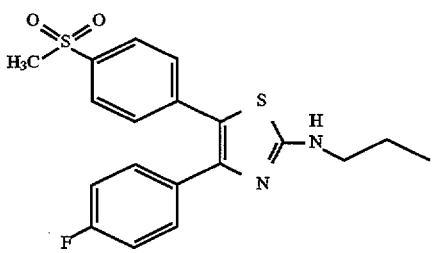

4-(4-Fluorophenyl)-5-(4-methylsulfonylphenyl)-2-(1-propylamino)thiazole

To a solution of 2-bromo-1-(4-fluorophenyl)-2-(4-methylsulfonylphenyl)ethanone (0.346 g, 0.932 mmol) (Example 26, Step 2) in ethanol (15 mL) in a 25 mL round bottom flask was added N-propylthiourea (0.116 g, 0.979 mmol) with stirring. The resulting solution was heated to reflux for 24 hours. The reaction was cooled to room temperature and concentrated in vacuo. The residue was dissolved in methylene chloride, washed successively with Na$_2$CO$_3$ (10% solution) and brine, dried over Na$_2$SO$_4$, filtered and reconcentrated in vacuo yielding 4-(4-fluorophenyl)-5-(4-methylsulfonylphenyl)-2-(1-propylamino) thiazole as a yellow crystalline solid (0.276 g, 76%): mp 181°–182° C. $^1$H NMR (DMSO-d$_6$) 400 mHz 5 7.97 (t, J=5.37 Hz, 1H), 7.78 (d, J=8.79 Hz, H), 7.42 (dd, J=5.86, 8.79, 2H), 7.37 (d, J=8.79, H), 7.15 (t, J=8.79 Hz, 2H), 3.21 (q, J=6.84, H), 3.18 (s, 3H), 1.60 (m, 2H), 0.91 (t, J=7.33, H). MS (EI): m/z 390 (M+). HRMS Δ=2.4 mmu.

EXAMPLE 32

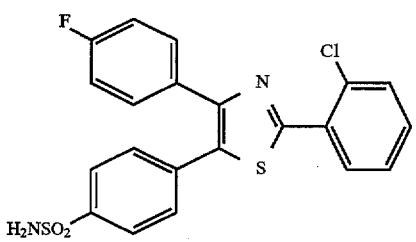

4-[4-(4-Fluorophenyl)-2-(2-chlorophenyl)-5-thiazolyl]benzensulfonamide

To a solution of the methyl sulfone (Example 16) (0.21 g, 0.47 mmol) in tetrahydrofuran (THF) (5 mL) at 0° C. under nitrogen was added 2M n-butyl magnesium chloride in THF (1.0 mL, 2.0 mmol) slowly, via syringe, and the mixture stirred at 0° C. for 30 minutes and then at room temperature (25° C.) for 2 hours. After cooling to 0° C., a 1.0M solution of triethyl borane in THF (2.5 mL, 2.5 mmol) was added and the mixture warmed to room temperature and stirred for 2 hours, and then heated to reflux overnight (18 hours). After cooling to room temperature and stirring for 3 hours, water (3 mL) was added followed by sodium acetate (1.2 g) and hydroxylamine-O-sulfonic acid (0.82 g). After stirring at room temperature overnight, the mixture was poured into 3 volumes of ethyl acetate, and the organic layer washed with water and brine and dried over $MgSO_4$. After solvent removal, the white solids (a mixture of product and starting material) was recrystalized from ethyl acetate/hexane to provide 0.11 g of a white solid. Anal. Calc'd for $C_{21}H_{14}N_2O_2S_2FCl$: C, 56.69; H, 3.17; N, 6.30. Found: C, 55.99; H, 2.97; N, 6.15.

EXAMPLE 33

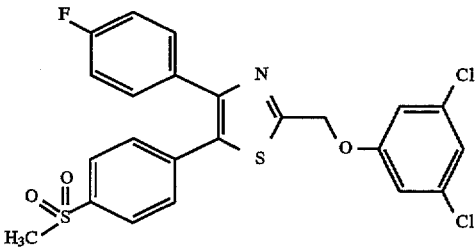

2-[(3,5-Dichlorophenoxy)methyl]-4-(4-fluorophenyl)-5-[4-(methylsulfonyl)phenyl]thiazole Step 1 Preparation of 2-((3,5-dichlorophenoxy) methyl)-4-(4-fluorophenyl)-5-(4-methylthiophenyl)thiazole:

A solution of 1-(4-fluorophenyl)-2-(4-methylthiophenyl)-2-bromoethanone, (Example 1, Step 3) (4.01 g, 11.8 mmol) and 3,5-dichlorophenoxy thioacetamide (2.80 g, 11.9 mmol) in 20 mL of acetonitrile and 10 mL of ethanol was heated to reflux for 1.2 hours. The solution was diluted with methanol, cooled to 0° C. in an ice bath and a precipitate formed that was removed by filtration to provide pure 4-(4-fluorophen-yl)5-(4-methylthiophenyl)-2-((3,5-dichlorophenoxy)-methyl)thiazole (4.19 g; 74%) which was used directly in the next step: mp 104.5°–105.0° C.; Mass spectrum M+H=476.

Step 2 Preparation of 2-((3,5-dichlorophenoxy) methyl)-4-(4-fluorophenyl)-5-(4-methylsulfonylphenyl)thiazole:

A dichloromethane (30 mL) solution of the thiazole from Step 1 (4.06 g, 8.52 mmol) was treated with m-chloroperoxybenzoic acid (5.98 g, 17.06 mmol) and stirred at room temperature for 0.75 hour. The solution was then washed successively with 10% aq. $NaHSO_3$, 10% $Na_2CO_3$, dried over anhydrous $MgSO_4$, filtered and concentrated in vacuo to give a white solid that was recrystallized from a mixture of dichloromethane and isooctane to afford 2.50 g (58%) of pure 2-((3,5-dichlorophenoxy)methyl)-4-(4-fluorophenyl)-5-(4-methylsulfonylphenyl)thiazole as a white solid: mp 171°–173° C.; $^1$H NMR ($CDCl_3$) 300 MHz 7.88 (d, J=8.5Hz, 2H), 7.54 (d, J=8.5Hz, 2H), 7.50–7.40 (m, 2H), 7.07–6.90 (m, 5H), 5.37 (s, 2H), 3.08 (s, 3H); $^{19}$F NMR ($CDCl_3$) 112.53 (m). High resolution mass spectrum calc'd. for $C_{23}H_{16}ClFNO_3S_2$ (MH$^+$): 506.9933. Found: 506.9932.

EXAMPLE 34

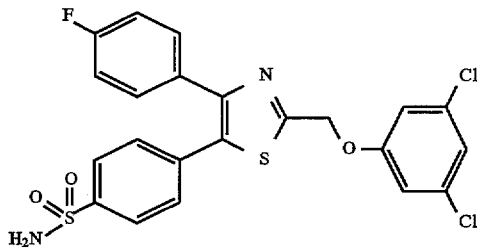

4-[2-((3,5-Dichlorophenoxy)methyl)-4-(4-fluorophenyl)-5-thiazolyl]benezenesulfonamide To a solution of 2-((3,5-dichlorophenoxy)methyl)-4-(4-fluorophenyl)-5-(4-methylsulfonylphenyl)thiazole (Example 33) (0.508 g, 1.0 mmol) in THF (5 mL) at 0° C. under nitrogen was added 2.0M n-butyl magnesium chloride in THF (1.6 mL, 3.2 mmol) slowly, via syringe, and the mixture stirred at 0° C. for 30 minutes and then at room temperature (25° C.) for 2 hours. After cooling to 0° C., a 1.0M solution of triethyl borane in THF (5 mL, 5 mmol) was added and the mixture was warmed to room temperature and stirred for 2 hours, and then heated to reflux for 36 hours. After cooling to room temperature and stirring for 3 hours, water (3 mL) was added followed by sodium acetate (1.2 g) and hydroxylamine-O-sulfonic acid (0.82 g). After stirring at room temperature overnight, the mixture was poured into 3 volumes of ethyl acetate, and the organic layer washed with water and brine and dried over $MgSO_4$. After solvent removal, the white solids (a mixture of product and starting material) were purified by flash chromatography on silica gel using 30% ethyl acetate/70% hexane to provide 4-[4-(4-fluorophenyl)-2-((3,5-dichlorophenoxy)methyl)-5-thiazolyl]benzenesulfonamide as a white solid (0.147 g): Anal. Calc'd for $C_{22}H_{15}N_2O_3S_2FCl_2$: C, 51.87; H, 2.97; N, 5.50. Found: C, 52.19; H, 2.84; N, 5.40

EXAMPLE 35

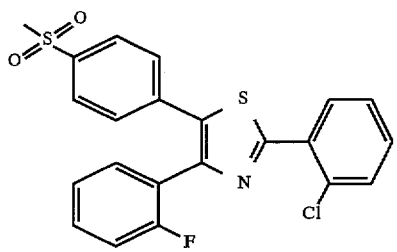

2-(2-Chlorophenyl)-4-(2-fluorophenyl)-5-(4-methylsulfonylphenyl)thiazole

Step 1 Preparation of 2- (2-fluorophenyl)-3-(4-methylthiophenyl)propenoic acid:

Acetic anhydride (60 mL), 4-(methylthio)benzaldehyde (7.05 g, 44 mmol), 2-fluorophenylacetic acid (7.79 g, 50.5 mmol), and triethylamine (5.50 g, 54.5 mmol) were placed in a 250 mL round bottom flask and heated to reflux for 1.75 hours. The reaction was cooled to 90° C., and water (100 mL) was added cautiously through an addition funnel. This caused the solution to reflux vigorously and the temperature to rise to 135° C. A yellow precipitate formed and after cooling to room temperature the solid was collected by filtration, washed with water, and recrystallized from toluene to provide 2-(2-fluorophenyl)-3-(4-methylthiophenyl) propenoic acid as yellow needles (7.98 g, 63%): mp 151.5°–156.0° C. $^1$H NMR (CDCl$_3$) 300 MHz 8.01 (s,1H), 7.41–7.00 (m, 8H), 2.43 (s, 3H). $^{19}$F NMR (CDCl$_3$) –113.40 (m). Mass spectrum M+H$^+$=289.

Step 2 Preparation of 1-(2-fluorophenyl)-2-(4-methylthiophenyl)ethanone:

A solution of 2-(2-fluorophenyl)-3-(4-methylthiophenyl) propenoic acid from Step 1 (7.86 g, 27.3 mmol) and triethylamine (2.80 g, 27.7 mmol) in 22 mL of anhydrous toluene was cooled to 0° C. and treated with diphenylphosphoryl azide (7.73 g, 28.1 mmol). The solution was stirred at 0° C. for 20 minutes and at room temperature for 3.50 hours. The reaction was poured into water, extracted with ether, dried over magnesium sulfate, and concentrated in vacuo to remove the ether. The remaining toluene solution was heated to reflux and a vigorous evolution of gas occurred. After 0.75 hours, 11 mL of tert-butyl alcohol was added to the reaction. After an additional twenty minutes, concentrated hydrochloric acid (5 mL) was added slowly and the reaction was heated at 90 ° C. overnight (14 hours). The solution was cooled to room temperature and diluted with ethyl acetate, washed with saturated aqueous NaHCO$_3$, brine, dried over anhydrous MgSO$_4$, filtered and concentrated in vacuo to provide a brown solid that was purified by crystallization from ether to afford 1-(2-fluorophenyl)-2-(4-methylthiophenyl)ethanone as a yellow solid (4.60 g, 65%): mp 58°–59.5° C. $^1$H NMR (CDCl$_3$) 300 MHz 7.84 (m, 1H), 7.52 (m, 1H), 7.23–7.08 (m, 6H), 4.25 (d, J=2.6Hz, 2H), 2.46 (s, 3H). $^{19}$F NMR (CDCl$_3$) –108.51 (m). Mass spectrum M+H$^+$=261.

Step 3 Preparation of 1-(2-fluorophenyl)-2-(4-methylthiophenyl)-2-bromo-ethanone:

A 100 mL three necked round bottomed flask equipped with reflux condenser, magnetic stir bar, thermometer adapter, and constant pressure addition funnel was charged with 1-(2-fluorophenyl)-2-(4-methylthiophenyl)ethanone from Step 2, (4.36 g, 16.7 mmol), acetic acid (30 mL) and 33% HBr in acetic acid (0.5 mL). The solution was stirred and treated with bromine (17 mL, 16.8 mmol, 1.0M in acetic acid) from the addition funnel at such a rate that the bromine color was discharged rapidly, ca, 15 min. After an additional 50 minutes at room temperature, the solution was concentrated in vacuo to give a brown oil. The crude haloketone was dissolved in dichloromethane and washed with 1N NaHSO$_3$, dried over anhydrous MgSO$_4$, filtered and concentrated in vacuo to give 1-(2-fluorophenyl)-2-(4-methylthiophenyl)-2-bromo-ethanone as an oil that solidified upon standing (4.83 g, 85%): mp 58°–63° C. $^1$H NMR (CDCl$_3$) 300 MHz 7.87 (td, J=7.6, 1.8Hz, 1H), 7.52 (m, 1H), 7.39 (d, J=8.3Hz, 2H), 7.27–7.03 (m, 4H), 6.34 (s, 1H), 2.45 (s, 3H). $^{19}$F NMR (CDCl$_3$) –108.51 (m). Mass spectrum M$^+$=338.

Step 4 Preparation of 2-(2-chlorophenyl)-4-(2-fluorophenyl) -5-(4-methylthiophenyl) thiazole;

A solution of 1-(2-fluorophenyl)-2-(4-methylthiophenyl) -2-bromo-ethanone from Step 3 (1.39 g, 4.1 mmol) and 2-chlorothiobenzamide (0.71 g, 4.1 mmol) in 10 mL of ethanol was heated to reflux for 4.4 hours. The solution was cooled to room temperature and poured into 25 mL of methanol, chilled with an ice bath whereupon crystals of pure product formed which were isolated by filtration and air dried to afford the thiazole (1.34 g, 79%): mp 117°–119° C. $^1$H NMR (CDCl$_3$) 300 MHz 8.37 (m, 1H), 7.62 (m, 2H), 7.49 (d, J=7.7Hz,1H), 7.32 (m, 7H), 7.22 (d, J=8.5Hz, 2H), 2.51 (s, 3H). Mass spectrum M$^+$+H=412.

Step Preparation of 2-(2-chlorophenyl)-4-(2-fluorophenyl)-5-(4-methylsulfonylphenyl) thiazole:

A solution of 2-(2-chlorophenyl)-4-(2-fluorophenyl)-5-(4-methylthiophenyl)thiazole (1.12 g, 2.72 mmol) in 20 mL of dichloromethane was treated with m-chloroperoxybenzoic acid (1.91 g, 5.53 mmol) at 0° C. for 20 minutes. The solution was washed with 10% aqueous NaHSO$_3$, 10% Na$_2$CO$_3$, dried over anhydrous MgSO$_4$, filtered and concentrated in vacuo to give a yellow solid that was purified by recrystallization from a mixture of dichloromethane and isooctane to provide 660 mg (55%) of pure product: mp 163°–166° C. $^1$H NMR (CDCl$_3$) 300 MHz 8.37 (m, 1H), 7.86 (d, J=8.5Hz, 2H), 7.63 (td, J=7.7, 1.8 Hz, 2 H), 7.53 (d, J=8.5Hz, 2H), 7.53 (m, 1H), 7.38 (m, 3H), 7.26 (t, J=7.4Hz, 1H), 7.05 (t, J=9.6Hz, 1H), 3.06 (s, 3H). $^{19}$F NMR (CDCl$_3$) –113.33 (m). High resolution mass spectrum calc'd. for C$_{22}$H$_{15}$ClFNO$_2$S$_2$: 443.0217. Found: 443.0176.

EXAMPLE 36

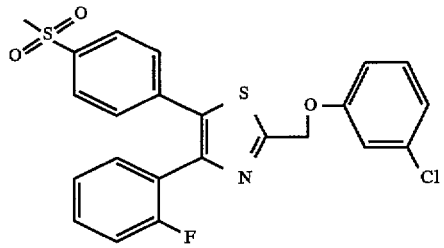

2-(3-Chlorophenoxy)methyl-4-(2-fluorophenyl)-5-[4-(methylsulfonyl)phenyl]thiazole Step 1 Preparation of 2- ( (3 -chlorophenoxy) methyl/-4-(2-fluorophenyl)-5-(4-methylthiophenyl)thiazole:

A solution of 1-(2-fluorophenyl)-2-(4-methylthiophenyl) -2-bromo ethanone, (1.64 g, 4.8 mmol) (Example 34, Step 3) and 3-chlorophenoxy thioacetamide (0.98 g, 4.8 mmol) in 25 mL of acetonitrile was heated to reflux for 14 hours. The solution was diluted with methanol, cooled to 0° C. in an ice bath and a precipitate formed that was removed by filtration to provide pure 2-((3-chlorophenoxy)methyl)-4-(2-fluorophenyl)-5-(4-methylthiophenyl)thiazole (0.69 g; 32%). The filtrate was concentrated in vacuo, and the residue dissolved in ethyl acetate, washed with water, brine, dried over anhydrous MgSO$_4$, filtered and concentrated in vacuo to provide additional product that was crystallized from a mixture of dichloromethane and isooctane to provide 200 mg of additional material for a total yield of 890 mg (42%): mp 115°–118° C.: $^1$H NMR (CDCl$_3$) 300 MHz 7.52–6.90 (m, 12H), 5.38 (s, 2H), 2.46 (s, 3H). $^{19}$F NMR (CDCl$_3$) –113.61 (m). High resolution mass spectrum calc'd. for C$_{23}$H$_{17}$ClFNOS$_2$ (M$^+$): 441.0424. Found: 441.0467.

Step 2 Preparation of 2-((3-Chlorophenoxy)methyl)-4-(2-fluorophenyl)-5-(4-methylsulfonylphenyl)thiazole:

A dichloromethane (5 mL) solution of 2-((3-chlorophenoxy)methyl)-4-(2-fluorophenyl)-5-(4-methylthiophenyl)thiazole from Step 1 (0.85 g, 1.9 mmol) was treated with m-chloroperoxybenzoic acid (1.33 g, 3.9 mmol) and stirred at room temperature for 15 hours. The solution was then washed with 10% aq. NaHSO$_3$, 10% Na$_2$CO$_3$, dried over anhydrous MgSO$_4$, filtered and concentrated in vacuo to give a white solid that was recrystallized from a mixture of dichloromethane and isooctane to afford 0.71 g (78%) of pure 4-(2-fluorophenyl)-5-(4-methylsulfonylphenyl)-2-((3-chlorophenoxy)methyl)thiazole as a white solid: mp 151.5°–153° C. $^1$H NMR (CDCl$_3$) 300 MHz 7.84 (d, J=8.3Hz, 2H), 7.50 (m, 1H), 7.46 (d, J=8.3Hz, 2H), 7.39 (m, 1H), 7.24 (m, 2H), 7.06 (m, 3H), 6.92 (m, 1H), 5.41 (s, 2H), 3.06 (s, 3H). $^{19}$F NMR (CDCl$_3$) –113.64 (m). High resolution mass spectrum calc'd. for C$_{23}$H$_{17}$ClFNO$_3$S$_2$ (MH$^+$): 473.0322. Found: 473.0346.

EXAMPLE 37

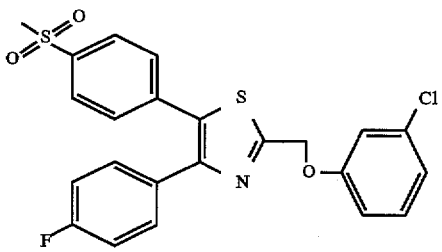

2-((3-Chlorophenoxy)methyl)-4-(4-fluorophenyl)-5-(4-methylsulfonylphenyl)thiazole Step 1 Preparation of 2-((3-Chlorophenoxy)methyl)-4-(4-fluorophenyl)-5-(4-methylthiophenyl) thiazole:

A solution of 1-(4-fluorophenyl)-2-(4-methylthiophenyl)-2-bromo-ethanone (1.98 g, 5.84 mmol) (Example 1, Step 3) and 3-chlorophenoxy thioacetamide (1.18 g, 5.85 mmol) in 15 mL of acetonitrile and 10 mL of ethanol was heated to reflux for 16 hours. The solution was diluted with methanol, cooled to 0° C. in an ice bath and a precipitate formed that was removed by filtration. The solid was air dried and then recrystallized from methanol to provide (1.67 g; 65%),of pure 2-((3-chlorophenoxy)methyl)-4-(4-fluorophenyl)-5-(4-methylthiophenyl)thiazole: mp 106°–110° C., $^1$NMR (CDCl$_3$) 300 MHz 7.50 (m, 2H), 7.30–7.15 (m, 5H), 7.09–6.87 (m, 5H), 5.38 (s, 2H), 2.50 (s, 3H). 19F NMR (CDCl$_3$) –113.58 (m). Mass spectrum M$^+$=441.

Step 2 Preparation of 2-((3-Chlorophenoxy)methyl)-4-(4-fluorophenyl)-5-(4-methylsulfonylphenyl)thiazole:

A dichloromethane (10 mL) solution of 2-((3-chlorophenoxy)methyl)-4-(4-fluorophenyl)-5-(4-methylthiophenyl)thiazole (0.65 g, 1.47 mmol) was treated with m-chloroperoxybenzoic acid (1.03 g, 2.98 mmol) and stirred at room temperature for 1.2 hours. The solution was washed with 10% aq. NaHSO$_3$, 10% Na$_2$CO$_3$, dried over anhydrous MgSO$_4$, filtered and concentrated in vacuo to give a white solid that was recrystallized from dichloromethane to afford 0.50 g (72%) of pure 2-((3-chlorophenoxy)methyl)-4-(4-fluorophenyl)- 5-(4-methylsulfonylphenyl)thiazole as a white solid: mp 128.5°–131° C. $^1$H NMR (CDCl$_3$) 300 MHz 7.89 (d, J=8.1 Hz, 2H), 7.52 (d, J=8.1Hz, 2H), 7.46 (m, 1H), 7.25 (t, J=8.5Hz, 1H), 7.03 (m, 3H), 6.95 (m, 1H), 5.39 (s, 2H), 3.08 (s, 3H). 19F NMR (CDCl$_3$) –112.43 (m). Mass spectrum M+H$^+$=474.

EXAMPLE 38

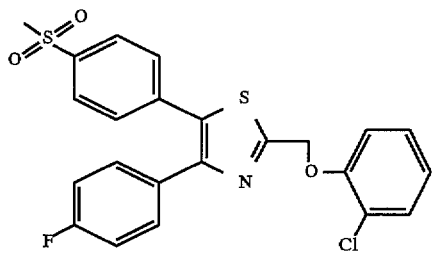

2-((2-Chlorophenoxy)methyl)-4-(4-fluorophenyl)-5-(4-methylsulfonylphenyl)thiazole Step 1 Preparation of 2-((2-chlorophenoxy)methyl)-4-(4-fluorophenyl)-5-(4-methylthiophenyl)thiazole:

A solution of 1-(4-fluorophenyl)-2-(4-methylthiophenyl)-2-bromo-ethanone (2.05 g, 6.04 mmol) (Example 1, Step 3) and 2-chlorophenoxy thioacetamide (1.21 g, 6.0 mmol) in 30 mL of acetonitrile was heated to reflux for 3 hours. The solution was diluted with methanol, cooled to 0° C. in an ice bath and a precipitate formed that was removed by filtration. The crude solid was further purified by flash chromatography over silica gel and the appropriate fractions were combined, concentrated in vacuo and crystallized from methanol to provide 2.60 g (98%) of pure 4-2- ( (2-chlorophenoxy) methyl)-4-(4-fluorophenyl)-5-(4-methylthiophenyl) thiazole: mp 126°–129° C., $^1$H NMR (CDCl$_3$) 300 MHz 7.55–7.39 (m, 4H), 7.28–6.90 (m, 8H), 5.44 (s, 2H), 2.49 (s, 3H). $^{19}$F NMR (CDCl$_3$) –114.00 (m). Mass spectrum M+H$^+$=442.

Step 2 Preparation of 2-((2-Chlorophenoxy)methyl)-4-(4-fluorophenyl)-5-(4-methylsulfonylphenyl)thiazole:

A dichloromethane (50 mL) solution of 2-((2-chlorophenoxy)methyl)-4-(4-fluorophenyl)-5-(4-methylthiophenyl)thiazole from Step 1 (2.65 g, 6.0 mmol) was treated with m-chloroperoxybenzoic acid (4.19 g, 12.1 mmol) and stirred at room temperature for 3 hours. The solution was washed with 10% aq. NaHSO$_3$, 10% Na$_2$CO$_3$, dried over anhydrous MgSO$_4$, filtered and concentrated in vacuo to give a white solid that was purfied by flash chromatography (silica gel) eluting with hexane/ethyl acetate to afford 2.08 g (73%) of pure 2-((2-chlorophenoxy) methyl)-4-(4-fluorophenyl)-5-(4-methylsulfonylphenyl) thiazole as a white solid, after concentration of the appropriate fractions: mp 189°–191° C. $^1$H NMR (CDCl$_3$) 300 MHz 7.89 (d, J=8.5 Hz, 2H), 7.53 (d, J=8.5Hz, 2H), 7.50–7.47 (m, 3H), 7.23 (m, 1H), 7.10–6.95 (m, 4H), 5.47 (s, 2H), 3.08 (s, 3H). $^{19}$F NMR (CDCl$_3$) –112.75 (m). High resolution mass spectrum calc'd. for C$_{23}$H$_{17}$ClFNO$_3$S$_2$: 473.0322. Found: 473.0374.

EXAMPLE 39

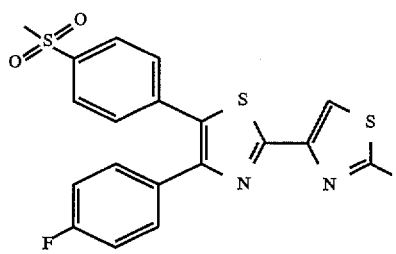

4-(4-Fluorophenyl)-5-[4-(methylsulfonyl)phenyl]-2-
(2-methyl-4-thiazolyl)thiazole Step Preparation of 4-(4-fluorophenyl)-5-(4-methylthiophenyl)-2-[2-(methyl)-4-thiazolyl)thiazole:

A solution of 1-(4-fluorophenyl)-2-(4-methylthiophenyl)-2-bromoethanone (9.69 g, 28.6 mmol) (Example 1, Step 3) and 2-methylthiazole-4-thiocarboxamide (3.90 g, 24.7 mmol) in 35 mL of acetonitrile and 20 mL of ethanol was heated to reflux for 1 hour. The solution was concentrated in vacuo and the residue was dissolved in ethyl acetate, washed with saturated aqueous NaHCO₃, brine, dried over anhydrous MgSO₄, filtered and concentrated in vacuo to give a yellow solid. The crude solid was purified by flash chromatography over silica gel eluting with 1:1 hexane:ethyl acetate. The appropriate fractions were combined and the solvent removed in vacuo to provide pure 4-(4-fluorophenyl)-5-(4-methylthiophenyl)-2-[2-(methyl)-4-thiazolyl]thiazole (4.79 g; 49%): mp 132.5°–135° C. $^1$H NMR (CDCl₃) 300 MHz 7.89 (s, 1H), 7.55 (m, 2H), 7.25 (d, J=8.5Hz, 2H), 7.17 (d, J=8.5Hz, 2H), 7.01 (t, J=8.8Hz, 2H), 2.78 (s, 3H), 2.49 (s, 3H). $^{19}$F NMR (CDCl₃) –113.80 (m). Mass spectrum M+H$^+$=399.

Step 2 Preparation of 4-(4-fluorophenyl)-5-(4-methylsulfonylphenyl)-2-[2-(methyl)-4-thiazolyl]thiazole:

A dichloromethane (15 mL) solution of 4-(4-(fluorophenyl)-5-(4-methylthiophenyl)-2-[2-(methyl)-4-thiazolyl]thiazole from Step 1 (0.71 g, 1.78 mmol) was treated with m-chloroperoxybenzoic acid (1.25 g, 3.62 mmol) and stirred at room temperature for 2 hours. The solution was washed with 10% aq. NaHSO₃, 10% Na₂CO₃, dried over anhydrous MgSO₄, filtered and concentrated in vacuo to give a white solid that was purfied by crystallization from a mixture of dichloromethane and isooctane to afford pure 4-(4-fluorophenyl)-5-(4-methylsulfonylphenyl)-2-[2-(methyl)thiazol-4-yl]thiazole (0.37 g, 48%) as a white solid: mp 184°–185.5° C. $^1$H NMR (CDCl₃) 300 MHz 7.93 (s, 1H), 7.88 (d, J=8.5Hz, 2H), 7.54 (d, J=8.5Hz, 2H), 7.53 (m, 2H), 7.04 (t, J=8.8Hz, 2H), 3.08 (s, 3H), 2.79 (s, 3H). 19F NMR (CDCl₃) –112.61 (m). Mass spectrum M$^+$=430.

EXAMPLE 40

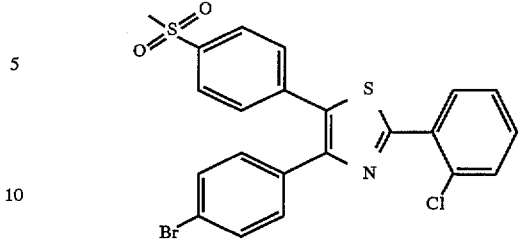

4-(4-Bromophenyl)-2-(2-chlorophenyl)-5-[4-(methylsulfonyl)phenyl]thiazole

Step 1 Preparation of 2-(4-bromophenyl) 3-(4-methylthiophenyl)propenoic acid:

A mixture of acetic anhydride (100 mL), 4-(methylthio)benzaldehyde (12.61 g, 82.8 mmol), 4-bromophenylacetic acid (17.79 g, 82.7 mmol), and triethylamine (8.48 g, 83.8 mmol) was heated to reflux for 4.25 hours. The reaction was cooled to 90° C., and water (100 mL) was added through an addition funnel. A yellow solid separated from the solution and was isolated by filtration and air dried and recrystallized from a mixture of ethyl acetate and isooctane to afford the acid (12.83 g, 44%): mp 187°–190° C. $^1$H NMR (acetone d$^6$) 300 MHz 7.83 (s,1H), 7.57 (d, J=8.5Hz, 1H), 7.20 (d, J=8.5Hz, 2H), 7.10 (d, J=8.1Hz, 2H), 7.08 (d, J=8.1Hz, 1H), 2.46 (s, 3H). Mass spectrum M$^+$+H=350.

Step 2 Preparation of 1-(4-bromophenyl)2-(4-methylthiophenyl)ethanone:

A solution of 3-(4-methylthiophenyl)-2-(4-bromophenyl)propenoic acid from Step 1 (12.66 g, 36 mmol) and triethylamine (4.27 g, 42 mmol) was dissolved in 60 mL of anhydrous toluene, cooled to 0° C. and treated with diphenylphosphoryl azide (10.04 g, 36 mmol). The solution was maintained at 0° C. for 0.5 hour and warmed to room temperature for 3.33 hours. The reaction was poured into water, extracted with ether, dried over magnesium sulfate, and concentrated in vacuo to remove the ether. The remaining toluene solution was heated to 100 ° C. for 1 hour. tert-Butyl alcohol (6.5 mL) was added to the reaction mixture. After an additional ten minutes, concentrated hydrochloric acid (4 mL) was cautiously added and the reaction maintained at 80° C. for 72 hours. After cooling with an ice bath, a solid separated and was isolated by filtration, washed with water, and air dried to afford pure white ketone (8.41 g, 72%): mp 158.5°–163° C. $^1$H NMR (acetone d$_6$) 300 MHz 8.00 (d, J=8.3Hz, 2H), 7.71 (d, J=8.3Hz, 2H), 7.24 (s, 4H), 4.35 (s, 2H), 2.47 (s, 3H). Mass spectrum M$^+$+H=321 and 323.

Step 3 Preparation of 2-bromo-1-(4-bromophenyl)-2-(4-methylthiophenyl)ethanone:

A solution of 1-(4-bromophenyl)-2-(4-methylthiophenyl) ethanone from Step 2 (8.40 g, 26 mmol) in acetic acid (135 mL) and 33% HBr in acetic acid (1.5 mL) was treated with a 0.99M solution of bromine in acetic acid (27 mL, 26.6 mmol) and stirred at room temperature for ten minutes. The solution was concentrated in vacuo and the residue taken up in dichloromethane, washed with 1N NaHSO₃, 10% Na₂CO₃, dried over anhydrous MgSO₄, filtered and concentrated in vacuo to give a gray solid which was recrystallized from a mixture of dichloromethane and isooctane to provide the bromoketone (8.50 g, 81%): mp 107°–111° C. ¹HNMR (CDCl₃) 300 MHz 7.83 (d, J=8.7Hz, 2H), 7.58 (d, J=8.7Hz, 2H), 7.41 (d, J=8.3Hz, 2H), 7.22 (d, J=8.3Hz, 2H), 6.27 (s, 1H), 2.47 (s, 3H). Mass spectrum M⁺+H=399, 401 and 403.

Step 4 Preparation of 4-(4-bromophenyl)-2-(2-chlorophenyl)-5-(4- methylthiophenyl)thiazole:

A solution of 2-bromo-1-(4-bromophenyl)-2-(4-methylthiophenyl)ethanone from Step 3 (1.18 g, 2.9 mmol) and 4-chlorothiobenzamide (520 mg, 3.0 mmol) in 40 mL of acetonitrile was heated to reflux for 1.75 hours. The solution was cooled to room temperature, poured into 100 mL of methanol and chilled with an ice bath, whereupon white crystals of pure product formed which were isolated by filtration and air dried. The product was further purified by flash chromatography over silica gel eluting with 8% ether in hexane to afford pure thiazole (1.10 g, 79%) which was used directly in the next step: mp 133°–135° C., ¹H NMR (CDCl₃) 300 MHz 8.35 (m, 1H), 7.52–7.21 (m, 11H), 2.51 (s, 3H). Mass spectrum M⁺+H=474.

Step 5 Preparation of 4-(4-bromophenyl)-2-(2-chlorophenyl)-5-(4-methylsulfonylphenyl)thiazole:

A solution of 4-(4-bromophenyl)-2-(2-chlorophenyl)-5-(4-methylthiophenyl)thiazole from Step 4 (1.06 g, 2.2 mmol) in 15 mL of dichloromethane was treated with m-chloroperoxybenzoic acid (1.60 g, 4.6 mmol) at room temperature for 0.08 hour. The solution was diluted with additional dichloromethane, washed with 10% aq. NaHSO₃, 10% Na₂CO₃, dried over anhydrous MgSO₄, filtered and concentrated in vacuo to give a white solid that was purified by recrystallization from a mixture of dichloromethane and isooctane to give the product (850 mg, 75%): mp 168°–184° C. ¹H NMR (CDCl₃) 300 MHz 8.38 (m, 1H), 7.92 (d, J=8.5Hz, 2H), 7.60 (d, J=8.5 Hz, 2H), 7.54–7.38 (m, 7H), 3.10 (s, 3H). High resolution mass spectrum calc'd. for C₂₂H₁₅BrClNO₂S: 502.9416. Found: 502.9436.

EXAMPLE 41

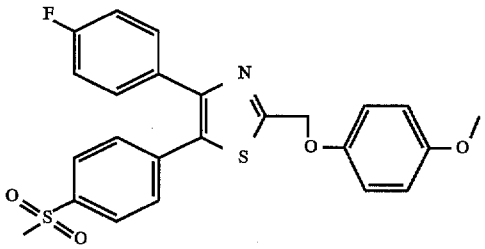

4-(4-Fluorophenyl)-2-[(4-methoxyphenoxy)methyl]-5-[4-(methylsulfonyl)phenyl]thiazole Step 1 Preparation of 4-(4-fluorophenyl)-5-(4-methylthiophenyl)-2-((4-methoxyphenoxy) methyl) thiazole:

A solution of 1-(4-fluorophenyl)-2-(4-methylthiophenyl)-2-bromo-ethanone, (Example 1, Step 3) (2.30 g, 6.8 mmol) and 4-methoxyphenoxy thioacetamide (1.35 g, 6.8 mmol) in 20 mL of acetonitrile was heated to reflux for 1.1 hours. The solution was concentrated in vacuo and the residue dissolved in ethyl acetate. The ethyl acetate solution was washed with saturated aqueous NaHCO₃, brine, dried over anhydrous MgSO₄, filtered and concentrated in vacuo to afford a solid that was recrystallized from a mixture of ethyl acetate and isooctane to provide pure 4- (4-fluorophenyl) -5-(4-methylthiophenyl)-2-((4-methoxyphenoxy) methyl) thiazole (1.60 g; 54%): mp 89°–92° C., ¹H NMR (CDCl₃) 300 MHz 7.47 (dd, J=3.2, 8.7Hz, 2H), 7.23 (d, J=8.5 Hz, 2H), 7.17 (d, J=8.5Hz, 2H), 6.98 (m, 4H), 6.86 (d, J=9.1 Hz, 2H), 5.33 (s, 2H), 3.78 (s, 3H), 2.49 (s,3H). ¹⁹F NMR (CDCl₃) −114.07 (m). Mass spectrum M⁺H+=438.

Step 2 Preparation of 4-(4-fluorophenyl)-5-(4-methylsulfonylphenyl)-2-((4-methoxyphenoxy) methyl) thiazole:

A dichloromethane (20 mL) solution of 4-(4-fluorophenyl)-5-(4-methylthiophenyl)-2-((4-methoxyphenoxy)methyl)thiazole from Step 1 (1.45 g, 3.3 mmol) was treated with m-chloroperoxybenzoic acid (2.32 g, 6.7 mmol) and stirred at room temperature for 0.42 hour. The solution was washed with 10% aqueous NaHSO₃, 10% Na₂CO₃, dried over anhydrous MgSO₄, filtered and concentrated in vacuo to give a tan solid that was recrystallized from a mixture of dichloromethane and isooctane to afford 0.93 g (60%) of pure 4-(4-fluorophenyl)-5-(4-methylsulfonylphenyl)-2-((4-methoxyphenoxy)methyl) thiazole as a light tan solid: mp 160°–164° C. ¹H NMR (CDCl₃) 300 MHz 7.88 (d, J=8.3Hz, 2H), 7.71 (d, J=8.3Hz, 2H), 7.45 (dd, J=5.4, 8.7Hz, 2H), 7.03 (d, J=8.7Hz, 5H), 6.98 (d, J=9.1Hz, 2H), 8.68 (d, J=9.1Hz, 2H), 5.35 (s, 2H), 3.77 (s, 3H), 3.08 (s, 3H). ¹⁹F NMR (CDCl₃) 112.80 (m). High resolution mass spectrum calc'd. for C₂₄H₂₀FNO₄S₂: 469.0818. Found: 469.0854.

EXAMPLE 42

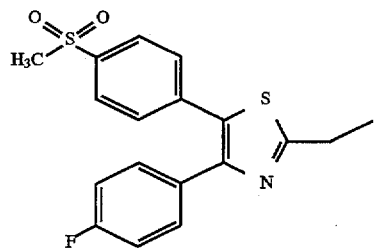

2-Ethyl-4-(4-fluorophenyl)-5-(4-methylsulfonylphenyl)thiazole

Step 1 Preparation of 2-ethyl-4-(4-fluorophenyl)-5-(4-methylthiophenyl)thiazole:

To a solution of 2-bromo-1-(4-fluorophenyl)-2-(4-methylthiophenyl)ethanone (Example 1, Step 3) (0.250 g, 0.737 mmol) in ethanol (9 mL) in a 25 mL round bottom flask was added thiopropionamide (0.066 g, 0.737 mmol) and the mixture heated to reflux overnight. The reaction was allowed to cool to room temperature, diluted with ethyl acetate (50 mL), washed with NaHCO₃ (10% solution), brine, dried over Na₂SO₄, filtered and concentrated in vacuo. The crude thiazole was recrystallized from methylene chloride and isooctane yielding 2-ethyl-4-(4-fluorophenyl)-5-(4 4-methylthiophenyl)thiazole (0.14 g, 57%) as pale yellow crystals: mp 73°–74° C.; ¹HNMR (CDCl₃) 300 mHz 7.55 (m, 2H), 7.26 (d, J=7.85, 2H), 7.21 (d, J=7.85, 2H), 7.03 (t, J=7.85, 2 H), 3.12 (q, J=7.50 Hz, 2H), 2.54 (s, 3H), 1.47 (t, J=7.50 Hz, 3 H); MS (FAB) m/z 330.08 (MH+), HRMS (EI) Δ=−4.2 mmu.

Step 2 Preparation of 2-ethyl-4-(4-fluorophenyl)-5-(4-methylsulfonylphenyl)thiazole:

To a solution of 2-ethyl-4-(4-fluorophenyl)-5-(4-methylthiophenyl)thiazole from step 1 (0.105 g, 0.32 mmol) in methylene chloride (5 mL) was added at room temperature MCPBA (0.21 g of 67% peroxide content MCPBA, 0.80 mmol) and the reaction was warmed to room temperature and stand for 2 hours. The crude reaction mixture was diluted with methylene chloride (50 mL) and the resulting solution was washed with NaHSO₃ solution (0.1M), NaHCO₃ saturated solution, and brine, dried over Na₂SO₄, filtered and concentrated in vacuo yielding a solid. This solid was flash chromatographed (hexane:ethyl acetate 1:1 with 2% acetic acid) yielding 4-(4-fluorophenyl)-5-(4-methylsulfonylphenyl)-2-ethylthiazole (0.080g, 69%) as a white foam: mp 156°–157° C.; ¹HNMR (CDCl₃) 300 mHz 7.86 (d, J=8.48 Hz, 2H), 7.45 (m, 4 H), 7.00 (t, 8.48 Hz, 2H), 3.13–3.05 (m, 5H), 1.44 (t, J=7.37 Hz, 3H); MS (FAB) m/z 362.07 (MH+), HRMS (MH+) Δ=–2.6 mmu.

EXAMPLE 43

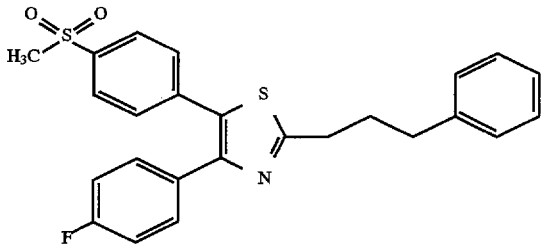

4-(4-Fluorophenyl)-5-(4-methylsulfonylphenyl)-2-(3-phenylpropyl)thiazole

Step 1 preparation of 4-phenylthiobutyramide:

To a solution of 4-phenylbutyramide (0.373 g, 2.28 mmol) in toluene (15 mL) was added Lawesson's reagent (0.461 g, 1.14 mmol). The reaction was refluxed overnight, cooled to room temperature and concentrated yielding an orange oil. Flash chromatography of this oil (1:1 hexane:methylene chloride with 1% acetic acid) yielded 4-phenylthiobutyramide (0.184 g) as a white solid: ¹HNMR (DMSO d₆) 400 mHz 9.33 (s, 1 H), 9.13 ( s, 1 H), 7.29–7.23 (m, 2 H), 7.20–7.15 (m, 3 H), 2.56 (t, J=7.58 Hz, 2 H), 2.50–2.42 (m, 2 H), 2.00–1.85 (m, 2 H).

Step 2 Preparation of 4-(4-fluorophenyl)-5-(4-methylthiophenyl)-2-(3-phenylpropyl)thiazole:

To a solution of 2-bromo-1-(4-fluorophenyl)-2-(4-methylthiophenyl)ethanone (Example 1, step 3) (0.100 g, 0.295 mmol) in ethanol (3 mL) in a 10 mL round bottom flask was added 4-phenylthiobutyramide from step 1 (0.055 g, 0.310 mmol) and the mixture heated to reflux overnight. The reaction was cooled to room temperature, diluted with ethyl acetate (50 mL), washed with Na₂CO₃ (10% solution), brine, dried over Na₂SO₄, filtered and concentrated in vacuo. The crude thiazole was flash chromatographed (9:1, hexane:ethyl acetate) yielding 4-(4-fluorophenyl)-5-(4-methylthiophenyl)-2-(3-phenylpropyl)thiazole (0.118 g, 95%) as crystalline solid: mp 62°–63° C.; ¹HNMR (CDCl₃) 300 mHz 7.49 (d of d, J=5.52 and 8.85, 2H), 7.33–7.14 (m, 9H), 6.98 (t, J=8.85, 2H), 3.05 (t, J=7.74, 2 H), 2.82 (t, J=7.74 Hz, 2H), 2.49 (s, 3H), 2.18 (m, 2 H); MS (FAB) m/z 420 (MH+).

Step 3 Preparation of 4- (4-fluorophenyl)-5-(4-methylsulfonylphenyl)-2-(3-phenylpropyl)thiazole:

To a solution of 4-(4-fluorophenyl)-5-(4-methylthiophenyl)-2-(3-phenylpropyl)thiazole from step 2 (0.11 g, 0.26 mmol) in methylene chloride (3 mL) was added at room temperature MCPBA (0.20 g of 67% peroxide content MCPBA, 0.79 mmol) and the reaction warmed to room temperature and stand for 2 days. The crude reaction mixture was diluted with methylene chloride (50 mL) and the resulting solution was washed with NaHSO₃ solution (0.1M), NaHCO₃ saturated solution, and brine, dried over Na₂SO₄, filtered and concentrated in vacuo. This product was flash chromatographed (1:1 hexane:ethyl acetate with 2% acetic acid) yielding 4-(4-fluorophenyl)-5-(4-methylsulfonylphenyl)-2-(3-phenylpropyl)thiazole 0.040 g, 34%) as an oily off-white foam: ¹HNMR (CDCl₃) 300 mHz 7.87 (d, J=8.31 Hz, 2H), 7.52–7.42 (m, 2 H), 7.38 (d, 8.68 Hz, 2H), 7.76–7.18 (m, 5 H), 7.11 (t, J=8.68 Hz, 2 H), 3.15 (t, J=7.55 Hz, 2H), 3.05 (s, 3 H), 2.83 (t, J=7.55 Hz, 2 H), 2.19 (m 2 H); MS (EI) m/z 452.12 (MH+), HRMS (MH+) Δ=–3.1 mmu.

EXAMPLE 44

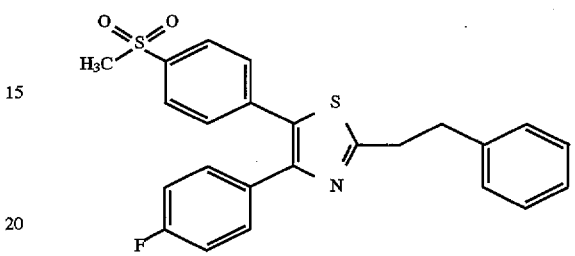

4-(4-Fluorophenyl)-5-(4-methylsulfonylphenyl)-2-(2-phenylethyl)thiazole

Step 1 Preparation of 3 -phenylthiopropionamide;

To a solution of 3-phenylpropionamide (1.653 g, 6.827 mmol) in toluene (20 mL) was added Lawesson's reagent (0.716 g, 1.77 mmol). The reaction was refluxed overnight, cooled to room temperature and concentrated yielding an orange oil. Flash chromatography of this oil (1:1 hexane:methylene chloride with 1% acetic acid) yielded 3-phenylthiopropionamide (0.070 g) as a white solid: mp 82°–83° C.; ¹HNMR (DMSO d₆) 300 mHz 9.35 (br s, 1 H), 9.15 (br s, 1 H), 7.34–7.10 (m, 2 H), 2.95 (t, J=8.48 Hz, 2 H), 2.72 (t, J=8.48 Hz, 2 H).

Step 2 Preparation of 4-(4-fluorophenyl)-5-(4-methylthiophenyl)-2-(2-phenylethyl)thiazole To a solution of 2-bromo-1-(4-fluorophenyl)-2-(4-methylthiophenyl)ethanone (Example 1, Step 3)(0.115 g, 0.340 mmol) in ethanol (4 mL) in a 10 mL round bottom flask was added 3-phenylthiopropionamide from Step 1 (0.059 g, 0.357 mmol) and the mixture was heated to reflux overnight. The reaction was cooled to room temperature, diluted with ethyl acetate (50 mL), washed with Na₂CO₃ (10% solution), brine, dried over Na₂SO₄, filtered and concentrated in vacuo yielding 4-(4-fluorophenyl)-5-(4-methylthiophenyl)-2-(2-phenylethyl)thiazole (0.090 g, 65%) as oily crystals: mp 97°–99° C.; ¹HNMR (CDCl₃) 300 mHz 7.50 (d of d, J=5.38 and 8.80, 2 H), 7.35–7.15 (m, 9H), 6.99 (t, J=8.80, 2H), 3.35 (t, J=8.80, 2 H), 3.19 (t, J=8.56 Hz, 2H), 2.49 (s, 3H); MS (EI) m/z 405.10 (MH+), HRMS (M+) Δ=0.0 mmu.

Step 3 Preparation of 4-(4-fluorophenyl)-5-(4-methylsulfonylphenyl)-2-(2-phenylethyl)thiazole To a solution of 4-(4-fluorophenyl)-5-(4-methylthiophenyl)-2-(2-phenylethyl)thiazole from Step 2 (0.080 g, 0.21 mmol) in methylene chloride (3 mL) was added at room temperature MCPBA (0.110 g of 67% peroxide content MCPBA, 0.42 mmol) and the reaction warmed to room temperature and let stand for 2 days. The crude reaction mixture was diluted with methylene chloride (50 mL) and the resulting solution was washed with NaHSO₃ solution (0.1M), NaHCO₃ saturated solution, and brine, dried over Na₂SO₄, filtered and concentrated in vacuo. This product was recrystallized from methylene chloride and isooctane yielding 4-(4-fluorophenyl)-5-(4- methylsulfonylphenyl)-2-(2-phenylethyl)thiazole (0.111 g, 100%) as a fluffy white solid: mp 153°–154° C.; ¹HNMR (CDCl₃) 400 mHz 7.86 (d, J=8.30 Hz, 2H), 7.48–7.42 (m, 4 H), 7.37–7.22 (m, 5 H), 7.02 (t, J=8.79 Hz, 2 H), , 5 H), 3.39 (t, J=6.84 Hz, 2H), 3.19 (t, J=7.32, 2 H), 3.08 (s, 3 H); MS (CI) m/z 438 (MH+), HRMS (MH+) Δ=2.4 mmu.

EXAMPLE 45

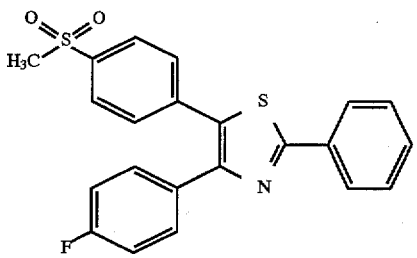

4-(4-Fluorophenyl)-5-(4-methylsulfonylphenyl)-2-phenylthiazole

To a solution of 2-bromo-1-(4-fluorophenyl)-2-(4-methylsulfonylphenyl)ethanone (Example 26, Step 2) (0.468 g, 1.26 mmol) in acetonitrile (10 mL) in a 25 mL round bottom flask was added thiobenzamide (0.164 g, 1.20 mmol) and the solution heated to reflux (19 hours). The reaction was cooled to room temperature. The resulting suspension was concentrated in vacuo, suspended in methylene chloride (100 mL) and washed with NaHCO₃ saturated solution (3×10 mL), dried over sodium sulfate, filtered and concentrated yielding 4-(4-fluorophenyl)-5-(4-methylsulfonylphenyl)-2-phenylthiazole (0.085 g, 16%) as a fine white powder: mp 188°–189° C., ¹HNMR (CDCl₃) 300 mHz 8.01 (m, 2H), 7.90 (d, J=8.48 Hz, 2 H), 7.62–7.55 (m, 4 H), 7.55–7.44 (m, 3 H), 7.04 (t, J=8.85 Hz, 2 H), 3.09 (s, 3H); MS (EI-thermospray) m/z 410 (MH+). HRMS (EI) Δ=–2.0 mmu.

EXAMPLE 46

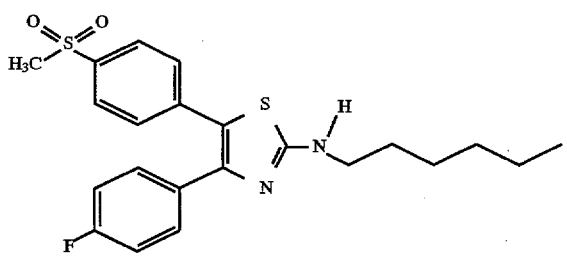

4-(4-Fluorophenyl)-2-n-hexylamino-5-(4-methylsulfonylphenyl)thiazole

To a solution of 2-bromo-1-(4-fluorophenyl)-2-(4-methylsulfonylphenyl)ethanone (Example 26, Step 2) (0.503 g, 1.35 mmol) in ethanol (10 mL) in a 25 mL round bottom flask was added N-hexylthiourea (0.239, 1.49 mmol). The solution was heated to reflux for 14 hours and the reaction was cooled to room temperature. The resulting suspension was concentrated in vacuo, suspended in methylene chloride (100 mL) and washed with NaHCO₃ saturated solution (3×10 mL), dried over sodium sulfate, filtered and concentrated yielding 4-(4-fluorophenyl)-2-n-hexylamino-5-(4-methylsulfonylphenyl)thiazole (0.420 g, 72%) as a white powder: mp 161°–162° C., ¹HNMR (DMSO d₆) 400 mHz 7.95 (t, J=5.38 Hz, 1 H), 7.77 (d, J=8.79 Hz, 2 H), 7.44–7.36 (m, 4 H), 7.15 (t, J=9.28, 2 H), 3.24 ( q , J=5.86, 2H), 3.18 (s, 3 H), 1.61–1.52 (m, 2 H), 1.38–1.20 (m, 6 H), 0.85 (t, J=6.84 Hz, 3 H); MS (FAB) m/z 433 (MH+). HRMS Δ=–0.9 mmu.

EXAMPLE 47

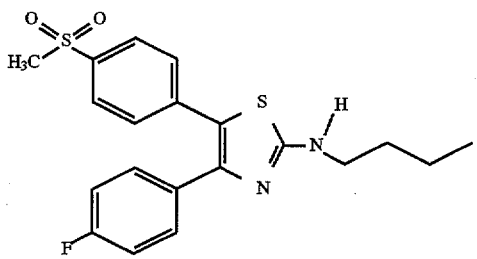

2-Butylamino-4-(4-fluorophenyl)-5-(4-methylsulfonylphenyl)thiazole

To a solution of 2-bromo-1-(4-fluorophenyl)-2-(4-methylsulfonylphenyl) ethanone (Example 26, Step 2) (0.384 g, 1.03 mmol) in ethanol (15 mL) in a 25 mL round bottom flask was added N-butylthiourea (0.144 g, 1.09 mmol). The solution was heated to reflux for 14 hours and the reaction was cooled to room temperature. The resulting suspension was concentrated in vacuo, suspended in methylene chloride (100 mL) and washed with NaHCO₃ saturated solution (3×10 mL), dried over sodium sulfate, filtered and concentrated yielding 2-butylamino-4-(4-fluorophenyl)-5-(4-methylsulfonylphenyl)thiazole (0.319 g, 77%) as an off-white fluffy solid: mp 134°–135° C., ¹HNMR (DMSO d₆) 7.94 (t, J=5.37 Hz, 1 H), 7.78 (d, J=8.79, 2 H), 7.45–7.36 (m, 4 H), 7.15 (t, J=8.79 Hz, 2H), 3.25 (q, J=5.37 Hz, 2 H), 3.18 (s, 3 H), 1.58–1.50 (m, 2 H), 1.41–1.32 (m, 2H), 0.90 (t, J=7.33 Hz, 3 H); MS (EI) m/z 404 (M+). HRMS Δ=1.1 mmu.

EXAMPLE 48

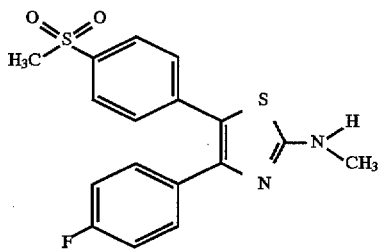

4-(4-Fluorophenyl)-5-(4-methylsulfonylphenyl)-2-methylaminothiazole

To a solution of 2-bromo-1-(4-fluorophenyl)-2-(4-methylsulfonylphenyl)ethanone (Example 26, Step 2) (0.355 g, 0.959 mmol) in ethanol (10 mL) in a 25 mL round bottom flask was added N-methylthiourea (0.086 g, 0.959 mmol). The solution was heated to reflux for 14 hours and cooled to room temperature. The resulting suspension was concentrated in vacuo, suspended in ethyl acetate (100 mL) and washed with NaHCO₃ saturated solution (3×10 mL), dried over sodium sulfate and filtered. Isooctane was added to the filtrate until the solution became cloudy yielding a pale yellow fluffy solid which was collected by vacuum filtration. This solid was dissolved in methylene chloride and washed with sodium carbonate solution (10% solution), dried over sodium sulfate, and concentrated yielding a solid. This solid was recrystallized from methylene chloride-isooctane yielding 4-(4-fluorophenyl)-5-(4-methylsulfonylphenyl)-2-methylaminothiazole (0.135 g, 39%) as a pale yellow powder: mp 243°–244° C.; $^1$HNMR 400 mHz 7.90 (q, J=4.76 Hz, 1 H), 7.81 (d, J=8.50 Hz, 2 H), 7.49–7.43 (m, 2 H), 7.41 (t, J=8.70 Hz, 2 H), 7.19 (t, J=8.95 Hz, 2 H), 3.22 ( s, 3 H), 2.90 (d, J=4.80 Hz, 3 H); MS (FAB) m/z 363 (M+H). HRMS Δ=–0.2 mmu.

EXAMPLE 49

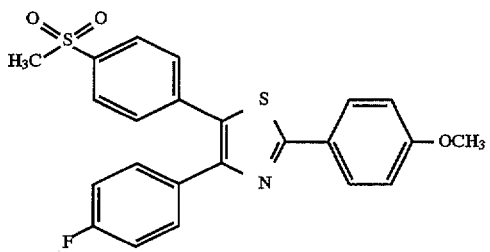

4-(4-Fluorophenyl)-5-(4-methylsulfonylphenyl)-2-(4-methoxyphenyl)thiazole

To a solution of 2-bromo-1- (4-fluorophenyl) -2- (4-methylsulfonylphenyl) ethanone (Example 26, Step 2) (0.500 g, 1.35 mmol) in isopropanol (10 mL) in a 25 mL round bottom flask was added p-methoxythiobenzamide (0.230 g, 1.35 mmol). The solution was heated to reflux for 30 hours and cooled to room temperature. The resulting suspension was concentrated in vacuo, suspended in methylene chloride (100 mL) and washed with NaHCO$_3$ saturated solution (3×10 mL), dried over sodium sulfate, filtered and concentrated yielding 4-(4-fluorophenyl)-5-(4-methylsulfonylphenyl)-2-(4-methoxyphenyl)thiazole (0.360 g, 61%) as a crystalline solid: mp 187°–189° C., $^1$HNMR (CDCl$_3$) 300 mHz 7.99 (d, 8.82 Hz, 2 H), 7.93 (d, J=8.50 Hz, 2 H), 7.63–7.53 (m, 4 H), 7.09 (t, J=8.63 Hz, 2 H), 7.03 (d, J=8.82 Hz, 2 H), 3.92 (s, 3 H), 3.13 (s, 3 H); MS m/z 440 (M+H). HRMS Δ=2.0 mmu.

EXAMPLE 50

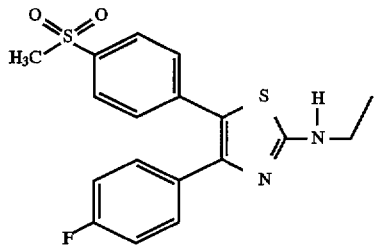

2-Ethylamino-4-(4-fluorophenyl)-5-(4-methylsulfonylphenyl)-thiazole

To a solution of 2-bromo-1-(4-fluorophenyl)-2-(4-methylsulfonylphenyl)ethanone (Example 26, Step 2) (0.405 g, 1.09 mmol) in ethanol (10 mL) in a 25 mL round bottom flask was added N-ethylthiourea (0.114 g, 1.09 mmol) and the solution was heated to reflux for 14 hours. The reaction was cooled to room temperature and the resulting suspension was concentrated in vacuo, suspended in methylene chloride (100 mL) and washed with NaHCO$_3$ saturated solution (3×10 mL), sodium carbonate solution (10%, 3×20 mL), dried over sodium sulfate, filtered and concentrated. The crude product was recrystallized from methylene chloride and isooctane yielding 2-ethylamino-4-(4-fluorophenyl)-5-(4-methylsulfonylphenyl)thiazole (0.218 g, 53%) as a white powdery crystals: mp 218°–219° C., $^1$HNMR (DMSO d$_6$) 400 mHz 7.94 (t, 5.38 Hz, 1 H), 7.78 (d, J=8.56 Hz, 2 H), 7.45–7.40 (m, 2 H), 7.37 (d, J=8.56 Hz, 2 H), 7.15 (t, J=9.05 Hz, 2 H), 3.31 (q, J=7.10 Hz, 2 H), 3.18 (s, 3 H), 1.18 (t, J=7.10 Hz, 3 H); MS m/z 377 (M+H). HRMS Δ=0.5 mmu.

EXAMPLE 51

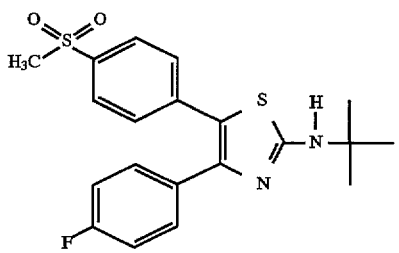

2-tert-Butylamino-4-(4-fluorophenyl)-5-(4-methylsulfonylphenyl)thiazole:

To a solution of 2-bromo-1-(4-fluorophenyl)-2-(4-methylsulfonylphenyl)ethanone (Example 26, Step 2) (0.406 g, 1.09 mmol) in ethanol (11 mL) in a 25 mL round bottom flask was added N-(t-butyl)thiourea (0.144 g, 1.09 mmol) and the solution heated to reflux (14 hours). The reaction was cooled to room temperature. The resulting suspension was concentrated in vacuo, suspended in methylene chloride (100 mL) and washed with NaHCO$_3$ saturated solution (3×10 mL), sodium carbonate solution (10%, 3×20 mL), dried over sodium sulfate, filtered and concentrated. The crude product was recrystallized from methylene chloride and isooctane yielding 4-(4-fluorophenyl)-5-(4-methylsulfonylphenyl)-2-tert-butylaminothiazole ( 0.226 g, 51%) as a yellow crystalline plates: mp 250°–253° C.; $^1$HNMR (DMSO d$_6$) 400 mHz 7.78 (d, J=8.32 Hz, 2 H), 7.70 (s, 1 H), 7.46–7.35 (m, 4 H), 7.15 (t, J=9.05 Hz, 2 H), 3.19 (s, 3 H), 1.40 (s, 9 H); MS m/z 405 (M+H). HRMS Δ=4.78 mmu.

EXAMPLE 52

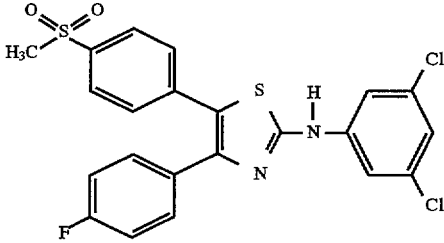

2-(3,5-Dichlorophenylamino)-4-(4-fluorophenyl)-5-(4-methylsulfonylphenyl)thiazole To a solution of 2-bromo-1-(4-fluorophenyl)-2-(4-methylsulfonylphenyl)ethanone (Example 26, Step 2)

(0.312, 0.841 mmol) in ethanol (10 mL) in a 25 mL round bottom flask was added N-(3,5-dichlorophenyl)thiourea (0.195 g, 0.882 mmol). The solution was heated to reflux (14 hours) and the reaction was cooled to room temperature. The resulting suspension was concentrated in vacuo, suspended in ethyl acetate (100 mL) and washed with sodium carbonate solution (10%, 3×20 mL), brine (1×20 mL), dried over sodium sulfate, filtered and concentrated, yielding a powdery solid. This solid was dissolved in ethyl acetate/ methylene chloride. Addition of isooctane resulted in the precipitation of 4-(4-fluorophenyl)-5-(4-methylsulfonylphenyl)-2-(3,5-dichlorophenylamino) thiazole (0.261 g, 63%) as a pale yellow powder: mp 287°–288° C.; $^1$HNMR (DMSO $d_6$) 400 mHz 10.84 (s, 1 H), 7.86 (d, J=8.79 Hz, 2 H), 7.73 (s, 2 H), 7.54–7.45 (m, 4 H), 7.22 (t, J=8.79 Hz, 2 H), 7.15 (s, 1 H), 3.22 (s, 3 H); MS m/z 492 (M+). HRMS Δ=4.8 mmu.

EXAMPLE 53

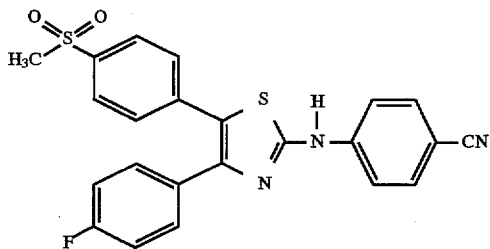

2-(4-Cyanophenylamino)-4-(4-fluorophenyl)-5-(4-methylsulfonylphenyl)-thiazole

To a solution of 2-bromo-1-(4-fluorophenyl)-2-(4-methylsulfonylphenyl)ethanone (Example 26, Step 2) (0.413, 1.11 mmol) in ethanol (10 mL) in a 25 mL round bottom flask was added N-(4-cyanophenyl)thiourea (0.207 g, 1.17 mmol). The solution was heated to reflux (24 hours) and the reaction was cooled to room temperature. The resulting suspension was concentrated in vacuo, suspended in methylene chloride (100 mL) and washed with sodium carbonate solution (10%, 3×20 mL), brine (1×20 mL), dried over sodium sulfate, filtered and concentrated yielding a solid. This solid was flash chromatographed (1:1, hexane:ethyl acetate with 1% acetic acid). The resulting product was recrystallized from methylene chloride and isooctane yielding 2-(4-cyanophenylamino)-4-(4-fluorophenyl)-5-(4-methylsulfonylphenyl)thiazole (0.266 g, 53%) as a pale yellow solid: mp 273°–274° C.; $^1$HNMR (DMSO $d_6$) 400 mHz 10.98 (s, 1 H), 7.86 (d, J=8.32 Hz, 2 H), 7.83 (d, J=9.05 Hz, 2 H), 7.76 (d, J=8.80 Hz, 2 H), 7.55–7.47 (m, 4 H), 7.21 (t, J=8.80 Hz, 2 H), 3.22 (s, 3 H); MS m/z 450 (M+H). HRMS Δ=2.6 mmu.

EXAMPLE 54

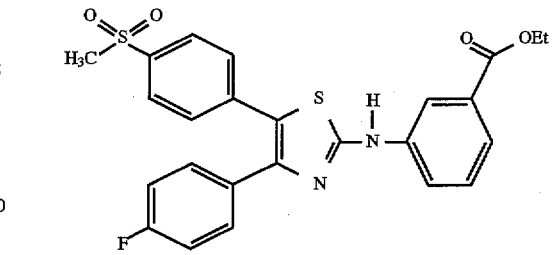

Ethyl-[3-[4-(4-fluorophenyl)-5-(4-methylsulfonylphenyl)-2-thiazolyl]amino]benzoate To a solution of 2-bromo-1-(4-fluorophenyl)-2-(4-methylsulfonylphenyl) ethanone (Example 26, Step 2) (0.444, 1.20 mmol) in ethanol (10 mL) in a 25 mL round bottom flask was added N-(3-ethoxycarbonylphenyl) thiourea (0.282 g, 1.26 mmol). The solution was heated to reflux (24 hours) and the reaction was cooled to room temperature. The resulting suspension was concentrated in vacuo, suspended in methylene chloride (100 mL) and washed with sodium carbonate solution (10%, 3×20 mL), brine (1×20 mL), dried over sodium sulfate, filtered and concentrated yielding a solid. The resulting product was recrystallized from methylene chloride and isooctane yielding ethyl [3-[4-(4-fluorophenyl)-5-(4-methylsulfonylphenyl)-2-thiazolyl]amino]benzoate (0.393 g, 66%) as a pale yellow fluffy solid: mp 208°–209° C.; $^1$HNMR (DMSO $d_6$) 400 mHz 10.68 (s, 1 H), 8.45 (s, 1 H), 7.91–7.84 (m, 3 H), 7.58–7.44 (m, 6 H), 7.19 (t, J=8.79 Hz, 2 H), 4.30 (q, J=6.84 Hz. 2 H), 3.21 (s, 3 H), MS m/z 496 (M+). HRMS Δ=0.03 mmu.

EXAMPLE 55

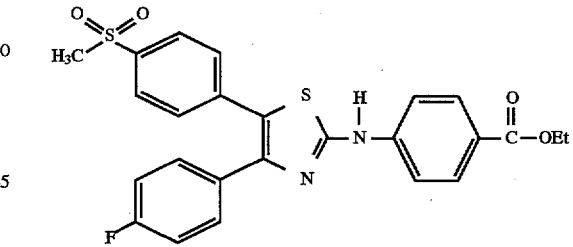

Ethyl [4-[4-(4-fluorophenyl)-5-(4-methylsulfonylphenyl)-2-thiazolyl]amino]benzoate To a solution of 2-bromo-1-(4-fluorophenyl)-2-(4-methylsulfonylphenyl)ethanone (Example 26, Step 2) (0.361, 0.972 mmol) in ethanol (10 mL) in a 25 mL round bottom flask was added N-(4-ethoxycarbonylphenyl) thiourea (0.229 g, 1.02 mmol). The solution was heated to reflux (24 hours) and the reaction was cooled to room temperature. The resulting suspension was concentrated in vacuo, suspended in methylene chloride (100 mL) and washed with sodium carbonate solution (10%, 3×20 mL), brine (1×20 mL), dried over sodium sulfate, filtered and concentrated yielding a solid. The resulting product was recrystallized from methylene chloride and isooctane yielding ethyl[4-[4-(4-fluorophenyl)-5-(4-methylsulfonylphenyl) -2-thiazolyl]amino]benzoate (0.277 g, 57%) as a fine, pale yellow crystals: mp 207°–208° C.; ¹HNMR (DMSO d₆) 400 mHz 10.87 (s, 1 H), 7.93 (d, J=8.79 Hz, 2 H), 7.87 (d, J=8.30 Hz, 2 H), 7.78 (d, J=8.79, 2 H), 7.57–7.49 (m, 4 H), 7.20 (t, J=9.28 Hz, 2 H), 4.26 ( q, J=7.32 Hz, 2 H), 3.21 (s, 3 H), 1.29 (t, J=7.32 Hz, 3 H). MS m/z 496 (M+). HRMS Δ=0.2 mmu.

EXAMPLE 56

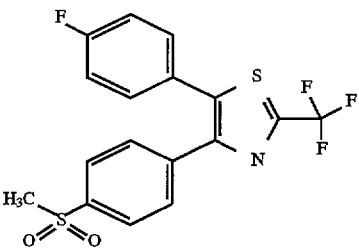

5-(4-Fluorophenyl)-A-(4-methylsulfonylphenyl)-2-trifluoromethylthiazole:

Step 1 Preparation of 5-(4-fluorophenyl)-4-(4-methylthiophenyl)-2-trifluoroformethylthiazole:

To a solution of trifluoroacetamide (13.7 g, 121.2 mmol) in toluene (30 mL) was added solid P₄S₁₀ (5.4 g, 12.1 mmol) and the mixture refluxed for 60 hours. The resulting orange "coarse" suspension was cooled to room temperature and the solid pulverized to form a fine suspension. One fourth of this toluene suspension (7.5 mL, ca. 30 mmol of theory) was transferred to a 25 mL round bottom flask and 2-bromo-2-(4-fluorophenyl)-1-(4-methylthiophenyl)ethanone (1.24 g, 3.66 mmol) (Example 20, Step 2) added in one portion. This suspension was heated to reflux for 1.5 hours, cooled to 50° C., and 1.0 N HCl solution (1 mL) added carefully and reflux continued for 1 hour more. This reaction was cooled to room temperature and let stand overnight. To this solution was added 2 N NaOH solution until the exotherm subsided and the reaction was stirred for 1 hour longer. The resulting black suspension was diluted with methylene chloride and washed with NaHCO₃ saturated solution, dried over Na₂SO₄, filtered and concentrated in vacuo yielding a brown semi-solid. This crude thiazole was flash chromatographed (9:1 hexane:methylene chloride) yielding 5-(4-fluorophenyl)-4-(4-methylthiophenyl)-2-trifluoromethylthiazole (0.28 g, 23%) as yellow oil which slowly solidified mp: 59°–60° C.; ¹HNMR (CDCl₃) 300 mHz 7.43 (d, J=8.48, 2 H), 7.40–7.32 (m, 2 H), 7.17 (d, J=8.48 Hz, 2 H), 7.08 (t, J=8.48, 2 H) 2.46 (s, 3 H); MS (EI) m/z 369 (M+H). HRMS Δ=–3.17 mmu.

Step 2 Preparation of 5-(4-fluorophenyl)-4-(4-methylsulfonylphenyl)-2-trifluoromethylthiazole:

To a solution of 2-trifluoromethyl-5-(4-fluorophenyl)-4-(4-methylthiophenyl)thiazole from Step 1 (0.25 g, 0.74 mmol) in methylene chloride (10 mL) at 0° C. was added MCPBA (0.50 g of 67% peroxide content reagent, 1.9 mmol) in three portions over 2 hours. After 3 hours total reaction time, the reaction was diluted with methylene chloride (150 mL) and this solution was washed with NaHSO₃ solution (0.1 M)/NaHCO₃ saturated solution (1:1 ratio, 3×50 mL), dried over MgSO₄, filtered and concentrated in vacuo. The resulting solid was recrystallized from methylene chloride and isooctane yielding 5-(4-fluorophenyl)-4-(4-methylsulfonylphenyl)-2-trifluoromethylthiazole (0.19 g, 70%) as opaque white crystals: mp 150°–151° C.; ¹HNMR (CDCl₃) 300 mHz 7.89 (d, J=8.48, 2 H), 7.71 (d, J=8.85, 2 H), 7.40–7.30 ( m, 2 H), 7.13 (t, J=8.48 Hz, 2 H), 3.06 (s, 3 H); 19F NMR (CDCl₃) 300 mHz –61.53, –109.98; MS (EI) m/z 402 (MH+). HRMS Δ=–1.161 mmu.

EXAMPLE 57

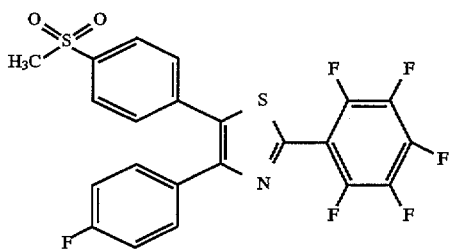

5 4-(4-Fluorophenyl))-5-(4-methylsulfonylphenyl)-2-(2,3,4,5,6-pentafluorophenyl)thiazole:

Step 1 Preparation of pentafluorothiobenzamide:

To a solution of pentafluorobenzamide (5.00 g, 23.69 mmol) in toluene (60 mL) was added Lawesson's reagent (5.70 g, 14.20 mmol) and the flask fitted with a drying tube. The reaction was refluxed overnight, cooled to room temperature, and isooctane (200 mL) was added causing a precipitate to form. The suspension was filtered (gravity) and the filtrate concentrated yielding an orange oil which solidified. Flash chromatography of this oil (1:1 hexane:methylene chloride with 2% acetic acid) yielded crude pentafluorothiobenzamide as a white solid (mp 92°–93° C.) which was used without any further purification.

Step 2 Preparation of 2-pentafluorophenyl-4-(4-fluorophenyl)-5-(4-methylthiophenyl)thiazole:

To a solution of 2-bromo-1-(4-fluorophenyl)-2-(4-methylthiophenyl)ethanone (Example 1, Step 3) (3.13 g, 9.22 mmol) in acetonitrile (90 mL) in a 250 mL round bottom flask was added pentafluorothiobenzamide from Step 1 (2.2 g, 9.69 mmol) and the mixture was heated to reflux for 16 hours. The resulting burgundy colored reaction solution was poured into hot methanol (400 mL) and the resulting solution was cooled to room temperature yielding a crystalline product. The crystals were collected by vacuum filtration, redissolved in hot acetonitrile and methanol, darco decolorizing carbon was added, and the mixture was heated on a steam bath to reflux for two minutes. The resulting black suspension was gravity filtered. The filtrate was diluted with methanol to enhance recrystallization yielding 2-pentafluorophenyl-4-(4-fluorophenyl)-5-(4-methylthiophenyl)thiazole as papery pale gray crystals (0.59 g, 14%): mp 131°–132° C.; ¹HNMR (CDCl₃) 300 mHz 7.60–7.50 (m, 2 H), 7.31 (d, J=8.11 Hz, 2 H), 7.23 (d, J=8.48 Hz, 2 H), 7.02 (t, J=8.48 Hz, 2 H), 2.52 ( s, 3 H); MS (EI) m/z 468 (M+H). HRMS Δ=1.66 mmu.

Step 3 Preparation of 2 -pentafluorophenyl-4-(4-fluorophenyl)-5-(4-methylsulfonylphenyl)thiazole:

To a solution of 2-pentafluorophenyl-4-(4-fluorophenyl)-5-(4-methylthiophenyl)thiazole from step 2 (0.55 g, 1.18 mmol) in methylene chloride (15 mL) in a 25 mL round bottom flask at 0° C. was added MCPBA (0.51 g of 67% peroxide reagent, 2.94 mmol) and the solution allowed to warm to room temperature and stand overnight. The reaction mixture was diluted with methylene chloride (100 mL), washed with NaHSO₃ solution (0.1M), NaHCO₃ saturated solution, dried over Na₂SO₄, filtered and concentrated in vacuo. The product was recrystallized from methylene chloride and isooctane yielding 2-pentafluorophenyl-4-(4-fluorophenyl)-5-(4-methylsulfonylphenyl)thiazole (0.48 g, 93%) as a long thin papery needles: mp 173°–174° C.; ¹HNMR (CDCl₃) 300 mHz 7.95 (d, J=8.48 Hz, 2 H), 7.61 (d, J=8.48, 2 H), 7.52 (d of d, J=5.16 and 8.48 Hz, 2 H), 7.05

(t, J=8.48 Hz, 2 H), 3.11 (s, 3 H); $^{19}$F NMR (CDCl$_3$) 300 mHz −111.9, −138.8, −150.5, −160.7; MS (EI) m/z 499 (M+H). HRMS Δ=5.146 mmu.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDS*, in *Non-steroidal Anti-Inflammatory Drugs*, (J. Lombardino, ed. 1985)). The % inhibition shows the % decrease from control paw volume determined in this procedure and the data for selected compounds in this invention are summarized in Table 1. Rat Carrageenan-induced Analgesia Test The analgesia test using rat carrageenan was performed with materials, reagents and procedures essentially as described by Hargreaves, et al., (Pain, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Examples | RAT PAW EDEMA % Inhibition @ 20 mg/kg body weight | ANALGESIA % Inhibition @ 20 mg/kg body weight |
| --- | --- | --- |
| 8 | 12 | — |
| 10 | 14 | — |
| 12 | 53 | — |
| 16 | 50 | 27 |
| 20 | 48 | — |
| 23 | 39.5 | — |
| 24 | 20* | — |
| 29 | 42 | 24 |
| 31 | 27.5* | — |
| 33 | 36 | 34ª |
| 35 | 16 | — |
| 37 | 9 | — |
| 39 | 19 | — |
| 41 | 4 | — |

TABLE I-continued

| Examples | RAT PAW EDEMA % Inhibition @ 20 mg/kg body weight | ANALGESIA % Inhibition @ 20 mg/kg body weight |
| --- | --- | --- |
| 45 | 19* | — |
| 46 | 25* | — |
| 47 | 12 | — |
| 48 | 15* | — |
| 49 | 6* | — |
| 50 | 11* | — |
| 51 | 14* | — |
| 52 | 7* | — |
| 56 | 20* | — |
| 57 | 2* | — |

*@ 10 mg/kg
ª@ 30 mg/kg

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of recombinant COX baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (Baculovirus Expression Vectors: *A Laboratory Manual* (1992)). Recombinant baculoviruses were isolated by transfecting 4 µg of baculovirus transfer vector DNA into SF9 insect cells (2×10e8) along with 200 ng of linearized baculovirus plasmid DNA by the calcium phosphate method. See M.D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5×10$^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000xG for 30 minutes, and the resultant supernatant was stored at −80° C. before being assayed for COX activity.

b. Assay for COX I and COX II activity:

COX activity was assayed as PGE$_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The PGE$_2$ formed was measured by standard ELISA technology (Cayman Chemical). Results are shown in Table II.

TABLE II

| Examples | Species murine (m)/human (h) | COX I ID$_{50}$ μM | COX II ID$_{50}$ μM |
|---|---|---|---|
| 1 | m | >100 | .1 |
|   | h | >10 | <.1 |
| 2 | h | >100 | <.1 |
| 3 | h | >100 | <.1 |
| 4 | m | 6.2 | <.1 |
|   | h | 70 | <.1 |
| 5 | h | >100 | <.1 |
| 6 | h | >100 | <.1 |
| 7 | h | >100 | <.1 |
| 8 | m | >100 | .2 |
| 9 | h | >100 | <.1 |
| 10 | h | >100 | <.1 |
| 11 | h | >100 | <.1 |
| 12 | m | 1.6 | <.1 |
|   | h | >10 | <.1 |
| 13 | m | >30 | 1.2 |
| 14 | m | 39.8 | .5 |
|   | h | >100 | .6 |
| 15 | h | >100 | .2 |
| 16 | m | >10 | <.1 |
|   | h | >100 | <.1 |
| 17 | m | >10 | .3 |
| 18 | m | 5.4 | .15 |
| 19 | m | .4 | <.1 |
| 20 | m | >10 | .1 |
| 21 | m | >10 | <.1 |
|   | h | >10 | <.1 |
| 22 | m | >100 | 11.2 |
| 23 | m | .7 | <.1 |
|   | h | 1.1 | <.1 |
| 24 | m | >10 | <.1 |
| 25 | h | 2.6 | <.1 |
| 26 | m | >100 | .5 |
| 27 | m | >10 | .2 |
| 28 | m | >10 | <.1 |
| 29 | m | .5 | .1 |
| 30 | m | .9 | .3 |
| 31 | m | >10 | .1 |
| 32 | h | .7 | <.1 |
| 33 | h | >100 | <.1 |
| 34 | h | <.1 | <.1 |
| 35 | m | >100 | <.1 |
| 36 | h | >100 | <.1 |
| 37 | m | >100 | <.1 |
| 38 | h | >100 | <.1 |
| 39 | m | >10 | .3 |
| 40 | h | >100 | <.1 |
| 41 | h | >100 | <.1 |
| 42 | m | 1.9 | <.1 |
| 43 | m | 100 | 1.3 |
| 44 | m | 1.7 | <.1 |
| 45 | m | >100 | <.1 |
| 46 | m | 1.4 | <.1 |
| 47 | m | 1.4 | <.1 |
| 48 | m | >10 | .3 |
| 49 | m | >10 | .3 |
| 50 | m | >10 | .3 |
| 51 | m | 11.9 | .3 |
| 52 | m | >100 | .5 |
| 53 | m | .2 | .9 |
| 54 | m | 1.1 | 1.3 |
| 55 | m | >10 | 3.5 |
| 56 | m | >100 | <.1 |
| 56 | h | >100 | <.1 |
| 57 | m | 4.9 | >.1 |
|   | h | >100 | <.1 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

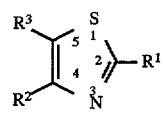

wherein $R^1$ is selected from hydrido, halo, amino, $C_1$–$C_{10}$ alkoxy, cyano, nitro, hydroxyl, aminocarbonyl, acyl, $C_1$–$C_{10}$ alkylaminocarbonyl, $C_6$–$C_{12}$ arylaminocarbonyl, $C_1$–$C_{10}$ alkyl, $C_2$–$C_{10}$ alkenyl, $C_2$–$C_{10}$ alkynyl, $C_1$–$C_{10}$ haloalkyl, $C_1$–$C_{10}$ haloalkoxy, $C_1$–$C_{10}$ alkylamino, $C_6$–$C_{12}$ arylamino, $C_1$–$C_{10}$ alkyl-$C_6$–$C_{12}$-arylamino, $C_6$–$C_{12}$ aryl-$C_1$–$C_{10}$-alkylamino, carboxyl, $C_1$–$C_{10}$ carboxyalkyl, $C_1$–$C_{10}$ alkoxycarbonyl, $C_1$–$C_{10}$ alkoxycarbonylalkyl, $C_1$–$C_{10}$ alkylamino-$C_1$–$C_{10}$alkyl, 5–10 membered heterocyclic-$C_1$–$C_{10}$-alkyl, $C_6$–$C_{12}$ aryl-$C_1$–$C_{10}$ alkyl, $C_1$–$C_{10}$ cyanoalkyl, N-$C_1$–$C_{10}$-alkylsulfonylamino, 5–10 membered heteroarylsulfonyl-$C_1$–$C_{10}$-alkyl, 5–10 membered heteroarylsulfonyl-$C_1$–$C_{10}$-haloalkyl, $C_6$–$C_{12}$ aryloxy-$C_1$–$C_{10}$-alkyl, $C_6$–$C_{12}$ aryl-$C_1$–$C_{10}$-alkyloxy-$C_1$–$C_{10}$-alkyl, $C_6$–$C_{12}$ aryl optionally substituted at a substitutable position with one or more radicals selected from halo, $C_1$–$C_{10}$ alkyl, $C_1$–$C_{10}$ alkoxy, $C_1$–$C_{10}$ alkylthio, $C_1$–$C_{10}$ alkylsulfinyl, $C_1$–$C_{10}$ haloalkyl, $C_1$–$C_{10}$ haloalkoxy, $C_1$–$C_{10}$ carboxyalkyl, $C_1$–$C_{10}$ alkoxycarbonyl, aminocarbonyl, amino, acyl and $C_1$–$C_{10}$ alkylamino, and 5–10 membered heterocyclic optionally substituted at a substitutable position with one or more radicals selected from halo, $C_1$–$C_{10}$ alkyl, $C_1$–$C_{10}$ alkoxy, $C_1$–$C_{10}$ alkylthio, $C_1$–$C_{10}$ alkylsulfinyl, $C_1$–$C_{10}$ haloalkyl, $C_1$–$C_{10}$ haloalkoxy, $C_1$–$C_{10}$ carboxyalkyl, $C_1$–$C_{10}$ alkoxycarbonyl, aminocarbonyl, amino, acyl and $C_1$–$C_{10}$ alkylamino;

wherein $R^2$ is selected from $C_6$–$C_{12}$ aryl, $C_3$–$C_{10}$ cycloalkyl, $C_3$–$C_{10}$ cycloalkenyl and 5–10 membered heterocyclic; wherein $R^2$ is optionally substituted at a substitutable position with one or more radicals selected from halo, $C_1$–$C_{10}$ alkylthio, $C_1$–$C_{10}$ alkylsulfinyl, $C_1$–$C_{10}$ alkylsulfonyl, $C_1$–$C_{10}$ haloalkylsulfonyl, sulfamyl, $C_1$–$C_{10}$ alkyl, $C_2$–$C_{10}$ alkenyl, $C_2$–$C_{10}$ alkynyl, cyano, carboxyl, $C_1$–$C_{10}$ carboxyalkyl, $C_1$–$C_{10}$ alkoxycarbonyl, aminocarbonyl, acyl, N-mono-$C_1$–$C_{10}$-alkylaminocarbonyl, N-mono-$C_6$–$C_{12}$-arylaminocarbonyl, N,N-di-$C_1$–$C_{10}$-alkylaminocarbonyl, N-$C_1$–$C_{10}$-alkyl-N-$C_6$–$C_{12}$-arylaminocarbonyl, $C_1$–$C_{10}$ haloalkyl, hydroxyl, $C_1$–$C_{10}$ alkoxy, $C_1$–$C_{10}$ hydroxyalkyl, $C_1$–$C_{10}$ haloalkoxy, amino, N-$C_1$–$C_{10}$-alkylamino, N,N-di-$C_1$–$C_{10}$-alkylamino, 5–10 membered heterocyclic and nitro; and wherein $R^3$ is selected from $C_6$–$C_{12}$ aryl, $C_3$–$C_{10}$ cycloalkyl, $C_3$–$C_{10}$ cycloalkenyl and 5–10 membered heterocyclic; wherein $R^3$ is optionally substituted at a substitutable position with one or more radicals selected from halo, $C_1$–$C_{10}$ alkylthio, $C_1$–$C_{10}$ alkylsulfinyl, $C_1$–$C_{10}$ alkylsulfonyl, $C_1$–$C_{10}$ haloalkylsulfonyl, sulfamyl, $C_1$–$C_{10}$ alkyl, $C_2$–$C_{10}$ alkenyl, $C_2$–$C_{10}$ alkynyl, cyano, carboxyl, $C_1$–$C_{10}$ carboxyalkyl, $C_1$–$C_{10}$ alkoxycarbonyl, aminocarbonyl, acyl, N-mono-$C_1$–$C_{10}$-alkylaminocarbonyl, N-mono-$C_6$–$C_{12}$-arylaminocarbonyl, N,N-di-$C_1$–$C_{10}$-alkylaminocarbonyl, N-$C_1$–$C_{10}$-alkyl-N-$C_6$–$C_{12}$-arylaminocarbonyl, $C_1$–$C_{10}$ haloalkyl, $C_1$–$C_{10}$ haloalkoxy, hydroxyl, $C_1$–$C_{10}$ alkoxy, $C_1$–$C_{10}$ hydroxyalkyl, amino, N-$C_1$–$C_{10}$-alkylamino, N,N-di-$C_1$–$C_{10}$-alkylamino, 5–10 membered heterocyclic and nitro;

provided one of $R^2$ and $R^3$ is phenyl substituted with methylsulfonyl, $C_1$ haloalkylsulfonyl or sulfamyl;

or a pharmaceutically-acceptable salt thereof.

2. Compound of claim 1 wherein $R^1$ is selected from hydrido, halo, amino, $C_1$–$C_{10}$ alkoxy, cyano, nitro, hydroxyl, aminocarbonyl, acyl, $C_1$–$C_{10}$ alkylaminocarbonyl, $C_6$–$C_{12}$ arylaminocarbonyl, $C_1$–$C_{10}$ alkyl, $C_2$–$C_{10}$ alkenyl, $C_2$–$C_{10}$ alkynyl, $C_1$–$C_{10}$ haloalkyl, $C_1$–$C_{10}$ haloalkoxy, $C_1$–$C_{10}$ alkylamino, $C_6$–$C_{12}$ arylamino, $C_6$–$C_{12}$ aryl-$C_1$–$C_{10}$-alkylamino, carboxyl, $C_1$–$C_{10}$ carboxyalkyl, $C_1$–$C_{10}$ alkoxycarbonyl, $C_1$–$C_{10}$ alkoxycarbonyl-$C_1$–$C_{10}$ -alkyl, $C_1$–$C_{10}$ alkylamino-$C_1$–$C_{10}$-alkyl, 5–10 membered heterocyclic-$C_1$–$C_{10}$-alkyl, $C_6$–$C_{12}$ aryl-$C_1$–$C_{10}$-alkyl, $C_1$–$C_{10}$ cyanoalkyl, N-$C_1$–$C_{10}$-alkylsulfonylamino, 5–10 membered heteroarylsulfonyl-$C_1$–$C_{10}$-alkyl, 5–10 membered heteroarylsulfonyl-$C_1$–$C_{10}$-haloalkyl, $C_6$–$C_{12}$ aryloxy-$C_1$–$C_{10}$-alkyl, $C_6$–$C_{12}$ aryl-$C_1$–$C_{10}$-alkyloxy-$C_1$–$C_{10}$-alkyl, $C_6$–$C_{12}$ aryl optionally substituted at a substitutable position with one or more radicals selected from halo, $C_1$–$C_{10}$ alkyl, $C_1$–$C_{10}$ alkoxy, $C_1$–$C_{10}$ alkylthio, $C_1$–$C_{10}$ alkylsulfinyl, $C_1$–$C_{10}$ haloalkyl, $C_1$–$C_{10}$ haloalkoxy, $C_1$–$C_{10}$ carboxyalkyl, $C_1$–$C_{10}$ alkoxycarbonyl, aminocarbonyl, amino, acyl and $C_1$–$C_{10}$ alkylamino, and 5–10 membered heterocyclic optionally substituted at a substitutable position with one or more radicals selected from halo, $C_1$–$C_{10}$ alkyl, $C_1$–$C_{10}$ alkoxy, $C_1$–$C_{10}$ alkylthio, $C_1$–$C_{10}$ alkylsulfinyl, $C_1$–$C_{10}$ haloalkyl, $C_1$–$C_{10}$ haloalkoxy, $C_1$–$C_{10}$ carboxyalkyl, $C_1$–$C_{10}$ alkoxycarbonyl, aminocarbonyl, amino, acyl and $C_1$–$C_{10}$ alkylamino; wherein $R^2$ is selected from $C_6$–$C_{12}$ aryl, $C_3$–$C_6$ cycloalkyl, $C_3$–$C_6$ cycloalkenyl and 5–10 membered heterocyclic; wherein $R^2$ is optionally substituted at a substitutable position with one or more radicals selected from halo, $C_1$–$C_{10}$ alkylthio, $C_1$–$C_{10}$ alkylsulfinyl, $C_1$–$C_{10}$ alkyl, $C_2$–$C_{10}$ alkenyl, $C_2$–$C_{10}$ alkynyl, cyano, carboxyl, $C_1$–$C_{10}$ carboxyalkyl, $C_1$–$C_{10}$ alkoxycarbonyl, aminocarbonyl, acyl, N-mono-$C_1$–$C_{10}$-alkylaminocarbonyl, N-mono-$C_6$–$C_{12}$-arylaminocarbonyl, N, N-di-$C_1$–$C_{10}$-alkylaminocarbonyl, N-$C_1$–$C_{10}$-alkyl-N-$C_6$–$C_{12}$-arylaminocarbonyl, $C_1$–$C_{10}$ haloalkyl, hydroxyl, $C_1$–$C_{10}$ alkoxy, $C_1$–$C_{10}$ hydroxyalkyl, $C_1$–$C_{10}$ haloalkoxy, amino, N-$C_1$–$C_{10}$-alkylamino, N,N-di-$C_1$–$C_{10}$-alkylamino, 5–10 membered heterocyclic and nitro; and wherein $R^3$ is phenyl substituted at a substitutable position with a radical selected from methylsulfonyl and sulfamyl; or a pharmaceutically-acceptable salt thereof.

3. Compound of claim 2 wherein $R^1$ is selected from halo, amino, $C_1$–$C_6$ alkoxy, cyano, nitro, hydroxyl, aminocarbonyl, acyl, $C_1$–$C_6$ alkylaminocarbonyl, phenylaminocarbonyl, $C_1$–$C_6$ alkyl, $C_2$–$C_6$ alkenyl, $C_2$–$C_6$ alkynyl, $C_1$–$C_6$ haloalkyl, $C_1$–$C_6$ haloalkoxy, $C_1$–$C_6$ alkylamino, phenylamino, phenyl-$C_1$–$C_6$-alkylamino, carboxyl, $C_1$–$C_6$ carboxyalkyl, $C_1$–$C_6$ alkoxycarbonyl, $C_1$–$C_6$ alkoxycarbonyl-C1-C6-alkyl, $C_1$–$C_6$ alkylamino-$C_1$–$C_6$-alkyl, 5–6 membered heterocyclicalkyl, phenyl-$C_1$–$C_6$-alkyl, $C_1$–$C_6$cyanoalkyl, phenyloxy-$C_1$–$C_6$-alkyl, N-$C_1$–$C_6$-alkylsulfonylamino, 5–6 membered heteroarylsulfonyl-$C_1$–$C_6$-alkyl, phenyl-$C_1$–$C_6$-alkyloxy-$C_1$–$C_6$-alkyl, 5–6 membered heteroarylsulfonyl-$C_1$–$C_6$-haloalkyl, aryl selected from phenyl, naphthyl and biphenyl, optionally substituted at a substitutable position with one or more radicals selected from halo, $C_1$–$C_6$ alkyl, $C_1$–$C_6$ alkoxy, $C_1$–$C_6$ alkylthio, $C_1$–$C_6$ alkylsulfinyl, $C_1$–$C_6$ haloalkyl, $C_1$–$C_6$ haloalkoxy, $C_1$–$C_6$ carboxyalkyl, $C_1$–$C_6$ alkoxycarbonyl, aminocarbonyl, amino, acyl and $C_1$–$C_6$ alkylamino, and 5–6 membered heterocyclic selected from thienyl, pyridyl, furyl, pyrazinyl, pyrrolyl, pyrazolyl and triazolyl, optionally substituted at a substitutable position with one or more radicals selected from halo, $C_1$–$C_6$ alkyl, $C_1$–$C_6$ alkoxy, $C_1$–$C_6$ alkylthio, $C_1$–$C_6$ alkylsulfinyl, $C_1$–$C_6$ haloalkyl, $C_1$–$C_6$ haloalkoxy, $C_1$–$C_6$ carboxyalkyl, $C_1$–$C_6$ alkoxycarbonyl, aminocarbonyl, amino, acyl and $C_1$–$C_6$ alkylamino; wherein $R^2$ is selected from phenyl, $C_3$–$C_6$ cycloalkyl, $C_3$–$C_6$ cycloalkenyl and 5–6 membered heterocyclic; wherein $R^2$ is optionally substituted at a substitutable position with one or more radicals selected from halo, $C_1$–$C_6$ alkylthio, $C_1$–$C_6$ alkylsulfinyl, $C_1$–$C_6$ alkyl, $C_2$–$C_6$ alkenyl, $C_2$–$C_6$ alkynyl, cyano, carboxyl, $C_1$–$C_6$ carboxyalkyl, $C_1$–$C_6$ alkoxycarbonyl, aminocarbonyl, acyl, N-mono-$C_1$–$C_6$-alkylaminocarbonyl, N-phenylaminocarbonyl, N,N-di-$C_1$–$C_6$-alkylaminocarbonyl, N-$C_1$–$C_6$-alkyl-N-phenylaminocarbonyl, $C_1$–$C_6$ haloalkyl, hydroxyl, $C_1$–$C_6$ alkoxy, $C_1$–$C_6$hydroxyalkyl, $C_1$–$C_6$ haloalkoxy, amino, N-$C_1$–$C_6$-alkylamino, N,N-di-$C_1$–$C_6$-alkylamino, 5–6 membered heterocyclic and nitro; and wherein $R^3$ is phenyl substituted at a substitutable position with a radical selected from methylsulfonyl, and sulfamyl; or a pharmaceutically-acceptable salt thereof.

4. Compound of claim 3 wherein $R^1$ is selected from fluoro, chloro, bromo, iodo, amino, methoxy, ethoxy, propoxy, butoxy, isopropoxy, tert-butoxy, cyano, nitro, hydroxy, aminocarbonyl, formyl, acetyl, N-methylaminocarbonyl, N-phenylaminocarbonyl, N,N-dimethylaminocarbonyl, N-methyl-N-phenylaminocarbonyl, methyl, ethyl, propyl, butyl, pentyl, isopropyl, isobutyl, tert-butyl, ethylenyl, propylenyl, butenyl, pentenyl, isopropylenyl, isobutylenyl, propargyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, N-methylamino, N-ethylamino, N-propylamino, N-butylamino, N-tert-butylamino, N-pentylamino, N-hexylamino, N,N-dimethylamino, carboxyl, N-benzylamino, carboxymethyl, methoxycarbonylmethyl, ethoxycarbonylmethyl, methylaminomethyl, morpholinomethyl, pyrrolidinylmethyl, piperazinylmethyl, piperidinylmethyl, pyridylmethyl, thienylmethyl, benzyl, phenethyl, phenpropyl, cyanomethyl, phenoxymethyl, benzyloxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylsulfonylamino, (2-thienyl)sulfonylmethyl, (2-thienyl)sulfonylbromomethyl, phenyl optionally substituted at a substitutable position with one or more radicals selected from fluoro, chloro, bromo, methyl, ethyl, propyl, butyl, pentyl, isopropyl, isobutyl, tert-butyl, methoxy, ethoxy, propoxy, butoxy, isopropoxy, tert-butoxy, methylthio, methylsulfinyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxymethyl, methoxycarbonyl, ethoxycarbonyl, aminocarbonyl, amino, formyl, methylamino and dimethylamino, and heterocyclic selected from morpholino, pyrrolidinyl, piperazinyl, piperidinyl, thienyl, pyridyl, furyl, pyrazinyl, pyrrolyl, pyrazolyl and triazolyl, optionally substituted at a substitutable position with one or more radicals selected from fluoro, chloro, bromo, methyl, ethyl, propyl, butyl, pentyl, isopropyl, isobutyl, tert-butyl, methoxy, ethoxy, propoxy, butoxy, isopropoxy, tert-butoxy, methylthio, methylsulfinyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxymethyl, methoxycarbonyl, ethoxycarbonyl, aminocarbonyl, amino, formyl, methylamino and dimethylamino; wherein $R^2$ is selected from phenyl, naphthyl, biphenyl, thienyl, pyridyl, furyl, pyrazinyl, pyrrolyl, pyrazolyl, triazolyl, cyclopropyl, cyclobutyl, cyclopentyl, cyclohexyl, cyclopropenyl, cyclobutenyl, cyclopentenyl, cyclohexenyl, morpholino, pyrrolidinyl, piperazinyl and piperidinyl; wherein $R^2$ is optionally substituted at a substitutable position with one or more radicals selected from fluoro, chloro, bromo, methylthio, methylsulfinyl, methyl, ethyl, propyl, butyl, pentyl, isopropyl,.isobutyl, tert-butyl, ethylenyl, propylenyl, butenyl, pentenyl, isopropylenyl, isobutylenyl, propargyl, cyano, carboxyl, carboxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, formyl, acetyl, N-methylaminocarbonyl, N-phenylaminocarbonyl, N,N-dimethylaminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, ethoxy, propoxy, butoxy, isopropoxy, tert-butoxy, hydroxymethyl, trifluoromethoxy, amino, N-methylamino, N,N-dimethylamino, pyridyl, furyl, pyrazinyl, pyrrolyl, pyrazolyl, morpholino, pyrrolidinyl, piperazinyl, piperidinyl, triazolyl and nitro; and wherein $R^3$ is aryl selected from phenyl, naphthyl and biphenyl, substituted at a substitutable position with a radical selected from methylsulfonyl and sulfamyl; or a pharmaceutically-acceptable salt thereof.

5. Compound of claim 1 wherein $R^1$ is selected from hydrido, halo, amino, $C_1$–$C_{10}$ alkoxy, cyano, nitro, hydroxyl, aminocarbonyl, acyl, $C_1$–$C_{10}$ alkylaminocarbonyl, $C_6$–$C_{12}$ arylaminocarbonyl, $C_1$–$C_{10}$ alkyl, $C_2$–$C_{10}$ alkenyl, $C_2$–$C_{10}$ alkynyl, $C_1$–$C_{10}$ haloalkyl, $C_1$–$C_{10}$ haloalkoxy, $C_1$–$C_{10}$ alkylamino, $C_6$–$C_{12}$ arylamino, $C_6$–$C_{12}$ aryl-$C_1$–$C_{10}$-alkylamino, carboxyl, $C_1$–$C_{10}$ carboxyalkyl, $C_1$–$C_{10}$ alkoxycarbonyl, $C_1$–$C_{10}$ alkoxycarbonyl-$C_1$–$C_{10}$-alkyl, $C_1$–$C_{10}$ alkylamino-$C_1$–$C_{10}$-alkyl, 5–10 membered heterocyclic-$C_1$–$C_{10}$-alkyl, $C_6$–$C_{12}$ aryl-$C_1$–$C_{10}$-alkyl, $C_1$–$C_{10}$ cyanoalkyl, N-$C_1$–$C_{10}$-alkylsulfonylamino, 5–10 membered heteroarylsulfonyl-$C_1$–$C_{10}$-alkyl, 5–10 membered heteroarylsulfonyl-$C_1$–$C_{10}$-haloalkyl, $C_6$–$C_{12}$ aryloxy-$C_1$–$C_{10}$-alkyl and $C_6$–$C_{12}$ aryl-$C_1$–$C_{10}$-alkyloxy-$C_1$–$C_{10}$-alkyl; wherein $R^2$ is phenyl substituted at a substitutable position with a radical selected from methylsulfonyl, and sulfamyl; and wherein $R^3$ is selected from $C_6$–$C_{12}$ aryl, $C_3$–$C_{10}$ cycloalkyl, $C_3$–$C_{10}$ cycloalkenyl and 5–10 membered heterocyclic; wherein $R^3$ is optionally substituted at a substitutable position with one or more radicals selected from halo, $C_1$–$C_{10}$ alkylthio, $C_1$–$C_{10}$ alkylsulfinyl, $C_1$–$C_{10}$ alkyl, $C_2$–$C_{10}$ alkenyl, $C_2$–$C_{10}$ alkynyl, cyano, carboxyl, $C_1$–$C_{10}$ carboxyalkyl, $C_1$–$C_{10}$ alkoxycarbonyl, aminocarbonyl, acyl, N-mono-$C_1$–$C_{10}$-alkylaminocarbonyl, N-mono-$C_6$–$C_{12}$-arylaminocarbonyl, N, N-di-$C_1$–$C_{10}$-alkylaminocarbonyl, N-$C_1$–$C_{10}$-alkyl-N-$C_6$–$C_{12}$-arylaminocarbonyl, $C_1$–$C_{10}$ haloalkyl, $C_1$–$C_{10}$ haloalkoxy, hydroxyl, $C_1$–$C_{10}$ alkoxy, $C_1$–$C_{10}$ hydroxyalkyl, amino, N-$C_1$–$C_{10}$-alkylamino, N,N-di-$C_1$–$C_{10}$-alkylamino, 5–10 membered heterocyclic and nitro; or a pharmaceutically-acceptable salt thereof.

6. Compound of claim 5 wherein $R^1$ is selected from halo, amino, $C_1$–$C_6$ alkoxy, cyano, nitro, hydroxy, aminocarbonyl, acyl, $C_1$–$C_6$ alkylaminocarbonyl, phenylaminocarbonyl, $C_1$–$C_6$ alkyl, $C_2$–$C_6$ alkenyl, $C_2$–$C_6$ alkynyl, $C_1$–$C_6$ haloalkyl, $C_1$–$C_6$ haloalkoxy, $C_1$–$C_6$ alkylamino, carboxyl, phenyl-$C_1$–$C_6$-alkylamino, $C_1$–$C_6$ carboxyalkyl, $C_1$–$C_6$ alkoxycarbonyl-$C_1$–$C_6$-alkyl, $C_1$–$C_6$ alkoxycarbonyl, $C_1$–$C_6$ alkylamino-$C_1$–$C_6$-alkyl, 5–6 membered heterocyclic-$C_1$-$C_6$-alkyl, $C_1$-$C_6$ N-alkylsulfonylamino, 5–6 membered heteroarylsulfonyl-$C_1$-$C_6$-alkyl, 5–6 membered heteroarylsulfonyl-$C_1$-$C_6$-haloalkyl, phenyl-$C_1$-$C_6$-alkyl, $C_1$-$C_6$ cyanoalkyl, phenyloxy-$C_1$-$C_6$-alkyl and phenyl-$C_1$-$C_6$-alkyloxy-$C_1$-$C_6$-alkyl; wherein $R^2$ is phenyl substituted at a substitutable position with a radical selected from methylsulfonyl, and sulfamyl; and wherein $R^3$ is selected from phenyl, $C_3$-$C_6$ cycloalkyl, $C_3$-$C_6$ cycloalkenyl and 5–6 membered heterocyclic; wherein $R^3$ is optionally substituted at a substitutable position with one or more radicals selected from halo, $C_1$-$C_6$ alkylthio, $C_1$-$C_6$ alkylsulfinyl, $C_1$-$C_6$ alkyl, $C_2$-$C_6$ alkenyl, $C_2$-$C_6$ alkynyl, cyano, carboxyl, $C_1$-$C_6$ carboxyalkyl, $C_1$-$C_6$ alkoxycarbonyl, aminocarbonyl, acyl, N-mono-$C_1$-$C_6$-alkylaminocarbonyl, N-phenylaminocarbonyl, N,N-di-$C_1$-$C_6$-alkylaminocarbonyl, N-$C_1$-$C_6$-alkyl-N-phenylaminocarbonyl, $C_1$-$C_6$ haloalkyl, hydroxyl, $C_1$-$C_6$ alkoxy, $C_1$-$C_6$ hydroxyalkyl, $C_1$-$C_6$ haloalkoxy, amino, $C_1$-$C_6$ N-alkylamino, N,N-di-$C_1$-$C_6$-alkylamino, 5–6 membered heterocyclic and nitro; or a pharmaceutically-acceptable salt thereof.

7. Compound of claim 6 wherein $R^1$ is selected from fluoro, chloro, bromo, iodo, amino, methoxy, ethoxy, propoxy, butoxy, isopropoxy, tert-butoxy, cyano, nitro, hydroxy, aminocarbonyl, formyl, acetyl, N-methylaminocarbonyl, N-phenylaminocarbonyl, N,N-dimethylaminocarbonyl, N-methyl-N-phenylaminocarbonyl, methyl, ethyl, propyl, butyl, pentyl, isopropyl, isobutyl, tert-butyl, ethylenyl, propylenyl, butenyl, pentenyl, isopropylenyl, isobutylenyl, propargyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, N-methylamino, N-ethylamino, N-propylamino, N-butylamino, N-tert-butylamino, N-pentylamino, N-hexylamino, N,N-dimethylamino, carboxyl, N-benzylamino, carboxymethyl, methoxycarbonylmethyl, ethoxycarbonylmethyl, methylaminomethyl, morpholinomethyl, pyrrolidinylmethyl, piperazinylmethyl, piperidinylmethyl, pyridylmethyl, thienylmethyl, benzyl, phenethyl, phenpropyl, cyanomethyl, phenoxymethyl, benzyloxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, morpholino, pyrrolidinyl, piperazinyl, piperidinyl, methylsulfonylamino, (2-thienyl)sulfonylmethyl and (2-thienyl)sulfonylbromomethyl; wherein $R^2$ is phenyl substituted at a substitutable position with a radical selected from methylsulfonyl, fluoromethylsulfonyl and sulfamyl; and wherein $R^3$ is selected from phenyl, naphthyl, biphenyl, thienyl, pyridyl, furyl, pyrazinyl, pyrrolyl, pyrazolyl, triazolyl, cyclopropyl, cyclobutyl, cyclopentyl, cyclohexyl, cyclopropenyl, cyclobutenyl, cyclopentenyl, cyclohexenyl, morpholino, pyrrolidinyl, piperazinyl and piperidinyl; wherein $R^3$ is optionally substituted at a substitutable position with one or more radicals selected from fluoro, chloro, bromo, methylthio, methylsulfinyl, methyl, ethyl, propyl, butyl, pentyl, isopropyl, isobutyl, tert-butyl, ethylenyl, propylenyl, butenyl, pentenyl, isopropylenyl, isobutylenyl, propargyl, cyano, carboxyl, carboxymethyl, carboxyethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, formyl, acetyl, N-methylaminocarbonyl, N-phenylaminocarbonyl, N,N-dimethylaminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, ethoxy, propoxy, butoxy, isopropoxy, tert-butoxy, hydroxymethyl, trifluoromethoxy, amino, N-methylamino, N,N-dimethylamino, pyridyl, furyl, pyrazinyl, pyrrolyl, pyrazolyl, morpholino, pyrrolidinyl, piperazinyl, piperidinyl, triazolyl and nitro; or a pharmaceutically-acceptable salt thereof.

8. Compound of claim 7 selected from compounds, and their pharmaceutically-acceptable salts or prodrugs, of the group consisting of 4-[(4-methylsulfonyl)phenyl]-5-(4-fluorophenyl)-2-(trifluoromethyl)thiazole;

4-[(4-methylsulfonyl)phenyl]-5-(4-chlorophenyl)-2-(2-chlorophenyl)thiazole;

4-[(4-methylsulfonyl)phenyl]-5-(4-methoxyphenyl)-2-(2-chlorophenyl)thiazole;

4-[(4-methylsulfonyl)phenyl]-5-(4-methylphenyl)-2-(2-chlorophenyl)thiazole;

4-[(4-methylsulfonyl)phenyl]-5-(4-bromophenyl)-2-(2-chlorophenyl)thiazole;

4-[(4-methylsulfonyl)phenyl]-5-(4-methylthiophenyl)-2-(2-chlorophenyl)thiazole;

4-[(4-methylsulfonyl)phenyl]-5-(3-fluoro-4-methoxyphenyl)-2-(2-chlorophenyl)thiazole;

4-[(4-methylsulfonyl)phenyl]-5-(3-chloro-4-methoxyphenyl)-2-(2-chlorophenyl)thiazole;

4-[(4-methylsulfonyl)phenyl]-5-(3-chloro-4-methylphenyl)-2-(2-chlorophenyl)thiazole;

4-[(4-methylsulfonyl)phenyl]-5-(3-methyl-4-chlorophenyl)-2-(2-chlorophenyl)thiazole;

4-[(4-methylsulfonyl)phenyl]-5-(3,4-methylenedioxyphenyl)-2-(2-chlorophenyl)thiazole;

4-[(4-methylsulfonyl)phenyl]-5-(3,5-difluoro-4-methoxyphenyl)-2-(2-chlorophenyl)thiazole;

4-[(4-methylsulfonyl)phenyl]-5-(3,5-dichloro-4-methoxyphenyl)-2-(2-chlorophenyl)thiazole;

5-(4-fluorophenyl)-5-[(4-methylsulfonyl)phenyl]-2-methylthiazole;

4-[(4-methylsulfonyl)phenyl]-5-(4-fluorophenyl)-2-(difluoromethyl)thiazole;

4-[(4-methylsulfonyl)phenyl]-5-(4-fluorophenyl)-2-(methylthio)thiazole;

4-[(4-methylsulfonyl)phenyl]-5-(4-fluorophenyl)-2-(phenylthio)thiazole;

4-[(4-methylsulfonyl)phenyl]-5-(4-fluorophenyl)-2-([3-chlorophenyl]thio)thiazole;

4-[(4-methylsulfonyl)phenyl]-5-(4-fluorophenyl)-2-([3,5-dichlorophenyl]thio)thiazole;

4-[(4-methylsulfonyl)phenyl]-5-(4-fluorophenyl)-2-([4-fluorophenyl]thio)thiazole;

4-[(4-methylsulfonyl)phenyl]-5-(4-fluorophenyl)-2-([4-methylphenyl]thio)thiazole;

4-[(4-methylsulfonyl)phenyl]-5-(4-fluorophenyl)-2-(benzylthio)thiazole;

4-[(4-methylsulfonyl)phenyl]-5-(4-fluorophenyl)-2-([3-chlorobenzyl]thio)thiazole;

4-[(4-methylsulfonyl)phenyl]-5-(4-fluorophenyl)-2-[(3,5-dichlorobenzyl)thio]thiazole;

4-[(4-methylsulfonyl)phenyl]-5-(4-fluorophenyl)-2-([4-fluorobenzyl]thio)thiazole;

4-[(4-methylsulfonyl)phenyl]-5-(4-fluorophenyl)-2-([4-methylbenzyl]thio)thiazole;

4-[(4-methylsulfonyl)phenyl]-5-(4-fluorophenyl)-2-(methylsulfonyl)thiazole;

4-[(4-methylsulfonyl)phenyl]-5-(4-fluorophenyl)-2-(phenylsulfonyl)thiazole;

4-[(4-methylsulfonyl)phenyl]-5-(4-fluorophenyl)-2-([3-chlorophenyl]sulfonyl)thiazole;

4-[(4-methylsulfonyl)phenyl]-5-(4-fluorophenyl)-2-([3,5-dichlorophenyl)sulfonyl]thiazole;

4-[(4-methylsulfonyl)phenyl]-5-(4-fluorophenyl)-2-([4-bromophenyl]sulfonyl)thiazole;

4-[(4-methylsulfonyl)phenyl]-5-(4-fluorophenyl)-2-([4-methylphenyl]sulfonyl)thiazole;

4-[(4-methylsulfonyl)phenyl]-5-(4- fluorophenyl)-2-(benzylsulfonyl)thiazole;

4-[(4-methylsulfonyl)phenyl]-5-(4-fluorophenyl)-2-(fluoromethylsulfonyl)thiazole;

4-[(4-methylsulfonyl)phenyl]-5-(4-fluorophenyl)-2-(acetyl)thiazole;

4-[(4-methylsulfonyl)phenyl]-5-(4-fluorophenyl)-2-(trifluoroacetyl)thiazole;

4-[(4-methylsulfonyl)phenyl]-5-(4-fluorophenyl)-2-(benzoyl)thiazole;

4-[(4-methylsulfonyl)phenyl]-5-(4- fluorophenyl)-2-(4-fluorobenzoyl)thiazole;

methyl[4-[(4-methylsulfonyl)phenyl]-5-(4-fluorophenyl)-2-thiazolyl]carboxylate;

ethyl[4-[(4-methylsulfonyl)phenyl]-5-(4-fluorophenyl)-2-thiazolyl]carboxylate;

4-[(4-methylsulfonyl)phenyl]-5-(4-fluorophenyl)-2-(hydroxymethyl)thiazole;

4-[(4-methylsulfonyl)phenyl]-5-(4-fluorophenyl)-2-(methoxymethyl)thiazole;

4-[(4-methylsulfonyl)phenyl]-5-(4-fluorophenyl)-2-(phenyloxymethyl)thiazole;

4-[(4-methylsulfonyl)phenyl]-5-(4-fluorophenyl)-2-(3-fluorophenyloxymethyl)thiazole;

4-[(4-methylsulfonyl)phenyl]-5-(4-fluorophenyl)-2-(4-fluorophenoxymethyl)thiazole;

4-[(4-methylsulfonyl)phenyl]-5-(4-fluorophenyl)-2-(benzyloxymethyl)thiazole;

4-[(4-methylsulfonyl)phenyl]-5-(4-fluorophenyl)-2-(cyanomethyl)thiazole;

4-[(4-methylsulfonyl)phenyl]-5-(4-fluorophenyl)-2-(2-quinolylmethoxymethyl)thiazole;

4-[(4-methylsulfonyl)phenyl]-5-(4-fluorophenyl)-2-(2-naphthylmethoxymethyl)thiazole;

4-[(4-methylsulfonyl)phenyl]-5-(4-fluorophenyl)-2-(N-phenylaminocarbonyl)thiazole;

4-[(4-methylsulfonyl)phenyl]-5-(4-fluorophenyl)-2-[(3,5-difluorophenyl) aminocarbonyl]thiazole;

4-[(4-methylsulfonyl)phenyl]-5-(4-fluorophenyl)-2-(benzylaminocarbonyl)thiazole;

4-[(4-methylsulfonyl)phenyl]-5-(4-fluorophenyl)-2-([3,5-dichlorobenzyl]aminocarbonyl)thiazole;

4-[(4-methylsulfonyl)phenyl]-5-(4-fluorophenyl)-2-([4-methylbenzyl]aminocarbonyl)thiazole;

4-[(4-methylsulfonyl)phenyl]-5-(4-fluorophenyl)-2-(benzoylamino)thiazole;

4-[(4-methylsulfonyl)phenyl]-5-(4-fluorophenyl)-2-(phenylacetyl)aminothiazole;

4-[5-(4-fluorophenyl)-2-(trifluoromethyl)-4-thiazolyl]benzenesulfonamide;

4-[5-(4-bromophenyl)-2-(2-chlorophenyl)-4-thiazolyl]benzenesulfonamide;

4-[5-(4-methylthiophenyl)-2-(2-chlorophenyl)-4-thiazolyl]benzenesulfonamide;

4-[5-(3-fluoro-4-methoxyphenyl)-2-(2-chlorophenyl)-4-thiazolyl]benzenesulfonamide;

4-[5-(3-chloro-4-methoxyphenyl)-2-(2-chlorophenyl)-4-thiazolyl]benzenesulfonamide;

4-[5-(3-chloro-4-methylphenyl)-2-(2-chlorophenyl)-4-thiazolyl]benzenesulfonamide;

4-[5-(3-methyl-4-chlorophenyl)-2-(2-chlorophenyl)-4-thiazolyl]benzenesulfonamide;

4-[5-(3,4-methylenedioxyphenyl)-2-(2-chlorophenyl)-4-thiazolyl]benzenesulfonamide;

4-[5-(3,5-difluoro-4-methoxyphenyl)-2-(2-chlorophenyl)-4-thiazolyl]benzenesulfonamide;

4-[5-(3,5-dichloro-4-methoxyphenyl)-2-(2-chlorophenyl)-4-thiazolyl]benzenesulfonamide;

4-[5-(4-chlorophenyl)-2-(2-chlorophenyl)-4-thiazolyl]benzenesulfonamide;

4-[5-(4-methoxyphenyl)-2-(2-chlorophenyl)-4-thiazolyl]benzenesulfonamide;

4-[5-(4-methylphenyl)-2-(2-chlorophenyl)- 4-thiazolyl]benzenesulfonamide;

4-[5-(4-fluorophenyl)-2-methyl-4-thiazolyl]benzenesulfonamide;

4-[5-(4-fluorophenyl)-2-([3-chlorophenyl]thio)-4-thiazolyl]benzenesulfonamide;

4-[5-(4-fluorophenyl)-2-([3,5-dichlorophenyl]thio)-4-thiazolyl]benzenesulfonamide;

4-[5-(4-fluorophenyl)-2-([4-fluorophenyl]thio)-4-thiazolyl]benzenesulfonamide;

4-[5-(4-fluorophenyl)-2-([4-methylphenyl]thio)-4-thiazolyl]benzenesulfonamide;

4-[5-(4-fluorophenyl)-2-(benzylthio)-4-thiazolyl]benzenesulfonamide;

4-[5-(4-fluorophenyl)-2-([3-chlorobenzyl]thio)-4-thiazolyl]benzenesulfonamide;

4-[5-(4-fluorophenyl)-2-([3,5-dichlorobenzyl]thio)-4-thiazolyl]benzenesulfonamide;

4-[5-(4-fluorophenyl)-2-([4-fluorobenzyl]thio)-4-thiazolyl]benzenesulfonamide;

4-[5-(4-fluorophenyl)-2-([4-methylbenzyl]thio)-4-thiazolyl]benzenesulfonamide;

4-[5-(4-fluorophenyl)-2-(methylsulfonyl)-4-thiazolyl]benzenesulfonamide;

4-[5-(4-fluorophenyl)-2-(phenylsulfonyl)-4-thiazolyl]benzenesulfonamide;

4-[5-(4-fluorophenyl)-2-([3-chlorophenyl]sulfonyl)-4-thiazolyl]benzenesulfonamide;

4-[5-(4-fluorophenyl)-2-([3,5-dichlorophenyl]sulfonyl)-4-thiazolyl]benzenesulfonamide;

4-[5-(4-fluorophenyl)-2-([4-bromophenyl]sulfonyl)-4-thiazolyl]benzenesulfonamide;

4-[5-(4-fluorophenyl)-2-([4-methylphenyl]sulfonyl)-4-thiazolyl]benzenesulfonamide;

4-[5-(4-fluorophenyl)-2-(benzylsulfonyl)-4-thiazolyl]benzenesulfonamide;

4-[5-(4-fluorophenyl)-2-(fluoromethylsulfonyl)-4-thiazolyl]benzenesulfonamide;

4-[5-(4-fluorophenyl)-2-(acetyl)-4-thiazolyl]benzenesulfonamide;

4-[5-(4-fluorophenyl)-2-(trifluoroacetyl)-4-thiazolyl]benzenesulfonamide;

4-[5-(4-fluorophenyl)-2-(benzoyl)-4-thiazolyl]benzenesulfonamide;

4-[5-(4-fluorophenyl)-2-(4-fluorobenzoyl)-4-thiazolyl]benzenesulfonamide;

methyl[4-[(4-aminosulfonyl)phenyl]-5-(4-fluorophenyl)-2-thiazolyl]carboxylate;

ethyl[4-[(4-aminosulfonyl)phenyl]-5-(4-fluorophenyl)-2-thiazolyl]carboxylate;

4-[5-(4-fluorophenyl)-2-(hydroxymethyl)-4-thiazolyl]benzenesulfonamide;

4-[5-(4-fluorophenyl)-2-(methoxymethyl)-4-thiazolyl]
benzenesulfonamide;

4-[5-(4-fluorophenyl)-2-(phenoxymethyl)-4-thiazolyl]
benzenesulfonamide;

4-[5-(4-fluorophenyl)-2-(3- fluorophenoxymethyl)-4-
thiazolyl]benzenesulfonamide;

4-[5-(4-fluorophenyl)-2-(4-fluorophenoxymethyl)-4-
thiazolyl]benzenesulfonamide;

4-[5-(4-fluorophenyl)-2-(benzyloxymethyl)-4-thiazolyl]
benzenesulfonamide;

4-[5-(4-fluorophenyl)-2-(cyanomethyl)-4-thiazolyl]
benzenesulfonamide;

4-[5-(4-fluorophenyl)-2-(2-quinolylmethoxymethyl)-4-
thiazolyl]benzenesulfonamide;

4-[5-(4-fluorophenyl)-2-(2-naphthylmethoxymethyl)-4-
thiazolyl]benzenesulfonamide;

4-[5-(4-fluorophenyl)-2-(N-phenylamide)-4-thiazolyl]
benzenesulfonamide;

4-[5-(4-fluorophenyl)-2-([3,5-difluorophenyl]amide)-4-
thiazolyl]benzenesulfonamide;

4-[5-(4-fluorophenyl)-2-(benzylamide)- 5-thiazolyl]
benzenesulfonamide;

4-[5-(4-fluorophenyl)-2-([3,5-dichlorobenzyl]amide)-4-
thiazolyl]benzenesulfonamide;

4-[5-(4-fluorophenyl)-2-([4-methylbenzyl]amide)-4-
thiazolyl]benzenesulfonamide;

4-[5-(4- fluorophenyl)-2-(benzoylamino)-4-thiazolyl]
benzenesulfonamide; and

4-[5-(4- fluorophenyl)-2-((phenylacetyl)amino)-4-thiazolyl]
benzenesulfonamide.

9. A compound of Formula II

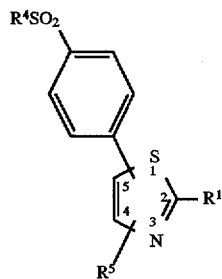

II wherein $R^1$ is selected from hydrido, $C_1-C_{10}$ alkyl, $C_1-C_{10}$ haloalkyl, $C_1-C_{10}$ cyanoalkyl, $C_1-C_{10}$ alkylamino, $C_6-C_{12}$ aryl-$C_1-C_{10}$-alkyl, $C_6-C_{12}$ arylamino, 5–10 membered heteroarylsulfonyl-$C_1-C_{10}$-alkyl, 5–10 membered heteroarylsulfonyl-$C_1-C_{10}$-haloalkyl, $C_6-C_{12}$ aryl-$C_1-C_{10}$-alkylamino, $C_6-C_{12}$ aryloxy-$C_1-C_{10}$-alkyl, $C_1-C_{10}$ alkoxycarbonyl, $C_6-C_{12}$ aryl optionally substituted at a substitutable position with one or more radicals selected from halo and $C_1-C_{10}$ alkoxy, and 5–10 membered heterocyclic optionally substituted at a substitutable position with one or more radicals selected from halo and $C_1-C_{10}$ alkyl;

wherein $R^4$ is selected from methyl and amino; and wherein $R^5$ is selected from $C_6-C_{12}$ aryl and 5–10 membered heteroaryl; wherein $R^5$ is optionally substituted at a substitutable position with one or more radicals selected from halo, $C_1-C_{10}$ alkyl and $C_1-C_{10}$ alkoxy;

or a pharmaceutically-acceptable salt thereof.

10. Compound of claim 9 wherein $R^1$ is selected from hydrido, $C_1-C_6$ alkyl, $C_1-C_6$ haloalkyl, $C_1-C_6$ cyanoalkyl, $C_1-C_6$ alkylamino, phenyl-$C_1-C_6$-alkyl, phenylamino, 5–6 membered heteroarylsulfonyl-$C_1-C_6$-alkyl, 5–6 membered heteroarylsulfonyl-$C_1-C_6$-haloalkyl, phenyl-$C_1-C_6$-alkylamino, phenyloxy-$C_1-C_6$-alkyl, $C_1-C_6$ alkoxycarbonyl, phenyl optionally substituted at a substitutable position with one or more radicals selected from halo and $C_1-C_6$ alkoxy, and 5–6 membered heterocyclic optionally substituted at a substitutable position with one or more radicals selected from halo and $C_1-C_6$ alkyl;

wherein $R^4$ is selected from methyl and amino; and wherein $R^5$ is selected from phenyl and 5–6 membered heteroaryl; wherein $R^5$ is optionally substituted at a substitutable position with one or more radicals selected from halo, $C_1-C_6$ alkyl and $C_1-C_6$ alkoxy;

or a pharmaceutically-acceptable salt thereof.

11. Compound of claim 10 wherein $R^1$ is selected from hydrido, methyl, ethyl, propyl, butyl, pentyl, isopropyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyanomethyl, cyanoethyl, cyanopropyl, methylamino, ethylamino, propylamino, butylamino, tert-butylamino, pentylamino, hexylamino, phenethyl, phenpropyl, benzyl, phenylamino, thienylsulfonylmethyl, thienylsulfonylbromomethyl, benzylamino, phenoxymethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, phenyl optionally substituted at a substitutable position with one or more radicals selected from fluoro, chloro, bromo, methoxy, ethoxy, propoxy, butoxy, isopropoxy and tert-butoxy, and a heterocyclic radical selected from thienyl, pyridyl, furyl, pyrazinyl, thiazolyl, pyrrolyl, pyrazolyl and triazolyl, optionally substituted at a substitutable position with one or more radicals selected from fluoro, chloro, bromo, methyl, ethyl, propyl, butyl, pentyl, isopropyl, isobutyl and tert-butyl;

wherein $R^4$ is methyl or amino; and wherein $R^5$ is selected from phenyl, pyridyl, furyl, pyrazinyl, pyrrolyl, pyrazolyl, triazolyl and thienyl; wherein $R^5$ is optionally substituted at a substitutable position with one or more radicals selected from fluoro, chloro, bromo, methyl, ethyl, propyl, butyl, pentyl, isopropyl, isobutyl, tert-butyl, methoxy, ethoxy, propoxy, butoxy, isopropoxy and tert-butoxy;

or a pharmaceutically-acceptable salt thereof.

12. Compound of claim 11 selected from compounds, and their pharmaceutically-acceptable salts or prodrugs, of the group consisting of 4-(4-fluorophenyl)-5-[(4-methylsulfonyl)phenyl]-2-
phenylthiazole;

4-(4-fluorophenyl)-5-[(4-methylsulfonyl)phenyl]-2-(4-
methoxyphenyl)thiazole;

4-(4-fluorophenyl)-5-[(4-methylsulfonyl)phenyl]-2-
trifluoromethyl-thiazole;

4-(4-fluorophenyl)-2-(N-hexylamino)-5-[(4-
methylsulfonyl)phenyl]thiazole;

2-(4-cyanophenylamino)-4-(4-fluorophenyl)-5[4-
(methylsulfonyl)phenyl]thiazole;

4-(4-fluorophenyl)-2-(N-methylamino)-5-[(4-
methylsulfonyl)phenyl]thiazole;

2-(N-ethylamino)-4-(4-fluorophenyl)-5-[(4-methylsulfonyl)
phenyl]thiazole;

2-(N-tert-butylamino)4-(4-fluorophenyl)-5-[(4-
methylsulfonyl)phenyl]thiazole;

ethyl 4-[[4-(4-fluorophenyl)-5-methylsulfonyl)phenyl]-2-
thiazolyl]amino]benzoate;

ethyl 3-[[4-(4-fluorophenyl) 5-[(4-methylsulfonyl)phenyl]-
2-thiazolyl]amino]benzoate;

4-(4-fluorophenyl) 5-[(4-methylsulfonyl)phenyl]-2-(2-phenylethyl)thiazole;

2-(N-(3,5-dichlorophenyl)amino)-4-(4-fluorophenyl)-5-[(4-methylsulfonyl)phenyl]thiazole;

2-(N-butylamino)-4-(4-fluorophenyl)-5-[(4-methylsulfonyl)phenyl]thiazole;

2-ethyl-4-(4-fluorophenyl)-5-[(4-methylsulfonyl)phenyl]thiazole 4-(4-fluorophenyl)-5-[(4-methylsulfonyl)phenyl]-2-(3-phenylpropyl)thiazole;

2-((3-chlorophenoxy) methyl)-4-(4-fluorophenyl)-5-[(4-methylsulfonyl)phenyl]thiazole;

4-(4-fluorophenyl)-5-[(4-methylsulfonyl)phenyl]-2-(2-methyl-4-thiazolyl)thiazole;

2-(2-chlorophenyl)-4-(2-fluorophenyl)-5-[(4-methylsulfonyl)phenyl]thiazole;

4-(4-fluorophenyl)-5-[(4-methylsulfonyl)phenyl]-2-(2,3,4,5,6-pentafluorophenyl)thiazole;

2-((2-chlorophenoxy) methyl)-4-(4-fluorophenyl)-5-methylsulfonyl)phenyl]thiazole;

2-(2-chlorophenyl)-4-(4-bromophenyl)- 5-[(4-methylsulfonyl)phenyl]thiazole;

2-((3-chlorophenoxy)methyl)-4-(2-fluorophenyl)-5-[(4-methylsulfonyl)phenyl]thiazole;

4-(2-fluorophenyl)-5-[(4-methylsulfonyl)phenyl]-2-((4-methoxyphenoxy)methyl)thiazole;

2-((4-chlorophenoxy)methyl)-4-(4-fluorophenyl)-5-[(4-methylsulfonyl)phenyl]thiazole;

2-(2-chlorophenyl)-4-phenyl-5-[(4-methylsulfonyl)phenyl]thiazole; 2-(2-chlorophenyl)-4-(3-fluorophenyl)-5-[(4-methylsulfonyl)phenyl]thiazole;

4-(2,4-difluorophenyl)-2-(2-chlorophenyl)-5-[(4-methylsulfonyl)phenyl]thiazole;

2-(2-chlorophenyl)-4-(2-methylphenyl)-5-[(4-methylsulfonyl)phenyl]thiazole;

2-(2-chlorophenyl)-5-[(4-methylsulfonyl)phenyl]-4-(2-thienyl)thiazole;

2-(2-chlorophenyl)-5-[(4-methylsulfonyl)phenyl]-4-(3-thienyl)thiazole;

4-(4-fluorophenyl)-5-[(4-methylsulfonyl)phenyl]-2-(4-pyridyl)thiazole;

2-(2-chlorophenyl)-4-(2-chlorophenyl)-5-[(4-methylsulfonyl)phenyl]thiazole;

2-(2-chlorophenyl)-4-(4-chlorophenyl)-5-[(4-methylsulfonyl)phenyl]thiazole;

2-(2-chlorophenyl)-4-(4-methoxyphenyl)-5-[(4-methylsulfonyl)phenyl]thiazole;

2-(3-chloro-4-fluorophenyl)-4-(4-fluorophenyl)-5-[(4-methylsulfonyl)phenyl]thiazole;

4-(4-fluorophenyl)-2-((2-thienyl)sulfonylmethyl)-5-[(4-methylsulfonyl)phenyl]thiazole;

4-(4-fluorophenyl)-2-((2-thienyl)sulfonylbromomethyl)-5-[(4-methylsulfonyl)phenyl]thiazole;

2-(2-chlorophenyl)-5-[(4-methylsulfonyl)phenyl]-4-(4-methylphenyl)thiazole;

2-(2-chlorophenyl)-4-(4-fluorophenyl)-5-[(4-methylsulfonyl)phenyl]thiazole;

ethyl[4-(4-fluorophenyl)-5-[(4-methylsulfonyl)phenyl]-2-thiazolyl]carboxylate;

2-(cyanomethyl)-4-(4-fluorophenyl)-5-[(4-methylsulfonyl)phenyl]thiazole;

2-(tert-butyl)-4-(4-fluorophenyl)-5-[(4-methylsulfonyl)phenyl]thiazole;

2-benzyl-4-(4-fluorophenyl)-5-[(4-methylsulfonyl)phenyl]thiazole;

5-(4-fluorophenyl)-4-[(4-methylsulfonyl)phenyl]-2-methylthiazole;

2-(3-[4-bromophenyl]propyl)-4-(4-fluorophenyl))-5-[(4-methylsulfonyl)phenyl]thiazole;

4-(4-fluorophenyl)-5-[(4-methylsulfonyl)phenyl]thiazole;

4-(4-fluorophenyl)-5-[(4-methylsulfonyl)phenyl]-2-trifluoromethylthiazole;

4-(4-fluorophenyl)-5-[(4-methylsulfonyl)phenyl]-2-(2-thienyl)thiazole;

2-(5-bromo-2-thienyl)-4-(4-fluorophenyl)-5-[(4-methylsulfonyl)phenyl]thiazole;

4-(4-fluorophenyl)-5-[(4-methylsulfonyl)phenyl]-2-(3-pyridyl)thiazole;

4-(4-fluorophenyl)-5-[(4-methylsulfonyl)phenyl]-2-methylthiazole;

2-benzylamino-4-(4-fluorophenyl)-5-[(4-methylsulfonyl)phenyl]thiazole;

4-(4-fluorophenyl)-5-[(4-methylsulfonyl)phenyl]-2-(1-piperidinyl)thiazole;

4-(4-fluorophenyl)-5-[(4-methylsulfonyl)phenyl]-2-(1-propylamino)thiazole;

2-[(3,5-dichlorophenoxy)methyl]-4-(4-fluorophenyl)-5-[4-(methylsulfonyl)phenyl]thiazole;

4-[4-(4-fluorophenyl)-2-(2-chlorophenyl)-5-thiazolyl]benzenesulfonamide; and

4-[4-(4-fluorophenyl)-2-((3,5-dichlorophenoxy)methyl)-5-thiazolyl]benzenesulfonamide.

13. Compound of claim 12 which is 4-(4-fluorophenyl)-5-[(4-methylsulfonyl)phenyl]-2-(2-chlorophenyl)thiazole, or a pharmaceutically-acceptable salt thereof.

14. Compound of claim 12 which is 2-((2,4-dichlorophenoxy)methyl)-4-(4-fluorophenyl)-5-[(4-methylsulfonyl)phenyl]thiazole, or a pharmaceutically-acceptable salt thereof.

15. A pharmaceutical composition comprising therapeutically-effective amount of a compound, said compound selected from a family of compounds of claim 1; or a pharmaceutically-acceptable salt thereof.

16. A pharmaceutical composition comprising a therapeutically-effective amount of a compound, said compound selected from a family of compounds of claim 9; or a pharmaceutically-acceptable salt thereof.

17. A pharmaceutical composition comprising a therapeutically-effective amount of a compound, said compound selected from a family of compounds of claim 10; or a pharmaceutically-acceptable salt thereof.

18. A pharmaceutical composition comprising a therapeutically-effective amount of a compound, said compound selected from a family of compounds of claim 11; or a pharmaceutically-acceptable salt thereof.

19. A pharmaceutical composition comprising a therapeutically-effective amount of a compound, said compound selected from a family of compounds of claim 12; or a pharmaceutically-acceptable salt thereof.

20. A pharmaceutical composition comprising a therapeutically-effective amount of a compound, said compound selected from a compound of claim 13; or a pharmaceutically-acceptable salt thereof.

21. A pharmaceutical composition comprising a therapeutically-effective amount of a compound, said compound selected from a compound of claim 14; or a pharmaceutically-acceptable salt thereof.

22. A method of treating inflammation or an inflammation-associated disorder in a subject, said method comprising administering to the subject having such inflammation or inflammation-associated disorder, a therapeutically-effective amount of a compound of claim 1; or a pharmaceutically-acceptable salt thereof.

23. A method of treating inflammation or an inflammation-associated disorder in a subject, said method comprising administering to the subject having such inflammation or inflammation-associated disorder, a therapeutically-effective amount of a compound of claim 9; or a pharmaceutically-acceptable salt thereof.

24. A method of treating inflammation or an inflammation-associated disorder in a subject, said method comprising administering to the subject having such inflammation or inflammation-associated disorder, a therapeutically-effective amount of a compound of claim 10; or a pharmaceutically-acceptable salt thereof.

25. A method of treating inflammation or an inflammation-associated disorder in a subject, said method comprising administering to the subject having such inflammation or inflammation-associated disorder, a therapeutically-effective amount of a compound of claim 11; or a pharmaceutically-acceptable salt thereof.

26. A method of treating inflammation or an inflammation-associated disorder in a subject, said method comprising administering to the subject having such inflammation or inflammation-associated disorder, a therapeutically-effective amount of a compound of claim 12; or a pharmaceutically-acceptable salt thereof.

27. A method of treating inflammation or an inflammation-associated disorder in a subject, said method comprising administering to the subject having such inflammation or inflammation-associated disorder, a therapeutically-effective amount of a compound of claim 13; or a pharmaceutically-acceptable salt thereof.

28. A method of treating inflammation or an inflammation-associated disorder in a subject, said method comprising administering to the subject having such inflammation or inflammation-associated disorder, a therapeutically-effective amount of a compound of claim 14; or a pharmaceutically-acceptable salt thereof.

29. The method of claim 22 for use in treatment of inflammation.

30. The method of claim 22 for use in treatment of an inflammation-associated disorder.

31. The method of claim 30 wherein the inflammation-associated disorder is arthritis.

32. The method of claim 31 wherein the inflammation-associated disorder is pain.

33. The method of claim 31 wherein the inflammation-associated disorder is fever.

34. Compound of claim 4 selected from compounds, and their pharmaceutically-acceptable salts or prodrugs, of the group consisting of 5-[(4-methylsulfonyl)phenyl]-4-(4-fluorophenyl)-2-phenylthiazole;

5-[(4-methylsulfonyl)phenyl]-4-(4-fluorophenyl)-2-(4-methoxyphenyl)thiazole;

5-[(4-methylsulfonyl)phenyl]-4-(4-fluorophenyl)-2-(4-chlorophenyl)thiazole;

5-[(4-methylsulfonyl)phenyl]-4-(4-fluorophenyl)-2-(N-hexylamino)thiazole;

5-[(4-methylsulfonyl)phenyl]-4-(4-fluorophenyl)-2-(N-methylamino)thiazole;

5-[(4-methylsulfonyl)phenyl]-4-(4-fluorophenyl)-2-(N-ethylamino)thiazole;

5-[(4-methylsulfonyl)phenyl]-4-(4-fluorophenyl)-2-(N-tert-butylamino)thiazole;

5-[(4-methylsulfonyl)phenyl]-4-(4-fluorophenyl)-2-(N-(4-phenoxyphenyl)amino)thiazole;

ethyl 4-[[5-[(4-methylsulfonyl)phenyl]-4-(4-fluorophenyl)-2-thiazolyl]amino]benzoate;

ethyl 3-[[5-[(4-methylsulfonyl)phenyl]-4-(4-fluorophenyl)-2-thiazolyl]amino]benzoate;

5-[(4-methylsulfonyl)phenyl]-4 -(4-fluorophenyl)-2-(2-phenylethyl)thiazole;

5-[(4-methylsulfonyl)phenyl]-4-(4-fluorophenyl)-2-(N-(3,5-dichlorophenyl)amino)thiazole;

5-[(4-methylsulfonyl)phenyl]-4-(4-fluorophenyl)-2-(N-butylamino)thiazole;

4-[5-[(4-methylsulfonyl)phenyl]-4-(4-fluorophenyl)-2-thiazolyl]aminobenzoic acid;

3-[5-[(4-methylsulfonyl)phenyl]-4-(4-fluorophenyl)-2-thiazolyl]aminobenzoic acid;

5-[(4-methylsulfonyl)phenyl]-4-(4-fluorophenyl)-2-ethylthiazole;

5-[(4-methylsulfonyl)phenyl]-4-(4-fluorophenyl)-2-(3-phenylpropyl)thiazole;

5-[(4-methylsulfonyl)phenyl]-4-(4-fluorophenyl)-2-((3-chlorophenoxy)methyl)thiazole;

5-[(4-methylsulfonyl)phenyl]-4-(4-fluorophenyl)-2-(2-methyl-4-thiazolyl)thiazole;

5-[(4-methylsulfonyl)phenyl]-4-(2-fluorophenyl)-2-(2-chlorophenyl)thiazole;

5-[(4-methylsulfonyl)phenyl]-4-(2,5-difluorophenyl)-2-(2-chlorophenyl)thiazole;

5-[(4-methylsulfonyl)phenyl]-4-(4-fluorophenyl)-2-(2,3,4,5,6-pentafluorophenyl)thiazole;

5-[(4-methylsulfonyl)phenyl]-4-(4-fluorophenyl)-2-((2-chlorophenoxy)methyl)thiazole;

5-[(4-methylsulfonyl)phenyl]-4-(4-bromophenyl)-2-(2-chlorophenyl)thiazole;

5-[(4-methylsulfonyl)phenyl]-4-(2-fluorophenyl)-2-((3-chlorophenoxy)methyl) thiazole;

5-[(4-methylsulfonyl)phenyl]-4-(4-fluorophenyl)-2-5((3,5-dichlorophenoxy)methyl)thiazole;

5-[(4-methylsulfonyl)phenyl]-4-(2-fluorophenyl)-2-((4-methoxyphenoxy)methyl)thiazole;

5-[(4-methylsulfonyl)phenyl]-4-(4-methylthiophenyl)-2-(2-chlorophenyl)thiazole;

5-[(4-methylsulfonyl)phenyl]-4-(3-fluoro-4-methoxyphenyl)-2-(2-chlorophenyl)thiazole;

5-[(4-methylsulfonyl)phenyl]-4-(3-chloro-4-methoxyphenyl)-2-(2-chlorophenyl)thiazole;

5-[(4-methylsulfonyl)phenyl]-4-(3-chloro-4-methylphenyl)-2-(2-chlorophenyl)thiazole;

5-[(4-methylsulfonyl)phenyl]-4-(3-methyl-4-chlorophenyl)-2-(2-chlorophenyl)thiazole;

5-[(4-methylsulfonyl)phenyl]-4-(3,4-methylenedioxyphenyl)-2-(2-chlorophenyl)thiazole;

5-[(4-methylsulfonyl)phenyl]-4-(3,5-difluoro-4-methoxyphenyl)-2-(2-chlorophenyl)thiazole;

5-[(4-methylsulfonyl)phenyl]-4-(3,5-dichloro-4-methoxyphenyl)-2-(2-chlorophenyl)thiazole;

5-[(4-methylsulfonyl)phenyl]-4-(4-fluorophenyl)-2-(difluoromethyl)thiazole;

5-[(4-methylsulfonyl)phenyl]-4-(4-fluorophenyl)-2-(methylthio)thiazole;

5-[(4-methylsulfonyl)phenyl]-4-(4-fluorophenyl)-2-(phenylthio)thiazole;

5-[(4-methylsulfonyl)phenyl]-4-(4-fluorophenyl)-2-([3-chlorophenyl]thio) thiazole;

5-[(4-methylsulfonyl)phenyl]-4-(4-fluorophenyl)-2-[(3,5-dichlorophenyl)thio]thiazole;

5-[(4-methylsulfonyl)phenyl]-4-(4-fluorophenyl)-2-fluorophenyl]thio)thiazole;

5-[(4-methylsulfonyl)phenyl]-4-(4-fluorophenyl)-2-([4-methylphenyl]thio)thiazole;

5-[(4-methylsulfonyl)phenyl]-4-(4-fluorophenyl)-2-(benzylthio)thiazole;

5-[(4-methylsulfonyl)phenyl]-4-(4-fluorophenyl)-2-([3-chlorobenzyl]thio)thiazole;

5-[(4-methylsulfonyl)phenyl]-4-(4- fluorophenyl)-2-[(3,5-dichlorobenzyl)thio]thiazole;

5-[(4-methylsulfonyl)phenyl]-4-(4- fluorophenyl)-2-([4-fluorobenzyl]thio)thiazole 5-[(4-methylsulfonyl)phenyl]-4-(4-fluorophenyl)-2-([4-methylbenzyl]thio)thiazole 5-[(4-methylsulfonyl)phenyl]-4-(4-fluorophenyl)-2-(methylsulfonyl)thiazole;

5-[(4-methylsulfonyl)phenyl]-4-(4-fluorophenyl)-2-(phenylsulfonyl)thiazole;

5-[(4-methylsulfonyl)phenyl]-4-(4-fluorophenyl)-2-([3-chlorophenyl]sulfonyl)thiazole;

5-[(4-methylsulfonyl)phenyl]-4-(4-fluorophenyl)-2-[(3,5-dichlorophenyl)sulfonyl]thiazole;

5-[(4-methylsulfonyl)phenyl]-4-(4-fluorophenyl)-2-([4-bromophenyl]sulfonyl)thiazole;

5-[(4-methylsulfonyl)phenyl]-4-(4-fluorophenyl)-2-([4-methylphenyl]sulfonyl)thiazole;

5-[(4-methylsulfonyl)phenyl]-4-(4-fluorophenyl)-2-(benzylsulfonyl)thiazole;

5-[(4-methylsulfonyl)phenyl]-4-(4-fluorophenyl)-2-(fluoromethylsulfonyl)thiazole;

5-[(4-methylsulfonyl)phenyl]-4-(4-fluorophenyl)-2-(acetyl)thiazole;

5-[(4-methylsulfonyl)phenyl]-4-(4-fluorophenyl)-2-(trifluoroacetyl)thiazole;

5-[(4-methylsulfonyl)phenyl]-4-(4-fluorophenyl)-2-(benzoyl)thiazole;

5-[(4-methylsulfonyl)phenyl]-4-(4-fluorophenyl)-2-(4-fluorobenzoyl)thiazole;

methyl [5-[(4-methylsulfonyl)phenyl]-4-(4-fluorophenyl)-2-thiazolyl]carboxylate;

ethyl [5-[(4-methylsulfonylphenyl]-4-(4-fluorophenyl)-thiazolyl]carboxylate;

5-[(4-methylsulfonyl)phenyl]-4-(4-fluorophenyl)-2-(hydroxymethyl)thiazole;

5-[(4-methylsulfonyl)phenyl]-4-(4-fluorophenyl)-2-(methoxymethyl)thiazole;

5-[(4-methylsulfonyl)phenyl]-4-(4-fluorophenyl)-2-(phenyloxymethyl)thiazole;

5-[(4-methylsulfonyl)phenyl]-4-(4-fluorophenyl)-2-(3-fluorophenyloxymethyl)thiazole;

5-[(4-methylsulfonyl)phenyl]-4-(4-fluorophenyl)-2-(4-fluorophenoxymethyl)thiazole;

5-[(4-methylsulfonyl)phenyl]-4-(4-fluorophenyl)-2-(benzyloxymethyl)thiazole;

5-[(4-methylsulfonyl)phenyl]-4-(4-fluorophenyl)-2-(cyanomethyl)thiazole;

5-[(4-methylsulfonyl)phenyl]-4-(4-fluorophenyl)-2-(2-quinolylmethoxymethyl)thiazole;

5-[(4-methylsulfonyl)phenyl]-4-(4-fluorophenyl)-2-(2-naphthylmethoxymethyl)thiazole;

5-[(4-methylsulfonyl)phenyl]-4-(4-fluorophenyl)-2-(N-phenylaminocarbonyl)thiazole;

5-[(4-methylsulfonyl)phenyl]-4-(4-fluorophenyl)-2-[(3,5-difluorophenyl) aminocarbonyl]thiazole;

5-[(4-methylsulfonyl)phenyl]-4-(4-fluorophenyl)-2-(benzylaminocarbonyl)thiazole;

5-[(4-methylsulfonyl)phenyl]-4-(4-fluorophenyl)-2-([3,5-dichlorobenzyl]aminocarbonyl)thiazole;

5-[(4-methylsulfonyl)phenyl]-4-(4-fluorophenyl)-2-([4-methylbenzyl]aminocarbonyl)thiazole;

5-[(4-methylsulfonyl)phenyl]-4-(4-fluorophenyl)-2-(benzoylamino)thiazole;

5-[(4-methylsulfonyl)phenyl]-4-(4-fluorophenyl)-2-(phenylacetyl)aminothiazole;

5-[(4-chlorophenoxy) methyl]-4-(4-fluorophenyl)-5-[(4-methylsulfonyl)phenyl]thiazole;

2-(2-chlorophenyl)-4-phenyl-5-[(4-methylsulfonyl)phenyl]thiazole;

2-(2-chlorophenyl)-4-(3-fluorophenyl)-5-[(4-methylsulfonyl)phenyl]thiazole;

4-(2,4-difluorophenyl)-2-(2-chlorophenyl)-5-[(4-methylsulfonyl)phenyl]thiazole;

2-(2-chlorophenyl)-4-(2-methylphenyl)-5-[(4-methylsulfonyl)phenyl]thiazole;

2-(2-chlorophenyl)-5-[(4-methylsulfonyl)phenyl]-4-(2-thienyl)thiazole;

2-(2-chlorophenyl)-5-[(4-methylsulfonyl)phenyl]-4-(3-thienyl)thiazole;

4-(4-fluorophenyl)-5-[(4-methylsulfonyl)phenyl]-2-(4-pyridyl)thiazole;

2-(2-chlorophenyl)-4-(2-chlorophenyl)-2- [(4-methylsulfonyl)phenyl]thiazole;

2-(2-chlorophenyl)-4-(4-chlorophenyl)-5-[(4-methylsulfonyl)phenyl]thiazole;

2-(2-chlorophenyl)-4-(4-methoxyphenyl)-5-[(4-methylsulfonyl)phenyl]thiazole;

2-(3-chloro-4-fluorophenyl)-4-(4-fluorophenyl)-5-[(4-methylsulfonyl)phenyl]thiazole;

2-((2-thienyl)sulfonylmethyl)-4-(4-fluorophenyl)-5-[(4-methylsulfonyl)phenyl]thiazole;

2-((2-thienyl)sulfonylbromomethyl)-4-(4-fluorophenyl)-5-[(4-methylsulfonyl)phenyl]thiazole;

2-(2-chlorophenyl)-5-[(4-methylsulfonyl)phenyl]-5-(4-methylphenyl)thiazole;

2-(2-chlorophenyl)-4-(4-fluorophenyl)-5-[(4-methylsulfonyl)phenyl]thiazole;

ethyl [4-(4-fluorophenyl)-5-[(4-methylsulfonyl)phenyl]-2-thiazolyl]carboxylate;

2-(cyanomethyl)-4-(4-fluorophenyl)-5-[(4-methylsulfonyl)phenyl]thiazole;

2-(tert-butyl)-4-(4-fluorophenyl)-5-[(4-methylsulfonyl)phenyl]thiazole;

4-(4-fluorophenyl)-5-[(4-methylsulfonyl)phenyl]-2-benzylthiazole;

2-(3-[4-bromophenyl]propyl)-4-(4-fluorophenyl))-5-[(4-methylsulfonyl)phenyl]thiazole;

4-(4-fluorophenyl)-5-[(4-5 methylsulfonyl)phenyl]thiazole;

4-(4-fluorophenyl)-5-[(4-methylsulfonyl)phenyl]-2-trifluoromethylthiazole;

4-(4-fluorophenyl)-5-[(4-methylsulfonyl)phenyl]-2-(2-thienyl)thiazole;

4-(4-fluorophenyl)-5-[(4-methylsulfonyl)phenyl]-2-(5-bromo-2-thienyl)thiazole;

4-(4-fluorophenyl)-5-[(4-methylsulfonyl)phenyl]-2-(3-pyridyl)thiazole;

4-(4-fluorophenyl)-5-[(4-methylsulfonyl)phenyl]-2-methylthiazole;

4-(4-fluorophenyl)-5-[(4-methylsulfonyl)phenyl]-2-benzylaminothiazole;

4-(4-fluorophenyl)-5-[(4-methylsulfonyl)phenyl]-2-(1-piperidinyl)thiazole;

4-(4-fluorophenyl)-5-[(4-methylsulfonyl)phenyl]-2-(1-propylamino)thiazole;

4-[4-(4-bromophenyl)-2-(2-chlorophenyl)-5-thiazolyl]benzenesulfonamide;

4-[4-(4-fluorophenyl)-2-phenyl-5-thiazolyl]benzenesulfonamide;

4-[4-(4-fluorophenyl)-2-(4-methoxyphenyl)-5-thiazolyl]benzenesulfonamide;

4-[4-(4-fluorophenyl)-2-(4-chlorophenyl)-5-thiazolyl]benzenesulfonamide;

4-[4-(4-fluorophenyl)-2-(N-hexylamino)-5-thiazolyl]benzenesulfonamide;

4-[4-(4-fluorophenyl)-2-(N-methylamino)-5-thiazolyl]
benzenesulfonamide;
4-[4-(4-fluorophenyl)-2-(N-ethylamino)-5-thiazolyl]
benzenesulfonamide;
4-[4-(4-fluorophenyl)-2-(N-tert-butylamino)-5-thiazolyl]
benzenesulfonamide;
4-[4-(4-fluorophenyl)-2-(N-(4-phenoxyphenyl) amino)-5-
thiazolyl]benzenesulfonamide;
ethyl 4-[[5-[(4-aminosulfonyl)phenyl]-4-(4-fluorophenyl)-
2-thiazolyl]amino]benzoate;
ethyl 3-[[5-[(4-aminosulfonyl)phenyl]-4-(4-fluorophenyl)-
2-thiazolyl]amino]benzoate;
4-[4-(4-fluorophenyl)-2-(2-phenylethyl-5-thiazolyl]
benzenesulfonamide;
4-[4-(4- fluorophenyl)-2-(N-(3,5-dichlorophenyl) amino)-5-
thiazolyl]benzenesulfonamide;
4-[4-(4-fluorophenyl)-2-(N-butylamino)-5-thiazolyl]
benzenesulfonamide;
4-[5-[(4-aminosulfonyl)phenyl]-4-(4-fluorophenyl)-2-
thiazolyl]amino]benzoic acid;
3-[5-[(4-aminosulfonyl)phenyl]-4-(4-fluorophenyl)-2-
thiazolyl]amino]benzoic acid;
4-[4-(4-fluorophenyl)-2-ethyl-5-thiazolyl]
benzenesulfonamide;
4-[4-(4-fluorophenyl)-2-(3-phenylpropyl)-5-thiazolyl]
benzenesulfonamide;
4-[4-(4-fluorophenyl)-2-(( 3-chlorophenoxy) methyl)-5-
thiazolyl]benzenesulfonamide;
4-[4-(4-fluorophenyl)-2-(2-methyl-4-thiazolyl)-5-thiazolyl]
benzenesulfonamide;
4-[4-(2-fluorophenyl)-2-(2-chlorophenyl)-5-thiazolyl]
benzenesulfonamide;
4-[4-(2,5-difluorophenyl)-2-(2-chlorophenyl)-5-thiazolyl]
benzenesulfonamide;
4-[4-(4-fluorophenyl)-2-(2,3,4,5,6-pentafluorophenyl)-5-
thiazolyl]benzenesulfonamide;
4-[4-(4-fluorophenyl)-2-((2-chlorophenoxy) methyl)-5-
thiazolyl]benzenesulfonamide;
4-[4-(2-fluorophenyl)-2-((3-chlorophenoxy) methyl)-5-
thiazolyl]benzenesulfonamide;
4-[4-(4-fluorophenyl)-2-((3,5-dichlorophenoxy) methyl)-5-
thiazolyl]benzenesulfonamide;
4-[4-(2-fluorophenyl)-2-((4-methoxyphenoxy)methyl)-5-
thiazolyl]benzenesulfonamide;
4-[4-(4-bromophenyl)-2-(2-chlorophenyl)-5-thiazolyl]
benzenesulfonamide;
4-[4-(4-methylthiophenyl)-2-(2-chlorophenyl)-5-thiazolyl]
benzenesulfonamide;
4-[4-(3-fluoro-4-methoxyphenyl)-2-(2-chlorophenyl)-5-
thiazolyl]benzenesulfonamide;
4-[4-(3-chloro-4-methoxyphenyl)-2-(2-chlorophenyl)-5-
thiazolyl]benzenesulfonamide;
4-[4-(3-chloro-4-methylphenyl)-2-(2-chlorophenyl)-5-
thiazolyl]benzenesulfonamide;
4-[4-(3-methyl-4-chlorophenyl)-2-(2-chlorophenyl)-5-
thiazolyl]benzenesulfonamide;
4-[4-(3,4-methylenedioxyphenyl)-2-(2-chlorophenyl)-5-
thiazolyl]benzenesulfonamide;
4-[4-(3,5-difluoro-4-methoxyphenyl)-2-(2-chlorophenyl)-5-
thiazolyl]benzenesulfonamide;
4-[4-(3,5-dichloro-4-methoxyphenyl)-2-(2-chlorophenyl)-
5-thiazolyl]benzenesulfonamide;
4-[4-(4-fluorophenyl)-2-(difluoromethyl)-5-thiazolyl]
benzenesulfonamide;
4-[4-(4-fluorophenyl)-2-(methylthio)-5-thiazolyl]
benzenesulfonamide;
4-[4-(4- fluorophenyl)-2-(phenylthio)-5-thiazolyl]
benzenesulfonamide;
4-[4-(4-fluorophenyl)-2-([3-chlorophenyl]thio)-5-thiazolyl]
benzenesulfonamide;
4-[4-(4-fluorophenyl)-2-([3,5-dichlorophenyl]thio)-5-
thiazolyl]benzenesulfonamide;
4-[4-(4-fluorophenyl)-2-([4-fluorophenyl]thio)-5-thiazolyl]
benzenesulfonamide;
4-[4-(4-fluorophenyl)-2-([4-methylphenyl]thio)-5-
thiazolyl]benzenesulfonamide;
4-[4-(4-fluorophenyl)-2-(benzylthio)-5-thiazolyl]
benzenesulfonamide;
4-[4-(4-fluorophenyl)-2-([3-chlorobenzyl]thio)-5-thiazolyl]
benzenesulfonamide;
4-[4-(4-fluorophenyl)-2-([3,5-dichlorobenzyl]thio)-5-
thiazolyl]benzenesulfonamide;
4-[4-(4-fluorophenyl)-2-([4-fluorobenzyl]thio)-5-thiazolyl]
benzenesulfonamide;
4-[4-(4-fluorophenyl)-2-([4-methylbenzyl]thio)-5-thiazolyl]
benzenesulfonamide;
4-[4-(4-fluorophenyl)-2-(methylsulfonyl)-5-thiazolyl]
benzenesulfonamide;
4-[4-(4-fluorophenyl)-2-(phenylsulfonyl)-5-thiazolyl]
benzenesulfonamide;
4-[4-(4-fluorophenyl)-2-([3-chlorophenyl]sulfonyl)-5-
thiazolyl]benzenesulfonamide;
4-[4-(4-fluorophenyl)-2-([3,5-dichlorophenyl]sulfonyl)-5-
thiazolyl]benzenesulfonamide;
4-[4-(4-fluorophenyl)-2-([4-bromophenyl]sulfonyl)-5-
thiazolyl]benzenesulfonamide;
4-[4-(4- fluorophenyl)-2-([4-methylphenyl]sulfonyl)-5-
thiazolyl]benzenesulfonamide;
4-[4-(4-fluorophenyl)-2-(benzylsulfonyl)-5-thiazolyl]
benzenesulfonamide;
4-[4-(4-fluorophenyl)-2-(fluoromethylsulfonyl)-5-thiazolyl]
benzenesulfonamide;
4-[4-(4-fluorophenyl)-2-(acetyl)-5-thiazolyl]
benzenesulfonamide;
4-[4-(4-fluorophenyl)-2-(trifluoroacetyl)-5-thiazolyl]
benzenesulfonamide;
4-[4-(4-fluorophenyl)-2-(benzoyl)-5-thiazolyl]
benzenesulfonamide;
4-[4-(4-fluorophenyl)-2-(4-fluorobenzoyl)-5-thiazolyl]
benzenesulfonamide;
methyl[5-[(4-aminosulfonyl)phenyl]-4-(4-fluorophenyl)-2-
thiazolyl]carboxylate;
ethyl[5-[(4-aminosulfonyl)phenyl]-4-(4-fluorophenyl)-2-
thiazolyl]carboxylate;
4-[4-(4-fluorophenyl)-2-(hydroxymethyl)-5-thiazolyl]
benzenesulfonamide;
4-[4-(4-fluorophenyl)-2-(methoxymethyl)-5-thiazolyl]
benzenesulfonamide;
4-[4-(4-fluorophenyl)-2-(phenoxymethyl)-5- thiazolyl]
benzenesulfonamide;
4-[4-(4-fluorophenyl)-2-(3-fluorophenoxymethyl)-5-
thiazolyl]benzenesulfonamide;
4-[4-(4-fluorophenyl)-2-(4-fluorophenoxymethyl)-5-
thiazolyl]benzenesulfonamide;
4-[4-(4-fluorophenyl)-2-(benzyloxymethyl)-5-thiazolyl]
benzenesulfonamide;
4-[4-(4-fluorophenyl)-2-(cyanomethyl)-5-thiazolyl]
benzenesulfonamide;
4-[4-(4-fluorophenyl)-2-(2-quinolylmethoxymethyl)-5-
thiazolyl]benzenesulfonamide;
4-[4-(4- fluorophenyl)-2-(2-naphthylmethoxymethyl)-5-
thiazolyl]benzenesulfonamide;
4-[4-(4- fluorophenyl)-2-(N-phenylamide)-5-thiazolyl]
benzenesulfonamide;
4-[4-(4-fluorophenyl)-2-[(3,5-difluorophenyl)amide]-5-
thiazolyl]benzenesulfonamide;

4-[4-(4-fluorophenyl)-2-(benzylamide)-5-thiazolyl]benzenesulfonamide;

4-[4-(4-fluorophenyl)-2-[(3,5-dichlorobenzyl) amide]-5-thiazolyl]benzenesulfonamide;

4-[4-(4-fluorophenyl)-2-[(4-methylbenzyl)amide]-5-thiazolyl]benzenesulfonamide;

4-[4-(4-fluorophenyl)-2-(benzoylamino)-5-thiazolyl]benzenesulfonamide;

4-[4-(4-fluorophenyl)-2-[(phenylacetyl) amino]-5-thiazolyl]benzenesulfonamide;

4-[4-(4-fluorophenyl)-2-(4-chlorophenoxy)-5-thiazolyl]benzenesulfonamide;

4-[4-phenyl-2-(2-chlorophenyl)-5-thiazolyl]benzenesulfonamide;

4-[4-(3-fluorophenyl)-2-(2-chlorophenyl)-5-thiazolyl]benzenesulfonamide;

4-[4-(2,4-difluorophenyl)-2-(2-chlorophenyl)-5-thiazolyl]benzenesulfonamide;

4-[4-(2-methylphenyl)-2-(2-chlorophenyl)-5-thiazolyl]benzenesulfonamide;

4-[4-(2-thienyl)-2-(2-chlorophenyl)-5-thiazolyl]benzenesulfonamide;

4-[4-(3-thienyl)-2-(2-chlorophenyl)-5-thiazolyl]benzenesulfonamide;

4-[4-(4-fluorophenyl)-2-(4-pyridyl)-5-thiazolyl]benzenesulfonamide;

4-[4-(2-chlorophenyl)-2-(2-chlorophenyl)-5-thiazolyl]benzenesulfonamide;

4-[4-(4-chlorophenyl)-2-(2-chlorophenyl)-5-thiazolyl]benzenesulfonamide;

4-[4-(4-methoxyphenyl)-2-(2-chlorophenyl)-5-thiazolyl]benzenesulfonamide;

4-[4-(4-fluorophenyl)-2-(3-chloro-4-fluorophenyl)-5-thiazolyl]benzenesulfonamide;

4-[4-(4-fluorophenyl)-2-((2-thienyl)sulfonylmethyl)-5-thiazolyl]benzenesulfonamide;

4-[4-(4-fluorophenyl)-2-(2-thienyl)-5-thiazolyl]benzenesulfonamide;

4-[4-(4-methylphenyl)-2-(2-chlorophenyl)-5-thiazolyl]benzenesulfonamide;

4-[4-(4-fluorophenyl)-2-(2-chlorophenyl)-5-thiazolyl]benzenesulfonamide;

ethyl 4-[(4-fluorophenyl)-5-[(4-aminosulfonyl)phenyl]-2-thiazolyl]carboxylate;

4-[4-(4-fluorophenyl)-2-(cyanomethyl)-5-thiazolyl]benzenesulfonamide;

4-[4-(4-fluorophenyl)-2-(tert-butyl)-5-thiazolyl]benzenesulfonamide;

4-[4-(4-fluorophenyl)-2-benzyl-5-thiazolyl]benzenesulfonamide;

4-[4-(4-fluorophenyl)-2-(3-(4-bromophenyl)propyl)-5-thiazolyl]benzenesulfonamide;

4-[4-(4-fluorophenyl)-5-thiazolyl]benzenesulfonamide;

4-[4-(4-fluorophenyl)-2-trifluoromethyl-5-thiazolyl]benzenesulfonamide;

4-[4-(4-fluorophenyl)-2-(2-thienyl)-5-thiazolyl]benzenesulfonamide;

4-[4-(4-fluorophenyl)-2-(5-bromo-2-thienyl)-5-thiazolyl]benzenesulfonamide;

4-[4-(4-fluorophenyl)-2-(3-pyridyl)-5-thiazolyl]benzenesulfonamide;

4-[4-(4-fluorophenyl)-2-(methyl)-5-thiazolyl]benzenesulfonamide;

4-[4-(4-fluorophenyl)-2-(1-benzylamino)-5-thiazolyl]benzenesulfonamide;

4-[4-(4-fluorophenyl)-2-(1-piperidinyl)-5-thiazolyl]benzenesulfonamide;

4-[4-(4-fluorophenyl)-2-(1-propylamino)-5-thiazolyl]benzenesulfonamide;

4-[4-(4-fluorophenyl)-2-(2-chlorophenyl)-5-thiazolyl]benzenesulfonamide; and

4-[4-(4-fluorophenyl)-2-((3,5-dichlorophenoxy)methyl)-5-thiazolyl]benzenesulfonamide.

* * * * *